United States Patent
Levin et al.

(10) Patent No.: US 10,618,907 B2
(45) Date of Patent: Apr. 14, 2020

(54) CELL-PERMEABLE, CELL-COMPATIBLE, AND CLEAVABLE LINKERS FOR COVALENT TETHERING OF FUNCTIONAL ELEMENTS

(71) Applicant: Promega Corporation, Madison, WI (US)

(72) Inventors: Sergiy Levin, Madison, WI (US); Rachel Friedman Ohana, Madison, WI (US); Thomas Kirkland, Madison, WI (US); Keith V. Wood, Madison, WI (US)

(73) Assignee: PROMEGA CORPORATION, Madison, WI (US)

( * ) Notice: Subject to any disclaimer, the term of this patent is extended or adjusted under 35 U.S.C. 154(b) by 0 days.

(21) Appl. No.: 15/172,860

(22) Filed: Jun. 3, 2016

(65) Prior Publication Data

US 2016/0355523 A1   Dec. 8, 2016

Related U.S. Application Data

(60) Provisional application No. 62/171,620, filed on Jun. 5, 2015.

(51) Int. Cl.
| | | |
|---|---|---|
| *C07D 491/22* | (2006.01) | |
| *C07D 231/40* | (2006.01) | |
| *C07D 487/04* | (2006.01) | |

(52) U.S. Cl.
CPC ......... *C07D 491/22* (2013.01); *C07D 231/40* (2013.01); *C07D 487/04* (2013.01)

(58) Field of Classification Search
CPC .. C07D 491/22; C07D 231/40; C07D 487/04; G01N 33/573; G01N 2333/914
See application file for complete search history.

(56) References Cited

U.S. PATENT DOCUMENTS

| | | |
|---|---|---|
| 4,812,409 A | 3/1989 | Babb et al. |
| 6,162,931 A | 12/2000 | Gee et al. |
| 7,238,842 B2 | 7/2007 | Wood et al. |
| 7,425,436 B2 | 9/2008 | Darzins et al. |
| 7,429,472 B2 | 9/2008 | Darzins et al. |
| 7,867,726 B2 | 1/2011 | Wood et al. |
| 8,557,970 B2 | 10/2013 | Encell et al. |
| 8,669,103 B2 | 3/2014 | Binkowski et al. |

(Continued)

FOREIGN PATENT DOCUMENTS

| | | |
|---|---|---|
| WO | WO2014/093671 | 6/2014 |
| WO | WO2014/151282 | 9/2014 |
| WO | WO2016/196956 | 12/2016 |

OTHER PUBLICATIONS

Luyai et al. Facile preparation of fluorescent neoglycoproteins using p-nitrophenyl anthranilate as a heterobifunctional linker. Bioconjugate Chem. 2009, vol. 20, pp. 1618-1624. (Year: 2009).*

(Continued)

*Primary Examiner* — Shafiqul Haq
(74) *Attorney, Agent, or Firm* — Casimir Jones SC; David W. Staple

(57) ABSTRACT

Provided herein are cell-permeable, cell-compatible, and chemoselectively-cleavable linkers for tethering (e.g., covalently) functional elements (e.g., a cellular interaction element and a capture element), and methods of use (e.g., intracellular capture and extracellular release of cellular targets) therewith.

10 Claims, 44 Drawing Sheets

Specification includes a Sequence Listing.

(56) References Cited

U.S. PATENT DOCUMENTS

| | | | | |
|---|---|---|---|---|
| 8,796,432 | B2* | 8/2014 | Ju | C07H 21/04 422/430 |
| 9,551,705 | B2* | 1/2017 | Hitko | G01N 33/54326 |
| 2007/0224620 | A1* | 9/2007 | Hartzell | G01N 33/5308 435/6.12 |
| 2009/0246142 | A1 | 10/2009 | Bhatla et al. | |
| 2011/0171673 | A1 | 7/2011 | Darzins et al. | |
| 2014/0199712 | A1 | 7/2014 | Hitko et al. | |
| 2014/0322794 | A1 | 10/2014 | Hitko et al. | |

OTHER PUBLICATIONS

Yang, Lihu. Facile cleavage of the carbamate linker of hydroxymethyl resin and its application in syntheses requiring strongly acidic conditions. Tetrahedron Letters 2000, vol. 41, pp. 6981-6984. (Year: 2000).*

Al et al., A method to site-specifically introduce methyllysine into proteins in E. coli. Chem Commun (Camb). Aug. 14, 2010;46(30):5506-8.

Amore et al., Development of a hypersensitive periodate-cleavable amino acid that is methionine- and disulfide-compatible and its application in MHC exchange reagents for T cell characterisation. Chembiochem. Jan. 2, 2013;14(1):123-31.

Crivat et al., Imaging proteins inside cells with fluorescent tags. Trends Biotechnol. Jan. 2012;30(1):8-16.

Crochet et al., Arene-ruthenium(II) complexes with hydrophilic P-donor ligands: versatile catalysts in aqueous media. Dalton Trans. Sep. 7, 2014;43(33):12447-62.

Gautier et al., An engineered protein tag for multiprotein labeling in living cells. Chem Biol. Feb. 2008;15(2):128-36.

Maurer et al., A periodate-cleavable linker for functional proteomics under slightly acidic conditions: application for the analysis of intracellular aspartic proteases. J Proteome Res. Jan. 4, 2013;12(1):199-207.

Rodenko et al., Class I major histocompatibility complexes loaded by a periodate trigger. J Am Chem Soc. Sep. 2, 2009;131(34):12305-13.

Sanchez et al., Metal-catalyzed uncaging of DNA-binding agents in living cells. Chem Sci. May 1, 2014;5(5):1901-1907.

Shaughnessy, Hydrophilic ligands and their application in aqueous-phase metal-catalyzed reactions. Chem Rev. Feb. 2009;109(2):643-710.

Streu et al., Ruthenium-induced allylcarbamate cleavage in living cells. Angew Chem Int Ed Engl. Aug. 25, 2006;45(34):5645-8.

Yang et al., A simple and effective cleavable linker for chemical proteomics applications. Mol Cell Proteomics. Jan. 2013;12(1):237-44.

International Search Report and Written Opinion for PCT/US2016/035752, dated Sep. 6, 2016, 8 pages.

Buckley et al., Small-molecule control of intracellular protein levels through modulation of the ubiquitin proteasome system. Angew Chem Int Ed Engl. Feb. 24, 2014;53(9):2312-30.

European Extended Search Report for EP16804539.1, dated Dec. 21, 2018, 7 pages.

* cited by examiner

Cy-Amphos t-Bu-Amphos

BDSPPB

Xantphos-S

DANPHOS o-DANPHOS p-DANPHOS

DAN2PHOS o-DAN2PHOS p-DAN2PHOS

- This linker structure displays minimal interference of allyl group with binding kinetics to HaloTag and cellular permeability

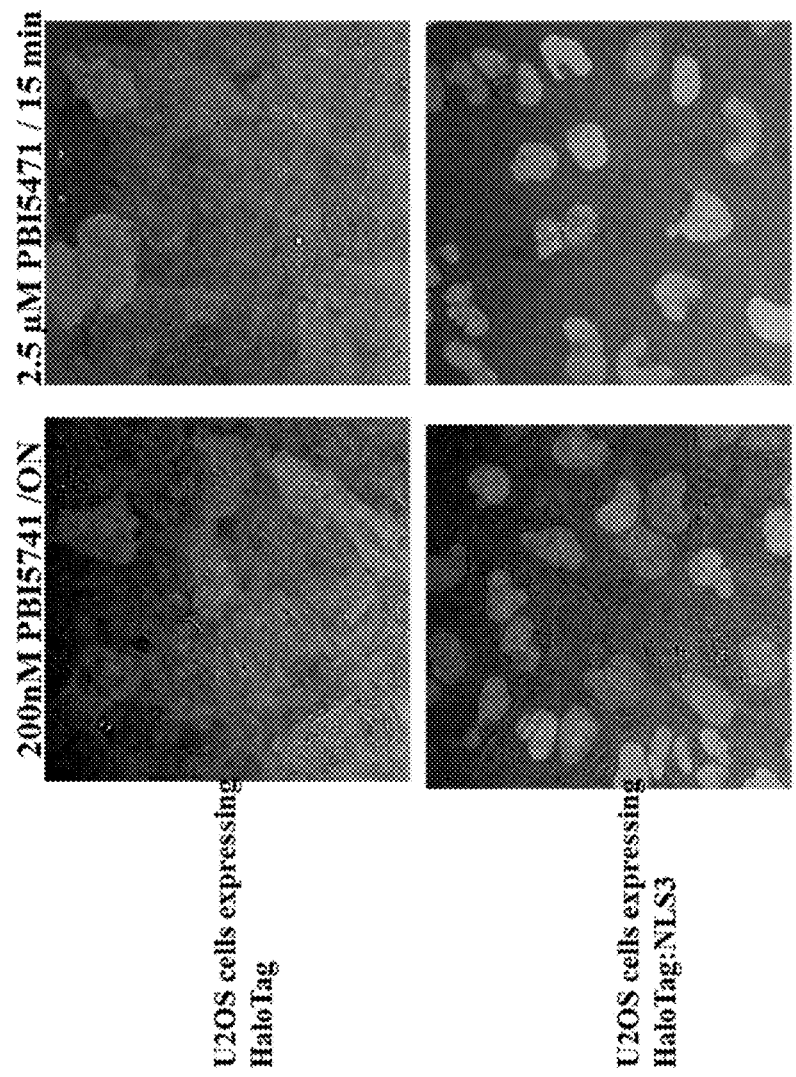

SDS-PAGE analysis of labeled cells

Enrichment of endogenous targets using different elution methods

Imaging of U2OS cells stably expressing HaloTag:NLS$_3$

SDS-PAG analysis

PBI6044

PBI5741

PBI6045

BIRB796-CA-T1
(PBI5446)

BIRB796-CA-T0

BIRB796-CA-T2Z
(PBI5813)

BIRB796-CA-T2E

BIRB796-CA-T3Z

BIRB796-CA-T3E

BIRB796-CA-T4Z

BIRB796-CA-T4E

Binding kinetics to HaloTag

*In lysate*

Binding kinetics to HaloTag
Inside intact cells

● CA-T4E (6140)
■ tri-amide (S83)
● all-PEG (SL_0729)

Interaction with the target (ABL1)

*Purified protein*

Interaction with the target (ABL1)

Cellular assay

- CA-T4E (6146)
- *tri-amide (S83)*
- *all-PEG (SL_0729)*

SEQUENCE LISTING

```
<160> NUMBER OF SEQ ID NOS: 7

<210> SEQ ID NO 1
<211> LENGTH: 5
<212> TYPE: PRT
<213> ORGANISM: Artificial sequence
<220> FEATURE:
<223> OTHER INFORMATION: Synthetic peptide

<400> SEQUENCE: 1

His His His His His
1               5

<210> SEQ ID NO 2
<211> LENGTH: 6
<212> TYPE: PRT
<213> ORGANISM: Artificial sequence
<220> FEATURE:
```

```
<223> OTHER INFORMATION: Synthetic peptide

<400> SEQUENCE: 2

His His His His His His
1               5

<210> SEQ ID NO 3
<211> LENGTH: 10
<212> TYPE: PRT
<213> ORGANISM: Artificial sequence
<220> FEATURE:
<223> OTHER INFORMATION: Synthetic peptide

<400> SEQUENCE: 3

Glu Gln Lys Leu Ile Ser Glu Glu Asp Leu
1               5                   10

<210> SEQ ID NO 4
<211> LENGTH: 8
<212> TYPE: PRT
<213> ORGANISM: Artificial sequence
<220> FEATURE:
<223> OTHER INFORMATION: Synthetic peptide

<400> SEQUENCE: 4

Asp Tyr Lys Asp Asp Asp Asp Lys
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic peptide

<400> SEQUENCE: 5

Trp Ser His Pro Gln Phe Glu Lys
1               5

<210> SEQ ID NO 6
<211> LENGTH: 5
<212> TYPE: PRT
<213> ORGANISM: Artificial sequence
<220> FEATURE:
<223> OTHER INFORMATION: Synthetic peptide

<400> SEQUENCE: 6

Gly Pro Ala Leu Ala
1               5

<210> SEQ ID NO 7
<211> LENGTH: 9
<212> TYPE: PRT
<213> ORGANISM: Artificial sequence
<220> FEATURE:
<223> OTHER INFORMATION: Synthetic peptide

<400> SEQUENCE: 7

Tyr Pro Tyr Asp Val Pro Asp Tyr Ala
1               5
```

CELL-PERMEABLE, CELL-COMPATIBLE, AND CLEAVABLE LINKERS FOR COVALENT TETHERING OF FUNCTIONAL ELEMENTS

CROSS-REFERENCE TO RELATED APPLICATIONS

The present invention claims priority to U.S. Provisional Patent Application Ser. No. 62/171,620, filed Jun. 5, 2015, which is incorporated by reference in its entirety.

FIELD

Provided herein are cell-permeable, cell-compatible, and/or chemoselectively-cleavable linkers for tethering (e.g., covalently) functional elements (e.g., a cellular interaction element and a capture element), and methods of use (e.g., intracellular binding and extracellular release of cellular targets) therewith.

BACKGROUND

Detection, isolation, and immobilization of cells, proteins, and molecules of interest are essential techniques for a variety of modern biological applications (e.g., basic molecular biology research, drug discovery, clinical diagnosis, etc.). Compositions and methods that provide advantages over existing techniques are in need.

SUMMARY

Provided herein are cell-permeable, cell-compatible, and/or chemoselectively-cleavable linkers for tethering (e.g., covalently) functional elements (e.g., a cellular interaction element and a capture element), and methods of use (e.g., intracellular binding and extracellular release of cellular targets) therewith.

In some embodiments, provided herein are chemoselectively-cleavable linkers (e.g., allyl-heteroatom linkers (e.g., allyl-carbamate-containing linkers), propargyl-containing linkers, etc.) for connecting molecular entities and/or functional elements (e.g., not limited to cellular interaction elements and capture elements, etc.). Although many embodiments herein specifically describe the linking of cellular interaction elements and capture elements, all embodiments herein are not so limited. The chemoselectively-cleavable linkers described herein may find use in connecting any two molecular entities (e.g., proteins, small molecules, nucleic acids combinations thereof, etc.). The linkers described herein, and the compounds or compositions comprising them, find use, for example, in labeling, detection, isolation, and/or immobilization of cellular targets (e.g., target proteins). In some embodiments, the linkers described herein are cell compatible, cell permeable, and/or chemoselectively-cleavable in a proteinaceous, or highly proteinaceous, environment (e.g., cellular environment, cell lysate, biochemical composition, in vitro, etc.). In some embodiments, the functional elements (e.g., cellular interaction elements and capture elements) in the structures described herein are cell compatible and cell permeable. In some embodiments, the structures comprising the linkers described herein (e.g., Z-Y-Q, wherein Z is a cellular interaction element, Q is a capture elements, and Y is a chemoselectively-cleavable linker) are cell compatible, cell permeable, and/or chemoselectively-cleavable in a proteinaceous, or highly proteinaceous, environment (e.g., cellular environment, cell lysate, biochemical composition, in vitro, etc.).

In some embodiments, provided herein are dual-function (e.g., linking two molecular entities), cell-permeable, cell-compatible, and/or chemoselectively-cleavable compositions. In some embodiments, the dual-function (e.g., linking two molecular entities), cell-permeable, cell-compatible, and/or chemoselectively-cleavable compositions comprise: (a) a first functional element; (b) a second functional element; and (c) a linker covalently tethering the first functional element to the second functional element, wherein said linker comprises a chemoselectively-cleavable moiety. In some embodiments, the first functional element can chemically interact (e.g., via covalent or non-covalent bonds) with a first molecular entity, and the second functional element can chemically interact (e.g., via covalent or non-covalent bonds) with a second molecular entity. In some embodiments, the first and second molecular entities are distinct in structure and/or function. In some embodiments, the first and second molecular entities are the same or similar in structure and/or function. In some embodiments, the chemical interaction of the first functional element with the first molecular entity and/or the second functional element with the second molecular entity may be selective or non-selective. In some embodiments, the first functional element and/or the second functional element comprise a reporter function (e.g., a fluorophore, a luciferase, an antibody, a nucleic acid, etc.). In some embodiments, the first functional element and/or the second functional element comprise a surface (e.g., microplate, particle).

In some embodiments, the dual-function (e.g., linking two molecular entities), cell-permeable, cell-compatible, and/or chemoselectively-cleavable compositions comprise: (a) a cellular interaction element; (b) a capture element; and (c) a linker covalently tethering the cellular interaction element to the capture element, wherein said linker comprises a chemoselectively-cleavable moiety. In some embodiments, the cellular interaction element is a small molecule or peptide. In some embodiments, the cellular interaction element is an inhibitor of an enzyme or cellular phenotype, an activator of an enzyme or cellular phenotype, or a modulator of an enzyme or cellular phenotype. In some embodiments, the capture element is a substrate or an inhibitor for an enzyme. In some embodiments, the capture element forms a specific covalent bond (e.g., a covalent substrate or suicide inhibitor) with a specific protein (e.g., an enzyme or mutant enzyme). In some embodiments, the capture element comprises a haloalkane group, a benzylguanine, a benzylcytosine, or a nitrophenyl phosphonate. In some embodiments, the capture element is an affinity element. In some embodiments, the chemoselectively-cleavable moiety is a transition metal (e.g., a d-block element of the periodic table) cleavable functional group. In some embodiments, the chemoselectively-cleavable moiety is a molybdenum-cleavable, tungsten-cleavable, iridium-cleavable, rhodium-cleavable, ruthenium-cleavable, platinum-cleavable, nickel-cleavable, copper-cleavable, iron-cleavable, cobalt-cleavable, palladium-cleavable, or ruthenium-cleavable moiety. In some embodiments, the chemoselectively-cleavable moiety is a Pd-cleavable or Ru-cleavable moiety. In some embodiments, the chemoselectively-cleavable moiety is selected from the group consisting of: an allyl-heteroatom group, a propargyl-heteroatom group, etc. In some embodiments, the chemoselectively-cleavable moiety comprises an allyl-heteroatom group selected from the group consisting of: allyl ether, allyl amine, allyl ester, allyl amide, allyl urea, allyl carbonate, and allyl carbamate. In some embodiments, the chemoselectively cleavable moiety comprises an allyl carbamate group. In some embodiments, the chemoselectively cleavable moiety comprises a propargyl-heteroatom group selected from the group consisting of: propargyl ether, propargyl amine, propargyl ester, propargyl amide, propargyl urea, propargyl carbonate, and propargyl carbamate. In some embodiments, the composition comprises the formula: Z-$L^1$-Y-$L^2$-Q, wherein Z is a cellular interaction element, Q is a capture element, wherein $L^1$ and $L^2$ are independently optionally present and are independent linker moieties, and Y is a chemoselectively-cleavable moiety.

In some embodiments, provided herein are methods comprising one or more of the steps of: (a) administering the dual-function, cell-permeable, cell-compatible, and/or chemoselectively-cleavable composition comprising a cellular interaction element, chemoselectively-cleavable moiety, and a capture element to a cell; (b) allowing binding of the cellular interaction element with a corresponding cellular target; (c) lysing said cell to produce a cell lysate; (d) contacting the capture element with a capture agent; and (e) contacting the chemoselectively-cleavable linker with a corresponding chemoselective agent, thereby releasing the cellular interaction element and the bound cellular target from the capture agent. In some embodiments, the capture agent is immobilized onto a surface.

In some embodiments, provided herein are systems comprising: (a) a dual-function, cell-permeable, cell-compatible, and/or chemoselectively-cleavable composition comprising a first functional element, chemoselectively-cleavable moiety, and a second functional element; and (b) one or more of: (i) a cell, cell lysate, or other proteinaceous environment, and/or (ii) a chemoselective agent. In some embodiments, provided herein are systems comprising: (a) a dual-function, cell-permeable, cell-compatible, and/or chemoselectively-cleavable composition comprising a cellular interaction element, chemoselectively-cleavable moiety, and a capture element; and (b) one or more of: (i) a cell, cell lysate, or other proteinaceous environment, (ii) a cellular target, (iii) a surface-displayed capture agent, and (iv) a chemoselective agent. In some embodiments, the cellular target is a fusion protein. In some embodiments, the fusion protein is a fusion of the cellular target with a reporter protein, e.g., NANO-LUC luciferase.

In some embodiments, provided herein are compositions of formula Z-$L^1$-Y-$L^2$-Q; wherein Z is a cellular interaction element (or other functional element), $L^1$ is a first linker moiety, Y is chemoselectively-cleavable moiety, $L^2$ is a second linker moiety, and Q is a capture element (or other functional element). In some embodiments, $L^1$ separates Z and Y by at least one atom linearly connected to Z and Y. In some embodiments, $L^1$ separates Z and Y by 1-200 (e.g., 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, or any ranges therebetween (e.g., 2-20, 5-10, 15-35, 25-100, etc.)) linearly connected atoms. In some embodiments, $L^2$ separates Q and Y by at least one atom linearly connected to Q and Y. In some embodiments, $L^2$ separates Q and Y by 1-200 (e.g., 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, or any ranges therebetween (e.g., 2-20, 5-10, 15-35, 25-100, etc.)) linearly connected atoms. In some embodiments, $L^1$ separates Z and Y by 2 or more linearly connected atoms. In some embodiments, $L^2$ separates Q and Y by 2 or more linearly connected atoms. In some embodiments, Z is a molecular entity that interacts (e.g., covalently or non-covalently binds) with a cellular component. In some embodiments, Q is a molecular entity that interacts (e.g., covalently or non-covalently binds) with a capture agent (e.g., antibody, mutant dehalogenase, streptavidin, etc.). In some embodiments, the Z and Q are cell-compatible and/or cell-permeable. In some embodiments, $L^1$ and $L^2$ independently comprise linear or branched, carbon-based moieties that may also comprise one or more C—, N, O—, S—, P—, and/or halogen-containing functional groups.

In some embodiments, provided herein are compositions of formula Z-$(L-Y)_n$-L-Q; wherein Z is a cellular interaction elements (or other functional element), each L is independently a linker moiety, each Y is independently a chemoselectively-cleavable moiety, Q is a capture element (or other functional element), and n is 1-20 (e.g., 1, 2, 3, 4, 5, 6, 7, 8, 9, 10, 11, 12, 13, 14, 15, 16, 17, 18, 19, 20, or any ranges therebetween). In some embodiments, each L is the same chemical moiety. In some embodiments, each Y is the same chemical moiety. In some embodiments, each L is independently selected from the L groups described herein. In some embodiments, each Y is independently selected from the L groups described herein.

In some embodiments, provided herein are chemoselectively-cleavable linkers (e.g., allyl-heteroatom linkers (e.g., allyl-carbamate-containing linkers), propargyl-containing linkers, etc.) for connecting haloalkane substrates to functional elements (e.g., tags, labels, reactive groups, peptides, target proteins, antibodies, nucleic acids, surfaces, small molecules, cellular interaction elements, etc.). Substrates and linkers described herein find use, for example, in labeling, detection, characterization of interactions, localization, etc., of proteins, cells, and molecules. In particular embodiments, the linkers provided herein comprise a chemically-cleavable unit (e.g., allyl carbamate) and find use within substrates for dehalogenase variants that form stable covalent bonds with their haloalkane substrates.

In some embodiments, provided herein are compounds of formula Z-Y-$L^1$-M-$L^2$-A-X; wherein Z is a cellular interaction element (or other functional element), Y is a chemoselectively-cleavable moiety e.g., allyl-heteroatom linkers (e.g., allyl-carbamate-containing linkers), propargyl-containing linkers, etc.), $L^1$ is a first linker moiety, M is an alkyl carbamate group, $L^2$ is a second linker moiety, A is an alkyl group, and X is a halogen. In some embodiments, $L^2$-A separates M and X by 6-18 linearly connected atoms. In some embodiments, $L^1$ separates Y and M by 2 or more (e.g., 2-100 (e.g., 2, 3, 4, 5, 6, 7, 8, 9 10, 11, 12, 14, 16, 18, 20, 25, 30, 35, 40, 45, 50, 60, 70, 80, 90, 100, or any ranges therebetween) linearly connected atoms. In some embodiments, A is $(CH_2)_6$. In some embodiments, $L^2$-A separates M and X by 2 or more (e.g., 2-100 (e.g., 2, 3, 4, 5, 6, 7, 8, 9 10, 11, 12, 14, 16, 18, 20, 25, 30, 35, 40, 45, 50, 60, 70, 80, 90, 100, or any ranges therebetween) linearly connected atoms. In some embodiments, $L^2$ does not comprise a carbamate group. In some embodiments, $L^2$ comprises linearly connected $CH_2$ and O groups. In some embodiments, $L^2$ consists of linearly connected $CH_2$ and O groups. In some embodiments, $L^2$ comprises $((CH_2)_2O)_x$, wherein x=0-5. In some embodiments, $L^2$ comprises $((CH_2)_2O)_2$. In some embodiments, $L^1$ comprises linearly connected $CH_2$ and O groups. In some embodiments, $L^1$ comprises $(CH_2)_2$. In some embodiments, $L^1$ comprises $O(CH_2)_2$.

In some embodiments, provided herein are compounds of formula Z-G-A-X; wherein Z is a cellular interaction element (or other functional element), A is an alkyl group, X is a halogen, and G comprises one or more (e.g., 1, 2, 3, 4, 5, 6, 7, 8, 9, 10, or ranges therebetween) chemoselectively-cleavable moieties Y (e.g., allyl-heteroatom linkers (e.g., allyl-carbamate-containing linkers), propargyl-containing linkers, etc.), and optionally one or more linker moieties L and/or one or more alkyl carbamate groups M. Non-limiting exemplary compounds include, for example, Z-Y$^1$-L$^1$-M-L$^2$-Y$^2$-A-X, Z-Y-L$^1$-M$^1$-M$^2$-L$^2$-A-X, Z-Y-L$^1$-M$^1$-L$^3$-M$^2$-L$^2$-A-X, Z-M-L$^1$-Y-L$^3$-Y-L$^2$-A-X, Z-M-L$^1$-Y$^1$-Y$^2$-L$^2$-A-X, etc.

In some embodiments, provided herein are compounds of formula Z-L$^3$-Y-L$^1$-M-L$^2$-A-X; wherein Z is a cellular interaction element (or other functional element), L$^3$ is a third linker moiety, Y is an chemoselectively-cleavable moiety e.g., allyl-heteroatom linkers (e.g., allyl-carbamate-containing linkers), propargyl-containing linkers, etc.), L$^1$ is a first linker moiety, M is an alkyl carbamate group, L$^2$ is a second linker moiety, A is an alkyl group, and X is a halogen. In some embodiments, L$^3$ separates Z and Y by 2 or more (e.g., 2-200 (e.g., 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, or any ranges therebetween (e.g., 2-20, 5-10, 15-35, 25-100, etc.))) linearly connected atoms. In some embodiments, L$^3$ comprises linearly connected CH$_2$ groups. In some embodiments, L$^3$ comprises linearly connected CH$_2$ and O groups. In some embodiments, L$^2$-A separates M and X by 1-200 (e.g., 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, or any ranges there between (e.g., 2-20, 5-10, 6-18, 15-35, 25-100, etc.)) linearly connected atoms. In some embodiments, L$^1$ separates Y and M by 2 or more (e.g., 2-18) linearly connected atoms. In some embodiments, A is (CH$_2$)$_6$. In some embodiments, L$^2$-A separates M and X by 12 linearly connected atoms. In some embodiments, L$^2$ does not comprise a carbamate group. In some embodiments, L$^2$ comprises linearly connected CH$_2$ and O groups. In some embodiments, L$^2$ consists of linearly connected CH$_2$ and O groups. In some embodiments, L$^2$ comprises ((CH$_2$)$_2$O)$_x$, wherein x=0-5. In some embodiments, L$^2$ comprises ((CH$_2$)$_2$O)$_2$. In some embodiments, L$^1$ comprises linearly connected CH$_2$ and O groups. In some embodiments, L$^1$ comprises (CH$_2$)$_2$. In some embodiments, L$^1$ comprises O(CH$_2$)$_2$.

In some embodiments, provided herein are compounds of a formula of one of: Z-Y-A-X; Z-L$^1$-Y-A-X; Z-Y-L$^2$-A-X; and Z-L$^1$-Y-L$^2$-A-X; wherein Z is a cellular interaction element (or other functional element); L$^1$, when present, is a first linker moiety; Y is an chemoselectively-cleavable moiety e.g., allyl-heteroatom linkers (e.g., allyl-carbamate-containing linkers), propargyl-containing linkers, etc.); L$^2$, when present, is a second linker moiety; A is an alkyl group, and X is a halogen. In some embodiments, A is (CH$_2$)$_6$. In some embodiments, Y and X are separated by at least 8 linearly connected atoms (e.g., 8 atoms, 9 atoms, 10 atoms, 11 atoms, 12 atoms, 13 atoms, 14 atoms, 15 atoms, 16 atoms, 17 atoms, 18 atoms, 19 atoms, 20 atoms, or more). In some embodiments, the compound comprises L$^2$, and L$^2$ comprises an alkyl carbamate group. In some embodiments, L$^1$ and/or L$^2$ are present and comprise linearly connected CH$_2$ and O groups.

In some embodiments, provided herein are methods of linking a cellular interaction element (or other functional element) to a capture agent (e.g., mutant dehalogenase, antibody, streptavidin, etc.) comprising: contacting a cell compatible and cell permeable composition comprising Z-L$^1$-Y-L$^2$-Q, Z-L$^1$-Y-Q, Z-Y-L$^2$-Q, Z-Y-L$^1$-M-L$^2$-Q, or Z-L$^3$-Y-L$^1$-M-L$^2$-Q with a capture element; wherein Z is a cellular interaction element (or other functional element), Y is an chemoselectively-cleavable moiety e.g., allyl-heteroatom linkers (e.g., allyl-carbamate-containing linkers), propargyl-containing linkers, etc.), L$^1$ is a first linker moiety, M is an alkyl carbamate group, L$^2$ is a second linker moiety, and L$^3$ (when present) is a third linker moiety, and Q is a capture element; wherein the capture agent specifically binds (covalently or non-covalently) the capture element.

In some embodiments, provided herein are methods of covalently linking a cellular interaction element (or other functional element) to a mutant dehalogenase, comprising: contacting a substrate comprising Z-L$^1$-Y-L$^2$-A-X, Z-L$^1$-Y-A-X, Z-Y-L$^2$-A-X, Z-Y-L$^1$-M-L$^2$-A-X, or Z-L$^3$-Y-L$^1$-M-L$^2$-A-X to a mutant dehalogenase; wherein Z is a cellular interaction element (or other functional element), Y is an chemoselectively-cleavable moiety, e.g., allyl-heteroatom linkers (e.g., allyl-carbamate-containing linkers), propargyl-containing linkers, etc.), L$^1$ is a first linker moiety, M is an alkyl carbamate group, L$^2$ is a second linker moiety, A is an alkyl group, X is a halogen, and L$^3$ (when present) is a third linker moiety; wherein the mutant dehalogenase comprises at least one amino acid substitution relative to a corresponding wild-type dehalogenase, wherein the at least one amino acid substitution results in the mutant dehalogenase forming a covalent bond with the substrate (e.g., Z-Y-L$^1$-M-L$^2$-A-X, Z-L$^3$-Y-L$^1$-M-L$^2$-A-X, etc.). In some embodiments, the at least one amino acid substitution in the mutant dehalogenase is a substitution at an amino acid residue in the corresponding wild-type dehalogenase that is associated with activating a water molecule which cleaves the bond formed between the corresponding wild-type dehalogenase and the substrate. In some embodiments, the at least one amino acid substitution in the mutant dehalogenase is a substitution at an amino acid residue in the corresponding wild-type dehalogenase that forms an ester intermediate with the substrate.

In some embodiments, methods further comprise releasing the cellular interaction element (or other functional element) from the capture agent (e.g., mutant dehalogenase) by exposing the complex to a chemoselective agent that cleaves the chemoselectively-cleavable moiety (Y).

In some embodiments, the chemoselectively-cleavable moiety is an allyl-containing moiety or propargyl-containing moiety, as described herein. In some embodiments, the chemoselective agent comprises, consists essentially of, or consists of a water-soluble transition metal complex (e.g., comprising Pd, Ru, etc.). In some embodiments, the transition metal is complexed by one or more water-soluble organic phosphine ligands. In some embodiments, the chemoselective agent is generated by the interaction of a transition metal salt with a suitable ligand (e.g., water-soluble organic phosphine ligand, nitrogen-based ligand, N-heterocyclic carbene, etc; See, e.g., Shaughnessy, K., H. Chem. Rev. 2009, 109, 643, herein incorporated by reference in its entirety). In some embodiments, a suitable transition metal salt as a source or palladium is a Palladium(II) salt and is selected from the group including but not limited to: Palladium acetate: Pd(OAc)$_2$, Palladium trifluoroacetate: Pd(TFA)$_2$, Palladium nitrate: Pd(NO$_3$)$_2$, Palladium chloride: PdCl$_2$, Palladium bromide: PdBr$_2$, Sodium tetrachloropalladate: Na$_2$PdCl$_4$, Potassium tetrachloropalladate: K$_2$PdCl$_4$, Lithium tetrachloropalladate: Li$_2$PdCl$_4$, Sodium tetrabromopalladate: Na$_2$PdBr$_4$, and Potassium tetrabromopalladate: K$_2$PdBr$_4$. In some embodiments, a water-soluble Pd(II) pre-chemoselective agent is selected from one of the Pd(OAc)$_2$ complexes depicted in FIG. 1. Analogous pre-chemoselective agents to those depicted in FIG. 1 for other palladium salts find use in embodiments described herein. In some embodiments, suitable sources of ruthenium for complexed-ruthenium chemoselective agents are understood in the art: Ai et al. *Chem. Commun.*, 2010, 46, 5506-5508; Streu & Meggers. *Angew. Chem. Int. Ed.* 2006, 45, 5645-5648; Sanchez et al. *Chem. Sci.* 2014, 5, 1901-1907; Crochet & Cadierno. *Dalton Trans.* 2014, 43, 12447-12462; herein incorporated by reference in their entireties. In some embodiments, suitable phosphine ligands for coordination of transition metals include monodentate phosphines and bidentate phosphines. Suitable phosphine ligands are described, for example, in Shaughnessy, K H. *Chem. Rev.* 2009, 109, 643; herein incorporated by reference in its entirety. Examples of phosphines that find use in coordination of transition metals for the formation of chemoselective agents herein include but are not limited to those depicted in FIG. 2. In some embodiments, suitable ligands for coordination of transition metals are hybrid ligands which contain nitrogen, phosphorus, N-heterocyclic carbenes (e.g., Arduengo carbenes), etc.

In some embodiments, the compositions and methods described herein provide for efficient chemoselective cleavage in a proteinaceous or highly proteinaceous environment. In some embodiments, the proteinaceous or highly proteinaceous environment comprises protein bound to or immobilized onto a surface (e.g., a magnetic particle). In some embodiments, conditions are provided (e.g., cleavage agent concentration, buffer, time, etc.) that allow for efficient cleavage without damaging (or with minimal damage) components of the system (e.g., cellular targets). In some embodiments, conditions are provided (e.g., cleavage agent concentration, buffer, time, etc.) that allow for efficient cleavage without interfering with subsequence sample analysis by mass spectrometry.

In some embodiments, provided herein are methods to identify, isolate, or immobilize a cellular target (e.g., target protein), comprising: (a) contacting a sample (e.g., cell) with a composition comprising a cellular interaction element tethered to a capture element (e.g., dehalogenase substrate) by a chemoselectively-cleavable moiety (e.g., Z-Y-Q or other structures described herein); (b) contacting the sample and with a capture agent for the capture element (e.g., on a solid support). In some embodiments, methods comprise lysing the cell prior to step (b). In some embodiments, methods further comprise contacting the sample with a chemoselective agent to cleave the chemoselectively-cleavable moiety. In some embodiments, the capture element is an affinity molecule, an inhibitor, or substrate that forms a covalent or otherwise stable bond with a protein or enzyme. In some embodiments, the capture element is a haloalkane, and the capture agent is a mutant dehalogenase, wherein the mutant dehalogenase comprises at least one amino acid substitution relative to a corresponding wild-type dehalogenase, wherein the at least one amino acid substitution results in the mutant dehalogenase forming a bond with the substrate which is more stable than the bond formed between the corresponding wild-type dehalogenase and the substrate, wherein the at least one amino acid substitution in the mutant dehalogenase is a substitution at an amino acid residue in the corresponding wild-type dehalogenase that is associated with activating a water molecule which cleaves a bond formed between the corresponding wild-type dehalogenase and the substrate or at an amino acid residue in the corresponding wild-type dehalogenase that forms an ester intermediate with the substrate; and (c) identifying the target molecule. In other embodiments, the capture element and capture agent are biotin/streptavidin, benzylguanine/$O^6$-alkylguanine-DNA transferase, benzylcytosine/modified $O^6$-alkylguanine-DNA transferase, cutinase/nitrophenyl phosphonate, or variants thereof. In some embodiments, the cellular interaction element (e.g., compound of interest) is a drug, drug compound, inhibitor, ligand, biomolecule, or small molecule. In some embodiments, the target molecule is a protein (e.g., enzyme, receptor, transcription factor, etc.). In some embodiments, methods further comprise releasing the cellular target from the mutant dehalogenase by contacting the complex with a chemoselective agent that cleaves the Y group.

In some embodiments, provided herein are methods for identifying a cellular target (e.g., molecule or protein) of a test ligand in a cell, comprising: (a) contacting the cell comprising a Z-Y-Q composition described herein (e.g., $Z-L^1-Y-L^2-Q$, $Z-Y-L^1-M-L^2-A-X$, $Z-L^3-Y-L^1-M-L^2-A-X$, etc.), wherein Z is the test ligand, Q is the capture element, and Y is a chemoselectively-cleavable moiety, wherein the test ligand binds the cellular target; (b) lysing the cell to create a cell lysate; (c) contacting the cell lysate with a capture agent (e.g., corresponding or specific to Q) attached to a surface or support; (d) washing away the unbound lysate; (e) contacting the surface or support with a chemoselective agent (e.g., corresponding or specific to Y) to release the cellular target from the surface or support; and (f) identifying the cellular target.

In some embodiments, provided herein are methods for detecting the presence or amount of a cellular target (e.g., molecule or protein) in a cell, comprising: (a) contacting the cell comprising a Z-Y-Q composition described herein (e.g., $Z-L^1-Y-L^2-Q$, $Z-Y-L^1-M-L^2-A-X$, $Z-L^3-Y-L^1-M-L^2-A-X$, etc.); (b) lysing the cell to create a cell lysate; (c) contacting the cell lysate with a capture agent (e.g., corresponding or specific to Q) attached to a surface or support; (d) washing away the unbound lysate; (e) contacting the surface or support with a chemoselective agent (e.g., corresponding or specific to Y); and (f) detecting or determining the presence or amount of the cellular target. In some embodiments, methods of detecting a protein within a cell that interacts with a molecule of interest are provided.

In some embodiments, provided herein are methods comprising, contacting a chemoselectively-cleavable construct comprising a first molecular entity linked to a second molecular entity by a transition metal cleavable linker with a transition metal ion or a chemoselective agent capable of releasing a transition metal ion under conditions in which the cleavable linker is cleaved by the transition metal ion and the first molecular entity is released from the second molecular entity. In some embodiments, the chemoselectively-cleavable moiety is selected from the group consisting of an allyl-heteroatom group and a propargyl-heteroatom group. In some embodiments, the chemoselectively-cleavable moiety comprises an allyl-heteroatom group selected from the group consisting of an allyl ether, allyl amine, allyl ester, allyl amide, allyl urea, allyl carbonate, and allyl carbamate. In some embodiments, the chemoselectively-cleavable moiety comprises an allyl carbamate group. In some embodiments, the chemoselectively-cleavable moiety comprises a propargyl-heteroatom group selected from the group consisting of a propargyl ether, propargyl amine, propargyl ester, propargyl amide, propargyl urea, propargyl carbonate, and propargyl carbamate. In some embodiments, the transition metal is Pd or Ru. In some embodiments, the conditions comprise a proteinaceous or highly proteinaceous environment. In some embodiments, the proteinaceous environment is a cell or cell lysate. In some embodiments, the proteinaceous environment comprises protein bound or immobilized onto a surface (e.g., magnetic particle). In some embodiments, the first molecular entity is a cellular interaction element and is bound to a cellular target. In some embodiments, the second molecular entity is a capture element and is bound to a capture agent. In some embodiments, the capture agent is bound to a surface.

In some embodiments, provided herein is the use of a chemoselectively-cleavable moiety (e.g., allyl-heteroatom linkers (e.g., allyl-carbamate-containing linkers), propargyl-containing linkers, etc.) to reversibly connect first and second molecular entities (e.g., capture element and cellular interaction element). In some embodiments, provided herein is the use of a chemoselective agent (e.g., comprising a transition metal (e.g., Pd, Ru, etc.)) to cleave a chemoselectively-cleavable moiety linking first and second molecular entities (e.g., capture element and cellular interaction element).

BRIEF DESCRIPTION OF THE DRAWINGS

FIGS. 9A and 9B shows A) Imaging of U2OS cells stably expressing HALOTAG or HALOTAG:NLS labeled with PBI-5741; B) SDS-PAGE analysis of labeled cells.

DEFINITIONS

Figure 1:
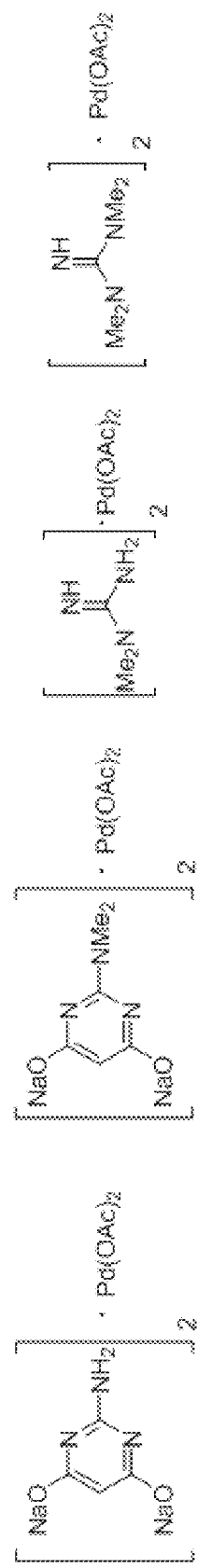
FIG. 1 shows structures of exemplary water-soluble $Pd(OAc)_2$ complexes.
Figure 2A:
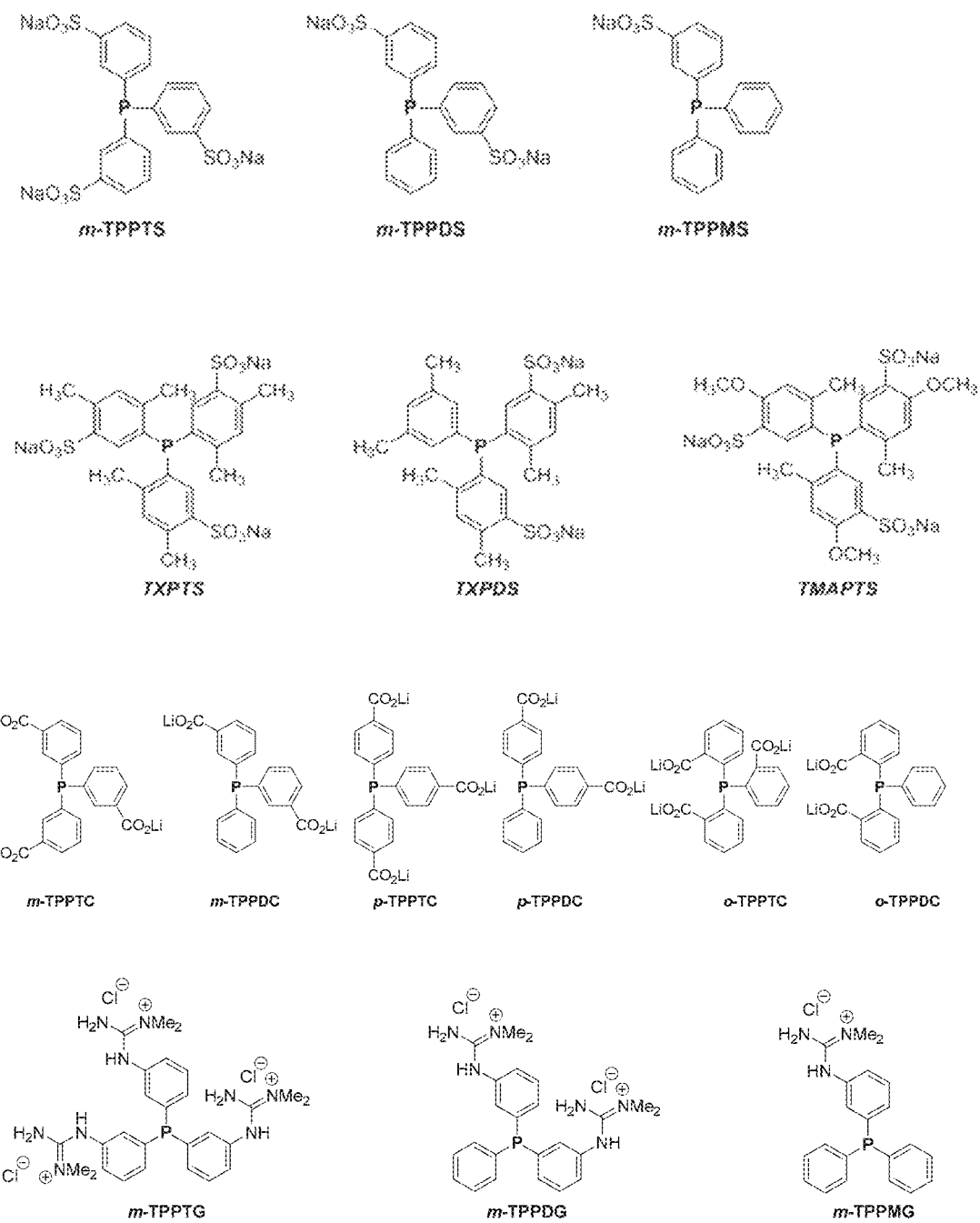
FIGS. 2A and 2B show structures of exemplary water soluble phosphines.
Figure 2B:
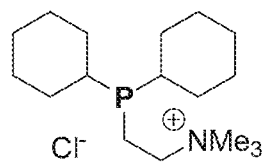
Figure 2B:
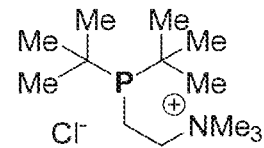
Figure 2B:
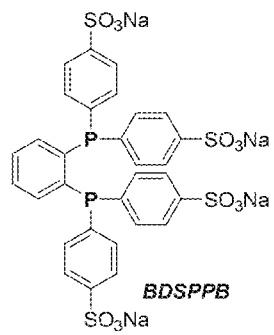
Figure 2B:
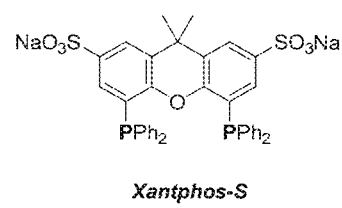
Figure 2B:
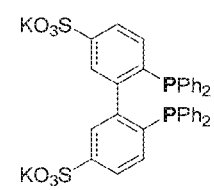
Figure 2B:
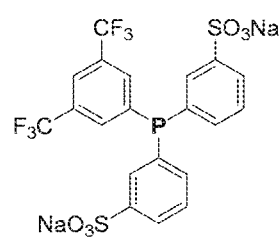
Figure 2B:
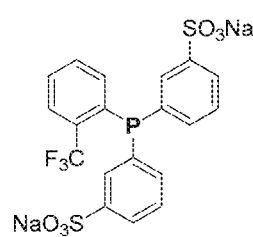
Figure 2B:
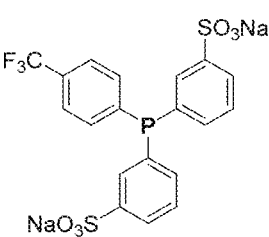
Figure 2B:
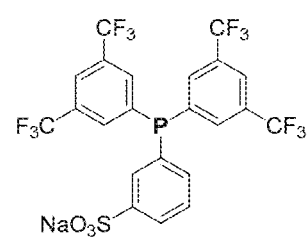
Figure 2B:
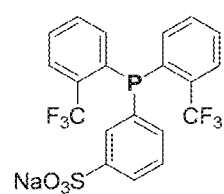
Figure 2B:
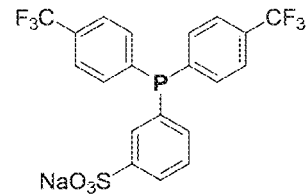

As used herein, the term "chemoselective" and linguistic variants thereof (e.g., "chemoselectively") refers to the chemically selective reactivity or catalytic activity of an agent ("chemoselective agent") for a particular functional group, moiety, or set of functional groups. A "chemoselectively-cleavable group" is a chemical moiety that is severed when exposed to appropriate conditions (e.g., the appropriate chemoselective agent).

As used herein, the term "cell permeable" refers to the capacity of a compound or other composition to cross the cell membrane of a living cell.

As used herein, the term "cell compatible" refers to the capacity of a compound, or other composition, to reside within a cell without itself decomposing or degrading substantially.

As used herein, the term "proteinaceous environment" refers to local conditions having a protein concentration greater than 0.1 mg/ml. A "highly proteinaceous environment" refers to local conditions having a protein concentration greater than 10 mg/ml.

As used herein, the term "cellular interaction element," depicted herein as a "Z" group, refers to any molecular moieties (e.g., small molecule (e.g., drug, toxin, reactive group, peptide, etc.), etc.) that interacts with (e.g., covalently binds or non-covalently binds), or potentially interacts with in the case of "test cellular interaction elements", a cellular component (e.g., protein, peptide, lipid, nucleic acid (e.g., specific sequence, etc.), etc.).

As used herein, the term "capture element," depicted herein as a "Q" group, refers to a molecular entity that forms a covalent or stable non-covalent interaction with a corresponding "capture agent".

As used herein, the term "functional elements" refers to the "cellular interaction elements" and "capture elements" linked by chemoselectively-cleavable linkers in the compositions, methods, and system herein. Other additional functional elements that may find use in embodiments described herein comprise "localization elements", "detection elements", etc.

As used herein, the term "linearly connected atoms" refers to the backbone atoms of a chain or polymer, excluding pendant, side chain, or H atoms that do not form the main chain or backbone.

As used herein, the term "wild-type" refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties (e.g., altered characteristics) when compared to the wild-type gene or gene product. It is noted that naturally-occurring mutants can be isolated; these are identified by the fact that they have altered characteristics when compared to the wild-type gene or gene product.

As used herein, the term "solid support" is used in reference to any solid or stationary material to which reagents such as substrates, mutant proteins, drug-like molecules, and other test components are or may be attached. Examples of solid supports include microscope slides, wells of microtiter plates, coverslips, beads, particles, resin, cell culture flasks, as well as many other suitable items. The beads, particles, or resin can be magnetic or paramagnetic.

As used herein, the term "compound of interest" is used to reference a drug, drug-like compound, biomolecule, small molecule, toxin, peptide, etc., that may bind to a target molecule, e.g., protein, nucleic acid, etc. In some embodiments, a compound of interest is used as a cellular interaction element or test cellular interaction element.

The following single letter code is used in the text and structures throughout when referring to the compositions described herein (unless otherwise indicated):

"A" is an alkane of 2 or more carbons;
"D" is a reactive group that forms a covalent linkage when reacted with "V";
"E" is a heteroatom (e.g., N, O, S, P);
"G" is any combination of Y, M, and/or L groups;
"L" is a linker moiety;
"M" is an alkyl carbamate;
"Q" is a capture element;
"R" is an organic functional group;
"V" is a reactive group that forms a covalent linkage when reacted with "D";
"X" is a halogen (e.g., Cl, Br, F, I, etc.)
"Y" is a chemoselectively-cleavable moiety, cleavable by interaction with an appropriate chemoselective agent (e.g., allyl-heteroatom (e.g., allyl carbamate), propargyl-heteroatom, etc.); and
"Z" is a cellular interaction element, capable of binding a cellular target.

DETAILED DESCRIPTION

Provided herein are cell-permeable, cell-compatible, and chemoselectively-cleavable linkers for tethering (e.g., covalently) functional elements (e.g., a cellular interaction element and a capture element), and methods of use (e.g., intracellular capture and extracellular release of cellular targets) therewith.

I. Structures

In some embodiments, compositions are provided comprising the general molecular formula Z-Y-Q, wherein Z is a cellular interaction element (or other functional element), Y is a chemoselectively-cleavable group, and Q is a capture element (or other functional element). Compositions may further comprise one or more linker moieties (e.g., $L^1$, $L^2$, etc.) and be of the general molecular formulas Z-L-Y-Q, Z-Y-L-Q or Z-$L^1$-Y-$L^2$-Q. Compositions may comprise two or more chemoselectively-cleavable moieties. In some embodiments, the combination of the cellular interaction element, chemoselectively-cleavable group, capture element, and optionally linker(s) is cell-permeable and cell-compatible. In some embodiments, the chemoselectively-cleavable group is cleavable under mild conditions (e.g., physiological conditions, near-neutral pH, near room temperature, etc.) in the presence of a chemoselective cleavage agent.

In some embodiments, a substrate minimally comprises a compound of the formula: Z-Y-Q, wherein Z is a cellular interaction element (or other functional element); wherein Y is an allyl carbamate group (e.g., —NHCOOCH$_2$CHCH—); wherein Q is capture element (or other functional element). In some embodiments, Z and Y may be separated by L (e.g., Z-L-Y-), wherein L is a multiatom straight or branched chain including C, N, S, or O. In some embodiments, Y and Q may be separated by M (e.g., -Y-M-A-), wherein M is an alkyl carbamate group. In some embodiments, Y and M may be separated by L (e.g., -Y-L-M-), wherein L is a multiatom straight or branched chain including C, N, S, or O. In some embodiments, M and A may be separated by L (e.g., -M-L-Q), wherein L is a multiatom straight or branched chain including C, N, S, or O. Suitable substrates comprise Z-Y-Q, Y-Q, R-Y-L$_2$-Q, Z-L$_1$-Y-L$_2$-Q, Z-Y-M-A-X, R-L-Y-M-Q, R-L-Y-M-M-Q, R-L-Y-L-Y-M-Q, Z-L-Y-L-M-Q, Z-L-Y-M-L$_2$-Q, Z-Y-L-M-Q, Z-Y-L-M-L-Q, Z-Y-M-L-Q, Z-L-Y-L-M-L-Q, Z-Y-L-Y-Q, R-L-Y-M-Y-L-Q, etc.

A. Chemoselectively-Cleavable Groups

In some embodiments, a chemoselectively-cleavable group is any chemical moiety that is capable of chemical cleavage when exposed to the appropriate chemoselective agent. In some embodiments, a chemoselectively-cleavable group is capable of serving as a linker (e.g., linear linker), connecting two other moieties (e.g., cellular interaction element and capture element). In some embodiments, the chemoselectively-cleavable group links two groups, and upon chemoselective cleavage of the chemoselectively-cleavable group, the two groups are released from each other. For example, the chemoselectively-cleavable group Y tethers cellular interaction element Z to capture agent Q (e.g., Z-Y-Q). Upon chemical cleavage of Y into $Y^1$ and $Y^2$, Z and Q become untethered (e.g., $Z^1$-$Y^1$ and $Y^2$-Q).

In some embodiments, suitable chemoselectively-cleavable groups are cell-permeable. In some embodiments, suitable chemoselectively-cleavable groups do not prevent the cell permeability of the compositions within which they are a component. In some embodiments, suitable chemoselectively-cleavable groups do not negatively impact the cell permeability of the compositions within which they are a component.

In some embodiments, suitable chemoselectively-cleavable groups are cell-compatible. In some embodiments, suitable chemoselectively-cleavable groups do not prevent the cell compatibility of the compositions within which they are a component. In some embodiments, suitable chemoselectively-cleavable groups do not negatively impact the cell compatibility of the compositions within which they are a component. Although not limited to the chemoselectively-cleavable moieties explicitly described herein, the following are example of chemoselectively-cleavable moieties that find use in embodiments herein.

1. Allyl-Containing Groups

Chemoselectively-cleavable groups that find use in the compositions and methods described herein include, but are not limited to, allyl-heteroatom groups. For example, chemoselectively-cleavable groups may be of the formula:

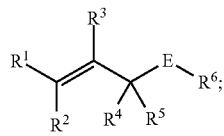

wherein E is a heteroatom (e.g., O, N, S (e.g., in any suitable oxidation state), P (e.g., in any suitable oxidation state), Se); wherein $R^1$, $R^2$, $R^3$, $R^4$, and $R^5$ each independently comprise: H, alkyl (e.g., methyl, ethyl, propyl, butyl, or longer, or branched versions thereof (e.g., isopropyl)), aryl, or heteroaryl; and wherein $R^6$ is an organic moiety, for example, selected from: alkyl (e.g., methyl, ethyl, propyl, butyl, or longer, or branched versions thereof (e.g., isopropyl)), aryl, heteroaryl, amides, esters, carbamates, carbonates, ureas, thioureas, sulfamides, sulfates, sulfites, phosphates, phosphonates, etc. In embodiments in which E is N or P, the E group may be further substituted with H or other organic or heterorganic functional groups described herein. In some embodiments, $R^6$ comprises:

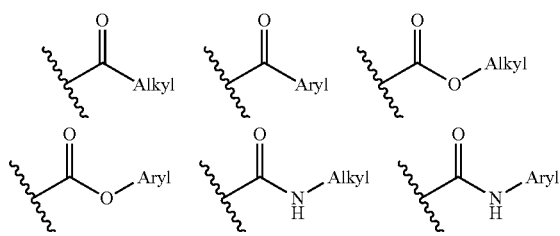

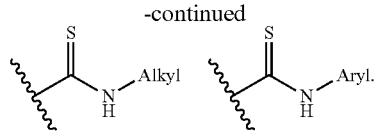

In some embodiments, a chemoselectively-cleavable group is an allyl ether, for example of the formula:

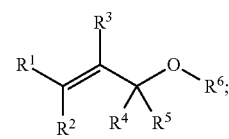

wherein $R^1$, $R^2$, $R^3$, $R^4$, and $R^5$ each independently comprise: H, alkyl (e.g., methyl, ethyl, propyl, butyl, or longer, or branched versions thereof (e.g., isopropyl)), aryl, or heteroaryl; and wherein $R^6$ comprises alkyl (e.g., methyl, ethyl, propyl, butyl, or longer, or branched versions thereof (e.g., isopropyl)), aryl, or heteroaryl.

In some embodiments, a chemoselectively-cleavable group is an allyl amine, for example of the formula:

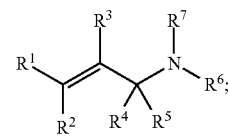

wherein $R^1$, $R^2$, $R^3$, $R^4$, $R^5$, and $R^7$ each independently comprise: H, alkyl (e.g., methyl, ethyl, propyl, butyl, or longer, or branched versions thereof (e.g., isopropyl)), aryl, or heteroaryl; and wherein $R^6$ comprises alkyl (e.g., methyl, ethyl, propyl, butyl, or longer, or branched versions thereof (e.g., isopropyl)), aryl, or heteroaryl.

In some embodiments, a chemoselectively-cleavable group is an allyl sulfide, for example of the formula:

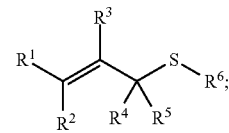

wherein $R^1$, $R^2$, $R^3$, $R^4$, and $R^5$ each independently comprise: H, alkyl (e.g., methyl, ethyl, propyl, butyl, or longer, or branched versions thereof (e.g., isopropyl)), aryl, or heteroaryl; and wherein $R^6$ comprises alkyl (e.g., methyl, ethyl, propyl, butyl, or longer, or branched versions thereof (e.g., isopropyl)), aryl, or heteroaryl.

In some embodiments, a chemoselectively-cleavable group is an allyl sulfoxide, for example of the formula:

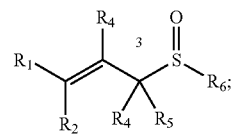

wherein $R^1$, $R^2$, $R^3$, $R^4$, and $R^5$ each independently comprise: H, alkyl (e.g., methyl, ethyl, propyl, butyl, or longer, or branched versions thereof (e.g., isopropyl)), aryl, or heteroaryl; and wherein $R^6$ comprises alkyl (e.g., methyl, ethyl, propyl, butyl, or longer, or branched versions thereof (e.g., isopropyl)), aryl, or heteroaryl.

In some embodiments, a chemoselectively-cleavable group is an allyl sulfone, for example of the formula:

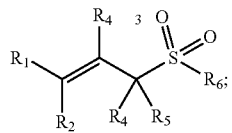

wherein $R^1$, $R^2$, $R^3$, $R^4$, and $R^5$ each independently comprise: H, alkyl (e.g., methyl, ethyl, propyl, butyl, or longer, or branched versions thereof (e.g., isopropyl)), aryl, or heteroaryl; and wherein $R^6$ comprises alkyl (e.g., methyl, ethyl, propyl, butyl, or longer, or branched versions thereof (e.g., isopropyl)), aryl, or heteroaryl.

In some embodiments, a chemoselectively-cleavable group is an allyl selenide, for example of the formula:

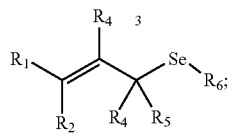

wherein $R^1$, $R^2$, $R^3$, $R^4$, and $R^5$ each independently comprise: H, alkyl (e.g., methyl, ethyl, propyl, butyl, or longer, or branched versions thereof (e.g., isopropyl)), aryl, or heteroaryl; and wherein $R^6$ comprises alkyl (e.g., methyl, ethyl, propyl, butyl, or longer, or branched versions thereof (e.g., isopropyl)), aryl, or heteroaryl.

In some embodiments, a chemoselectively-cleavable group is an allyl ester, for example of the formula:

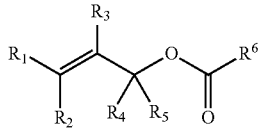

wherein $R^1$, $R^2$, $R^3$, $R^4$, and $R^5$ each independently comprise: H, alkyl (e.g., methyl, ethyl, propyl, butyl, or longer, or branched versions thereof (e.g., isopropyl)), aryl, or heteroaryl; and wherein $R^6$ comprises alkyl (e.g., methyl, ethyl, propyl, butyl, or longer, or branched versions thereof (e.g., isopropyl)), aryl, or heteroaryl.

In some embodiments, a chemoselectively-cleavable group is an allyl amide, for example of the formula:

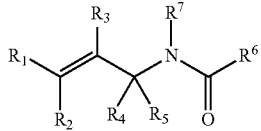

wherein $R^1$, $R^2$, $R^3$, $R^4$, $R^5$, and $R^7$ each independently comprise: H, alkyl (e.g., methyl, ethyl, propyl, butyl, or longer, or branched versions thereof (e.g., isopropyl)), aryl, or heteroaryl; and wherein $R^6$ comprises alkyl (e.g., methyl, ethyl, propyl, butyl, or longer, or branched versions thereof (e.g., isopropyl)), aryl, or heteroaryl.

In some embodiments, a chemoselectively-cleavable group is an allyl urea, for example of the formula:

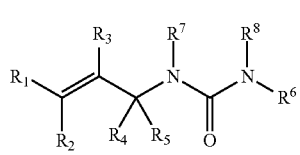

wherein $R^1$, $R^2$, $R^3$, $R^4$, $R^5$, $R^7$, and $R^8$ each independently comprise: H, alkyl (e.g., methyl, ethyl, propyl, butyl, or longer, or branched versions thereof (e.g., isopropyl)), aryl, or heteroaryl; and wherein $R^6$ comprises alkyl (e.g., methyl, ethyl, propyl, butyl, or longer, or branched versions thereof (e.g., isopropyl)), aryl, or heteroaryl.

In some embodiments, a chemoselectively-cleavable group is an allyl carbonate, for example of the formula:

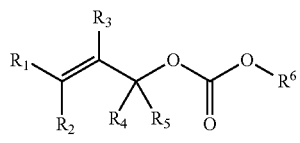

wherein $R^1$, $R^2$, $R^3$, $R^4$, and $R^5$ each independently comprise: H, alkyl (e.g., methyl, ethyl, propyl, butyl, or longer, or branched versions thereof (e.g., isopropyl)), aryl, or heteroaryl; and wherein $R^6$ comprises alkyl (e.g., methyl, ethyl, propyl, butyl, or longer, or branched versions thereof (e.g., isopropyl)), aryl, or heteroaryl.

In some embodiments, a chemoselectively-cleavable group is an allyl carbamate, for example of the formula:

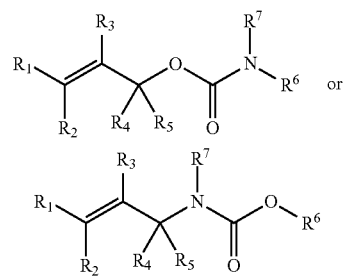

wherein $R^1$, $R^2$, $R^3$, $R^4$, $R^5$, and $R^7$ each independently comprise: H, alkyl (e.g., methyl, ethyl, propyl, butyl, or longer, or branched versions thereof (e.g., isopropyl)), aryl, or heteroaryl; and wherein $R^6$ comprises alkyl (e.g., methyl, ethyl, propyl, butyl, or longer, or branched versions thereof (e.g., isopropyl)), aryl, or heteroaryl.

In some embodiments, a chemoselectively-cleavable group is an allyl bis-heteroatom, for example of the formula:

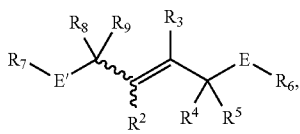

wherein $R^2$-$R^9$ each independently comprise: H, alkyl (e.g., methyl, ethyl, propyl, butyl, or longer, or branched versions thereof (e.g., isopropyl)), aryl, or heteroaryl, and wherein the double bond configuration is either E or Z, for example:

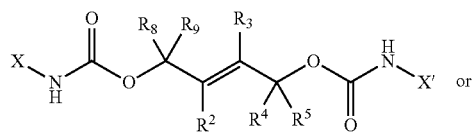

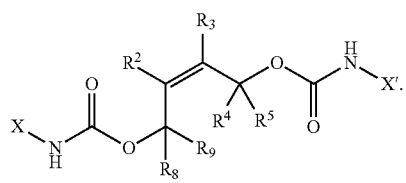

In some embodiments, E and E' are independently selected from N, S, and O, and E and E' may be the same or different heteroatoms. In some embodiments, $R^6$ and $R^7$ independently comprise:

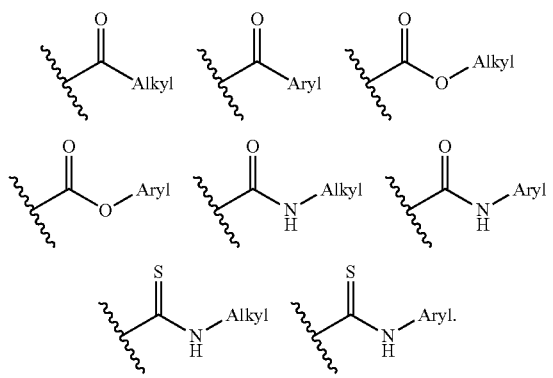

In general, chemoselectively-cleavable groups of the allyl-heteroatom type (e.g., allyl carbamates, allyl carbonates, allyl ureas, allyl amides, allyl esters, allyl amines, allyl ethers, etc.) are cleavable by allylic substitution (e.g., catalyzed by Pd or Ru). For example:

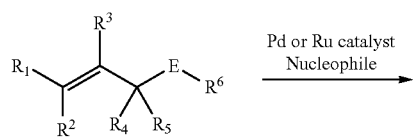

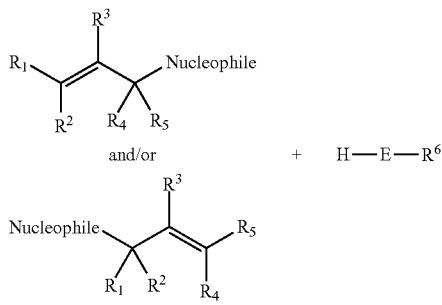

In some embodiments, exposure of compositions comprising a chemoselectively-cleavable allyl-heteroatom linker to Pd or Ru catalyst (e.g., under otherwise physiologic or intracellular conditions) results in cleavage of the linker.

2. Propargyl-Containing Groups

Chemoselectively-cleavable groups that find use in the compositions and methods described herein include, but are not limited to, propargyl-heteroatom groups. For example, chemoselectively-cleavable groups may be of the formula:

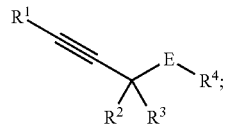

wherein E is a heteroatom (e.g., O, N, S, P); wherein $R^1$, $R^2$, and $R^3$ each independently comprise: H, alkyl (e.g., methyl, ethyl, propyl, butyl, or longer, or branched versions thereof (e.g., isopropyl)), aryl, or heteroaryl; and wherein $R^4$ is an organic moiety, for example, selected from: alkyl (e.g., methyl, ethyl, propyl, butyl, or longer, or branched versions thereof (e.g., isopropyl)), aryl, heteroaryl, amides, esters, carbamates, carbonates, ureas, thioureas, sulfonamides, sulfates, sulfites, phosphates, phosphonates, etc. In embodiments in which E is N or P, the E group may be further substituted with H or other organic or heterorganic functional groups described herein. In some embodiments, $R^4$ comprises:

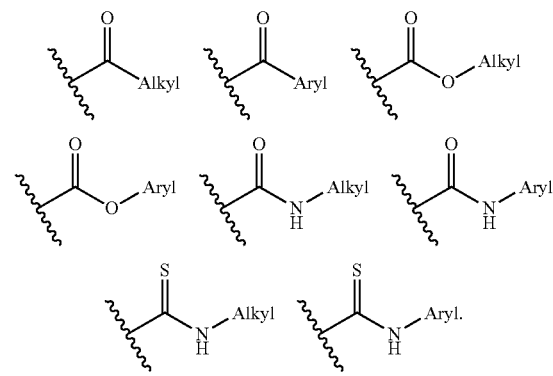

In some embodiments, a chemoselectively-cleavable group is a propargyl ether, for example of the formula:

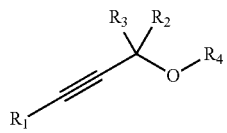

wherein $R^1$, $R^2$, and $R^3$ each independently comprise: H, alkyl (e.g., methyl, ethyl, propyl, butyl, or longer, or branched versions thereof (e.g., isopropyl)), aryl, or heteroaryl; and wherein $R^4$ comprises alkyl (e.g., methyl, ethyl, propyl, butyl, or longer, or branched versions thereof (e.g., isopropyl)), aryl, or heteroaryl.

In some embodiments, a chemoselectively-cleavable group is a propargyl amine, for example of the formula:

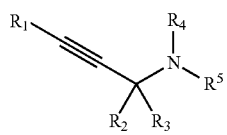

wherein $R^1$, $R^2$, $R^3$, and $R^4$ each independently comprise: H, alkyl (e.g., methyl, ethyl, propyl, butyl, or longer, or branched versions thereof (e.g., isopropyl)), aryl, or heteroaryl; and wherein $R^5$ comprises alkyl (e.g., methyl, ethyl, propyl, butyl, or longer, or branched versions thereof (e.g., isopropyl)), aryl, or heteroaryl.

In some embodiments, a chemoselectively-cleavable group is a propargyl ester, for example of the formula:

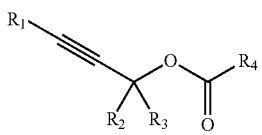

wherein $R^1$, $R^2$, and $R^3$ each independently comprise: H, alkyl (e.g., methyl, ethyl, propyl, butyl, or longer, or branched versions thereof (e.g., isopropyl)), aryl, or heteroaryl; and wherein $R^4$ comprises alkyl (e.g., methyl, ethyl, propyl, butyl, or longer, or branched versions thereof (e.g., isopropyl)), aryl, or heteroaryl.

In some embodiments, a chemoselectively-cleavable group is a propargyl amide, for example of the formula:

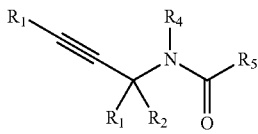

wherein $R^1$, $R^2$, $R^3$, and $R^4$ each independently comprise: H, alkyl (e.g., methyl, ethyl, propyl, butyl, or longer, or branched versions thereof (e.g., isopropyl)), aryl, or heteroaryl; and wherein $R^5$ comprises alkyl (e.g., methyl, ethyl, propyl, butyl, or longer, or branched versions thereof (e.g., isopropyl)), aryl, or heteroaryl.

In some embodiments, a chemoselectively-cleavable group is a propargyl urea, for example of the formula:

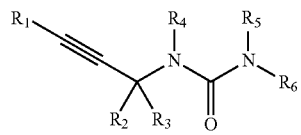

wherein $R^1$, $R^2$, $R^3$, $R^4$, and $R^5$ each independently comprise: H, alkyl (e.g., methyl, ethyl, propyl, butyl, or longer, or branched versions thereof (e.g., isopropyl)), aryl, or heteroaryl; and wherein $R^6$ comprises alkyl (e.g., methyl, ethyl, propyl, butyl, or longer, or branched versions thereof (e.g., isopropyl)), aryl, or heteroaryl.

In some embodiments, a chemoselectively-cleavable group is a propargyl carbonate, for example of the formula:

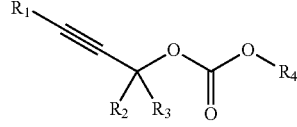

wherein $R^1$, $R^2$, and $R^3$ each independently comprise: H, alkyl (e.g., methyl, ethyl, propyl, butyl, or longer, or branched versions thereof (e.g., isopropyl)), aryl, or heteroaryl; and wherein $R^4$ comprises alkyl (e.g., methyl, ethyl, propyl, butyl, or longer, or branched versions thereof (e.g., isopropyl)), aryl, or heteroaryl.

In some embodiments, a chemoselectively-cleavable group is a propargyl carbamate, for example of the formula:

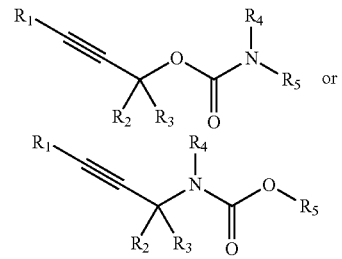

wherein $R^1$, $R^2$, $R^3$, and $R^4$ each independently comprise: H, alkyl (e.g., methyl, ethyl, propyl, butyl, or longer, or branched versions thereof (e.g., isopropyl)), aryl, or heteroaryl; and wherein $R^5$ comprises alkyl (e.g., methyl, ethyl, propyl, butyl, or longer, or branched versions thereof (e.g., isopropyl)), aryl, or heteroaryl.

In general, chemoselectively-cleavable groups of the propargyl-heteroatom type are cleavable by palladium- or other transition-metal-mediated cleavage. For example:

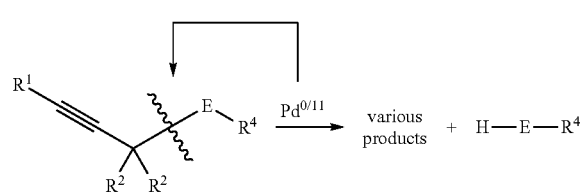

In some embodiments, exposure of compositions comprising a chemoselectively-cleavable propargyl-heteroatom linker to Pd or Ru catalyst (e.g., under otherwise physiologic or intracellular conditions) results in cleavage of the linker (Li et al. Nat. Chem. 2014, 6, 352; herein incorporated by reference in its entirety).

B. Linker Moieties

In some embodiments, linker moieties (e.g., $L^1$, $L^2$, etc.), for example, connecting the chemoselectively-cleavable group and the cellular interaction element or capture element, are provided as part of the compositions herein. In some embodiments, a "linker" connecting a cellular interaction element or capture element comprises a chemoselectively-cleavable moiety (Y) and 0, 1, 2, of more "linker moieties" ($L^1$, $L^2$, etc.). In some embodiments, linker moieties are straight or branched chains comprising any combination of alkyl, alkenyl, or alkynyl chains, and main-chain heteroatoms (e.g., O, S, N, P, etc.). In some embodiments, linker moieties comprises one or more backbone groups selected from of: —O—, —S—, —CH=CH—, =C=, a carbon-carbon triple bond, C=O, NH, SH, OH, CN, etc. In some embodiments, a linker moiety comprises one or more substituents, pendants, side chains, etc., comprising any suitable organic functional groups.

In some embodiments, the linker provides sufficient distance between functional elements and the chemoselectively-cleavable moiety to allow each element/moiety to function undisturbed by the presence of other elements/moieties. For example, linkers provide sufficient distance to allow a capture element to bind a capture agent, a cellular interaction element to bind a cellular target, and a chemoselectively-cleavable moiety to be cleaved by a chemoselective agent substrate (e.g., without or with reduced interference between moieties/elements).

A linker moiety, as used herein, is not a single covalent bond (such single covalent bond connections are depicted as Z-Y or Y-Q, for example). In some embodiments, the linker separates first and second functional elements (e.g., Z, Q) by about 5 angstroms to about 1000 angstroms, inclusive, in length. Suitable linkers separate first and second functional elements (e.g., Z, Q) by about 5 Å, 10 Å, 20 Å, 50 Å, 100 Å, 150 Å, 200 Å, 300 Å, 400 Å, 500 Å, 600 Å, 700 Å, 800 Å, 900 Å, 1000 Å, and any suitable ranges therein (e.g., 5-100 Å, 50-500 Å, 150-700 Å, etc.). In some embodiments, the linker separates first and second functional elements (e.g., Z, Q) by about 1-200 atoms (e.g., 1, 2, 3, 4, 5, 6, 7, 8, 9, 10, 15, 20, 25, 30, 35, 40, 45, 50, 60, 70, 80, 90, 100, 120, 140, 160, 180, 200, or any suitable ranges therein (e.g., 2-20, 10-50, etc.)).

In particular embodiments, a linker moiety comprises an alkyl carbamate group (e.g., $(CH_2)_nOCONH$, $(CH_2)_nNHCOO$, etc.). In some structures herein, alkyl carbamate is depicted as M. In some embodiments, the alkyl carbamate is oriented such the NH end is oriented toward the functional element (e.g., Z, Q), and the COO end is oriented toward the chemoselectively-cleavable moiety. In some embodiments, the alkyl carbamate is oriented such the COO end is oriented toward the functional element (e.g., Z, Q), and the NH end is oriented toward the chemoselectively-cleavable moiety. In some embodiments, a linker or linker moiety comprises a single alkyl carbamate group. In some embodiments, a linker or linker moiety comprises two or more alkyl carbamate groups (e.g., 2, 3, 4, 5, 6, 7, 8, etc.).

In some embodiments, a linker moiety is configured to separate a functional element (e.g., Z or Q (e.g., A-X)) and an allyl carbamate (Y) or alkyl carbamate (M) by a distance that optimizes the functionality of the Z group (e.g., interaction between the capture element (e.g., A-X, biotin, epitope, etc.) and capture agent (e.g., mutant dehalogenase, streptavidin, antibody). In certain embodiments, Z or Q and M or Y are separated by 1-200 linearly connected atoms (e.g., 1, 2, 3, 4, 5, 6, 7, 8, 9, 10, 15, 20, 25, 30, 35, 40, 45, 50, 60, 70, 80, 90, 100, 120, 140, 160, 180, 200, or any suitable ranges therein (e.g., 2-20, 10-50, 6-18 (e.g., $(CH2)_6O(CH_2)_2O(CH_2)_2$, $(CH_2)_{6-18}$, etc.), etc.). In some embodiments in which a composition comprises -Y-L-A-X or -M-L-A-X (and L does not comprise an M or Y), A and L together comprise 1-200 linearly connected atoms (e.g., 1, 2, 3, 4, 5, 6, 7, 8, 9, 10, 15, 20, 25, 30, 35, 40, 45, 50, 60, 70, 80, 90, 100, 120, 140, 160, 180, 200, or any suitable ranges therein (e.g., 2-20, 10-50, 6-18)). In some embodiments, A and $L^2$ comprises 9-15 linearly connected atoms (e.g., 9, 10, 11, 12, 13, 14, 15). In some embodiments, A and $L^2$ comprises 12 linearly connected C, N, and/or O atoms (e.g., $(CH_2)_6O(CH_2)_2O(CH_2)_2$, $(CH_2)_6(CH_2)_3O(CH_2)_2$, $(CH_2)_6O(CH_2)_2(CH_2)_3$, etc.).

In some embodiments, a linker is configured to separate the Z or Q group and the most proximal carbamate (e.g., M or Y) by a distance that decreases the interaction between the functional group and carbamate. In some embodiments, a linker moiety comprises more than 1 linearly connected C, S, N, and/or O atoms. In some embodiments, a linker moiety comprises one or more alkyl carbamate groups. In some embodiments, a linker moiety comprises one or more alkyl groups (e.g., methyl, ethyl, propyl, butyl, pentyl, hexyl, etc.). In some embodiments, a linker moiety comprises one or more $O(CH_2)_2$ or $(CH_2)O$ groups (1, 2, 3, 4, 5, 6, 7, 8, 9, 10, 15, 20, 25, 30, 35, 40, 45, 50, 60, 70, 80, 90, 100). In some embodiments, a linker moiety comprises 1-200 linearly connected atoms (e.g., 1, 2, 3, 4, 5, 6, 7, 8, 9, 10, 15, 20, 25, 30, 35, 40, 45, 50, 60, 70, 80, 90, 100, 120, 140, 160, 180, 200, or any suitable ranges therein (e.g., 2-20, 10-50, 6-18)). In some embodiments, a linker moiety is 1-200 linearly connected atoms (e.g., 1, 2, 3, 4, 5, 6, 7, 8, 9, 10, 15, 20, 25, 30, 35, 40, 45, 50, 60, 70, 80, 90, 100, 120, 140, 160, 180, 200, or any suitable ranges therein (e.g., 2-20, 10-50, 6-18)) in length.

C. Functional Elements

Provided herein are compositions comprising two functional elements (e.g., a capture element (Q) and a cellular interaction element (Z)) useful in the compositions and methods described herein. The functional elements are molecular or macromolecular entities that provide a function, or potential function, to the compositions to which they are attached. Such functions may be useful in the isolation, purification, detection, localization, immobilization, etc., of a composition described herein or a protein or fusion bound thereto. In some embodiments, a functional element interacts with a cellular entity (e.g., a cellular interaction element). In some embodiments, a functional element binds a capture agent (e.g., a capture element). Although embodiments herein are most typically described as a chemoselectively-cleavable linker connecting a capture agent and cellular interaction element, embodiments are not so limited. In some embodiments, the chemoselectively-cleavable linkers described herein connect other pairs of functional elements (e.g., a detection element, a cellular localization element, etc.).

In some embodiments, first functional element (e.g., a cellular interaction element (Z)) is covalently linked to a second functional element (e.g., a capture elements (Q)) via a chemoselectively-cleavable moiety (Y) and optionally one or more linker moieties (e.g., L, L1, L2, etc.). Suitable arrangements for compositions within the scope provided herein include, for example, Z-Y-Q, Z-L-Y-Q, Z-$L^1$-Y-$L^2$-Q, etc. In some embodiments, the functional elements retain their functional property (e.g. binding to a cellular target, binding to a capture agent, etc.) in the context of such a composition.

In some embodiments, the compositions described herein are cell compatible and/or cell permeable. Therefore, suitable functional elements (e.g., cellular interaction elements, capture elements) are ones that are cell compatible and/or cell permeable within the context of such compositions. In some embodiments, a composition comprising functional elements linked by a chemoselectively-cleavable linker, when added extracellularly, is capable of crossing the cell membrane to enter a cell (e.g., via diffusion, endocytosis, active transport, passive transport, etc.). In some embodiments, suitable functional elements are selected based on cell compatibility and cell permeability in addition to their particular function.

1. Cellular Interaction Elements

In some embodiments, compositions comprise a cellular interaction element linked to another functional element (e.g., capture element) by a chemoselectively-cleavable linker. Cellular interaction elements are physiologically and/or pharmacologically active substances that interact with one or more cellular (e.g., intracellular) components. In some embodiments, cellular interaction elements include, but are not limited to, small molecules (e.g., drugs, drug-like molecules, toxins, test compounds, etc.), amino acids (e.g., a naturally occurring amino acid or a non-natural amino acid), a peptide, a nucleic acid (e.g., DNA, RNA), etc.

In some embodiments, a cellular interaction element binds (e.g., covalently or non-covalently) to a cellular target under intracellular conditions. In some embodiments, a cellular interaction element forms a stable interaction with a cellular target under intracellular conditions, and maintains such an interaction under mild processing and analysis conditions (e.g., near neutral pH (e.g., pH 6.5, 6.6, 6.7, 6.8, 6.9, 7.0, 7.1, 7.2, 7.3, 7.4, 7.5, and any suitable ranges therein), room temperature, low concentration of denaturants or other destabilizing molecules, etc.).

In some embodiments, a cellular target comprises any suitable binding/interaction partner (e.g., receptor, enzyme) for a cellular interaction element (e.g., small molecule, peptide, nucleic acid, lipid, etc.). In particular embodiments, a cellular target is a protein that binds to or otherwise interacts with (e.g., stably interacts with) a cellular interaction element. In more particular embodiments, a cellular target is a receptor protein or an enzyme that binds to or otherwise interacts with (e.g., stably interacts with) a small molecule cellular interaction element.

Embodiments herein are not limited by the identity, type, or class of cellular targets.

In some embodiments, the cellular target is an endogenous cellular component of cells in which an assay is to be performed. In other embodiments, the cellular target is expressed in cells in which an assay is to be performed. In some embodiments, the cellular target is expressed at or near the endogenous levels (e.g., native abundance) for the cellular target (e.g., no overexpression of cellular targets). In some embodiments, methods herein allow for capture of endogenous cellular targets present in cells (or cell lysates). In some embodiments, methods herein allow for capture of cellular targets present in cells at or near their natural or endogenous abundance, thereby maximizing the biological relevance of an assay. In certain embodiments, because the methods allow for capture at endogenous levels of cellular target, the methods are useful for the capture of unknown targets of a cellular interaction element.

2. Capture Element

In some embodiments, compositions comprise a capture element linked to another functional element (e.g., cellular interaction element) by a chemoselectively-cleavable linker. Capture elements are molecular entities that form a stable complex by non-covalent interactions or form a covalent connection with a particular capture agent.

In some embodiments, a capture element is a substrate for a protein (e.g., enzyme), and the capture agent is that protein. In some embodiments, a capture element is a "covalent substrate" or one that forms a covalent bond with a protein or enzyme that it reacts with. The substrate may comprise a reactive group (e.g., a modified substrate) that forms a covalent bond with the enzyme upon interaction with the enzyme, or the enzyme may be a mutant version that is unable to reconcile a covalently bound intermediate with the substrate. In some embodiments, the substrate is recognized by a mutant protein (e.g., mutant dehalogenase) which forms a covalent bond thereto. In such embodiments, while the interaction of the substrate and a wild-type version of the protein (e.g., dehalogenase) results in a product and the regeneration of the wild-type protein, interaction of the substrate (e.g., haloalkane) with the mutant version of the protein (e.g., dehalogenase) results in stable bond formation (e.g., covalent bond formation) between the protein and substrate. The substrate may be any suitable substrate for any mutant protein that has been altered to form an ultra-stable or covalent bond with its substrate that would ordinarily only transiently bound by the protein. In some embodiments, the protein is a mutant hydrolase or dehalogenase. In some embodiments, the protein is a mutant dehalogenase and the substrate is a haloalkane. In some embodiments, the haloalkane comprises an alkane (e.g., $C_2$-$C_{20}$) capped by a terminal halogen (e.g., Cl, Br, F, I, etc.). In some embodiments, the haloalkane is of the formula A-X, wherein X is a halogen (e.g., Cl, Br, F, I, etc.), and wherein A is an alkane comprising 2-20 carbons. In certain embodiments, A comprises a straight-chain segment of 2-12 carbons. In certain embodiments, A is a straight-chain segment of 2-12 carbons. In some embodiments, the haloalkane may comprise any additional pendants or substitutions that do not interfere with interaction with the mutant dehalogenase.

In some embodiments, a capture agent is a SNAP-Tag and a capture element is benzyl guanine (See, e.g., Crivat G, Taraska J W (January 2012). *Trends in Biotechnology* 30 (1): 8-16; herein incorporated by reference in its entirety). In some embodiments, a capture agent is a CLIP-Tag and a capture element is benzyl cytosine (See, e.g., Gautier, et al. Chem Biol. 2008 February; 15(2):128-36; herein incorporated by reference in its entirety).

Systems comprising mutant proteins (e.g., mutant hydrolases (e.g., mutant dehalogenases) that covalently bind their substrates (e.g., haloalkane substrates) are described, for example, in U.S. Pat. Nos. 7,238,842; 7,425,436; 7,429,472; 7,867,726; each of which is herein incorporated by reference in their entireties.

In certain embodiments, the substrate is a substrate for a dehalogenase, e.g., a haloalkane dehalogenase, or a dehalogenase that cleaves carbon-halogen bonds in an aliphatic or aromatic halogenated substrate, such as a substrate for *Rhodococcus, Staphylococcus, Pseudomonas, Burkholderia, Agrobacterium* or *Xanthobacter* dehalogenase, or a substrate for a serine beta-lactamase. In some embodiments, a substrate optionally includes a linker which physically separates one or more functional groups from the reactive group in the substrate. For example, a substrate may include a linker of sufficient length, structure, charge, and hydrophobicity so that the one or more functional groups of the substrate do not disturb the interaction of the protein (e.g., dehalogenase) and reactive group (e.g., haloalkane) of the substrate.

In some embodiments, a capture element is an "affinity molecule" and a capture agent is an "acceptor" (e.g., small molecule, protein, antibody, etc.) that selectively interacts with such an affinity molecule. Examples of such pairs would include: an antibody as a the capture agent and an antigen as the capture element; a His-tag as the capture element and a nickel column as the capture agent; a protein and small molecule with high affinity as the capture agent and capture element, respectively (e.g., streptavidin and biotin), etc. Thus, a composition that includes an affinity molecule is separated from, for example, a cell-based on the selective interaction of the affinity molecule with the acceptor (e.g., an acceptor molecule that may be biological or non-biological in origin). The acceptor molecule may be free in solution or attached to a solid support. In some embodiments, a cellular interaction element or other functional element linked to the affinity molecule is subsequently released from the acceptor by chemoselective cleavage of the chemoselectively-cleavable linker (e.g., allowing detection or purification of a cellular target bound to the cellular capture agent).

For example, the specific molecule with which the affinity molecule interacts (referred to as the acceptor molecule) could be a small organic molecule, a chemical group such as a sulfhydryl group (—SH), or a large biomolecule such as an antibody or other naturally occurring ligand for the affinity molecule. The binding is normally chemical in nature and may involve the formation of covalent or non-covalent bonds or interactions such as ionic or hydrogen bonding. The acceptor molecule might be free in solution or bound to a solid or semi-solid surface, a polymer matrix, or reside on the surface of a solid or semi-solid substrate. The interaction may also be triggered by an external agent such as light, temperature, pressure, or the addition of a chemical or biological molecule that acts as a catalyst. The detection and/or separation of the complex from the reaction mixture occurs because of the interaction, normally a type of binding, between the affinity molecule and the acceptor molecule.

Examples of affinity molecules include molecules such as immunogenic molecules (e.g., epitopes of proteins, peptides, carbohydrates, or lipids (e.g., any molecule which is useful to prepare antibodies specific for that molecule)); biotin, avidin, streptavidin, and derivatives thereof; metal binding molecules; and fragments and combinations of these molecules. Exemplary affinity molecules include His5 (HHHHH)(SEQ ID NO: 1), HisX6 (HHHHHH)(SEQ ID NO: 2), C-myc (EQKLISEEDL) (SEQ ID NO: 3), Flag (DYKDDDDK) (SEQ ID NO: 4), SteptTag (WSHPQFEK) (SEQ ID NO: 5), HA Tag (YPYDVPDYA) (SEQ ID NO: 7), thioredoxin, cellulose binding domain, chitin binding domain, S-peptide, T7 peptide, calmodulin binding peptide, C-end RNA tag, metal binding domains, metal binding reactive groups, amino acid reactive groups, inteins, biotin, streptavidin, and maltose binding protein. In some embodiments, affinity interactions facilitate extracellular (e.g., following cell lysis) attachment of compositions described herein to various surfaces. Suitable surfaces include resins for chromatographic separation, plastics such as tissue culture surfaces or binding plates, microtiter dishes and beads, ceramics and glasses, particles including magnetic particles, polymers and other matrices. In some case, these materials may be part of biomolecular sensing devices such as optical fibers, chemfets, and plasmon detectors.

Another example of an affinity molecule is dansyllysine. Antibodies which interact with the dansyl ring are commercially available (Sigma Chemical; St. Louis, Mo.) or can be prepared using known protocols such as described in Antibodies: A Laboratory Manual (Harlow and Lane, 1988). For example, the anti-dansyl antibody is immobilized onto the packing material of a chromatographic column. This method, affinity column chromatography, accomplishes separation by causing the complex between a mutant hydrolase and a substrate to be retained on the column due to its interaction with the immobilized antibody, while other molecules pass through the column. The complex may then be released by disrupting the antibody-antigen interaction. Specific chromatographic column materials such as ion-exchange or affinity Sepharose, Sephacryl, Sephadex and other chromatography resins are commercially available (Sigma Chemical; St. Louis, Mo.; Pharmacia Biotech; Piscataway, N.J.). Dansyllysine may conveniently be detected because of its fluorescent properties.

When employing an antibody as an acceptor molecule, separation can also be performed through other biochemical separation methods such as immunoprecipitation and immobilization of antibodies on filters or other surfaces such as beads, plates or resins. For example, compositions may be isolated by coating magnetic beads with an affinity molecule-specific or other functional-element-specific antibody. Beads are oftentimes separated from the mixture using magnetic fields.

Methods to detect and/or isolate complexes having affinity molecules include chromatographic techniques including gel filtration, fast-pressure or high-pressure liquid chromatography, reverse-phase chromatography, affinity chromatography and ion exchange chromatography. Other methods of protein separation are also useful for detection and subsequent isolation of complexes between a mutant hydrolase and a substrate, for example, electrophoresis, isoelectric focusing and mass spectrometry.

3. Other Functional Groups

The compositions described herein comprise two functional elements tethered together by a chemoselectively-cleavable moiety. In most embodiments described herein, the functional elements are a cellular interaction element and a capture element; however, the embodiments with the scope provided herein are not so limited. Rather compositions may comprise other function elements having diverse functions tethered to a cellular interaction element or a capture element or to each other. Provided below are other exemplary functional elements that may find use in embodiments described herein.

In some embodiments, functional elements include, but are not limited to, small molecules (e.g., drugs, drug-like molecules, toxins, test compounds, etc.), amino acids (e.g., a naturally occurring amino acid or a non-natural amino acid), peptides, a polypeptides, proteins, a nucleic acids (e.g., DNA, RNA), a His-tag, a FLAG tag, a Strep-tag, an enzyme, a cofactor, a coenzyme, a peptide or protein substrate for an enzyme, for instance, a branched peptide substrate (e.g., Z-aminobenzoyl (Abz)-Gly-Pro-Ala-Leu-Ala-4-nitrobenzyl amide (NBA) (SEQ ID NO: 6), a suicide substrate, or a receptor, one or more nucleotides (e.g., ATP, ADP, AMP, GTP or GDP) including analogs thereof, e.g., an oligonucleotide, double stranded or single stranded DNA corresponding to a gene or a portion thereof, e.g., DNA capable of binding a protein such as a transcription factor, RNA corresponding to a gene, for instance, mRNA which lacks a stop codon, or a portion thereof, double stranded RNA for RNAi or vectors therefor, a glycoprotein, a polysaccharide, a peptide-nucleic acid (PNA), lipids including lipid bilayers, a drug (e.g., a chemotherapeutic such as doxorubicin, 5-fluorouracil, or camptosar (CPT-11; Irinotecan)), an aminoacylated tRNA such as an aminoacylated initiator tRNA or an aminoacylated amber suppressor tRNA, a molecule which binds $Ca^{2+}$, a molecule which binds $K^+$, a molecule which binds $Na^+$, a molecule which is pH sensitive, a radionuclide, a molecule which is electron opaque, a contrast agent, e.g., barium, iodine or other MRI or X-ray contrast agent, a molecule which fluoresces in the presence of NO or is sensitive to a reactive oxygen, a nanoparticle, e.g., an immunogold particle, paramagnetic nanoparticle, upconverting nanoparticle, or a quantum dot, a nonprotein substrate for an enzyme, an inhibitor of an enzyme, either a reversible or irreversible inhibitor, a chelating agent, a cross-linking group, for example, a succinimidyl ester or aldehyde, glutathione, biotin or other avidin binding molecule, avidin, streptavidin, cAMP, phosphatidylinositol, heme, a ligand for cAMP, a metal, NTA, and, in one embodiment, includes one or more dyes, e.g., a xanthene dye, a calcium sensitive dye, e.g., 1-[2-amino-5-(2,7-dichloro-6-hydroxy-3-oxy-9-xanthenyl)-phenoxy]-2-(2'-amino-5'-methylphenoxy)ethane-N,N,N',N'-tetraacetic acid (Fluo-3), a sodium sensitive dye, e.g., 1,3-benzenedicarboxylic acid, 4,4'-[1,4,10,13-tetraoxa-7,16-diazacyclooctadecane-7,16-diylbis(5-methoxy-6,2-benzofurandiyl)]bis (PBFI), a NO sensitive dye, e.g., 4-amino-5-methylamino-2',7'-difluorescein, or other fluorophore (e.g., carboxy rhodamine analog, see e.g., U.S. Ser. No. 13/682,589. In some embodiments, the functional element is a hapten or an immunogenic molecule, e.g., one which is bound by antibodies specific for that molecule. In some embodiments, the functional group comprises a radionuclide or a coordinator of a radionuclide, e.g., $^3H$, $^{14}C$, $^{35}S$, $^{125}I$, $^{131}I$, including a molecule useful in diagnostic methods.

In certain embodiments, functional elements have a detectable property that allows for detection of the composition and/or a protein or fusion bound thereto. Detectable functional elements include those with a characteristic electromagnetic spectral property such as emission or absorbance, magnetism, electron spin resonance, electrical capacitance, dielectric constant or electrical conductivity as well as functional groups which are ferromagnetic, paramagnetic, diamagnetic, luminescent, electrochemiluminescent, fluorescent, phosphorescent, chromatic, antigenic, or have a distinctive mass. A functional element includes, but is not limited to, a nucleic acid molecule (e.g., DNA or RNA (e.g., an oligonucleotide or nucleotide), a protein (e.g., a luminescent protein, a peptide, a contrast agent (e.g., MRI contract agent), a radionuclide, an affinity tag (e.g., biotin or streptavidin), a hapten, an amino acid, a lipid, a lipid bilayer, a solid support, a fluorophore, a chromophore, a reporter molecule, a radionuclide, an electron opaque molecule, a MRI contrast agent (e.g., manganese, gadolinium(III), or iron-oxide particles), or a coordinator thereof, and the like. Methods to detect a particular functional element, or to isolate a composition comprising a particular functional element and anything bound thereto, are known to the art.

In some embodiments, a functional group is or comprises a solid support. Suitable solid supports include a sedimental particle such as a magnetic particle, a sepharose, or cellulose bead; a membrane; glass, e.g., glass slides; cellulose, alginate, plastic, or other synthetically prepared polymer (e.g., an Eppendorf tube or a well of a multi-well plate); self-assembled monolayers; a surface plasmon resonance chip; or a solid support with an electron conducting surface; etc.

In some embodiments, a functional element is a photoaffinity labeling group. In some embodiments, a functional element is a ligand for a cellular target having one or more light (e.g., UV) activatable groups (e.g., azide group) for attachment to the cellular target.

Exemplary detectable functional elements include haptens (e.g., molecules useful to enhance immunogenicity such as keyhole limpet hemacyanin), cleavable labels (e.g., photocleavable biotin) and fluorescent labels (e.g., N-hydroxysuccinimide (NHS) modified coumarin and succinimide or sulfonosuccinimide modified BODIPY (which can be detected by UV and/or visible excited fluorescence detection), rhodamine (R110, rhodols, CRG6, Texas Methyl Red (TAMRA), RoxS, FAM, or fluorescein), coumarin derivatives (e.g., 7 aminocoumarin, and 7-hydroxycoumarin, 2-amino-4-methoxynapthalene, 1-hydroxypyrene, resorufin, phenalenones or benzphenalenones (U.S. Pat. No. 4,812, 409)), acridinones (U.S. Pat. No. 4,810,636), anthracenes, and derivatives of alpha and beta-naphthol, fluorinated xanthene derivatives including fluorinated fluoresceins and rhodols (e.g., U.S. Pat. No. 6,162,931), and bioluminescent molecules (e.g., luciferase (e.g., Oplophorus-derive luciferase (See e.g., U.S. application Ser. No. 12/773,002; U.S. application Ser. No. 13/287,986; herein incorporated by reference in their entireties) or GFP or GFP derivatives). A fluorescent (or bioluminescent) functional element may be used to sense changes in a system, like phosphorylation, in real-time. A fluorescent molecule, such as a chemosensor of metal ions may be employed to label proteins which bind the composition. A bioluminescent or fluorescent functional group such as BODIPY, rhodamine green, GFP, or infrared dyes, finds use as a functional element and may, for instance, be employed in interaction studies (e.g., using BRET, FRET, LRET or electrophoresis).

Another class of functional elements includes molecules detectable using electromagnetic radiation and includes, but is not limited to, xanthene fluorophores, dansyl fluorophores, coumarins and coumarin derivatives, fluorescent acridinium moieties, benzopyrene based fluorophores, as well as 7-nitrobenz-2-oxa-1,3-diazole, and 3-N-(7-nitrobenz-2-oxa-1,3-diazol-4-yl)-2,3-diamino-propionic acid. Preferably, the fluorescent molecule has a high quantum yield of fluorescence at a wavelength different from native amino acids and more preferably has high quantum yield of fluorescence that can be excited in the visible, or in both the UV and visible, portion of the spectrum. Upon excitation at a preselected wavelength, the molecule is detectable at low concentrations either visually or using conventional fluorescence detection methods. Electrochemiluminescent molecules such as ruthenium chelates and its derivatives or nitroxide amino acids and their derivatives are detectable at femtomolar ranges and below.

In addition to fluorescent molecules, a variety of molecules with physical properties based on the interaction and response of the molecule to electromagnetic fields and radiation find use in the compositions and methods described herein. These properties include absorption in the UV, visible and infrared regions of the electromagnetic spectrum, presence of chromophores which are Raman active, and can be further enhanced by resonance Raman spectroscopy, electron spin resonance activity and nuclear magnetic resonances and molecular mass, e.g., via a mass spectrometer.

II. Systems

In some embodiments, the compositions described herein are provided with one or more additional elements, compositions, components, devices, etc. in a system. For example, a cell permeable/compatible composition (as described herein) is provided with or administered to cells. Similarly, a composition may be provided with a solid support, to which a functional element on the composition may be attached. Further, a composition comprising an enzyme substrate (e.g., haloalkane) may be provided with a mutant protein (e.g., dehalogenase) that forms a covalent bond with the substrate. Some elements, compositions, components, devices, etc. that find use in various systems within the scope herein are described below.

In some embodiments, systems comprise a solid support. Suitable solid supports include a sedimental particle such as a magnetic particle, a sepharose, or cellulose bead; a membrane; glass, e.g., glass slides; cellulose, alginate, plastic, or other synthetically prepared polymer (e.g., an Eppendorf tube or a well of a multi-well plate); self-assembled monolayers; a surface plasmon resonance chip; or a solid support with an electron conducting surface; etc.

In some embodiments, a system comprises a chemoselectively-cleavable composition, as described herein, and a protein capable of stable interaction with a functional element on the protein. In some embodiments, the protein is a mutant version of an enzyme that has been altered to form a covalent bond with its substrate. In some embodiments, the mutant protein is a mutant protein, hydrolase and/or dehalogenase, as described in more detail in, for example, U.S. Pat. Nos. 7,238,842; 7,425,436; 7,429,472; 7,867,726; each of which is herein incorporated by reference in their entireties. In some embodiments, the mutant protein, hydrolase, and/or dehalogenase comprises at least one amino acid substitution relative to a corresponding wild-type protein, hydrolase or dehalogenase. Mutant proteins (e.g., mutant dehalogenases) are not limited to those prepared via recombinant techniques (e.g., site-directed mutagenesis or recursive mutagenesis) and comprise one or more amino acid substitutions which render the mutant protein (e.g., mutant dehalogenase) capable of forming a stable (e.g., covalent) bond with a substrate, such as a substrate comprising one or more functional groups. In some embodiments, the mutant proteins are mutant hydrolases. In certain embodiments, the mutant proteins are mutant dehalogenases. The at least one amino acid substitution results in the mutant protein forming a bond with the substrate which is more stable than the bond formed between the corresponding wild-type protein and the substrate (e.g., a covalent bond). The at least one amino acid substitution in the mutant protein is a substitution at an amino acid residue in the corresponding wild-type protein that is associated with activating a water molecule which cleaves the bond formed between the corresponding wild-type protein and the substrate or at an amino acid residue in the corresponding wild-type protein that forms an ester intermediate with the substrate. In some embodiments, the mutant protein comprises at least two amino acid substitutions relative to a corresponding wild-type protein, wherein one substitution is in a residue which, in the wild-type protein, is associated with activating a water molecule or in a residue which, in the wild-type protein, forms an ester intermediate by nucleophilic attack of a substrate for the hydrolase, and another substitution in a residue which, in the wild-type protein, is at or near a binding site(s) for a hydrolase substrate, but is not in a residue that in the corresponding wild-type protein is associated with activating a water molecule or which forms ester intermediate with a substrate. In one embodiment, the second substitution is in a residue which, in the wild-type protein lines the site(s) for substrate entry into the catalytic pocket of the protein. The additional substitution(s) preferably increase the rate of stable covalent bond formation of those mutants binding to a substrate of a corresponding wild-type protein. Details of the sequences and mutations of proteins, hydrolases and dehalogenases are described, for example, in U.S. Pat. Nos. 7,238,842; 7,425,436; 7,429,472; 7,867,726; each of which is herein incorporated by reference in their entireties.

In some embodiments, stable interactions between elements are achieved by the use of known capture/binding systems, such as SNAP-Tag and/or CLIP-Tag.

In various embodiments, systems comprise fusion proteins comprising a mutant protein (e.g., mutant dehalogenase) and amino acid sequences of a protein or peptide of interest (e.g., a drug target, a marker protein (e.g., a selectable marker protein, affinity tag (e.g., a polyhistidine sequence)), an enzyme of interest (e.g., luciferase, RNasin, RNase, and/or GFP), a nucleic acid binding protein, an extracellular matrix protein, a secreted protein, an antibody or a portion thereof such as Fc, a bioluminescence protein, a receptor ligand, a regulatory protein, a serum protein, an immunogenic protein, a fluorescent protein, a protein with reactive cysteines, a receptor protein (e.g., NMDA receptor, a channel protein (e.g., an ion channel protein such as a sodium-, potassium- or a calcium-sensitive channel protein including a HERG channel protein)), a membrane protein, a cytosolic protein, a nuclear protein, a structural protein, a phosphoprotein, a kinase, a signaling protein, a metabolic protein, a mitochondrial protein, a receptor associated protein, a fluorescent protein, an enzyme substrate (e.g., a protease substrate), a transcription factor, a protein destabilization sequence, or a transporter protein (e.g., EAAT1-4 glutamate transporter), as well as targeting signals (e.g., a plastid targeting signal, such as a mitochondrial localization sequence, a nuclear localization signal or a myristoylation sequence, that directs the mutant hydrolase to a particular location)).

In certain embodiments, a fusion protein is expressed from a recombinant DNA which encodes the mutant protein (e.g., mutant dehalogenase) and at least one protein of interest or formed by chemical synthesis. The protein of interest may be fused to the N-terminus or the C-terminus of the mutant protein. In some embodiments, the fusion protein comprises a protein of interest at the N-terminus and another protein, e.g., a different protein, at the C-terminus, of the mutant protein (e.g., mutant dehalogenase). For example, the protein of interest may be a fluorescent protein or an antibody. Optionally, the proteins in the fusion are separated by a connector sequence (e.g., one having at least 2 amino acid residues, such as one having 13 to 17 amino acid residues). The presence of a connector sequence in a fusion protein does not substantially alter the function of either protein in the fusion relative to the function of each individual protein. Thus, for a fusion of a mutant dehalogenase and a luciferase (e.g., Renilla luciferase, Oplophorus-derived luciferase (See e.g., U.S. application Ser. No. 12/773,002; U.S. application Ser. No. 13/287,986; herein incorporated by reference in their entireties)), the presence of a connector sequence does not substantially alter the stability of the bond formed between the mutant dehalogenase and a substrate therefor or the activity of the luciferase. For any particular combination of proteins in a fusion, a wide variety of connector sequences may be employed. In some embodiments, the connector sequence is a sequence recognized by an enzyme (e.g., a cleavable sequence (e.g., enzyme cleavable, chemically cleavable, photocleavable, etc.)).

III. Methods

Provided herein are methods utilizing cell-compatible and cell-permeable compositions comprising a pair of functional elements (e.g., capture element and cellular interaction element) linked by a chemoselectively-cleavable linker.

In some embodiments, a dual-function chemoselectively-cleavable composition (e.g., cellular interaction and capture) is introduced extracellularly to a cell or cell population. Due to its cell permeability, the composition enters the cell by an appropriate mechanism (e.g., passive transport).

In some embodiments, a cell is exposed to a cell-compatible/permeable composition comprising two functional elements linked by a chemoselectively-cleavable linker (e.g., Z-Y-Q, Z-L-Y-Q, Z-$L^1$-Y-$L^2$-Q, etc.) under conditions such that the composition enters the cell. According to the identity of the functional elements displayed on the composition, the composition will interact with one or more cellular components become subcellularly localized, etc. Subsequently, upon exposure to a chemoselective agent, the chemoselective moiety is cleaved, and the functional groups are unlinked. In some embodiments, prior to exposing the chemoselectively-cleavable composition to the chemoselective agent, one or more of the following steps is performed: detecting a function element of the composition, allowing a functional element to interact (e.g., bind) a cellular component, lysing or permeabilizing the cell (e.g., to cellular components not permeable to an intact cell), binding a functional element to a surface or solid support, etc.

In some embodiments, a dual-function chemoselectively-cleavable composition comprises a first functional element (e.g., cellular interaction element) configured to interact with a cellular target (e.g., intracellular protein) and a second functional element (e.g., capture element) configured to bind to a capture agent (e.g., mutant dehalogenase, antibody, streptavidin, etc.) connected by a chemoselectively-cleavable moiety (e.g., optionally comprising linker moieties connecting the chemoselectively-cleavable moiety to one or both functional elements). In some embodiments, upon exposure of cell to the dual-function chemoselectively-cleavable composition, the composition enters the cell (e.g., by any suitable mechanism (e.g., passive diffusion, active transport, endocytosis, etc.). In some embodiments, time is allowed for the first functional element to interact (e.g., covalently or non-covalently bind) with the cellular component. In some embodiments, the cell is lysed, and the lysate is exposed to the capture agent (e.g., in solution, on a solid surface, etc.). Time is provided to allow for the second functional element to bind to a capture agent. In some embodiments, the captured composition bound to the cellular component is exposed to a chemoselective agent to cleave the chemoselectively-cleavable moiety, resulting in release of the cellular component from the capture agent. In some embodiments, the liberated cellular target and/or cellular interaction element is detected, characterized, identified, analyzed, etc.

In embodiments in which one of the functional elements of the composition is a cellular interaction element, the composition is allowed to reside within the cell for an appropriate time period (e.g., <1 sec., 1 sec., 2 sec., 5 sec., 10 sec., 20 sec., 30 sec., 1 min., 2 min., 5 min., 10 min., 20 min. 30 min., 45 min., 1 hour, 2 hours, 6 hours, 1 day, 2 days, or more, or any suitable ranges there between). In some embodiments, when a cellular target for the cellular interaction element is present within the cell, interaction (e.g., covalent binding, non-covalent binding, etc.) between the cellular target and the cellular interaction element will occur (e.g., on the appropriate timescale, given appropriate cellular conditions (e.g., cell cycle timing), given proper localization of the cellular target and the cellular interaction element within the cell, etc.). In some embodiments, following interaction of the cellular target and the cellular interaction element, the cell or cells are lysed or further permeabilized (e.g., such that the cellular target can exit the cell). In embodiments in which one of the functional elements of the composition is a capture element, the cell, composition, and/or cell lysate is exposed to a capture agent (e.g., in solution or attached to a solid support). In some embodiments, capture of the capture element of the composition provides immobilization of a cellular target bound to the cellular interaction element. In some embodiments, following capture (e.g., immobilization), unbound cellular components (e.g., those that do not interact with the cellular interaction element) are washed away or otherwise removed. In some embodiments, the cellular interaction element (e.g., and bound cellular target, if present) is liberated from the capture agent (e.g., and solid support) by chemoselective cleavage of the chemoselectively-cleavable moiety. In some embodiments, the liberated cellular target and/or cellular interaction element is detected, characterized, identified, analyzed, etc.

In certain embodiments, provided herein is a sensitive method for discovery and validation of the cellular targets (e.g., protein or protein complexes) of bioactive agents (e.g., small and/or drug-like molecules) in cells. In some embodiments, a bioactive agent or library thereof is employed as cellular interaction element(s) in the compositions described herein and exposed to cell(s) comprising only endogenous proteins or expressing a cellular target of interest. The compositions and methods allow capture, purification/isolation, liberation, and characterization of the bioactive agent, cellular target, and/or pair thereof that resulting in a positive interaction (e.g., binding event). In some embodiments, because mild conditions are used for liberating the cellular complex, the interaction between the cellular interaction element and cellular target is not disturbed during processing and analysis.

In some embodiments, the methods find use as a part of, or a companion to, phenotypic screening assays. For example, a set of small molecules that yield the desired phenotypic response in a phenotypic screen are each tethered to capture elements (e.g., by chemical synthesis or enzymatic means) by a chemoselectively-cleavable linker. Cells are treated with the dual-function (e.g., cellular interaction and post-interaction capture) which engages the cellular target (optionally fused with a reporter) and re-generates the phenotypic response. In some embodiments, cells are then lysed, and the cellular target, now linked to the cellular interaction element, is captured by binding of the capture element with a capture agent (e.g., displayed on a surface or substrate). In some embodiments, the capture agent is in solution and is subsequently bound to a solid surface after capture of the capture element. In other embodiments, the capture agent is bound to a solid surface (e.g., well, microplate, bead, etc.) upon interaction with the capture element.

In some embodiments, methods are provided for the capture or "pull down" of endogenous targets (e.g., known and unknown targets of a bioactive agent). In some embodiments, a bioactive agent is employed as a cellular interaction element. A chemoselectively-cleavable composition employing such a cellular interaction element is introduced to cells and passes into the intracellular space. Endogenous protein(s) (or other endogenous targets) are bound to bound to cellular interaction element and are then captured (e.g., pulled down) by a capture agent (e.g., displayed on a surface (e.g., bead)), typically following lysis of the cell(s). Such pull-down methods can be followed by analysis to identify the targets (e.g., proteins) captured. Analysis techniques may include Western blotting, gel electrophoresis, mass spectrometry, nuclear magnetic resonance spectroscopy, functional analysis, etc.

In some embodiments, attaching a bioactive molecule (e.g., cell interaction element) to a capture element via a chemoselectively-cleavable moiety (and optionally one or more linker moieties) creates a dual-function composition that maintains the cell permeability of the parent bioactive molecule. In some embodiments, the dual-function composition finds use in a variety of applications, including, for example, in protein pull-down from cells by means of solid-supported capture, as previously described in WO/2014093671 and WO/2014151282 (herein incorporated by reference in their entireties). The compositions and linkers described herein allow for chemoselective release of captured targets. This chemoselective cleavage provides a mode of release that is independent of a small molecule-protein interaction and allows for efficient release of the protein from the resin with minimal background. The cleavable linker cleavage rate is not affected by the off rate of the bioactive small molecule from the target protein and allows for efficient cleavage even in the case of covalent attachment of the cellular target from the cellular interaction element. Previous approaches for release of captured targets from resin include non-specific elution under denaturing conditions and specific elution via competition. A downside of non-specific elution is the denaturation of target proteins and release of non-specifically bound proteins from the resin. Specific elution using unmodified bioactive compound has advantage over denaturation by releasing only specifically bound proteins, but the efficiency of release is strongly dependent on solubility and residence time of the small molecule with each target; long residence time and/or low drug solubility results in inefficient release of the target protein. The chemoselectively-cleavable linkers described herein overcome these disadvantages. In some embodiments, the linkers described herein allow for selective release of captured cellular target from a solid support regardless of the type of drug-protein interaction. The ability to selectively release captured target regardless of solubility or kinetics/thermodynamics of the system components provides significant advantage over existing methodologies.

In some embodiments, a first functional element of a composition herein is a photoaffinity group. In some such embodiments, methods comprise: (a) contacting a reaction mix, cell, cell lysate, etc., containing a target with a dual-function composition comprising a photoaffinity group, a chemoselectively-cleavable moiety, and a second functional group; (b) activating the photoaffinity group (e.g., by exposure to light) to induce binding of the target; and (c) contacting the chemoselectively-cleavable moiety with a chemoselective agent to release the photoaffinity group and bound target from the second functional group. In some embodiments, methods further comprise one or more steps between (b) and (c) or detecting, isolating, purifying, etc. the target-bound composition.

In some embodiments, a first functional element of a composition herein is a solid surface and a second functional element is a cellular interaction element, capture element, photoaffinity group, affinity element, or other group capable of binding (covalently or non-covalently) a target. In some such embodiments, methods comprise: (a) contacting a dual-function composition comprising a solid surface, a chemoselectively-cleavable moiety, and a second functional element capable of binding (covalently or non-covalently) a target with a reaction mixture, cell lysate, etc. comprising the target; (b) allowing binding of the target to the second functional element; and (c) contacting the chemoselectively-cleavable moiety with a chemoselective agent to release the second functional element and bound target from the surface. In some embodiments, methods further comprise one or more steps between (b) and (c) or detecting, isolating, purifying, etc. the target-bound composition.

IV. Allyl Carbamate Structures

The following provides an exemplary set of dual-function, cell-permeable, cell-compatible, and chemoselectively cleavable compositors. Similar compositions comprising different chemoselectively cleavable groups (e.g., propargyl groups, etc.), capture elements (e.g., affinity molecules), and/or other functional elements (e.g., detectable moiety) in place of the cellular interaction element (Z) are within the scope of embodiments herein.

Provided herein are allyl-carbamate (Y) containing linkers for connecting haloalkane substrates (A-X) to cellular interaction elements (Z). In particular, the linkers provided herein comprise a chemically-cleavable allyl carbamate unit and find use within substrates for dehalogenase variants that form covalent bonds with their haloalkane substrates. Provided herein are chemical linkers that find use, for example, in connecting two chemical moieties (e.g., a functional group and a dehalogenase substrate). In some embodiments, the linkers are cell-permeable and chemically-cleavable. In some embodiments, the linkers described herein bear certain structural similarities with previously described chloroalkane carbamates (U.S. Pub. No. 2014/0322794; herein incorporated by reference in its entirety). In some embodiments, the linkers described herein, like the linkers described in U.S. Pub. No. 2014/0322794, comprise one or more alkyl carbamate structural motifs. However, whether or not an alkyl carbamate is present, the linkers described in some embodiments herein comprise one or more allyl carbamate units. The inclusion of the allyl carbamate allows the linkers (and compounds or substrates comprising such linkers) to exhibit both cell permeability and cell compatibility. In some embodiments, the allyl carbamate group further renders the linkers (and compounds or substrates comprising such linkers) chemoselectively cleavable. In some embodiments, the linkers described herein are one or more (e.g., all) of cell-permeable, stable in cells, lack non-specific binding, and cleave under mild conditions.

Figure 3:
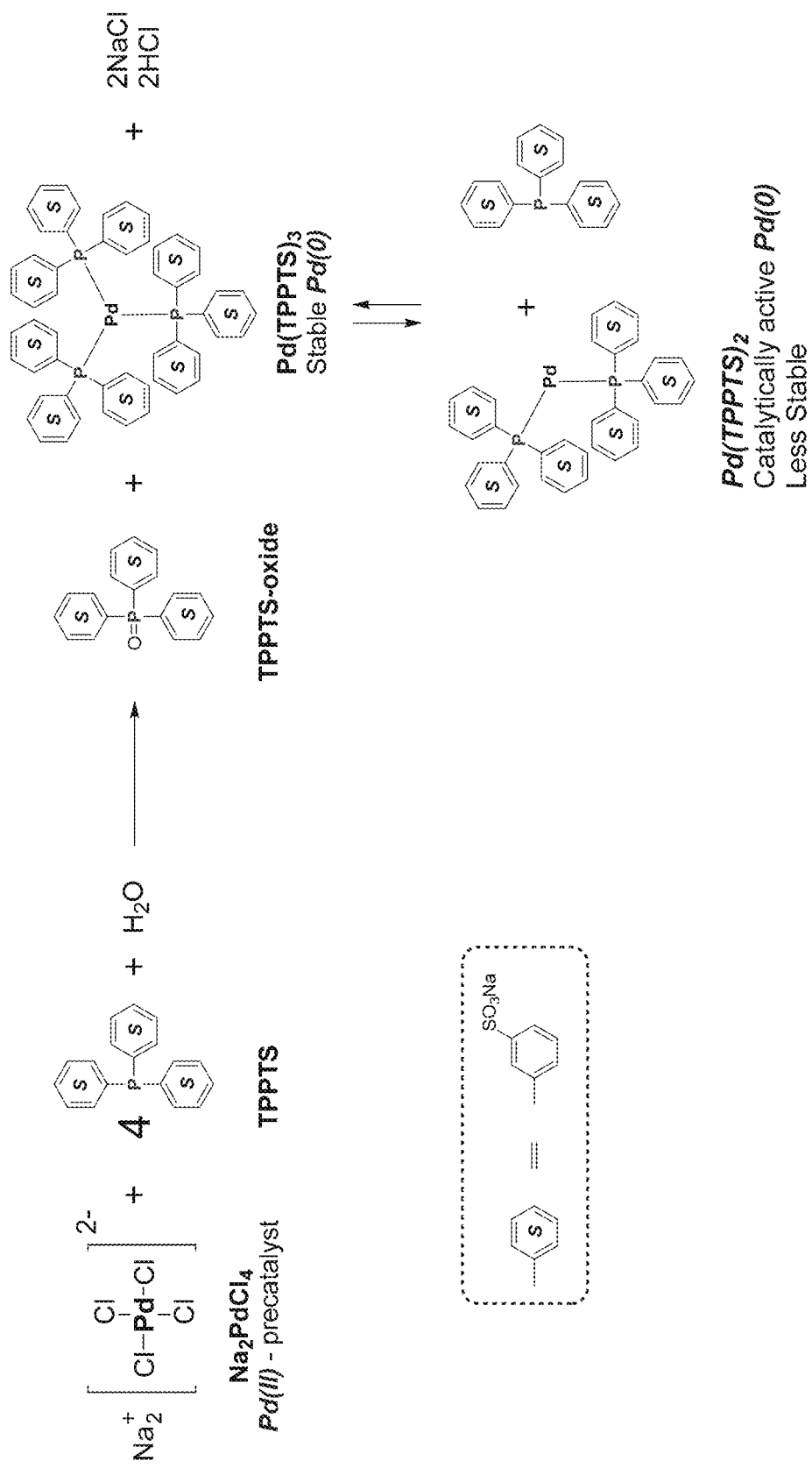
FIG. 3 shows an exemplary reaction scheme for generating chemoselective agents from a transition metal salt and coordinating ligand.

In some embodiments, the chemoselective-cleavage of the allyl carbamate linker occurs upon treatment with transition metal complex (e.g., a coordinated Palladium (Pd) or Ruthenium (Ru)). In some embodiments, a chemoselective agent is produced by the coordination of a transition metal (e.g., Pd, Ru, etc.) from transition metal salt by a ligand (e.g., one or more water soluble phosphine ligands) that stabilizes the transition metal in a catalytically active state (e.g., Pd(0), Ru(II), etc.) (See, e.g., FIG. 3). In this mechanism (to which the embodiments described herein are not limited), the catalytically-active complex $Pd(TPPTS)_2$ exists in equilibrium with a more stable, but catalytically less active, water soluble complex $Pd(TPPTS)_3$. $Pd(TPPTS)_3$ is generated by a reaction of water-soluble organic phosphines and Pd(II) salt. Phosphine (e.g. TPPTS) performs a dual role in generation of catalytically active Pd(0) specie. First, one equivalent of TPPTS is sacrificed to reduce Pd(II) to Pd (0). Second, TPPTS is involved in stabilization of Pd(0) specie in its catalytically-active form. Other phosphines are capable of both reducing Pd(II) to catalytically-active Pd(0) and stabilizing Pd(0) specie in solution. In some embodiments, reduction is accomplished by another reducing reagent (e.g., hydrogen, CO, formic acid, etc.).

Figure 4:
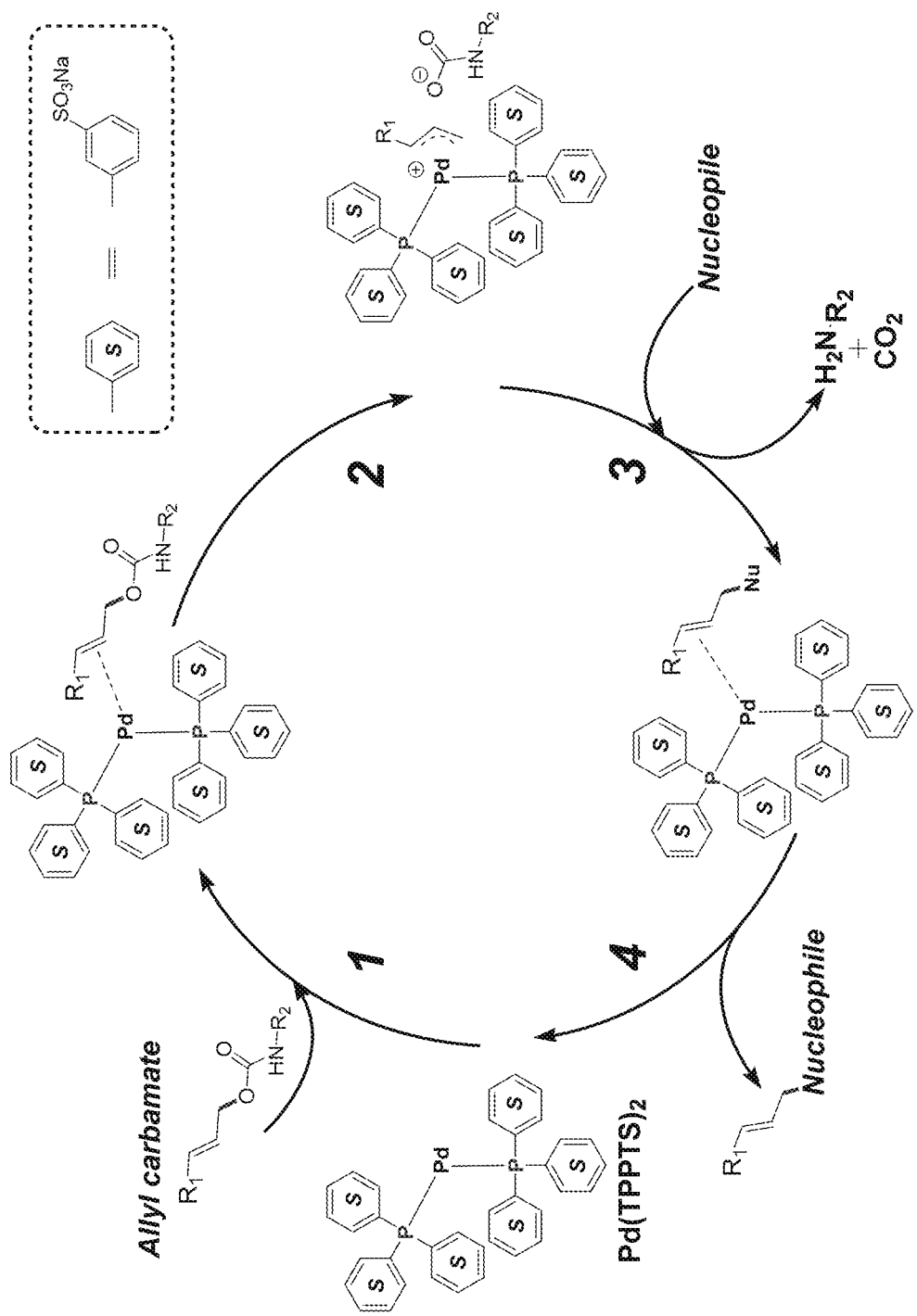
FIG. 4 shows an exemplary catalytic cycle for cleavage of an allyl carbamate linker with a chemoselective agent.
Figure 5:
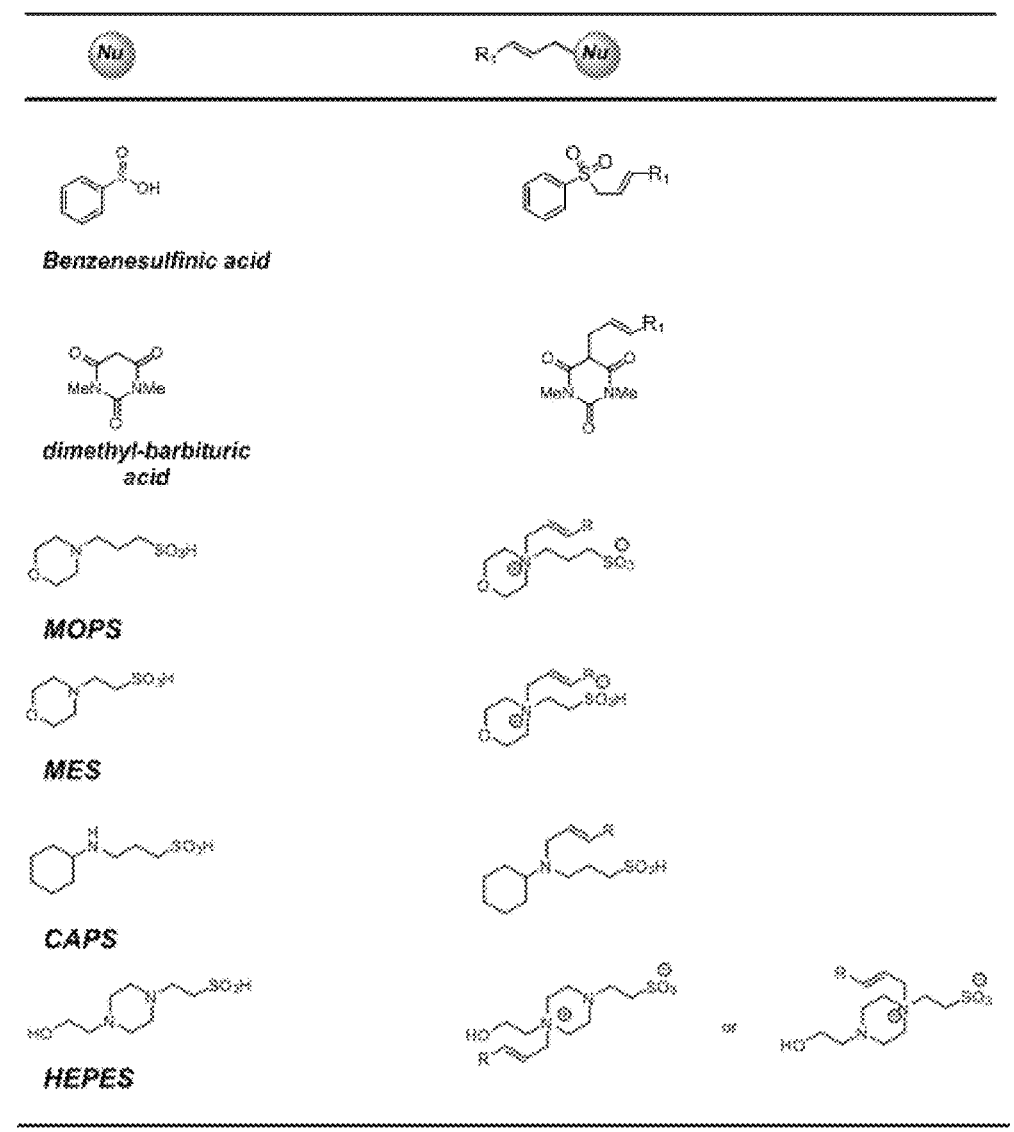
FIG. 5 shows exemplary nucleophiles before (left) and after (right) reaction with the cleaved allyl carbamate.

A general mechanism for the cleavage of an allyl carbamate linker by a transition metal coordination complex is depicted in FIG. 4; although the cleavage is not limited to any particular mechanism of action and an understanding of the mechanism of action is not necessary to practice the embodiments described herein. In FIG. 4, an allyl carbamate linking R1 and R2 moieties is cleaved by a $Pd(TPPTS)_2$ complex (or other moiety (e.g., phosphines) capable of both reducing Pd(II) to catalytically-active Pd(0), and stabilizing Pd(0) specie in solution); although the general scheme depicted in FIG. 4 applies to other allyl carbamate-containing linkers, compounds, and substrates as well as other chemoselective agents (e.g., other transition metals (e.g., Ru) and/or other coordinating ligands). In the general mechanism depicted in FIG. 4 (to which the embodiments described herein are not limited), the catalytically-active complex $Pd(TPPTS)_2$ destabilizes the allyl carbamate (step 1) and/or stabilizes the cleavage intermediates (step 2) to drive cleavage of the otherwise stable allyl carbamate group. The carbamate intermediate is then converted to an amine and $CO_2$ (step 3) while the allyl intermediate is trapped by reaction with a nucleophile (step 4). Suitable nucleophiles for completion of the cleavage reaction include, but are not limited to: MOPS, MES, CAPS, HEPES, benzenesulfinic acids, carbon nucleophiles (e.g., dimedone, dimethyl-barbituric acid, etc.) (FIG. 5).

In some embodiments, a composition comprises a compound of the formula: $Z-Y-L^1-M-L^2-A-X$, wherein Z is a cellular interaction element; wherein Y is an allyl carbamate group (e.g., —$NHCOOCH_2CHCH$—); wherein the $L^1$ is a multiatom straight or branched chain including C, N, S, or O; M is an alkyl carbamate group; wherein the $L^2$ is a multiatom straight or branched chain including C, N, S, or O; wherein A is an alkane of at least 2 carbons (e.g., 2, 3, 4, 5, 6, 7, 8, 9, 10, 11, 12, etc.), wherein X is a halogen (e.g., Cl, F, Br, I, etc.), and wherein A-X is a substrate for a dehalogenase.

In some embodiments, a substrate comprises a compound of the formula: $Z-L^3-Y-L^1-M-L^2-A-X$, wherein Z is a cellular interaction element; wherein $L^3$ is a multiatom straight or branched chain including C, N, S, or O; wherein Y is an allyl carbamate group (e.g., —$NHCOOCH_2CHCH$—); wherein the $L^1$ is a multiatom straight or branched chain including C, N, S, or O; M is an alkyl carbamate group; wherein the $L^2$ is a multiatom straight or branched chain including C, N, S, or O; wherein A is an alkane of at least 2 carbons (e.g., 2, 3, 4, 5, 6, 7, 8, 9, 10, 11, 12, etc.), wherein X is a halogen (e.g., Cl, F, Br, I, etc.), and wherein A-X is a substrate for a dehalogenase.

In some embodiments, a substrate minimally comprises a compound of the formula: Z-Y-A-X, wherein Z is a cellular interaction element; wherein Y is an allyl carbamate group (e.g., —$NHCOOCH_2CHCH$—); wherein A is an alkane of at least 2 carbons (e.g., 2, 3, 4, 5, 6, 7, 8, 9, 10, 11, 12, etc.), wherein X is a halogen (e.g., Cl, F, Br, I, etc.), and wherein A-X is a substrate for a dehalogenase. In some embodiments, Z and Y may be separated by $L^3$ (e.g., $Z-L^3-Y-$), wherein $L^3$ is a multiatom straight or branched chain including C, N, S, or O. In some embodiments, Y and A may be separated by M (e.g., -Y-M-A-), wherein M is an alkyl carbamate group. In some embodiments, Y and M may be separated by $L^1$ (e.g., $-Y-L^1-M-$), wherein $L^1$ is a multiatom straight or branched chain including C, N, S, or O. In some embodiments, M and A may be separated by $L^2$ (e.g., $-M-L^2-A-$), wherein $L^2$ is a multiatom straight or branched chain including C, N, S, or O. Suitable substrates comprise Z-Y-A-X, $R-L_1-Y-A-X$, R-Y-$L_2$-A-X, $Z-L_1-Y-L_2$-A-X, Z-Y-M-A-X, $R-L_1$-Y-M-A-X, $R-L_1$-Y-M-M-A-X, $R-L_1$-Y-L-Y-M-A-X, $Z-L_1-Y-L_2$-M-A-X, $Z-L_1$-Y-M-$L_2$-A-X, Z-Y-$L_1$-M-A-X, Z-Y-$L_1$-M-$L_2$-A-X, Z-Y-M-$L_1$-A-X, $Z-L_1-Y-L_2-M-L_3$-A-X, Z-Y-L-Y-A-X, R-L-Y-M-Y-L-A-X, etc.

EXPERIMENTAL

Example 1

Figure 6:
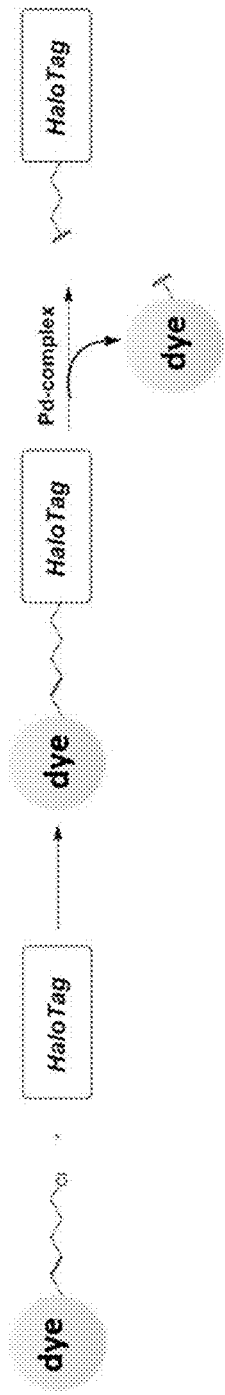
FIG. 6 shows a dye-chloroalkane conjugate reaction with HALOTAG (upper left) followed by Pd-catalyzed, chemoselective cleavage of an allyl carbamate conjugate (PBI-5696).
Figure 6:
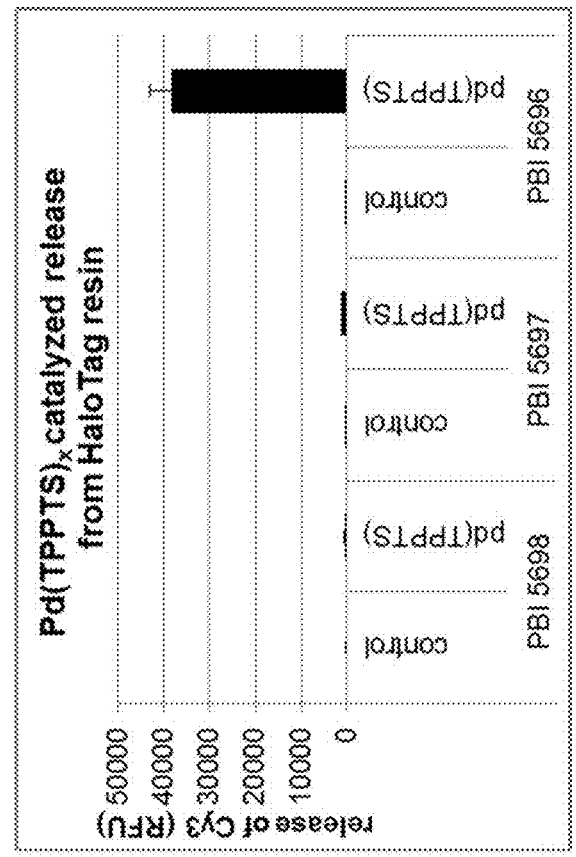
Figure 6:
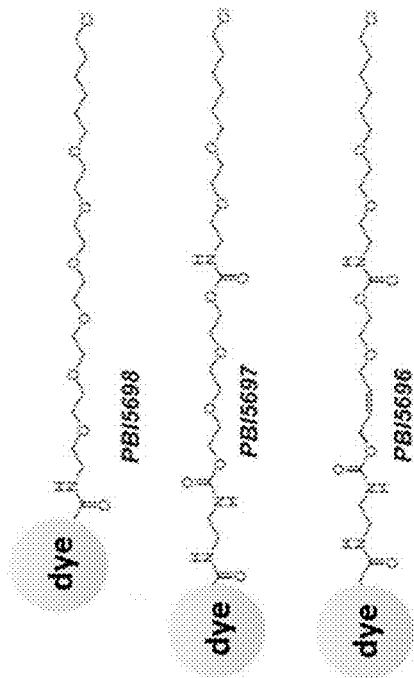

The following example demonstrates the chemoselective cleavage catalyzed by a palladium:TPPTS complex. Multiple chloroalkane linkers of similar size containing or lacking an allyl-carbamate group in their chemical structure were synthesized and conjugated to a Cy3 fluorescent dye (FIG. 6). PBI-5696 contains an allyl-carbamate group while PBI-5698 and PBI-5697 contain an alkyl-carbamate group. The Cy3:chloroalkane conjugates were incubated with an immobilized HALOTAG protein (HALOTAG coated beads; Promega Corporation), and following covalent binding of the conjugates to immobilized HALOTAG, the beads were treated with 2 mM palladium: TPPTS complex and examined for release of the Cy3 dye from the resin. Under these cleavage conditions, only the Cy3:chloroalkane conjugate that contained the allyl-carbamate group (i.e., PBI-5696) was cleaved resulting in the release of the Cy3 dye from the beads (FIG. 6). These results indicate that the palladium-catalyzed cleavage is selective to an allyl carbamate group.

Example 2

Figure 7A:
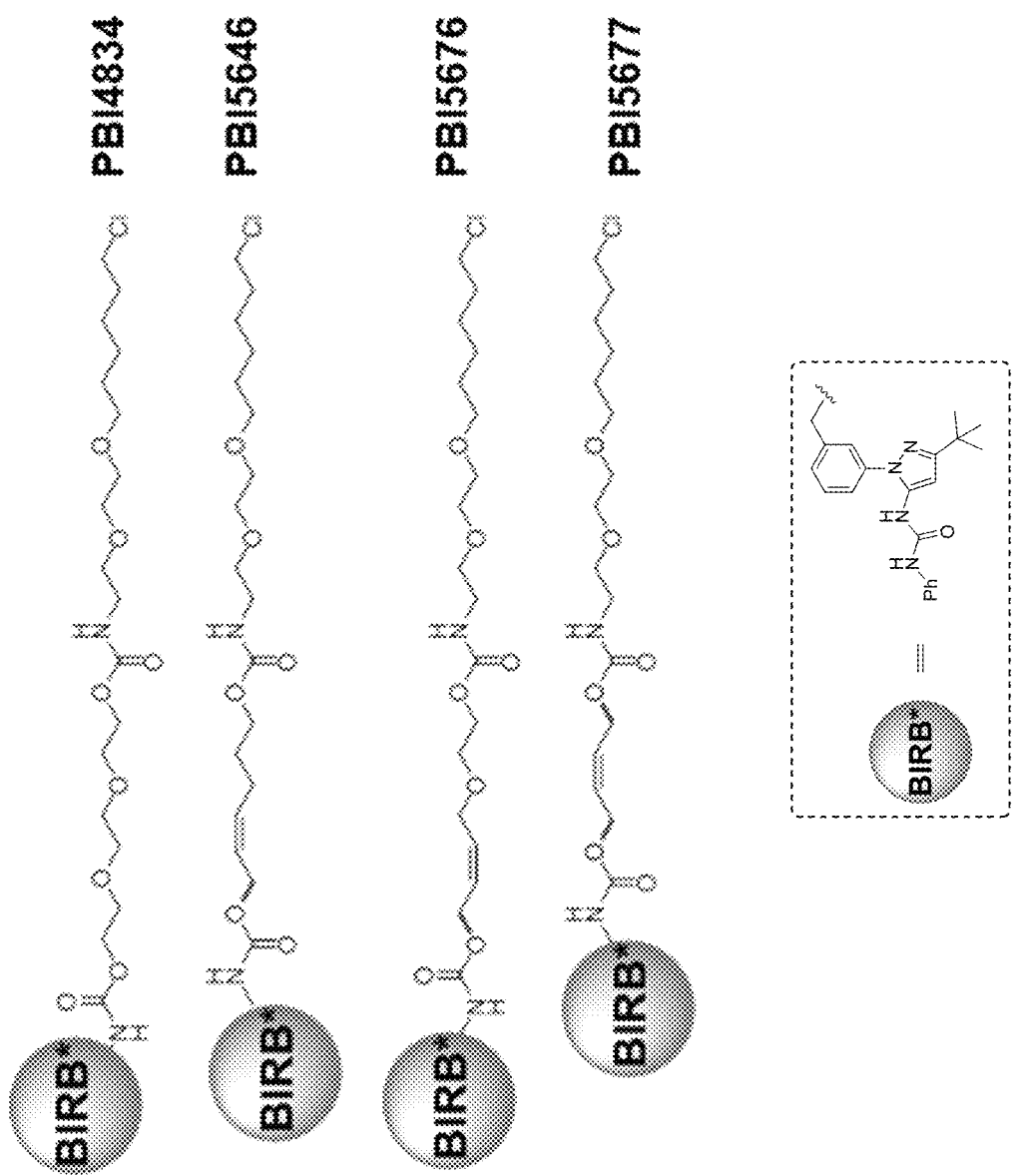
FIGS. 7A-7C show the binding kinetics of BIRB* chloroalkane conjugates to HALOTAG in lysate and cells.
Figures 7B, 7C:
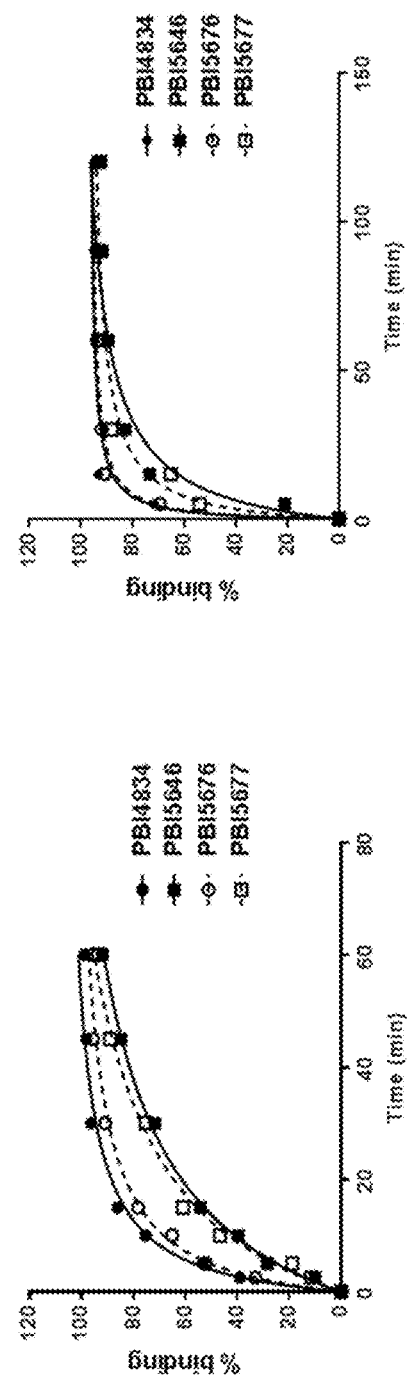

The following example describes insertion of an allyl carbamate group into the chemical structure of the chloroalkane linker and optimization of this insertion for minimal perturbation to the structure of the chloroalkane linker. The chloroalkane linker can be chemically attached to bioactive compounds to allow for selective isolation of their interacting cellular protein targets. This chloroalkane linker was optimized for minimal impact on a compound's bioactivity and cellular permeability as well as rapid covalent binding to a HALOTAG protein. In this example (FIGS. 7A-7C), the chloroalkane linker was conjugated to BIRB* (PBI-4834) and an allyl carbamate group was incorporated into the linker in 3 different configurations to generate PBI-5646, PBI-5676 and PBI-5677. The 4 BIRB* conjugates were compared for binding kinetics to a HALOTAG protein in a cell lysate or inside live cells. Binding kinetics to HALOTAG in lysate was measured by adding the BIRB*-chloroalkane conjugates to a lysate prepared from cells expressing a HALOTAG fusion protein at a final concentration of 1 µM. After 0-60 minutes incubation, a fraction of each reaction taken at different time points (each containing a different BIRB* conjugate) was removed, HALGOTAG TMR-fluorescent ligand (Promega Corporation) was added to a final concentration of 1 µM and allowed to bind to the HALOTAG protein (which remained unbound). The time point fractions were resolved on SDS-PAGE and scanned on a Typhoon 9400 fluorescent imager (GE Healthcare). Bands were quantitated using IMAGEQUANT (GE Healthcare), and binding kinetics were determined as the percent binding with time relative to time zero when no chloroalkylated compound was added. PBI-5676 exhibited similar binding kinetic to HALOTAG as PBI-4834 indicating that in this configuration, the allyl carbamate group displayed minimal perturbation to the chloroalkane binding kinetic to HALOTAG.

Binding kinetics to HALOTAG inside cells was measured by treating live cells expressing a HALOTAG protein with the BIRB* chloroalkane conjugates at a final concentration of 10 µM. After 0-120 minutes incubation time points, the medium was replaced with medium containing 5 µM HALOTAG TMR-fluorescent ligand, and the cells were incubated for additional 15 minutes allowing the TMR-fluorescent ligand to bind to the HALOTAG protein (which remained unbound). After the media was removed, the cells were lysed with a detergent lysis buffer, and the time points were analyzed as described above. PBI-5676 exhibited similar binding kinetics to HALOTAG as PBI-4834 indicating that, in this configuration, the allyl carbamate group displayed minimal impact on cellular permeability.

Taken together, the results in this example demonstrate that in an optimized configuration, the incorporation of an allyl-carbamate group into the chloroalkane linker chemical structure has minimal impact on its features (e.g., rapid binding kinetics to HALOTAG and minimal impact on cellular permeability).

Example 3

Figure 8A:
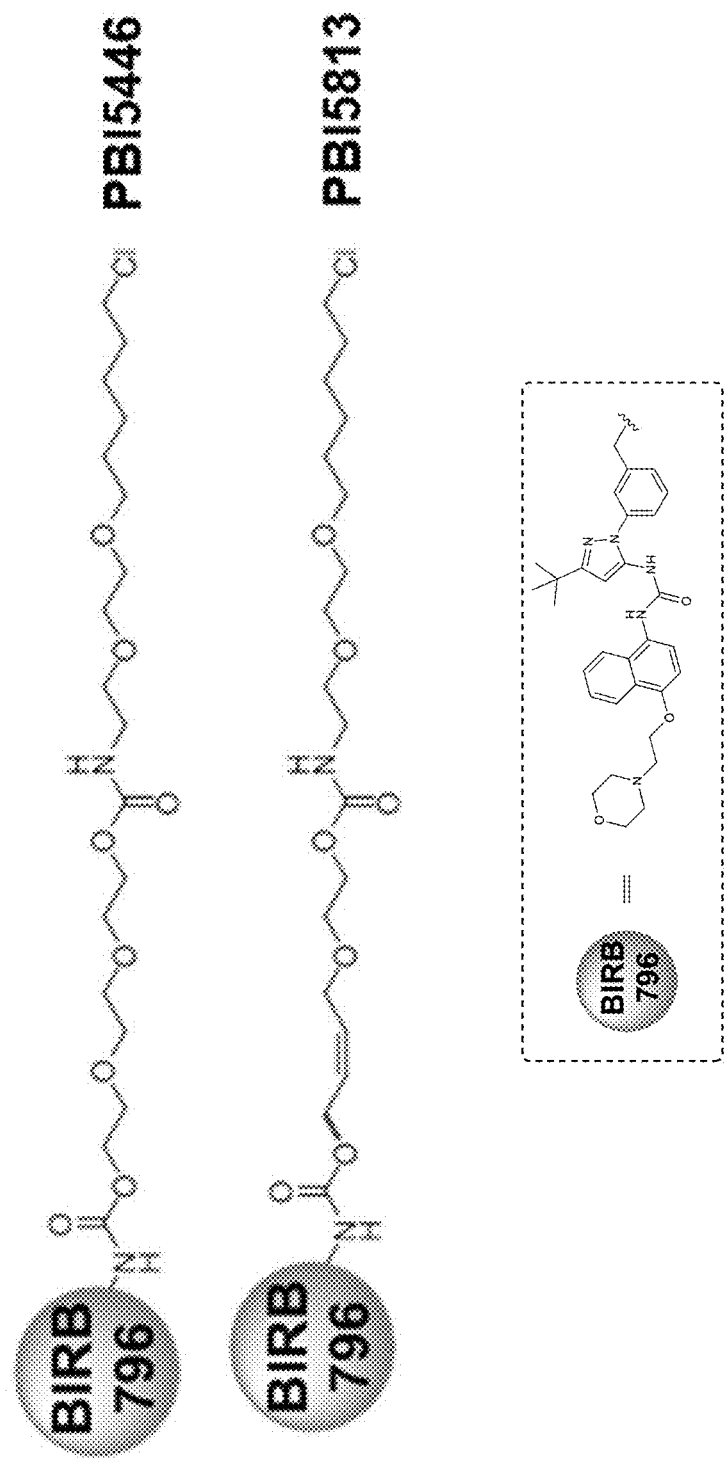
FIGS. 8A-8C show the binding kinetics of BIRB796 chloroalkane conjugates to HALOTAG in cells, and the inhibition of THFα secretion in THP-1 cells by BIRB76 conjugates (PBI-5446 and PBI-5813).
Figure 8C:
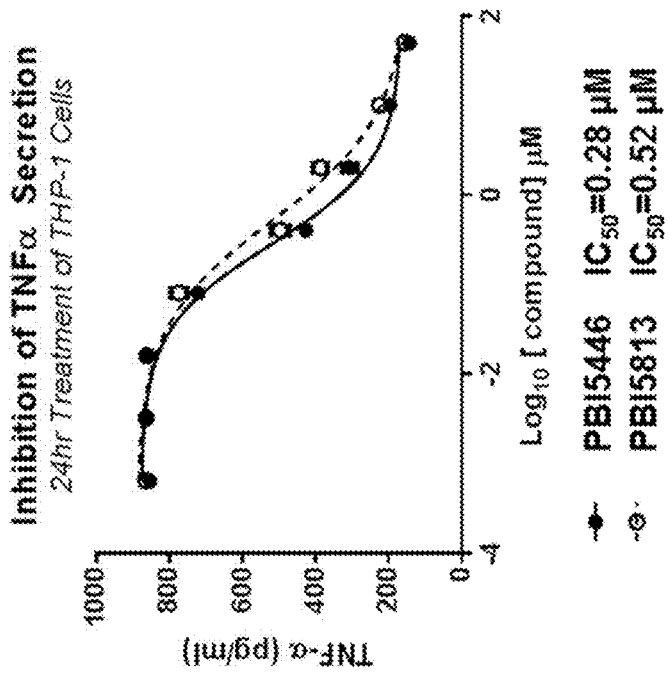
Figure 8B:
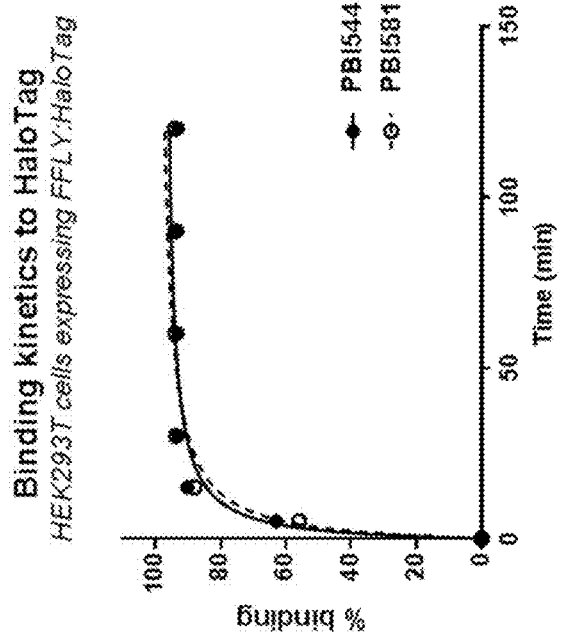

The following example further demonstrates the generality of the minimal perturbation imposed by the allyl-carbamate group to the chloroalkane linker structure and features (e.g., minimal impact on binding kinetics to HALOTAG, compound bioactivity, and cellular permeability). BIRB796 was conjugated to a chloroalkane linker (PBI-5446) and an allyl-carbamate group was inserted into the linker at the optimized configuration determined above to generate PBI-5813 (FIGS. 8A-8C). Both conjugates were compared for binding kinetics to HALOTAG inside live cells and for bioactivity. Binding kinetics to HALOTAG inside cells was measured by treating live cells expressing a HALOTAG protein with the BIRB796 chloroalkane conjugates at a final concentration of 10 µM. After 0-120 minutes incubation time points, the medium was replaced with medium containing 5 µM HALOTAG TMR-fluorescent ligand, and the cells were incubated for additional 15 minutes to allow the TMR fluorescent ligand to bind to the HALOTAG protein (which remained unbound). After the media was removed, the cells were lysed with a detergent lysis buffer, the samples at the various time points resolved on SDS-PAGE, and the images scanned on a Typhoon 9400 fluorescent imager. Bands were quantitated, and the binding kinetics were determined as the percent binding with time relative to time zero when no chloroalkylated compound was added. Both conjugates displayed similar binding kinetics to HALOTAG inside live cells indicating that the allyl-carbamate group at the optimized configuration displayed minimal perturbation to cellular permeability and binding kinetics to HALOTAG (FIGS. 8A-8C).

Bioactivity was measured through inhibition of TNFα secretion in LPS stimulated THP-1 cells (FIGS. 8A-8C). THP-1 cells were plated into wells of 96-well plates at 100,000 cells/well, treated with serial dilutions of BIRB796 conjugates for 2 hours, and then stimulated for 24 hours with LPS (Sigma) at final concentration of 250 ng/ml. The supernatant was analyzed for human TNFα secretion by ELISA (R&D Systems). Both conjugates displayed similar inhibition of TNFα secretion indicating that the incorporation of the allyl-carbamate group at this configuration had no impact on bioactivity of BIRB796. Thus, it imposes minimal impact on the chloroalkane features.

Example 4

Figure 9B:
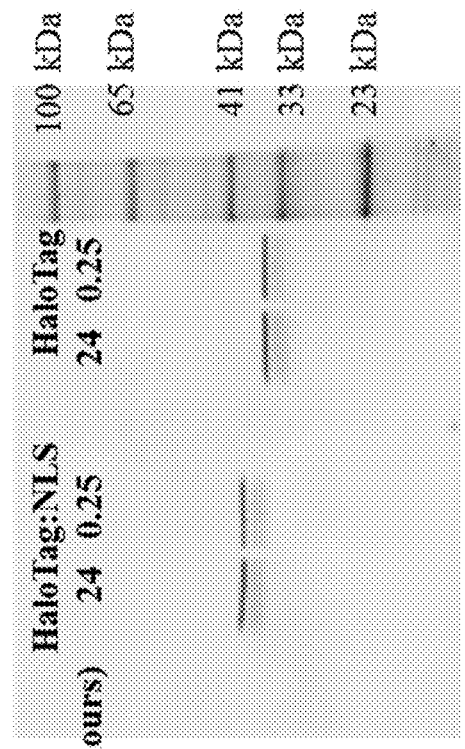

The following example demonstrates the cellular stability of the allyl carbamate group. For these experiments, the chloroalkane containing an allyl-carbamate at the optimized configuration was conjugated to tetramethylrhodamine (TMR) (PBI-5741). U2OS cells stably expressing HALOTAG and HALOTAG:NLS$_3$ displaying ubiquitous and nuclear expression respectively were treated for 24 hours with 200 nM PBI-5741 or were grown for 24 h and then treated for 15 min with 2.5 µM PBI-5741. Cells were then washed 3× with media prior to imaging on a Nikon confocal microscope. Following imaging, cells were collected, lysed with a detergent lysis buffer, resolved on SDS-PAGE, and images scanned on a Typhoon 9400 fluorescent imager. These labeling treatments resulted in the covalent binding of the TMR conjugate to HALOTAG. Any cellular cleavage of the allyl carbamate group would result with loss of the dye, and thus the loss of labeling intensity. The cell imaging and gel analysis results (FIG. 9) demonstrate similar labeling intensities after 24 hours and 15 minutes of labeling, indicating cellular stability of the allyl-carbamate group over 24 hours.

Example 5

Figure 10:
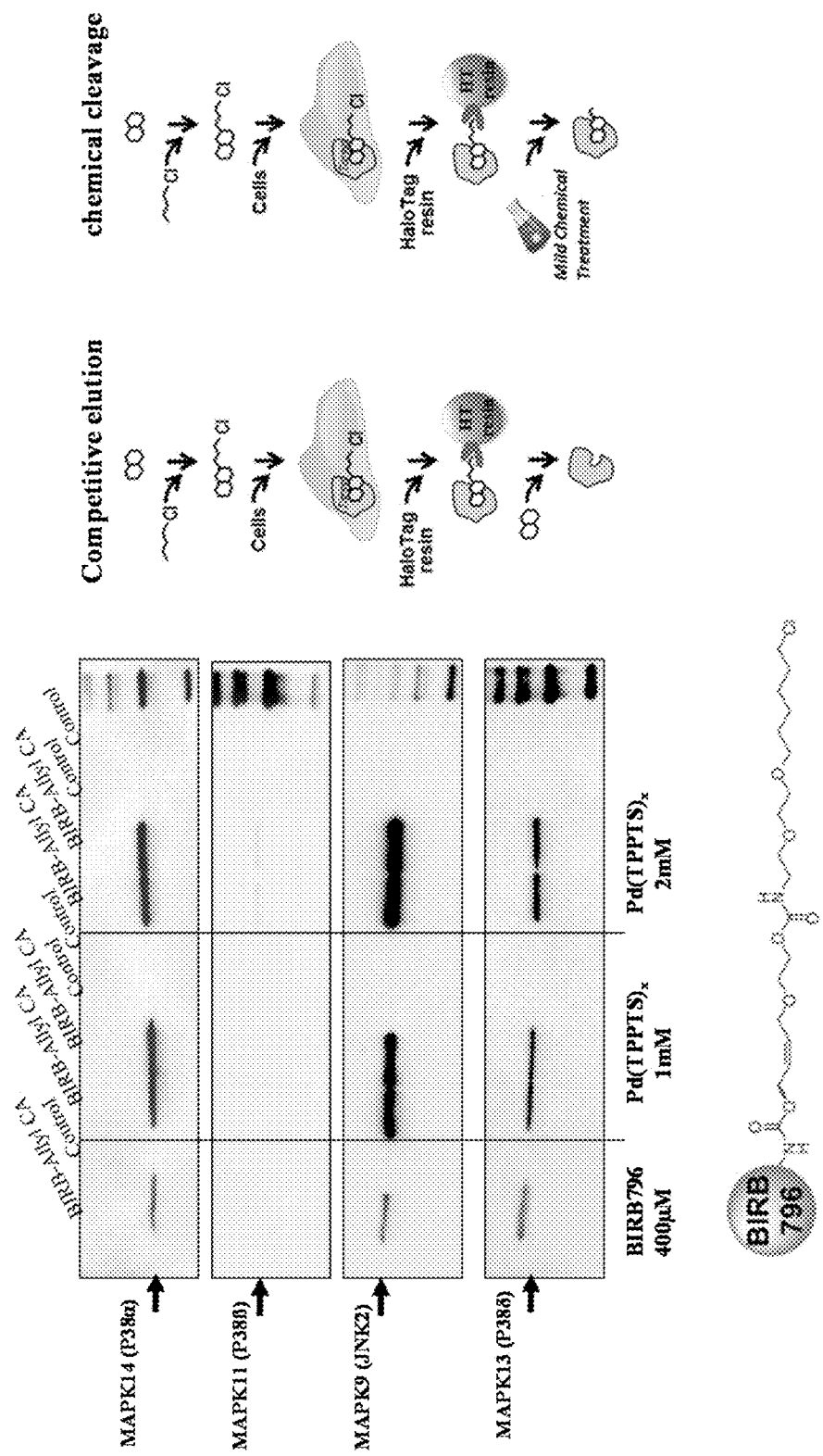
FIG. 10 shows enrichment of endogenous targets using different elution methods.

Enrichment experiments conducted during development of embodiments described herein demonstrated enhanced enrichment for endogenous targets with long residence time using palladium-catalyzed target release versus release by competitive drug elution (FIG. 10). BIRB796, which exhibits slow off-rates to its targets, was conjugated to a chloroalkane containing an allyl-carbamate group (PBI-5813). In this example, 2×10$^7$ HepG2 cells were plated in 150 mm dish, and after 16 hours, a final concentration of 20 µM BIRB796 conjugate (PBI-5813) was added to 3 dishes while 3 control dishes remained untreated. Following a 2 h incubation, the media was removed; cells were quickly washed with PBS, lysed for 10 min in a detergent-based lysis buffer, and centrifuged at 3000×g for 1 min. Clear lysates were than added to 75 ul of settled HALOTAG coated beads and incubated with shaking for 15 min. Following binding, the unbound fraction was removed, the HALOTAG coated beads were washed 3×, and the captured targets were specifically released from the beads by competitive elution (400 µM unconjugated BIRB797) or chemical cleavage (1 or 2 mM Palladium:TPPTS at 1:2 molar ratio). The released targets were subjected to western blot analysis (FIG. 10) with anti-MAPK14 antibody (ABCAM); anti-MAPK11 antibody (Cell signaling); anti-MAPK9 antibody (Cell signaling); and anti-MAPK13 antibody (Thermo Fisher). Results in FIG. 10 indicate enhanced enrichment of known BIRB796 targets utilizing target release by chemical cleavage over competitive drug elution. These results demonstrate the advantage of chemical cleavage over competitive drug elution for enrichment of targets exhibiting long residence time.

Example 6

Figure 11:
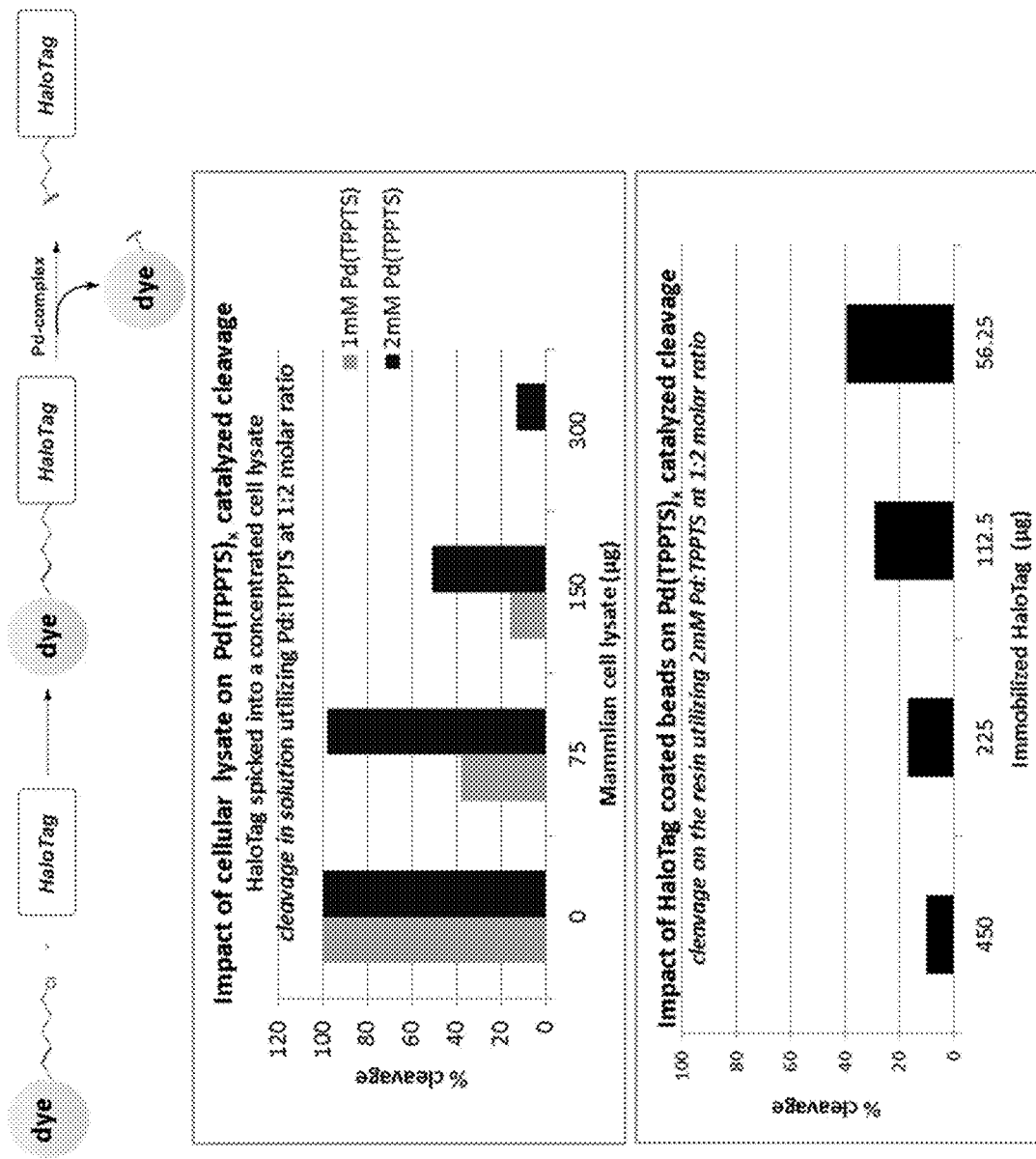
FIG. 11 shows the impact of cellular lysate and HALOTAG coated beads on the efficiency of Pd-catalyzed cleavage.

Experiments conducted during development of embodiments described herein demonstrated that in a protein rich environment (e.g., concentrated cell lysate or protein-coated beads), the efficiency of palladium catalyzed cleavage is significantly reduced and is directly correlated to the protein concentration (FIG. 11). In experiments testing the impact of protein concentration on palladium catalyzed cleavage in solution, 5 µg of HALOTAG was spiked into increasing concentrations of HEK293 cell lysate. HALOTAG was allowed to covalently bind to 4 µM PBI-5741 (TMR conjugated to a chloroalkane containing an allyl carbamate group) for 30 min and then cleaved for 30 min with 1 mM or 2 mM Pd(TPPTS)$_x$ at 1:2 molar ratio of Pd to TPPTS while control sample remained untreated. Samples were resolved on SDS-PAGE, scanned on a Typhoon 9400 fluorescent imager, and bands were quantitated using IMAGEQUANT. Cleavage of the allyl carbamate group would result with loss of the dye, and thus a reduced labeling intensity of the HALOTAG protein. Cleavage efficiency was determined as the percent of lost signal relative to control that was not treated with Pd(TPPTS)$_x$. Results indicate that cleavage efficiency in the presence of increasing concentrations of cell lysate was significantly lower compared to cleavage efficiency in buffer and was directly correlated to protein concentration.

In experiments testing the impact of protein concentration on palladium-catalyzed cleavage on the beads, increasing amounts of HALOTAG coated beads were incubated with 20 µM PBI-5741 for 30 min while control sample was not incubated with the beads. Following covalent binding of PBI-5741 to immobilized HALOTAG, beads were treated with 2 mM Pd(TPPTS)$_x$ at 1:2 molar ratio of Pd to TPPTS for 30 min. Cleavage of the allyl carbamate group would result with release of the dye from the beads. Samples of released dye together with the control dye were resolved on SDS-PAGE, scanned on a Typhoon 9400 fluorescent imager, and bands were quantitated using IMAGEQUANT. Cleavage efficiency was determined as the percent of released dye relative to control dye that was not incubated with the beads. Results indicate that cleavage efficiency was directly correlated to the amount of immobilized protein and was significantly reduced in the presence of increasing amounts of protein coated beads.

Example 7

Figure 12:
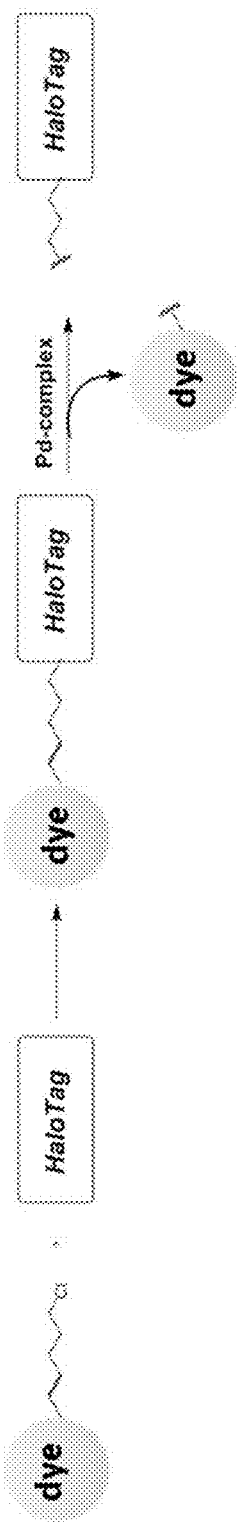
FIG. 12 shows the impact of buffer composition on the efficiency of Pd-catalyzed cleavage.
Figure 12:
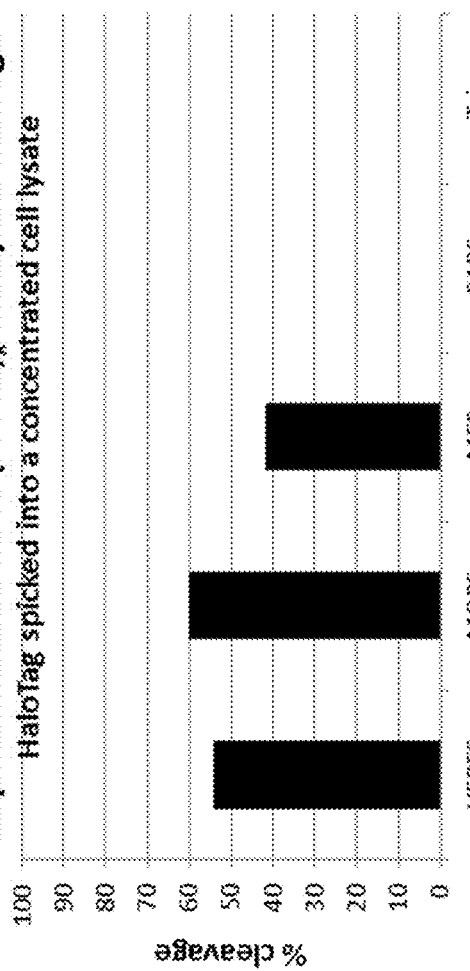

This example demonstrates that certain buffer compositions can affect the palladium-catalyzed cleavage of an allyl carbamate group (FIG. 12). In this example, HALOTAG was spiked into high concentrations of HEK293 cell lysate (150 µg) and then allowed to covalently bind to PBI-5741 for 30 min. Labeling reactions were then treated for 30 min with 2 mM Pd(TPPTS)$_x$ at 1:2 molar ratio of Pd to TPPTS prepared in different buffers while control sample remained untreated. Samples were resolved on SDS-PAGE, scanned on a Typhoon 9400 fluorescent imager, and bands were quantitated using IMAGEQUANT. Cleavage of the allyl carbamate group would result with loss of the dye, and thus a reduced labeling intensity of the HALOTAG protein. Cleavage efficiency was determined as the percent of lost signal relative to control that was not treated with Pd(TPPTS)$_x$. Results in FIG. 12 indicate that buffer composition plays a crucial role in palladium-catalyzed cleavage efficiency. While cleavage in HEPES, MOPS, and MES buffers was efficient, cleavage in CAPS and TRIS buffers was completely suppressed.

Example 8

Figure 13:
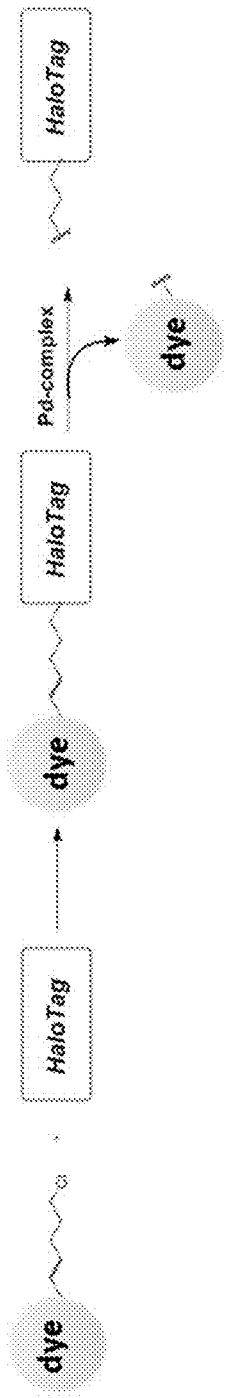
FIG. 13 shows the impact of buffer and nature of the phosphine ligand on the efficiency of Pd-catalyzed cleavage.
Figure 13:
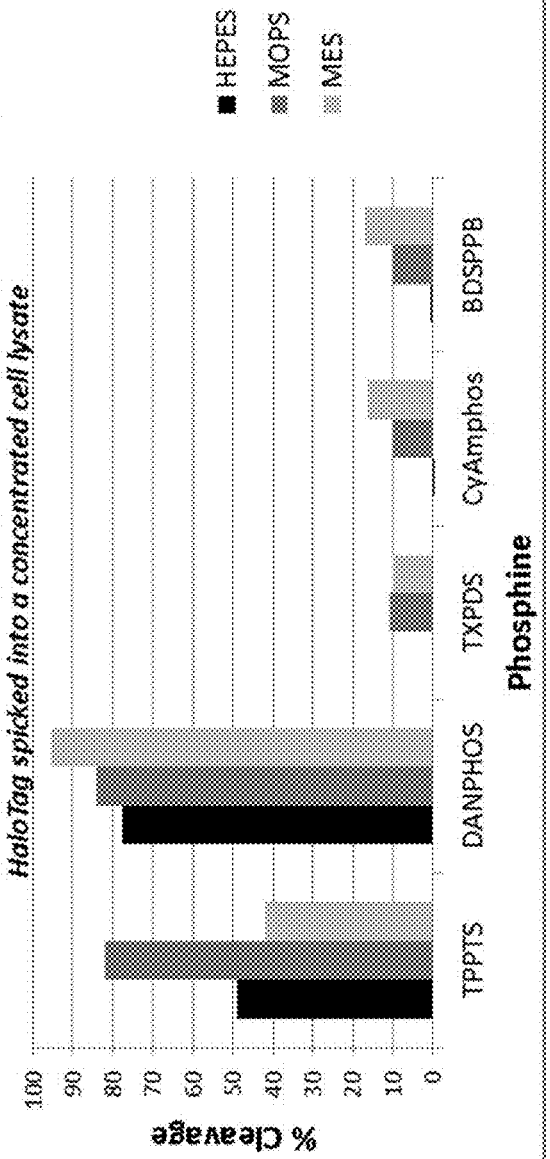

This example demonstrates that the nature of phosphine and buffer composition can affect the palladium catalyzed cleavage of allyl carbamate group (FIG. 13). In this example, HALOTAG protein was spiked into high concentrations of HEK293 cell lysate (150 µg) and then allowed to covalently bind to PBI-5741 for 30 min. Labeling reactions were then treated for 30 min with 2 mM Pd(phosphine)$_x$ at 1:2 molar ratio of Pd to phosphine prepared in different buffers while control sample remained untreated. Samples were resolved on SDS-PAGE, scanned on a Typhoon 9400 fluorescent imager, and bands were quantitated using IMAGEQUANT. Cleavage of the allyl-carbamate group would result in loss of the dye, and thus a reduced labeling intensity of the HALOTAG protein. Cleavage efficiency was determined as the percent of lost signal relative to control that was not treated with Pd(phosphine)$_x$. Results in FIG. 13 indicate that the nature of phosphine, as well as the buffer composition, plays a crucial role in palladium-catalyzed cleavage efficiency. Electron-poor phosphine DANPHOS outperformed the other phosphines in all buffers tested (HEPES, MOPS, MES), TPPTS displayed higher cleavage efficiency in MOPS buffer compared to MES and HEPES buffers while TXPDS (electron-rich phosphine), Cy-Amphos (positively charged and electron-rich), and BDSPPB (bidentate ligand) exhibited significantly lower cleavage efficiency (FIG. 13).

Example 9

Figure 14:
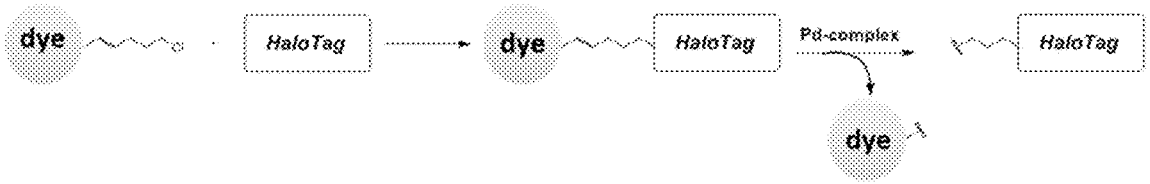
FIG. 14 shows cleavage efficiency on the HALOTAG coated beads as well as the impact of buffer, nature of phosphine ligand, and Pd-Phosphine ratio on the cleavage efficiency.
Figure 14:
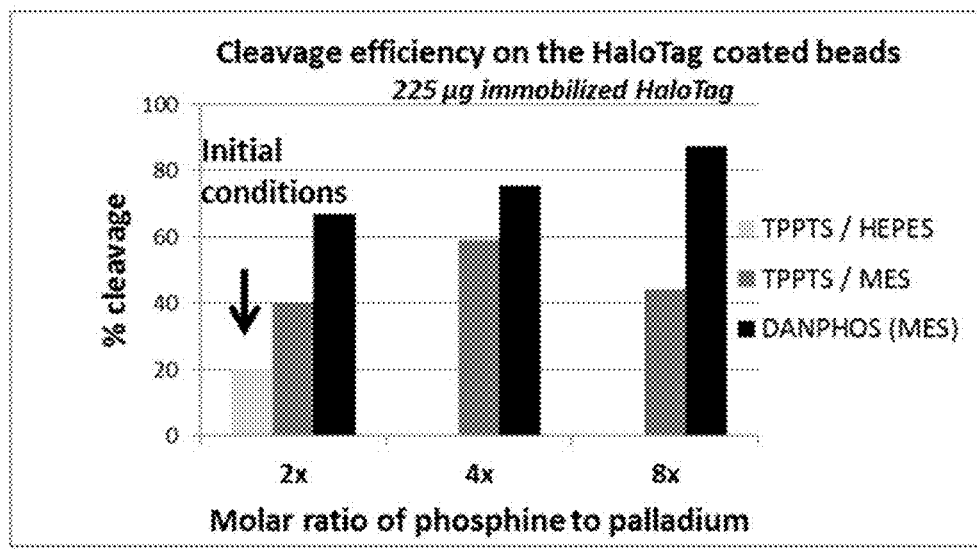
Figure 14:
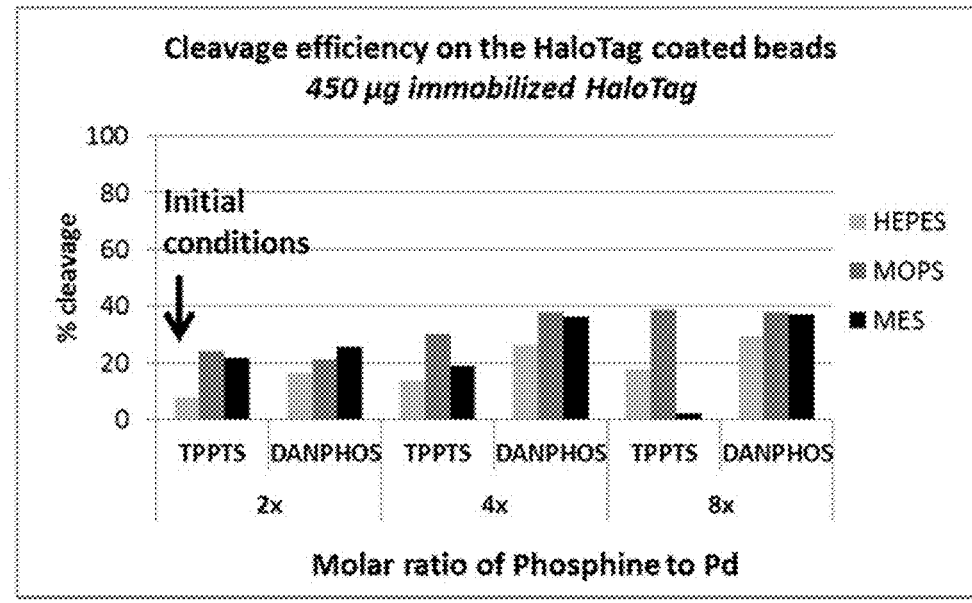

This example demonstrates that the nature of phosphine and buffer composition can affect the allyl carbamate cleavage efficiency on the beads (FIG. 14). The experiments in FIG. 14 were done at two different amounts of HALOTAG coated beads (beads containing 225 or 450 µg immobilized HALOTAG). Beads were incubated with 60 µM PBI-5741 for 30 min while control sample was not incubated with the beads. Following covalent binding of PBI-5741 to immobilized HALOTAG, beads were treated for 30 min with 2 mM Pd(TPPTS)$_x$ or 2 mM Pd(DANPHOS)$_x$ at 1:2, 1:4, and 1:8 molar ratios of Pd to phosphine, which were prepared in different buffers. Cleavage of the allyl-carbamate group would result in release of the dye from the beads. The released dyes together with the control dye were resolved on SDS-PAGE, scanned on a Typhoon 9400 fluorescent imager, and bands were quantitated using IMAGEQUANT. Cleavage efficiency was determined as the percent of released dye relative to control dye that was not incubated with the beads. Results indicate that higher molar ratios of Pd:phosphine is needed for cleavage on the resin. In addition, DANPHOS outperformed TPPTS in all 3 tested buffers (HEPES, MES, MOPS).

Example 10

Figure 15:
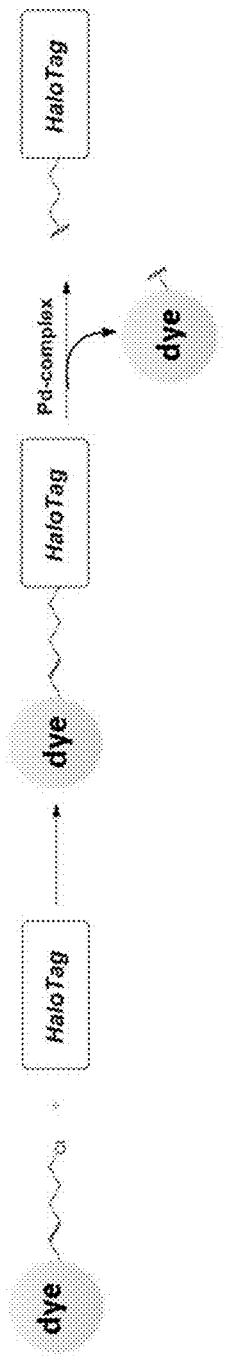
FIG. 15 shows the impact of premade Pd-phosphine complex on the cleavage efficiency.
Figure 15:
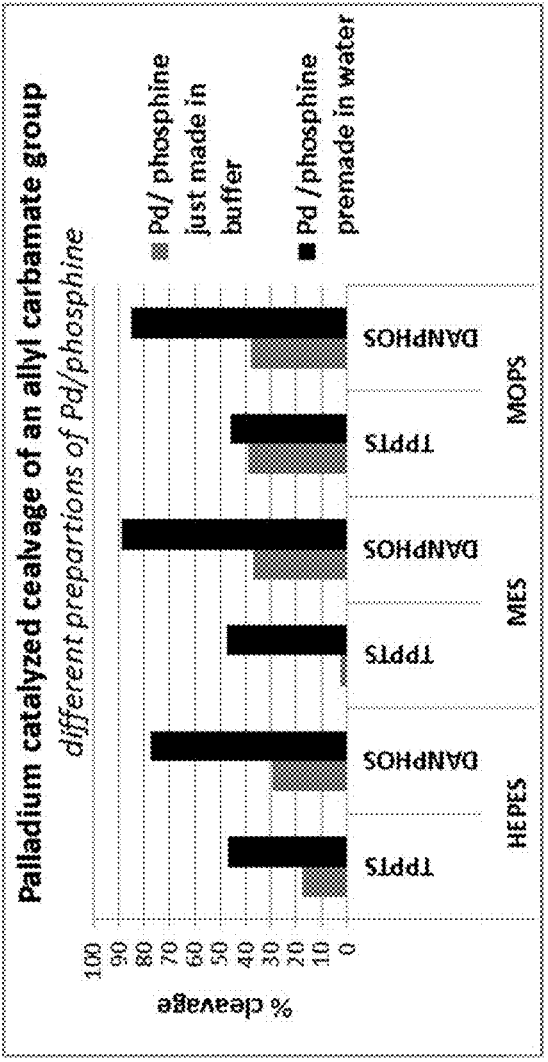

The following example demonstrates that palladium: phosphine complexes premade in water and stored under oxygen-depleted conditions are more active than complexes prepared in buffer and used immediately. In these experiments (FIG. 15), HALOTAG coated beads containing (450 µg immobilized HALOTAG) were incubated with 60 µM PBI-5741 for 30 min while control sample was not incubated with the beads. Following covalent binding of PBI-5741 to immobilized HALOTAG, beads were treated for 60 min with 2 mM of Pd(TPPTS)$_x$ or Pd(DANPHOS)$_x$ at 1:8 molar ratios of Pd to phosphine. The Pd-phosphine complexes were either prepared in the different buffers and used immediately or premade in water as 4 mM solutions and stored under oxygen depleted conditions. The premade solutions were diluted into the same buffers to create the 2 mM solution and then used immediately. Cleavage of the allyl carbamate group would result with release of the dye from the beads. The released dyes together with the control dye were resolved on SDS-PAGE, scanned on a Typhoon 9400 fluorescent imager, and bands were quantitated using IMAGEQUANT. Cleavage efficiency was determined as the percent of released dye relative to control dye that was not incubated with the beads. Higher cleavage efficiency of the allyl carbamate group was observed with the premade palladium:phosphine complexes in all three buffers. These results indicate that the premade Pd-phosphine complexes contained higher concentration of active catalyst resulting with higher cleavage efficiency. In addition, results also indicated that DANPHOS outperformed TPPTS in all 3 tested buffers (HEPES, MES, MOPS).

Example 11

Figure 16:
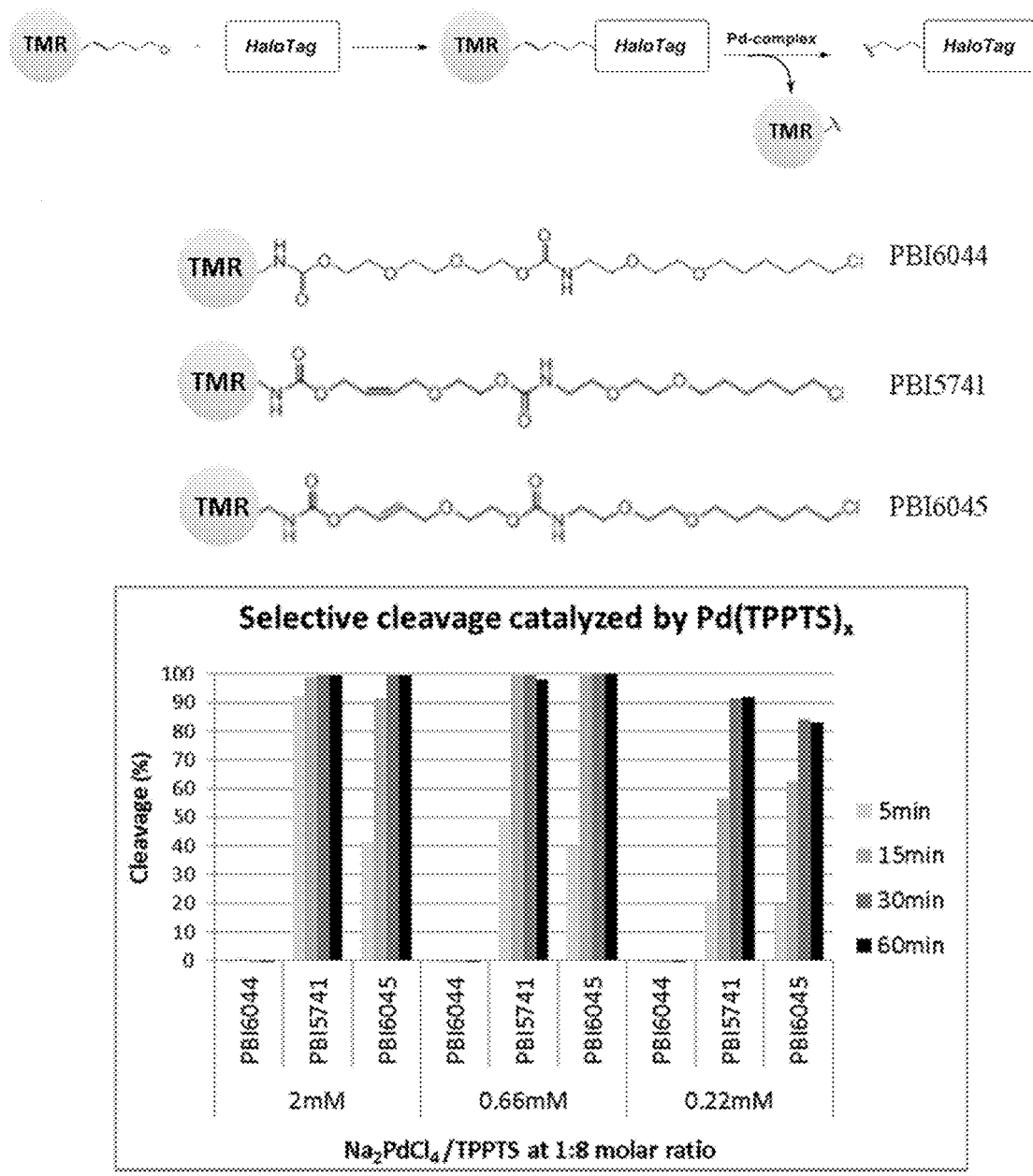
FIG. 16 shows a TMR-chloroalkane conjugate reaction with HALOTAG (upper left) followed by Pd-catalyzed, chemoselective cleavage of an allyl carbamate conjugates (PBI-5741 and PBI-6045).

The following example demonstrates the chemoselective-cleavage catalyzed by the premade palladium:TPPTS complex (1:8 molar ratio of Pd to phosphine). Multiple chloroalkane linkers of similar size containing or lacking an allyl-carbamate group in their chemical structure were synthesized and conjugated to a TMR fluorescent dye (FIG. 16). PBI-5741 and PBI-6045 contained an allyl-carbamate group while PBI-6044 contained an alkyl-carbamate group. In this example, purified HALOTAG protein was allowed to covalently bind to TMR-chloroalkane conjugates for 30 min. Labeling reactions were then treated for 30 min with 2 mM, 0.66 mM, and 0.22 mM Pd(TPPTS)$_x$ at 1:8 molar ratio of Pd to TPPTS while control sample remained untreated. Samples were resolved on SDS-PAGE, scanned on a Typhoon 9400 fluorescent imager, and bands were quantitated using IMAGEQUANT. Cleavage of the allyl carbamate group would result with loss of the dye, and thus a reduced labeling intensity of the HALOTAG protein. Cleavage efficiency was determined as the percent of lost signal relative to control that was not treated with Pd(TPPTS)$_x$. Results in FIG. 16 indicate that, under these cleavage conditions, only the TMR chloroalkane conjugates containing an allyl-carbamate group (e.g., PBI-5741 and PBI-6045) were cleaved, and the cleavage efficiency was time and concentration dependent. These results indicate that the palladium-catalyzed cleavage is selective to an allyl carbamate group.

Example 12

Figure 17A:
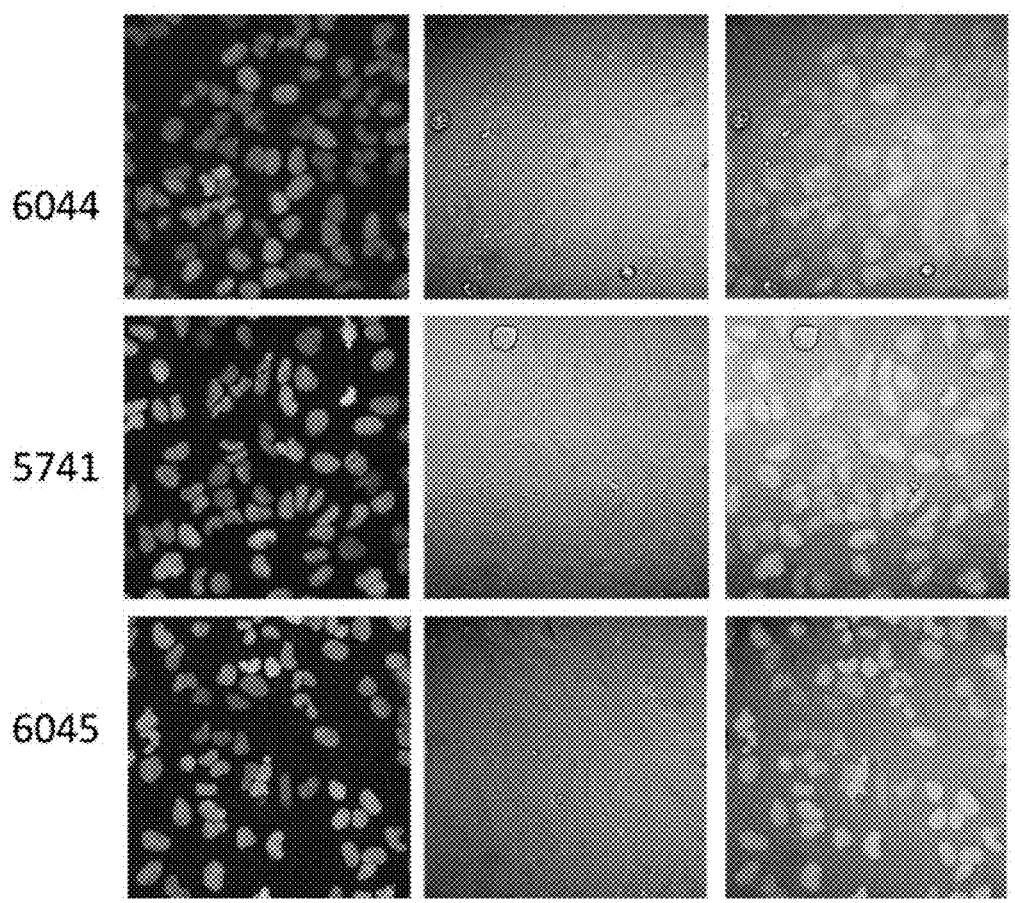
FIGS. 17A and 17B shows A) Imaging of U2OS cells stably expressing HALOTAG or HALOTAG:NLS labeled with PBI-5741; PBI-6044; PBI-6045; B) SDS-PAGE analysis of labeled cells.
Figure 17B:
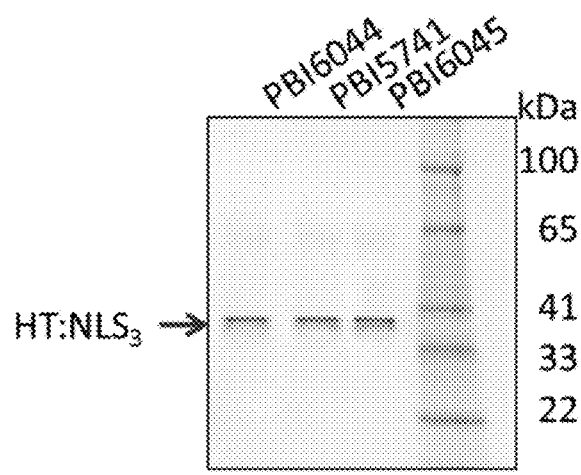
Figure 17B:
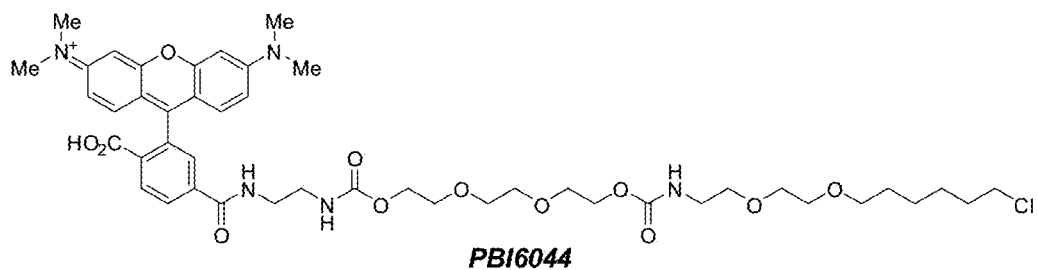

The following example demonstrates the cellular stability of the allyl carbamate group. For these experiments, U2OS cells stably expressing HALOTAG:NLS$_3$ (displaying nuclear expression) were treated for 24 h with 200 nM of the TMR chloroalkane conjugates. Two of the conjugates, PBI-5741 and PBI-6045, contained an allyl carbamate group while PBI-6044 contained an alkyl-carbamate group. Cells were washed 1× with media prior to imaging on a Nikon confocal microscope. Following imaging, cells were collected, lysed with a detergent lysis buffer, resolved on SDS-PAGE, and images scanned on a Typhoon 9400 fluorescent imager. These labeling treatments resulted with covalent binding of the TMR conjugates to HALOTAG. Any cellular cleavage of the allyl carbamate group would result with loss of the dye, and thus a loss of labeling intensity. The cell imaging and gel analysis results (FIGS. 17A-17B) demonstrate similar labeling intensities for all 3 conjugates indicating cellular stability of the allyl carbamate group over 24 hours.

Example 13

Figure 18:
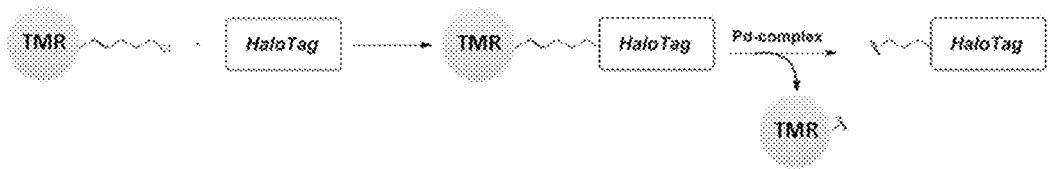
FIG. 18 shows the impact of HALOTAG coated beads (magnetic and non-magnetic) on the efficiency of Pd-catalyzed cleavage
Figure 18:
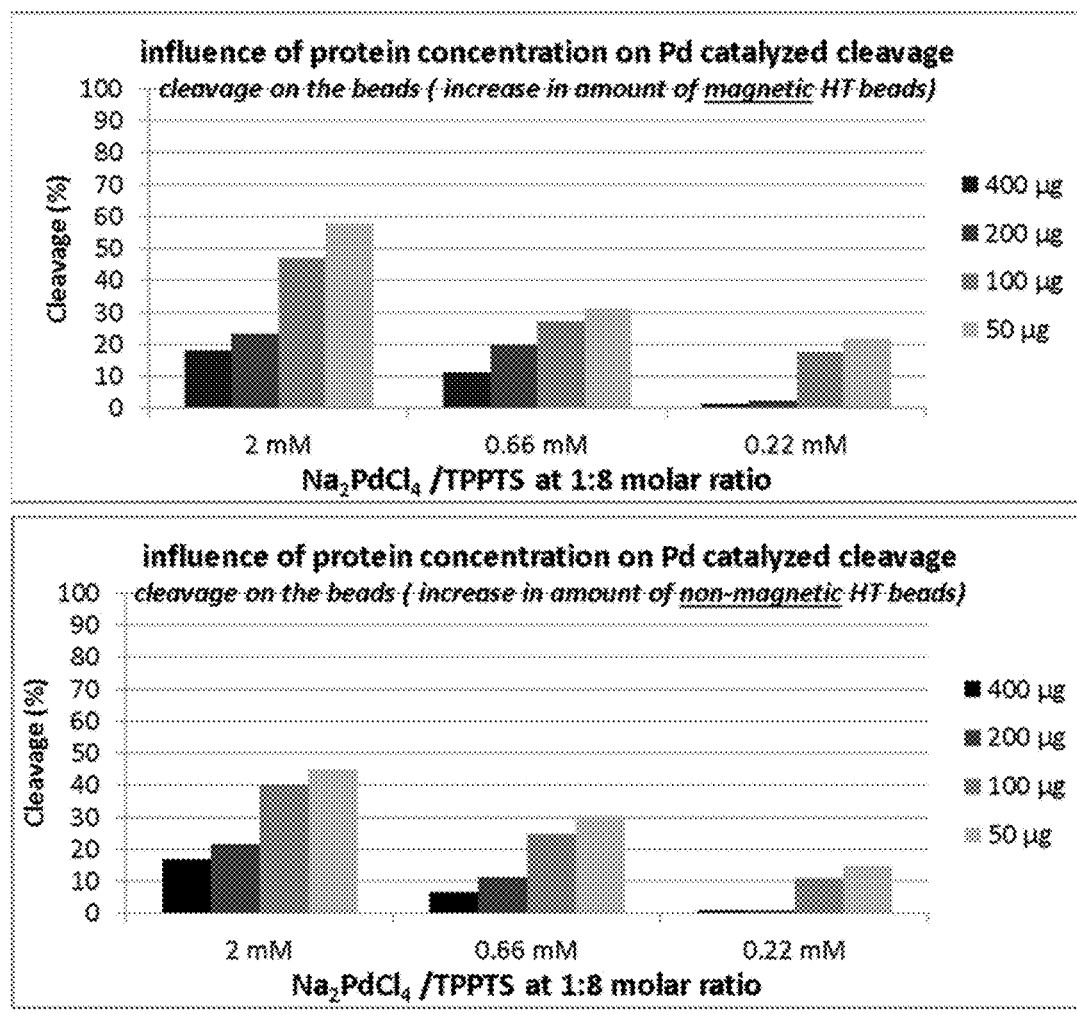

Experiments conducted during development of embodiments described herein demonstrated that, in a protein rich environment (e.g., protein coated beads), the efficiency of palladium-catalyzed cleavage is significantly reduced and is directly correlated to protein concentration (FIG. 18). In these experiments, increasing amounts of HALOTAG coated magnetic or non-magnetic beads were incubated for 30 min with 20 µM PBI-5741 while control sample was not incubated with the beads. Following covalent binding of PBI-5741 to immobilized HALOTAG, beads were treated with 2 mM, 0.66 mM, or 0.22 mM premade Pd(TPPTS)$_x$ complex at 1:8 molar ratio of Pd to TPPTS for 30 min in HEPES buffer. Cleavage of the allyl carbamate group would result with release of the dye from the beads. Samples of released dye together with the control dye were resolved on SDS-PAGE, scanned on a Typhoon 9400 fluorescent imager, and bands were quantitated using IMAGEQUANT. Cleavage efficiency was determined as the percent of released dye relative to control dye that was not incubated with the beads. Results indicate that cleavage efficiency was directly correlated to the amount of immobilized protein and was significantly reduced in the presence of increasing amounts of protein coated beads.

Example 14

Figure 19A:
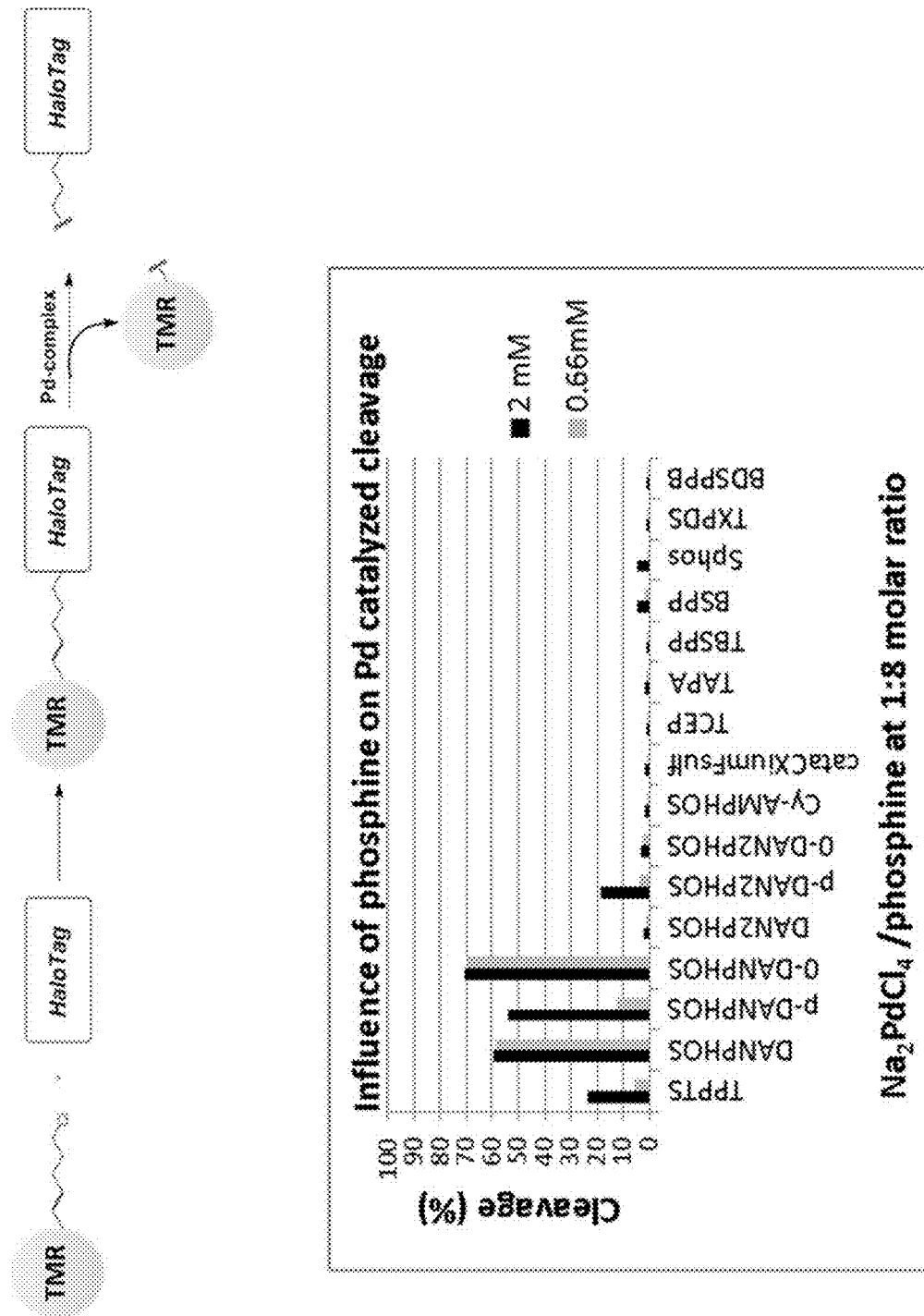
FIGS. 19A and 19B shows influence of phosphine on Pd-catalyzed cleavage
Figure 19B:
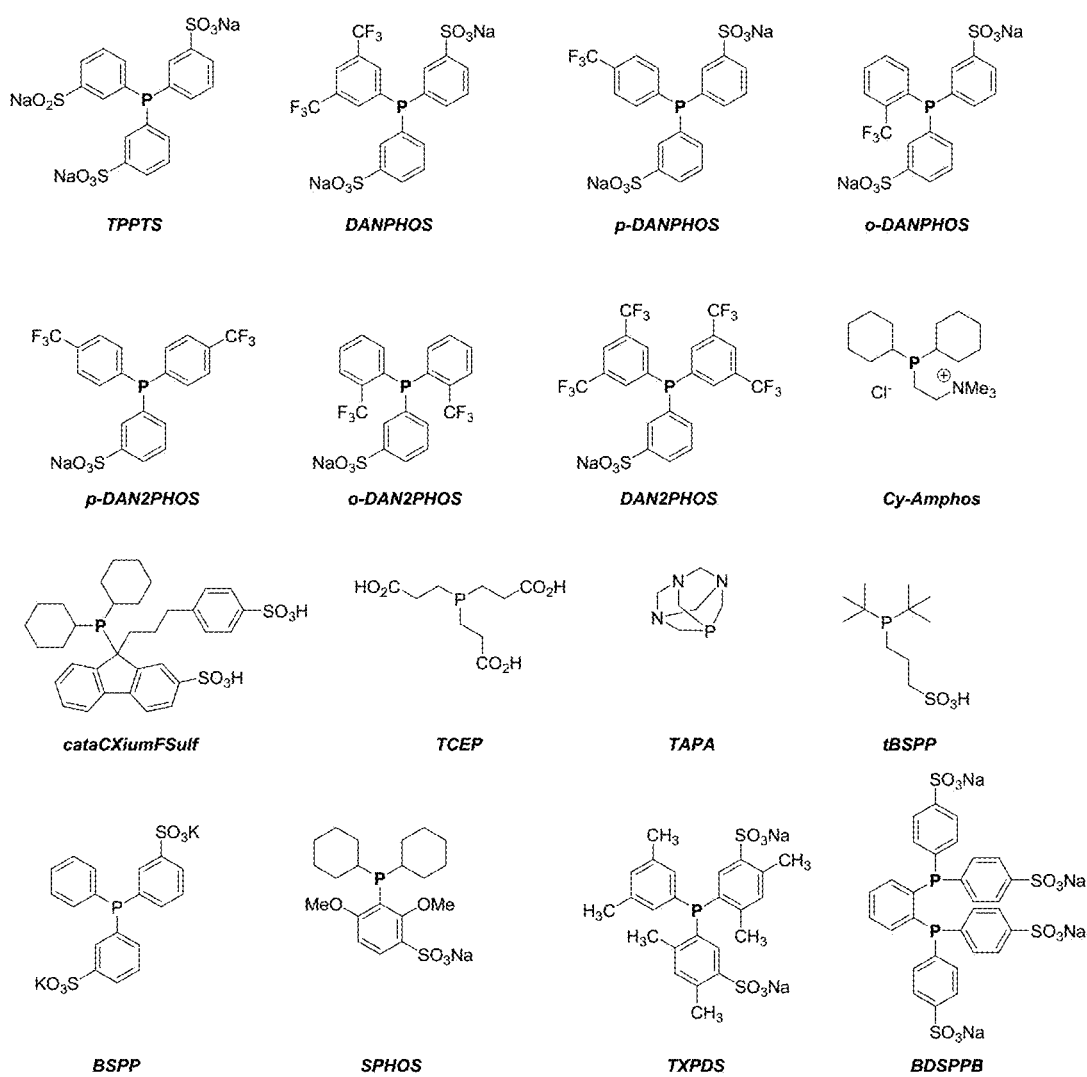

This example demonstrates that the nature of phosphine can affect palladium-catalyzed cleavage of an allyl carbamate group (FIG. 19). In these experiments, HALOTAG coated magnetic beads (containing 400 µg immobilized HALOTAG protein) were incubated with 60 µM PBI-5741 for 30 min while control sample was not incubated with the beads. Following covalent binding of PBI-5741 to immobilized HALOTAG protein, beads were treated with 2 mM or 0.66 mM premade Pd(phosphine) complexes at 1:8 molar ratio for 30 min in HEPES buffer. Cleavage of the allyl carbamate group would result with release of the dye from the beads. Samples of released dye together with the control dye were resolved on SDS-PAGE, scanned on a Typhoon 9400 fluorescent imager, and bands were quantitated using IMAGEQUANT. Cleavage efficiency was determined as the percent of released dye relative to control dye that was not incubated with the beads. Results in FIG. 19 indicate that the nature of phosphine plays a crucial role in palladium catalyzed cleavage efficiency. Electron-poor phosphines from the DANPHOS family, especially DANPHOS and o-DANPHOS, outperformed the other phosphines.

Example 15

Figure 20:
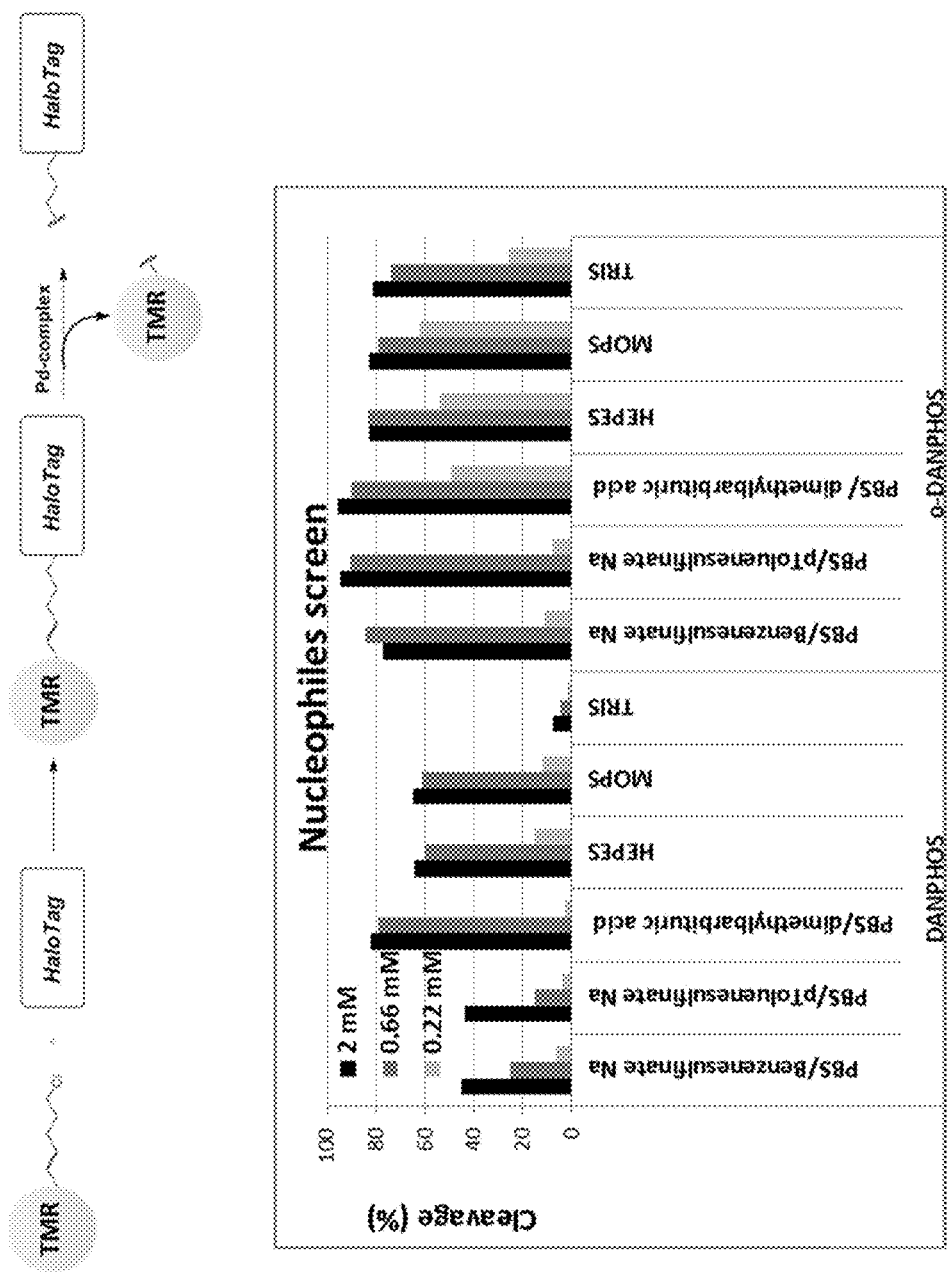
FIG. 20 shows influence of the nature of the nucleophile on the efficiency of Pd-catalyzed cleavage (examples are for DANPHOS and o-DANPHOS, ratio of Pd to phosphione was retained at 8:1).

This example demonstrates that the nature of nucleophile can affect palladium-catalyzed cleavage of an allyl carbamate group (FIG. 20). In these experiments, HALOTAG coated magnetic beads (containing 400 µg immobilized HALOTAG protein) were incubated with 60 µM PBI-5741 for 30 min while control sample was not incubated with the beads. Following covalent binding of PBI-5741 to immobilized HALOTAG protein, beads were treated for 30 min with 2 mM, 0.66 mM, or 0.22 mM premade Pd(DANPHOS)$_x$ or Pd(o-DANPHOS)$_x$ complexes at 1:8 molar ratio of Pd to phosphine in multiple amine buffers or non-amine buffer containing different nucleophiles. Cleavage of the allyl carbamate group would result with release of the dye from the beads. Samples of released dye together with the control dye were resolved on SDS-PAGE, scanned on a Typhoon 9400 fluorescent imager, and bands were quantitated using IMAGEQUANT. Cleavage efficiency was determined as the percent of released dye relative to control dye that was not incubated with the beads. Results in FIG. 20 indicate that the nature of nucleophile plays a crucial role in palladium-catalyzed cleavage efficiency. In addition, the combination of phosphine and nucleophile is very important. For Pd-DANPHOS complex, the highest cleavage efficiency was achieved using PBS buffer supplemented with 5 mM dimethylbarbituric acid. For o-DANPHOS the highest cleavage efficiency was achieved using MOPS buffer. Furthermore, o-DANPHOS outperformed DANPHOS especially at the 0.22 mM concentrations.

Example 16

Figure 21:
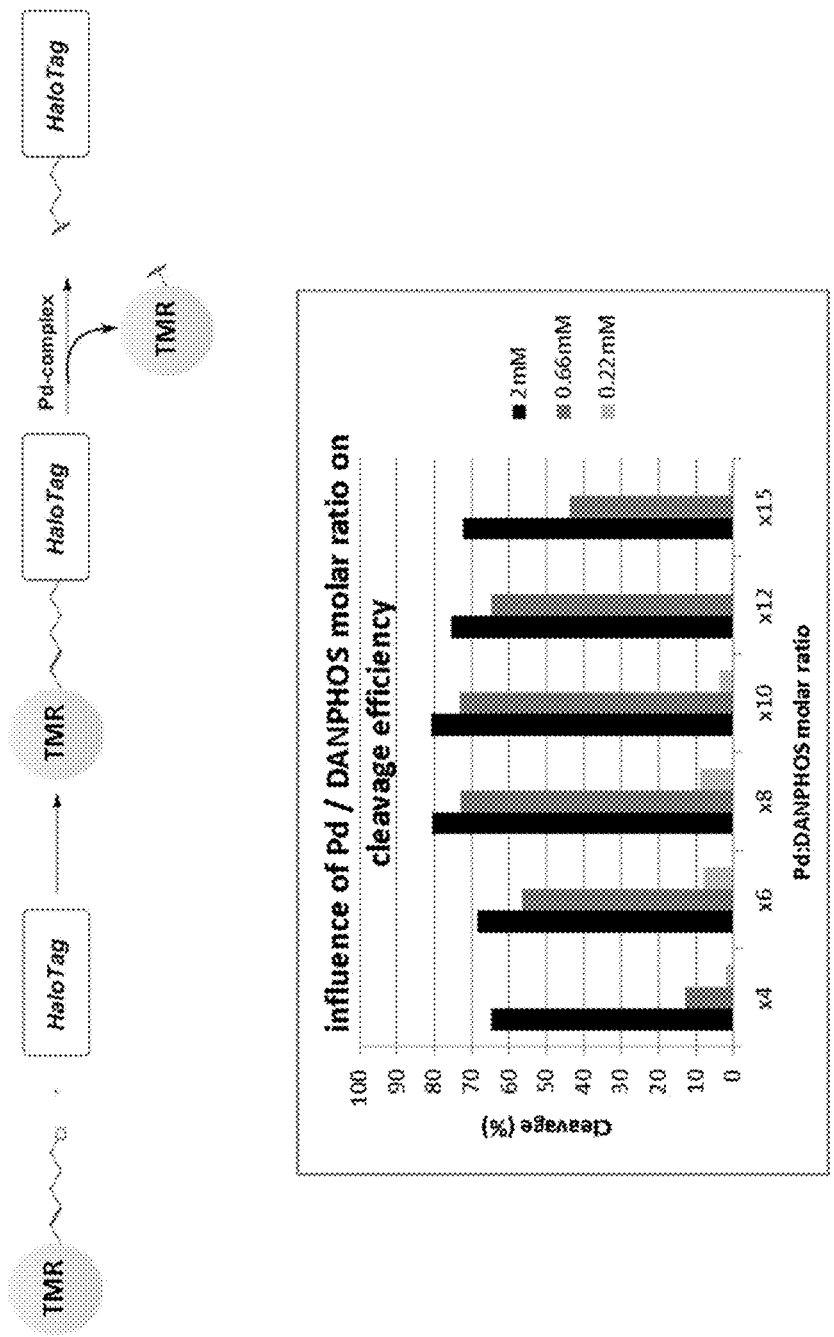
FIG. 21 shows influence of Pd-DANPHOS ratio on the cleavage efficiency

Experiments conducted during development of embodiments described herein demonstrated that the efficiency of palladium-catalyzed cleavage is dependent on the molar ratio of the premade Pd-phosphine solutions (FIG. 21). In these experiments, HALOTAG coated beads containing (400 µg immobilized HALOTAG protein) were incubated with 60 µM PBI-5741 for 30 min while control sample was not incubated with the beads. Following covalent binding of PBI-5741 to immobilized HALOTAG protein, beads were treated for 30 min with 2 mM, 0.6 mM, or 0.22 mM of Pd-DANPHOS complex at 1:4, 1:6, 1:8, 1:10, 1:12 and 1:15 molar ratios of Pd to DANPHOS in PBS/dimethylbarbituric acid. Cleavage of the allyl carbamate group would result with release of the dye from the beads. The released dyes, together with the control dye, were resolved on SDS-PAGE, scanned on a Typhoon 9400 fluorescent imager, and bands were quantitated using IMAGEQUANT. Cleavage efficiency was determined as the percent of released dye relative to control dye which was not incubated with beads. Higher cleavage efficiencies were observed for premade solutions of $Pd(DANPHOS)_x$ at a molar ratio of Pd to DANPHOS of 1:6 and above.

Example 17

Figure 22:
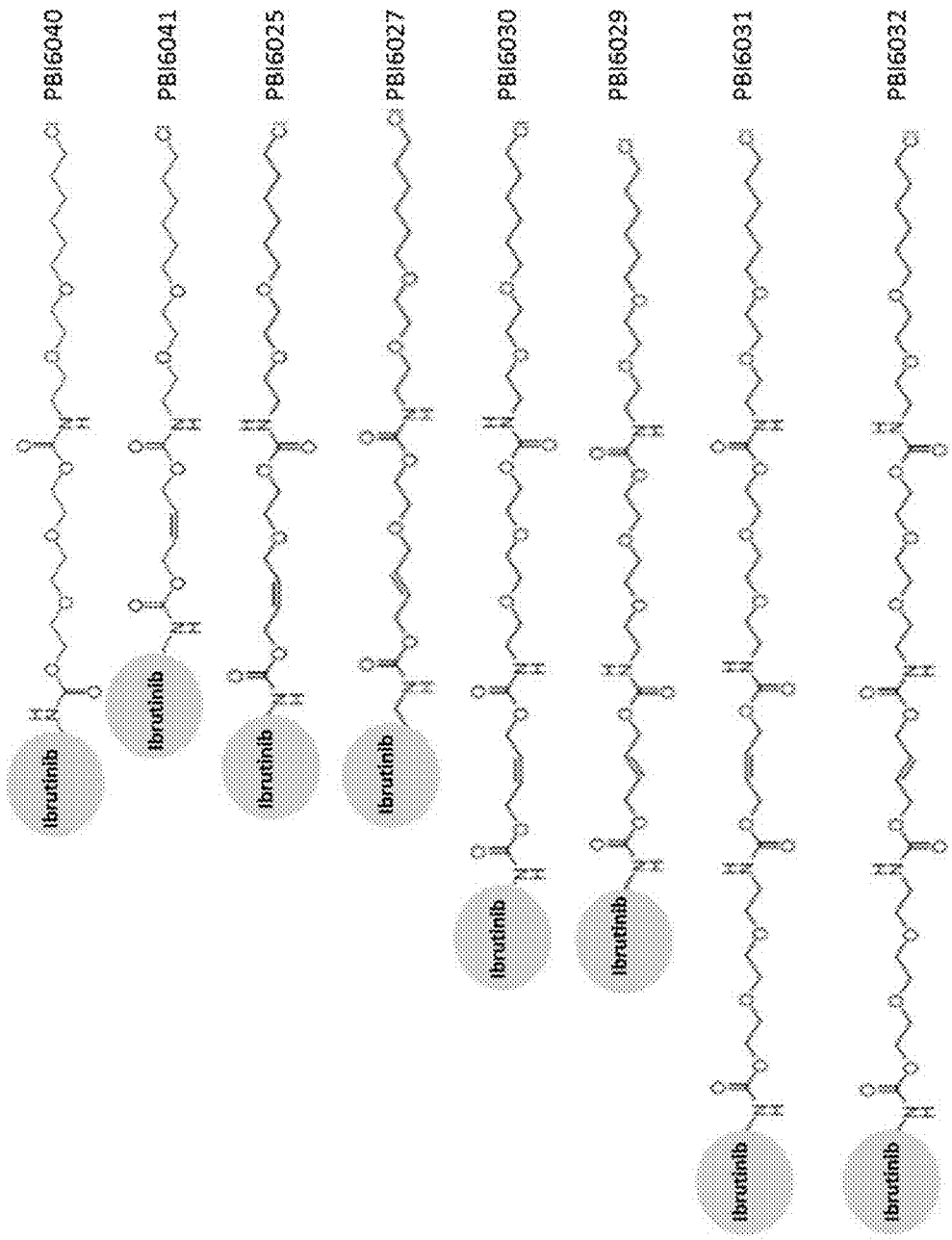
FIG. 22 shows structures of Ibrutinib-Chloroalkanes conjugates
Figure 23B:
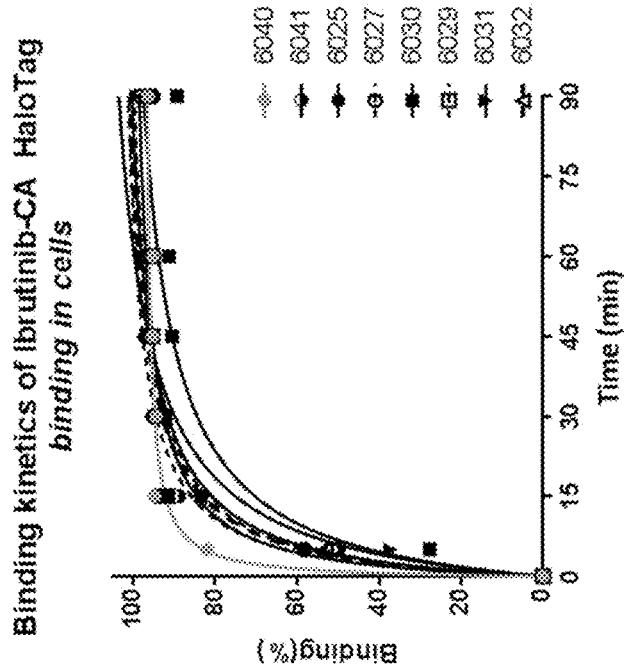
FIGS. 23A and 23B show binding kinetics of Ibrutinib-Chloroalkanes to HALOTAG in lysate (A) and cells (B)
Figure 23A:
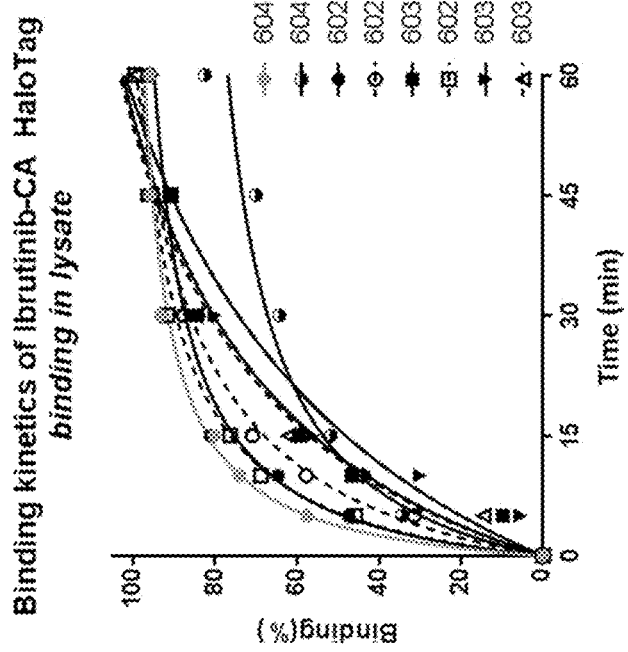
Figure 24A:
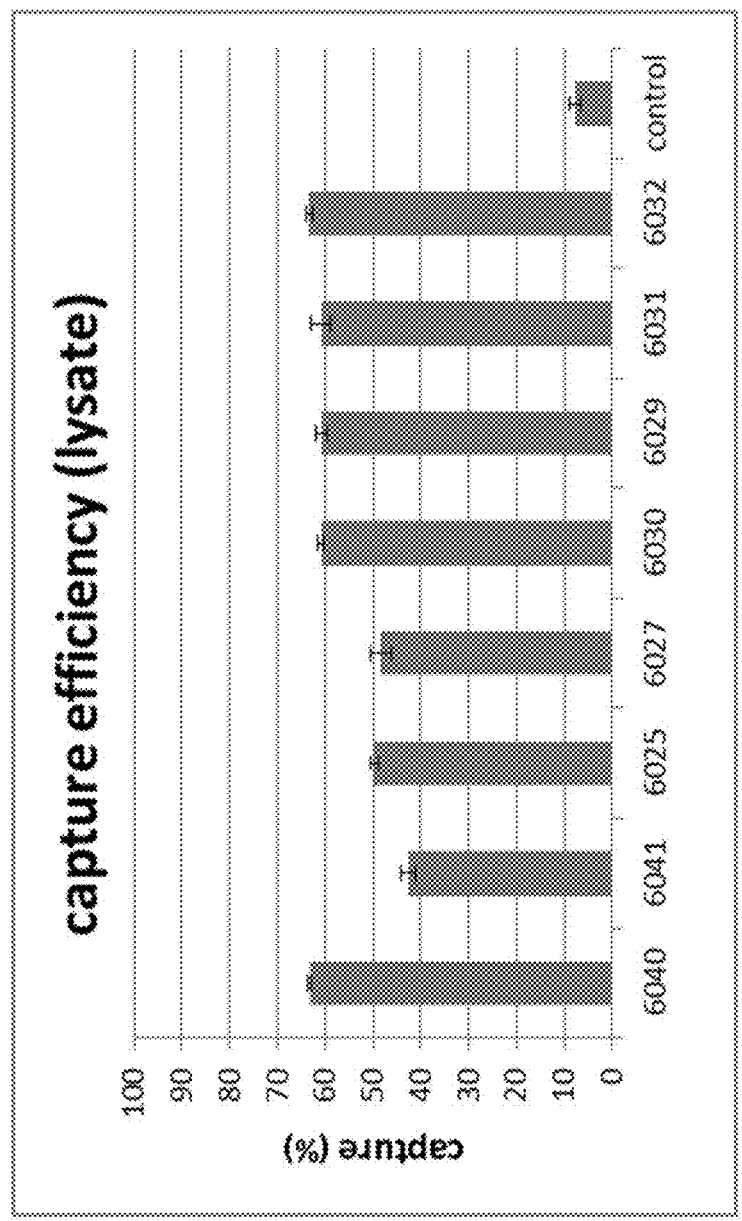
FIGS. 24A and 24B show capture efficiency of BTK:NLuc fusion on the HALOTAG coated beads by Ibrutinib-CA using various Ibrutinib-Chloroalkanes (A) and Western Blot analysis of release of NANOLUC (Nluc) by TEV proteolytic cleavage, release of BTK:Nluc fusion by 2 mM "$Pd(DANPHOS)_x$," at 1:8 ratio of Pd to DANPHOS and release BTK:Nluc fusion by 0.66 mM "$Pd(DANPHOS)_x$," at 1:8 ratio of Pd to DANPHOS.
Figure 24B:
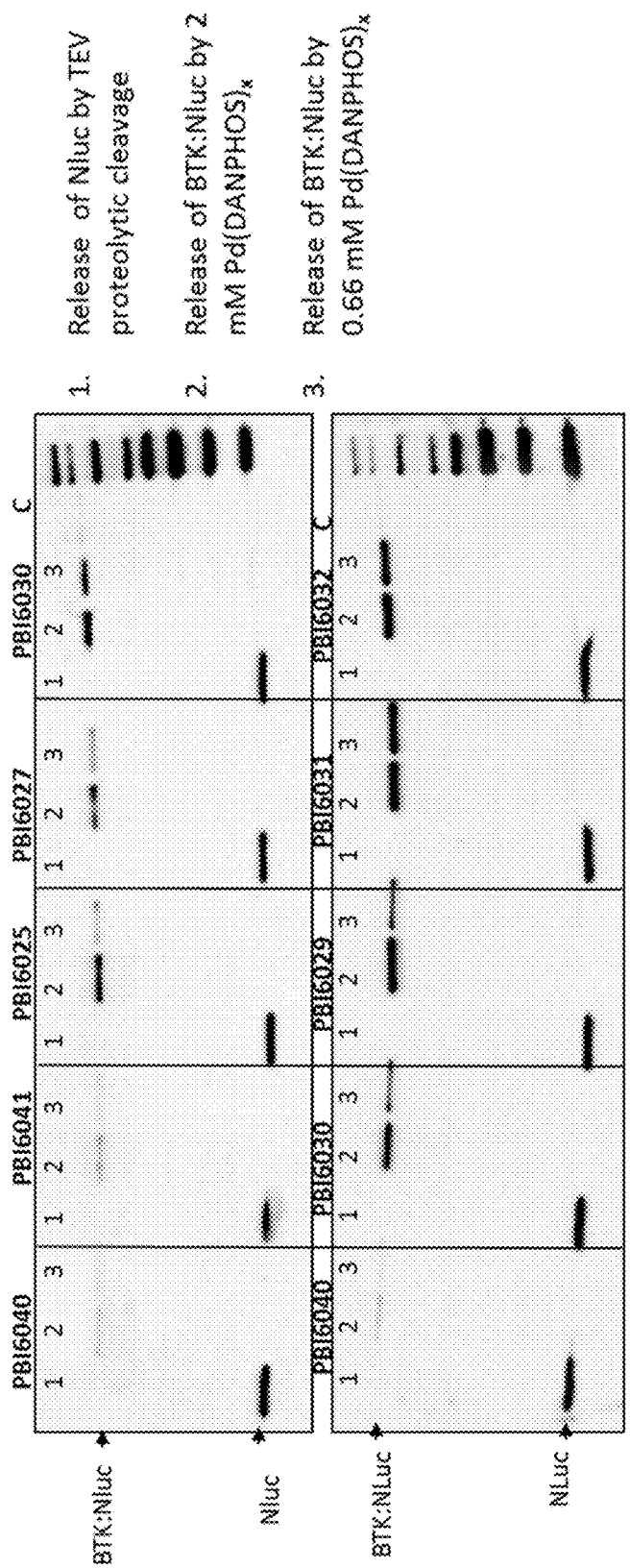

The following example describes insertion of an allyl-carbamate group into the chemical structure of the chloroalkane linker and optimization of this insertion for efficient palladium-catalyzed cleavage and minimal perturbation to the features of the chloroalkane linker (e.g., rapid binding to HALOTAG and minimal interference with a compound's cellular permeability). The chloroalkane linker can be chemically attached to a bioactive compound to allow for selective isolation of their interacting cellular protein targets. In this example, the chloroalkane linker was conjugated to Ibrutinib, a covalent kinase inhibitor, to generate PBI-6040. To optimize the insertion of the allyl carbamate group, 7 additional linkers of different length containing the allyl carbamate group in multiple configurations were generated and conjugated to Ibrutinib (FIG. 22). These Ibrutinib conjugates were compared for binding kinetics to a HALOTAG protein in a cell lysate or inside live cells (FIG. 23), capture of a BTK:NLuc fusion protein (BTK is a target of Ibrutinib) (FIG. 24A), and efficiency of palladium catalyzed cleavage (FIG. 24B).

Binding kinetics to HALOTAG in lysate (FIG. 23A) was measured by treating a lysate prepared from cells, expressing a HALOTAG fusion protein, with the Ibrutinib chloroalkane conjugates at a final concentration of 1 µM for up 60 minutes. After a specified incubation time, an aliquot was removed and treated with HALOTAG TMR-fluorescent ligand (Promega Corporation) at a final concentration of 1 µM to label the remaining unbound HALOTAG fusion protein. The aliquots were resolved on SDS-PAGE and scanned on a Typhoon 9400 fluorescent imager (GE Healthcare). Bands were quantitated using IMAGEQUANT (GE Healthcare), and binding kinetics was determined as the percent binding over time relative to time zero when no chloroalkane-tagged compound added. All linkers, except of the shorter linker PBI-6041, displayed good binding kinetic to HALOTAG with the longest linkers, PBI-6031 and PBI-6032, exhibiting relative slower binding. These results indicate that for all configurations, except PBI-6041, the insertion of the allyl carbamate group did not have with any significant interference with the chloroalkane binding to the HALOTAG protein.

Binding kinetics to HALOTAG inside cells (FIG. 23B) was measured by treating live cells, expressing a HALOTAG fusion protein, with the Ibrutinib chloroalkane conjugates at a final concentration of 10 µM for up to 90 minutes. Medium was then replaced with medium containing 5 µM HALOTAG TMR-fluorescent ligand, and the cells were incubated for additional 15 minutes to label the remaining unbound HALOTAG fusion protein. Cells were then lysed with a detergent lysis buffer, and the samples at the various time points were analyzed as described above. All conjugates displayed similar binding kinetics to HALOTAG indicating that the insertion of the allyl carbamate group exhibited minimal interference with cellular permeability. Furthermore, the length of these linkers had also minimal impact on cellular permeability.

To interrogate capture efficiency of an interacting cellular target, a known target of Ibrutinib, BTK, was genetically fused to NANOLUC (NLuc) luciferase reporter (Promega Corporation). Since Ibrutinib is a covalent inhibitor of BKT, a TEV recognition site was incorporated between BTK and NLuc to allow proteolytic release of NLuc from the beads. Following a 2 hour treatment of cell lysate (from cells expressing the BTK:NLuc fusion) with 1 µM Ibrutinib chloroalkane conjugates (final concentration), the Ibrutinib chloroalkane conjugates, and their interacting BTK:NLuc target, were captured onto HALOTAG coated magnetic beads (Promega Corporation). Capture efficiency was determined as the percent of lost in bioluminescence in the unbound fractions relative to the untreated cell lysate. Results in FIG. 24A indicate that for the shorter linkers, PBI-6041, PBI-6025, and PBI-6027, the insertion of the allyl carbamate group reduced capture efficiency relative to PBI-6040, which does not contain an allyl carbamate group. However, for the longer linkers, PBI-6029, PBI-6030, PBI-6031, and PBI-6032, the insertion of the allyl carbamate group did not interfere with capture efficiency.

To interrogate the efficiency of palladium-catalyzed cleavage of these linkers, the release of BTK:NLuc fusion covalently captured onto the HALOTAG beads was determined by two methods: i) TEV proteolytic cleavage and ii) palladium-catalyzed cleavage (FIG. 24B). TEV proteolytic cleavage of the fusion would lead to the release of NLuc while palladium catalyzed cleavage of the allyl carbamate group within the chloroalkane linker would result with the release of BTK:NLuc. Western analysis of the released proteins using an anti-NLuc antibody indicated significant release of NLuc by TEV proteolytic cleavage for all the tested linkers. However, a lower release was observed for the shorter linker PBI-6041, consistent with its lower binding kinetics to HALOTAG, and its lower capture of BTK:Nluc. Significant release of BTK:NLuc by $Pd(DANPHOS)_x$ treatment was detected only for linkers containing an allyl carbamate group. In addition, higher palladium-catalyzed cleavage efficiency was observed for the longer linkers. PBI-6030 and PBI-6029 displayed similar release efficiency by TEV and 2 mM $Pd(DANPHOS)_x$, while the longer PBI-6031 and PBI-6032 displayed similar release efficiency by TEV and 2 mM and 0.66 mM Pd(DAN-PHOS)$_x$.

Taken together, these results demonstrate that the incorporation of the allyl carbamate group into the longer chloroalkane linkers enabled efficient palladium-catalyzed cleavage while displaying minimal interference with cell permeability and binding kinetics to HALOTAG.

Example 18

Figure 25:
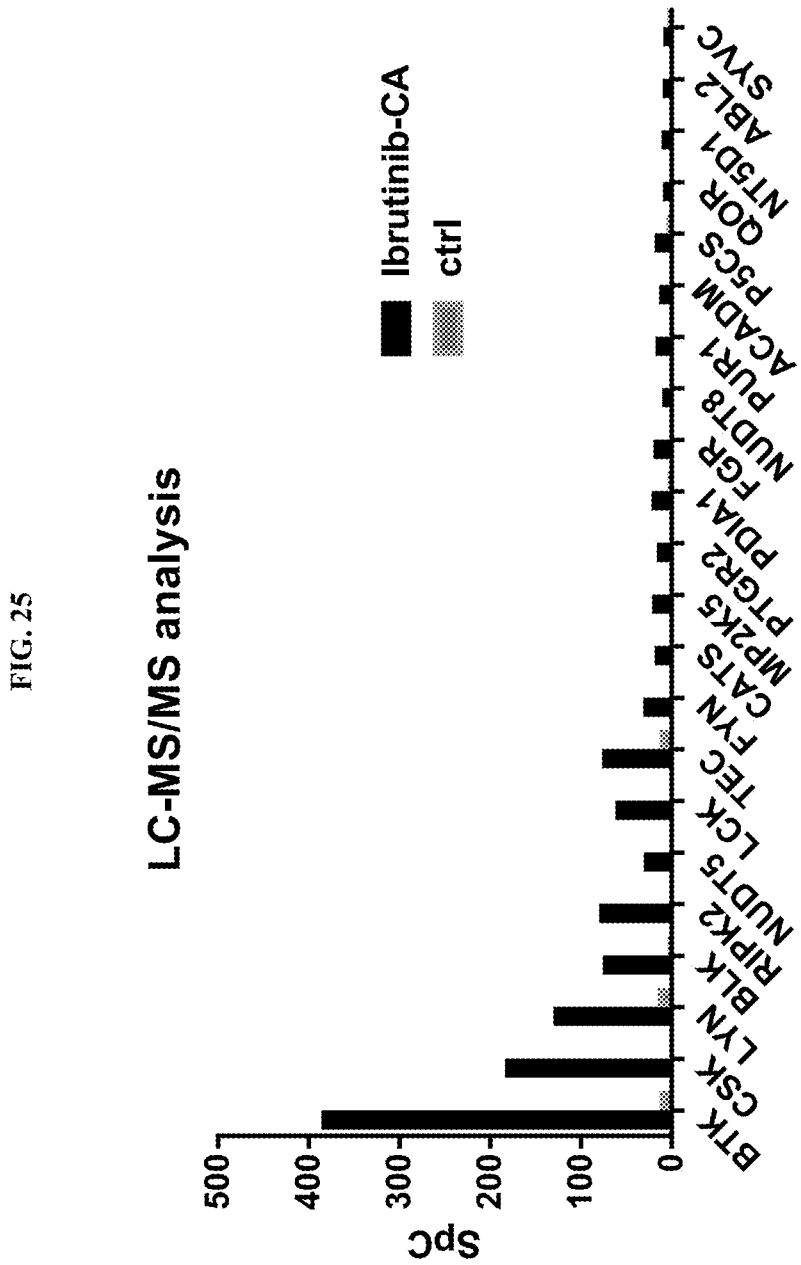
FIG. 25 shows Mass spec analysis of targets enriched from Ramos cells by ibrutinib-CA-T4E (PBI6132).
Figure 26:
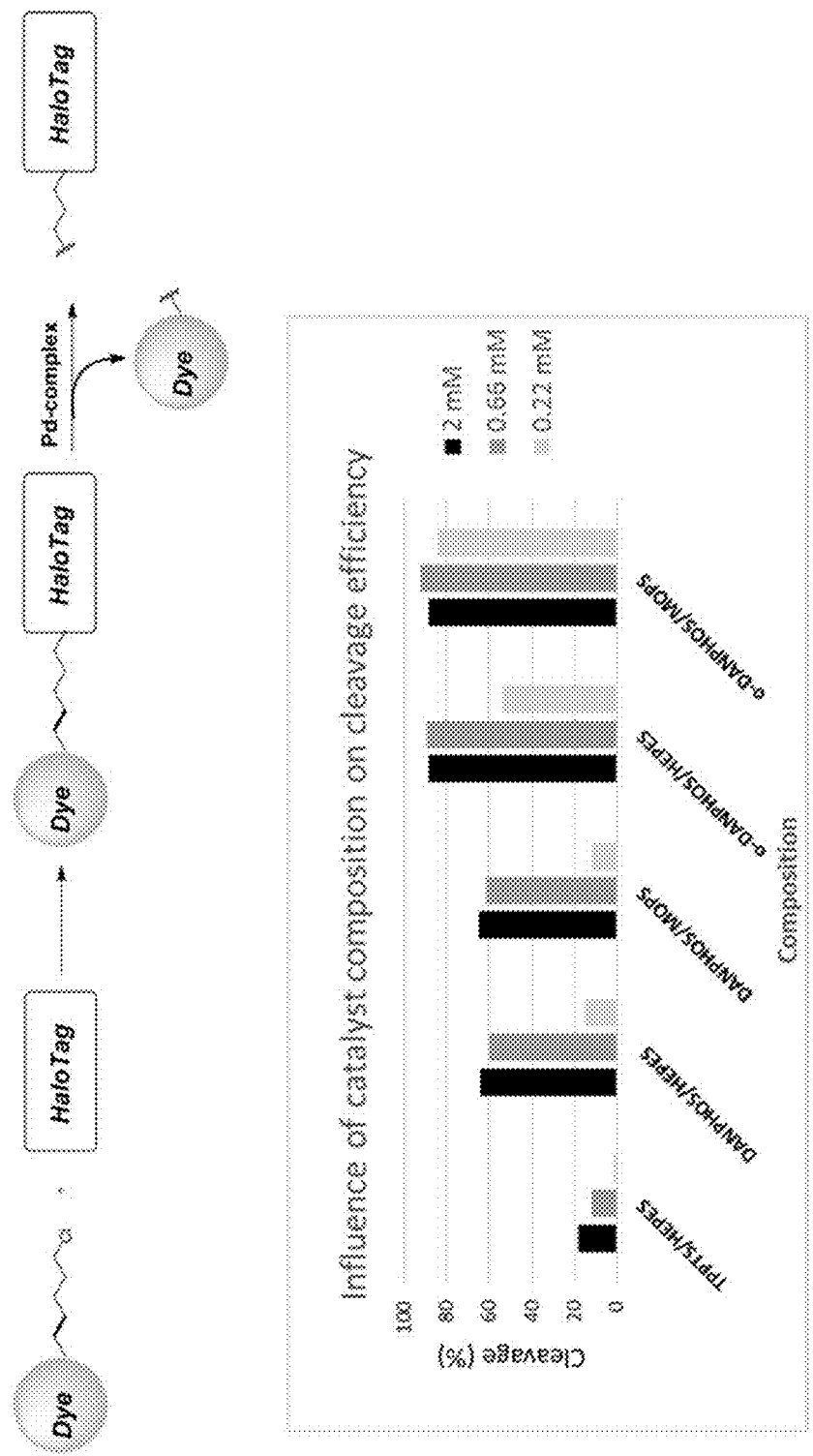
FIG. 26 shows the influence of catalyst composition on cleavage efficiency in a proteinaceous environment.

The following example demonstrates the capability of palladium catalyzed elution to enrich targets that interact covalently with the bioactive compound. Ibrutinib binds covalently to a cysteine in the ATP binding pocket of its primary target, BTK. In addition, Ibrutinib has been reported to interact either covalently or reversibly with other tyrosine kinases, depending on the presence of a corresponding cysteine in the ATP binding pocket. Following 2.5 hour treatment of Ramos cells with a final concentration of 20 µM ibrutinib-CA-T4E (control cells remained untreated), cells were lysed, and the chloroalkane conjugates, together with their bound targets, were captured onto HALOTAG coated magnetic beads (Promega Corporation). Targets were then released by 6 mM palladium catalyst and subjected to LC-MS/MS analysis (FIG. 25). Mass spectrometry analysis indicated enrichment of multiple tyrosine kinases including kinases predicted to interact covalently (i.e., BTK, BLK and TEC). These results demonstrate the applicability of palladium-catalyzed elution to covalent interactions that cannot be addressed by other elution methods.

Example 19

The following example (See, e.g., FIG. 27) demonstrates that the nature of the phosphine and nucleophile can affect palladium-catalyzed cleavage of an allyl-carbamate linkage in a proteinaceous environment. In these experiments, HALOTAG coated magnetic beads (containing 400 µg immobilized HALOTAG protein) were incubated with 60 µM PBI-5741 for 30 min. Control dye, PBI-5741, was incubated with beads that do not contain any immobilized HALOTAG protein. Following covalent binding of PBI-5741 to the immobilized HALOTAG protein, beads were treated with either 2 mM, 0.66 mM, or 0.22 mM premade Pd(phosphine) complexes at 1:8 molar ratio for 30 min in HEPES or MOPS buffer. Cleavage of the allyl-carbamate group would result with release of the dye from the beads. Samples of released dye, together with the control dye, were resolved on SDS-PAGE, scanned on a Typhoon 9400 fluorescent imager, and bands quantitated using IMAGEQUANT. Cleavage efficiency was determined as the percent of released dye relative to control dye. Results indicate that the nature of the phosphine and nucleophile play a crucial role in palladium catalyzed cleavage efficiency. Electron-poor phosphines from the DANPHOS family, especially DANPHOS and o-DANPHOS, outperformed TPPTS, a commonly used phosphine.

Example 20

Figure 27:
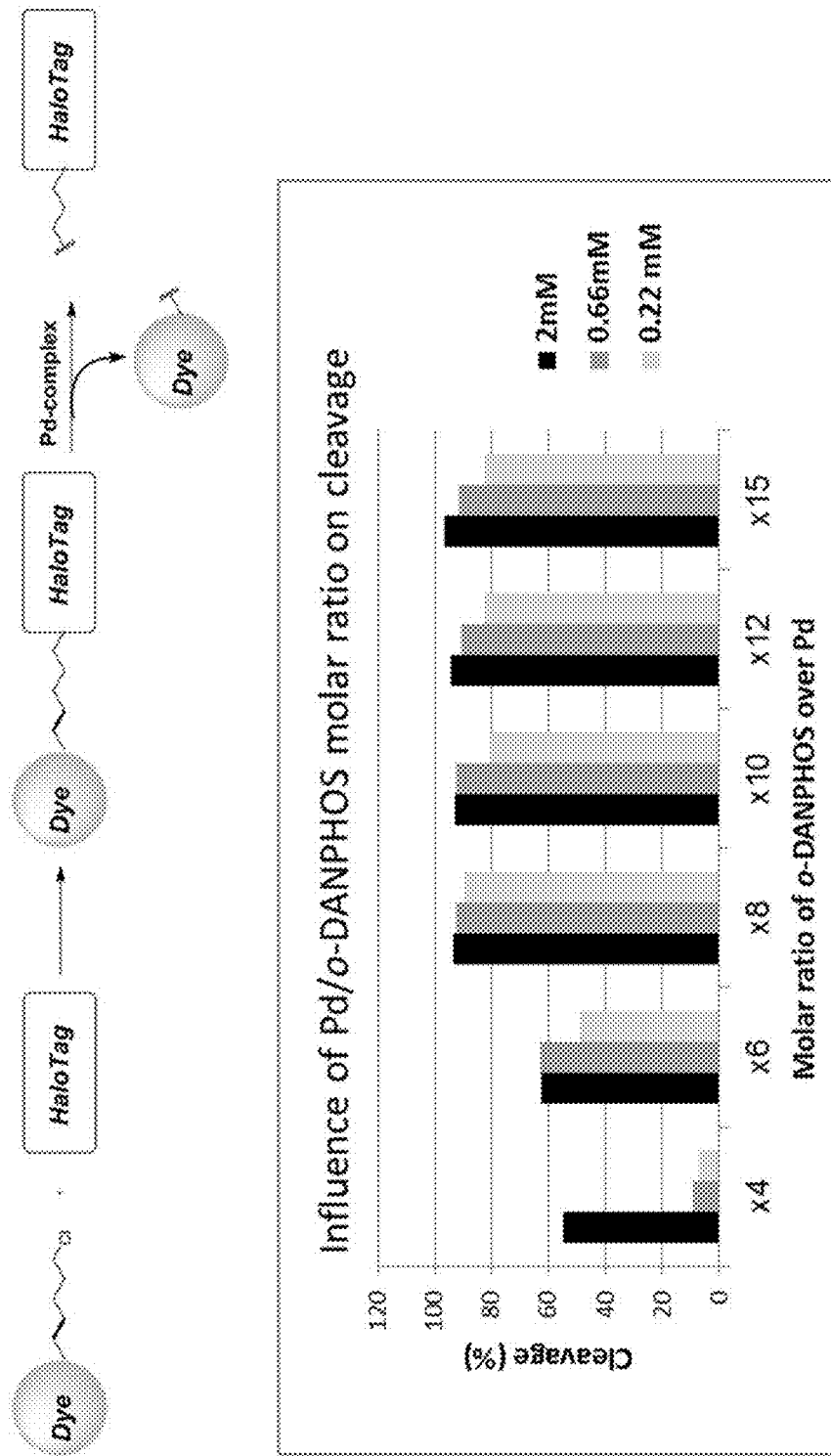
FIG. 27 shows the influence of Pd/o-DANPHOS molar ratio on cleavage efficiency in a proteinaceous environment.

Experiments conducted during development of embodiments described herein demonstrated that the efficiency of palladium-catalyzed cleavage is dependent on the molar ratio of the Pd-phosphine solutions (See, e.g., FIG. 27; See also FIG. 21 and Example 16 for DANPHOS). In these experiments, HALOTAG coated beads (containing 400 µg immobilized HALOTAG protein) were incubated with 60 µM PBI-5741 for 30 min while control dye PBI-5741 was incubated with beads that do not contain immobilized HALOTAG protein. Following covalent binding of PBI-5741 to the immobilized HALOTAG protein, the beads were treated for 30 min with either 2 mM, 0.6 mM, or 0.22 mM of Pd-o-DANPHOS complex at 1:4, 1:6, 1:8, 1:10, 1:12, and 1:15 molar ratios of Pd to o-DANPHOS. Cleavage of the allyl-carbamate linkage would result with release of the dye from the beads. The released dyes, together with the control dye, were resolved on SDS-PAGE, scanned on a Typhoon 9400 fluorescent imager, and bands quantitated using IMAGEQUANT. Cleavage efficiency was determined as the percent of released dye relative to control dye. Higher cleavage efficiencies were observed for solutions of Pd-o-DANPHOS at a molar ratio of Pd to o-DANPHOS of 1:8 to 1:10.

Example 21

Figure 28:
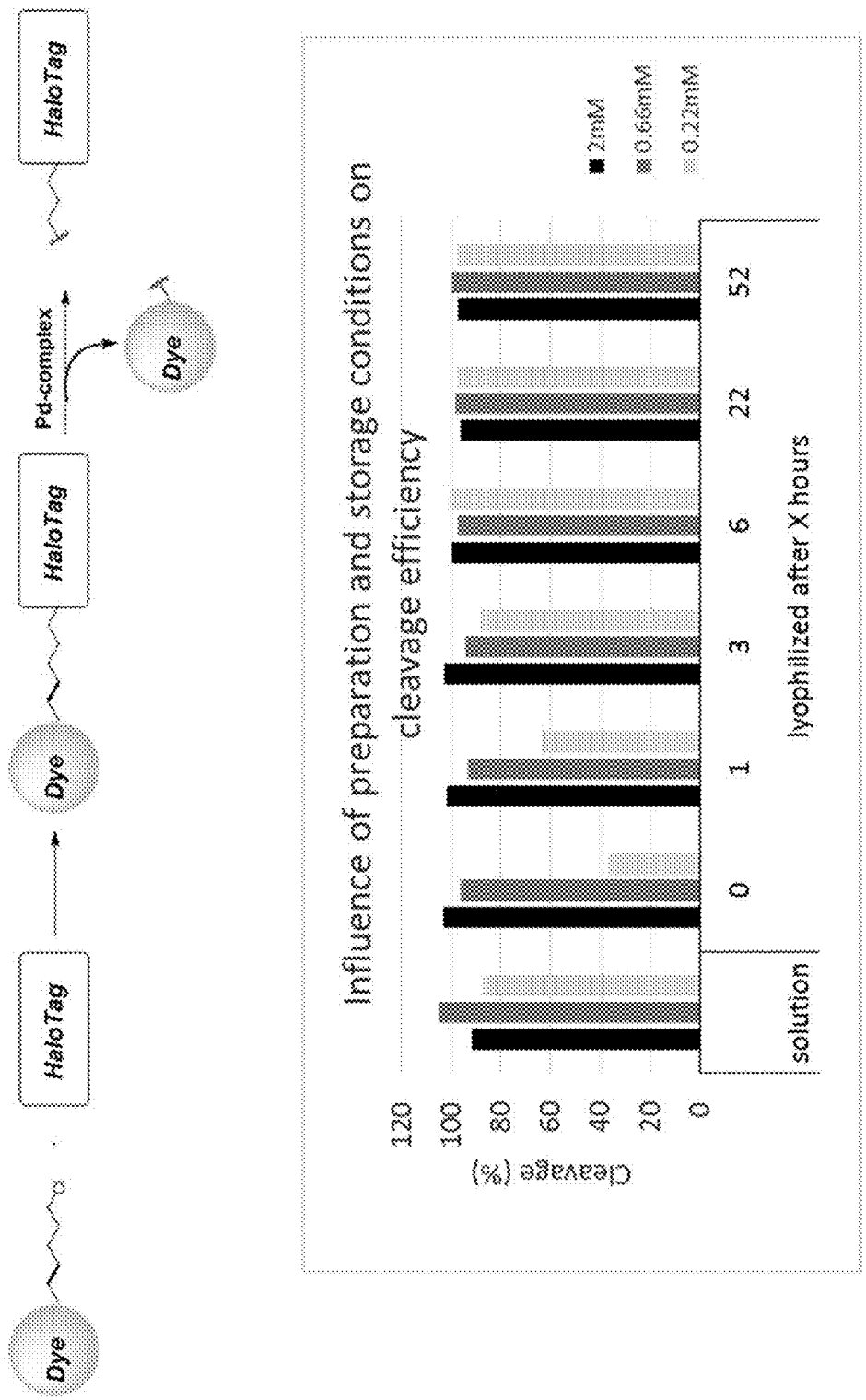
FIG. 28 shows the influence of storage conditions on cleavage efficiency in a proteinaceous environment.

This example demonstrates that the active catalyst can be stored either as a solution in sealed glass ampules or in a lyophilized form (See, e.g., FIG. 28). When lyophilized, it is crucial that the palladium be sufficiently reduced prior to lyophilization. In these experiments, HALOTAG coated magnetic beads (containing 400 µg immobilized HALOTAG protein) were incubated with 60 µM PBI-5741 for 30 min while control dye PBI-5741 was incubated with beads that do not contain immobilized HALOTAG protein. Following covalent binding of PBI-5741 to immobilized HALOTAG protein, the beads were treated for 30 min with 0.66 mM Pd/o-DANPHOS, which was prepared from catalyst stored either as a solution or in a lyophilized form (lyophilized immediately or 1, 3, 6, 22, and 52 hours after preparation). Cleavage of the allyl-carbamate linkage would result with release of the dye from the beads. Samples of released dye together with the control dye were resolved on SDS-PAGE, scanned on a Typhoon 9400 fluorescent imager, and bands quantitated using IMAGEQUANT. Cleavage efficiency was determined as the percent of released dye relative to control dye. Results indicate that catalysts stored in solution or lyophilized 6 hours or more after preparation retained their activity.

Example 22

Scheme 1: Preparation of an Active Catalyst:
General Procedure for the Prepartion of Catalyst Solution:

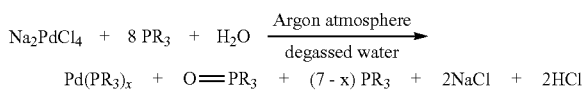

Operations were performed under argon atmosphere (Schlenk technique). Water was degassed by 3× freeze-pump-thaw cycles.

o-DANPHOS (188 mg, 0.32 mmol, 97% pure) was placed in a sealed vial and equipped with stir bar. Air was evacuated, and the vial backfilled with argon (3× repetitions). Degassed water (9 mL) was added via cannula resulting in the formation of a clear solution. In a separate sealed vial, Na$_2$PdCl$_4$ (11.8 mg, 0.04 mmol) was placed, air evacuated, and the vial backfilled with argon (3× repetitions). Degassed water (1 mL) was added to solid Na$_2$PdCl$_4$, resulting in the formation of a brown solution. The brown aqueous solution of Na$_2$PdCl$_4$ (1 mL, 11.8 mg/mL) solution was added to the stirred phosphine solution, resulting in the formation of a clear yellow solution. The clear, yellow solution of Pd-o-DANPHOS complex was allowed to mix for an appropriate amount of time under argon. When a sufficient amount of time had passed, the yellow solution was transferred to:

- 1 mL aliquots in glass ampules and fire sealed either under Argon or under vacuum. Solutions stored at 4° C., protected from light;
- 1 mL aliquots in glass ampules, ampules were sealed with septa and solution carefully frozen on liquid nitrogen and upon lyophilization, glass ampules were fire-sealed and stored at −80° C., protected from light; and
- 1 mL aliquots in septa-sealed glass vials, solution frozen on liquid nitrogen or dry ice and lyophilized. Lyophilized residue was stored in sealed glass vials at −80° C.

Scheme 2: Preparation of an Active Catalyst from Pd(OAc)$_2$:

General Procedure for the Preparation of Catalyst Solution from Pd(OAc)$_2$:

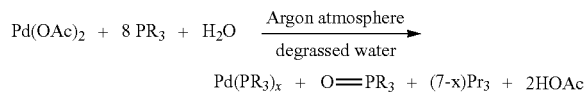

Example for 4 mM Pd-DANPHOS 1:8 Solution

DANPHOS (96 mg, 0.16 mmol, 97% pure) and Pd(OAc)$_2$ (4.5 mg, 0.02 mmol) were placed in a sealed vial equipped with stir bar. Air was evacuated, and the vial backfilled with argon (3× repetitions). Degassed water (5 mL) was added via cannula and upon stirring, resulted in the formation of a clear solution. (Pd(OAc)$_2$ reacts and dissolves slowly). The clear yellow solution of Pd-DANPHOS complex was allowed to mix for 20 hours under argon before packaging into vials.

The efficiency of the catalyst does NOT depend on the Pd source. Both Na$_2$PdCl$_4$ and Pd(OAc)$_2$, have been experimentally shown that under identical conditions, both exhibited very similar efficiencies.

Example 23

Figure 29:
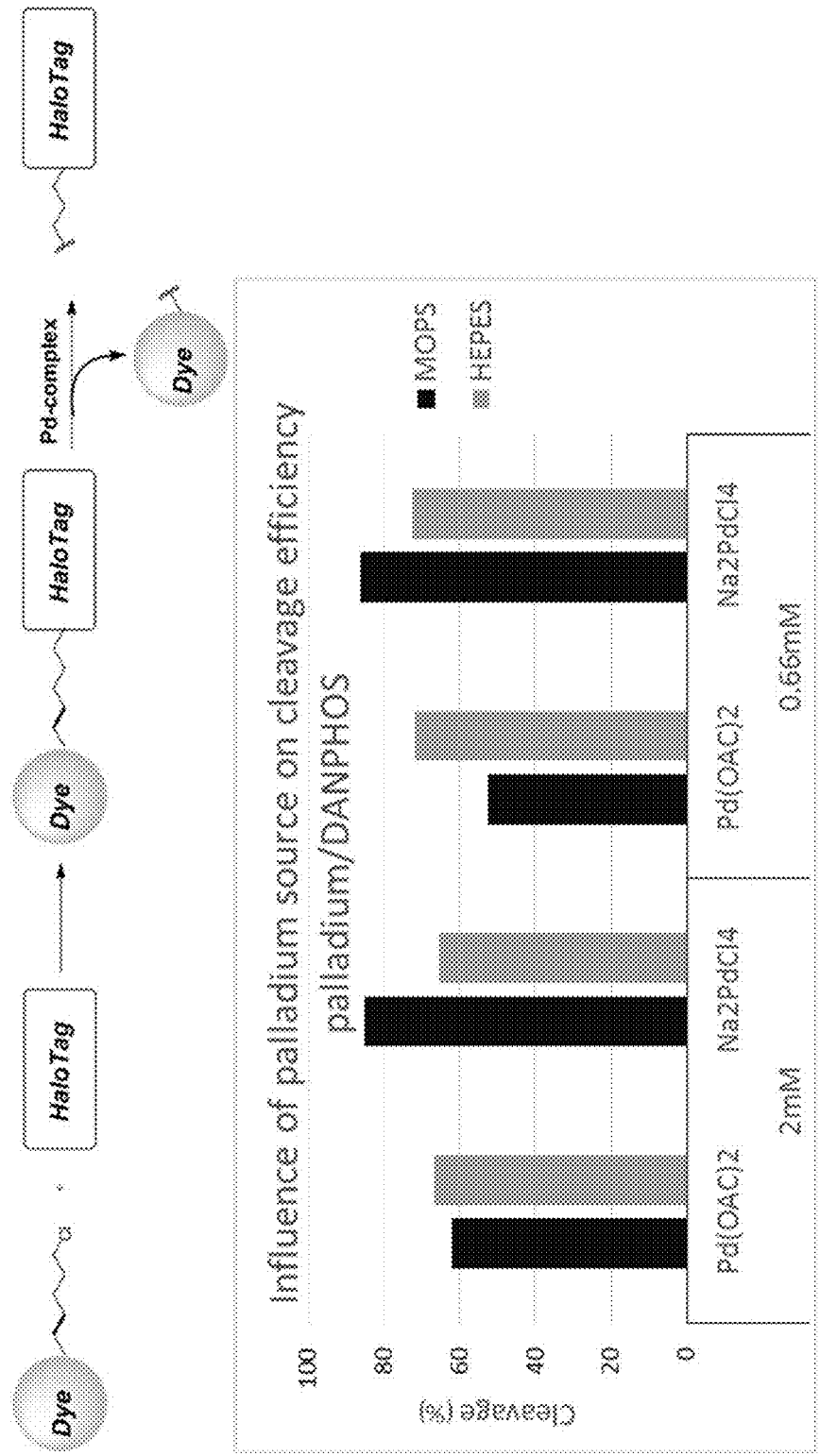
FIG. 29 shows the influence of palladium source on cleavage efficiency in a proteinaceous environment.

The following example demonstrates that catalysts prepared from two different source of palladium salt have similar reactivity (See, e.g., FIG. 29). HALOTAG coated beads (containing 400 µg immobilized HALOTAG protein) were incubated with 60 µM PBI-5741 for 30 min while control dye PBI-5741 was incubated with beads that do not contain immobilized HALOTAG protein. Following covalent binding of PBI-5741 to immobilized HALOTAG protein, the beads were treated for 30 min with 2 mM Pd/DANPHOS catalyst prepared from two sources of palladium salt Pd(OAC)$_2$ or Na$_2$PdCl$_4$ at 1:8 molar ratios of Pd to phosphine. The Pd/DANPHOS complexes were reconstituted in either in HEPES or MOPS buffers. Cleavage of the allyl-carbamate group would result with release of the dye from the beads. The released dyes together with the control dye were resolved on SDS-PAGE, scanned on a Typhoon 9400 fluorescent imager, and bands quantitated using IMAGEQUANT. Cleavage efficiency was determined as the percent of released dye relative to control dye. Similar cleavage efficiency of the allyl-carbamate group was observed for catalysts prepared from both sources of palladium salt.

Example 24

Figure 30:
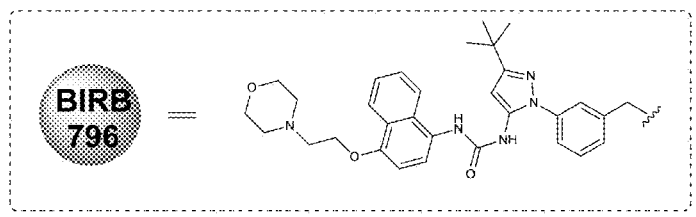
FIG. 30 shows structures of BIRB796-Chloroalkanes conjugates.
Figure 30:
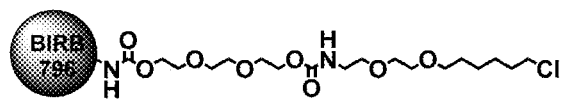
Figure 30:
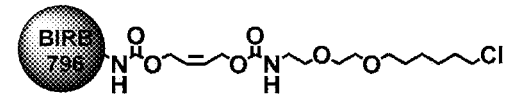
Figure 30:
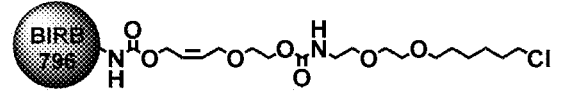
Figure 30:
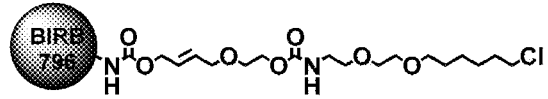
Figure 30:
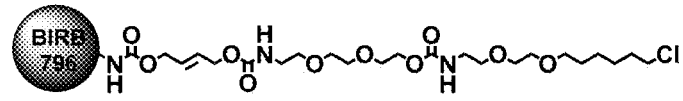
Figure 30:
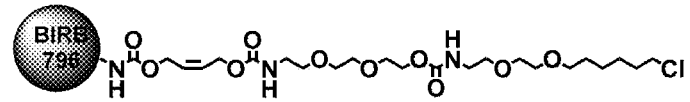
Figure 30:
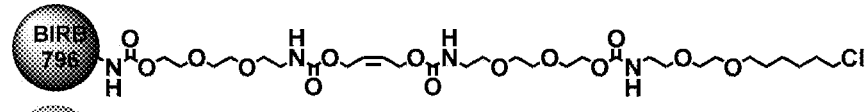
Figure 30:
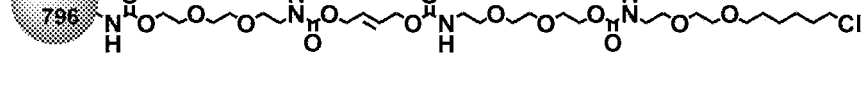
Figure 31A:
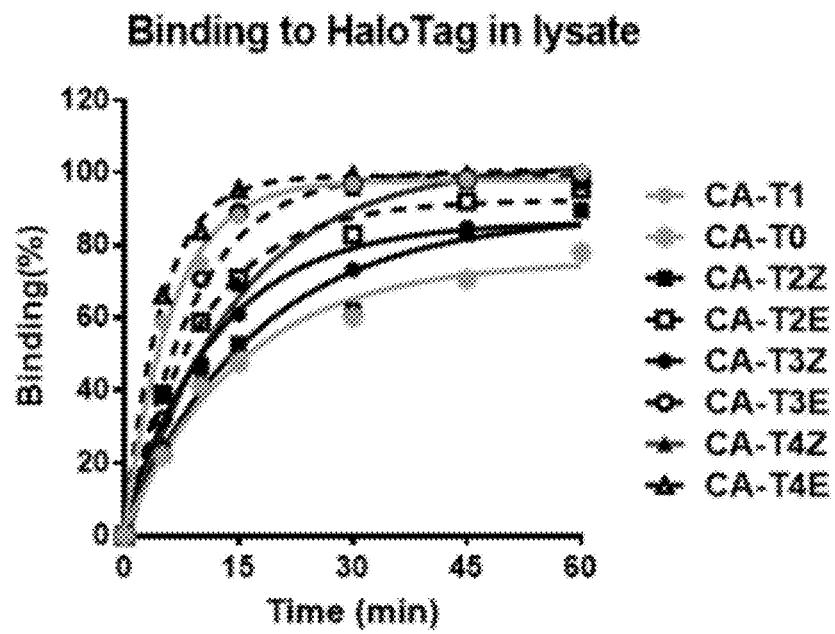
FIGS. 31A and 31B show the influence of linkers on binding kinetics of the BIRB796-Chloroalkane conjugates to HALOTAG (A) in lysate and (B) inside intact cells.
Figure 31B:
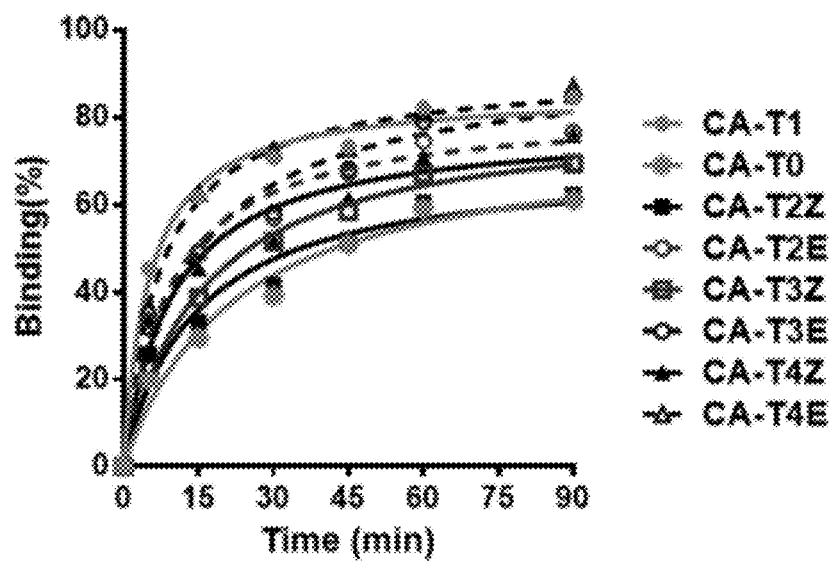
Figure 32:
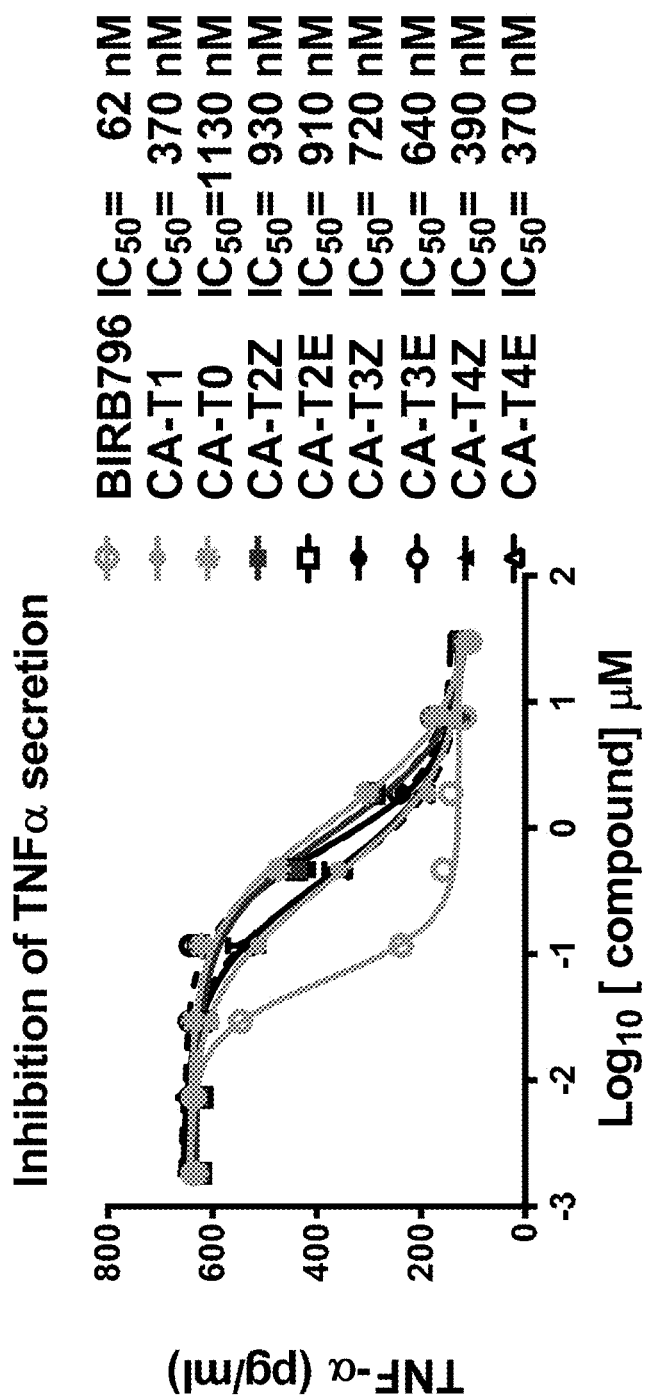
FIG. 32 shows influence of linkers on BIRB796 potency.
Figure 33:
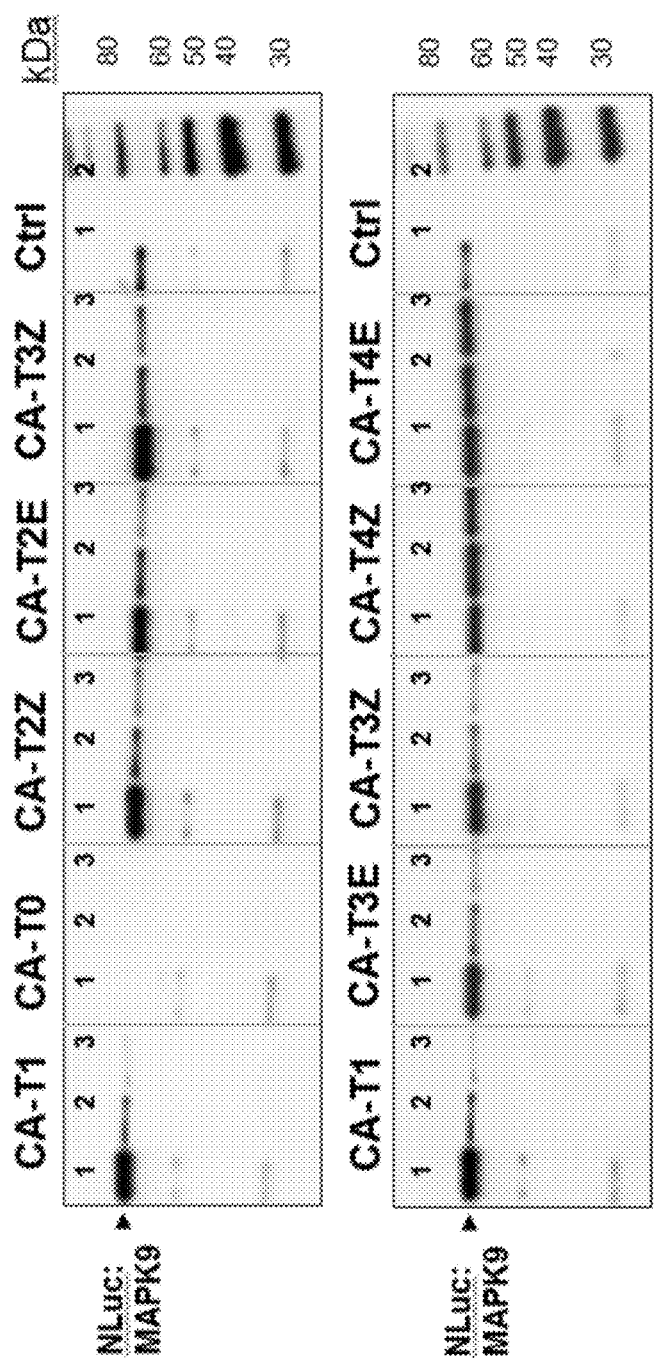
FIG. 33 shows influence of linkers on enrichment of NLuc:MAPK9 by BIRB796 conjugates using different elution methods. Analysis by Western using NLuc antibody.

The following example describes insertion of an allyl-carbamate group into the chemical structure of the chloroalkane linker and optimization of this insertion for efficient palladium catalyzed cleavage and minimal perturbation to the features of the chloroalkane linker (e.g., rapid binding to HALOTAG and minimal interference with compound's potency and cellular permeability). The chloroalkane linker can be chemically attached to a bioactive compounds to allow for selective isolation of their interacting cellular targets. In this example, the chloroalkane linker was conjugated to BIRB796 to generate BIRB796-CA-T1. To optimize the insertion of the allyl carbamate group, 7 additional linkers of different length containing the allyl carbamate group in two different configurations were generated and conjugated to BIRB796 (FIG. 30). The conjugates were compared for binding kinetics to a HALOTAG protein in a cell lysate and inside live cells (FIG. 31), influence on BIRB796 potency (FIG. 32), and efficiency of palladium catalyzed linker cleavage (FIG. 33).

Binding kinetics to HALOTAG in lysate (FIG. 31A) were measured by treating a lysate prepared from cells expressing a HALOTAG fusion protein with the BIRB796 chloroalkane conjugates at a final concentration of 1 µM for up to 60 minutes. After a specified incubation time, an aliquot was removed and treated with HALOTAG TMR-fluorescent ligand (Promega Corporation) at a final concentration of 1 µM to label the remaining unbound HALOTAG fusion protein. The aliquots were resolved on SDS-PAGE and scanned on a Typhoon 9400 fluorescent imager (GE Healthcare). Bands were quantitated using IMAGEQUANT (GE Healthcare), and binding kinetics was determined as the percent binding over time relative to time zero where no chloroalkane-tagged compound was added. Linkers with a trans-double bond (i.e. CA-T2E, CA-T3E and CA-T4E) displayed faster binding to HALOTAG than respective linkers with a cis-double bond. The binding kinetics of the longer linker CA-T4E was most similar to the non-cleavable linker CA-T1 demonstrating minimal influence on binding to HALOTAG.

Binding kinetics to HALOTAG inside cells (FIG. 31B) were measured by treating live cells expressing a HALOTAG fusion protein, with the BIRB796 chloroalkane conjugates at a final concentration of 10 µM for up to 90 minutes. Medium was then replaced with medium containing 5 µM HALOTAG TMR-fluorescent ligand, and the cells were incubated for additional 15 minutes to label the remaining unbound HALOTAG fusion protein. Cells were then lysed with a detergent lysis buffer, and the samples at the various time points were analyzed as described above. The linkers displayed similar relative influence on binding kinetics to HALOTAG in cells and in lysate indicating that regardless of their length, cellular permeability was not a limiting factor for their binding.

Inhibition of mitogen-activated protein kinases (MAPK) by BIRB796 reduces production of proinflammatory cytokines such as TNFα. Influence of the linkers on BIRB796 potency was tested by comparing the BIRB796 conjugates for inhibition of TNFα secretion from LPS-stimulated THP-1 cells (FIG. 32). THP-1 cells were plated in 96-well plates at 100,000 cells/well, treated with serial dilutions of BIRB796 (Cayman Chemical) and BIRB796-chloroalkane conjugates for 2 h, and then stimulated with LPS (Sigma) at final concentration of 250 ng mL−1 for 24 h. Supernatants were analyzed for human TNFα secretion by ELISA (R&D systems). Results indicates inverse correlation between the length of the cleavable chloroalkane linker and its influence on BIRB796 potency. Only the longer linkers, CA-T4Z and CA-T4E, exhibited potency similar to non-cleavable linker CA-T1.

To interrogate the efficiency of palladium-catalyzed cleavage of these linkers, the release of a MAPK9, a known BIRB796 target, genetically fused to NANOLUC (NLuc) (NLuc: MAPK9) captured onto the HALOTAG beads was determined by two methods: i) SDS and ii) palladium-catalyzed cleavage (FIG. 33). Following a 2 hour treatment of cell lysate (from cells expressing the NLuc:MAPK9 fusion) with a final concentration of luM BIRB796 chloroalkane conjugates, the conjugates and the bound NLuc:MAPK9 were captured onto HALOTAG coated magnetic beads (Promega Corporation). NLuc:MAPK9 was then released by treatment with either 1% SDS, 2 mM palladium catalyst, or 0.66 mM palladium catalyst. Western analysis of the released proteins using an anti-NLuc antibody indicated significant release of NLuc:MAPK9 by SDS for all the tested linkers except of CA-T0, which is consistent with its lower binding kinetics to HALOTAG. Significant release of NLuc:MAPK9 by the palladium catalyst was detected only for the longer linkers.

Taken together, these results demonstrate that the incorporation of the allyl carbamate linkage into the longer chloroalkane linkers enabled efficient palladium-catalyzed cleavage while displaying minimal interference on cell permeability and binding kinetics to HALOTAG.

Example 25

Figure 34:
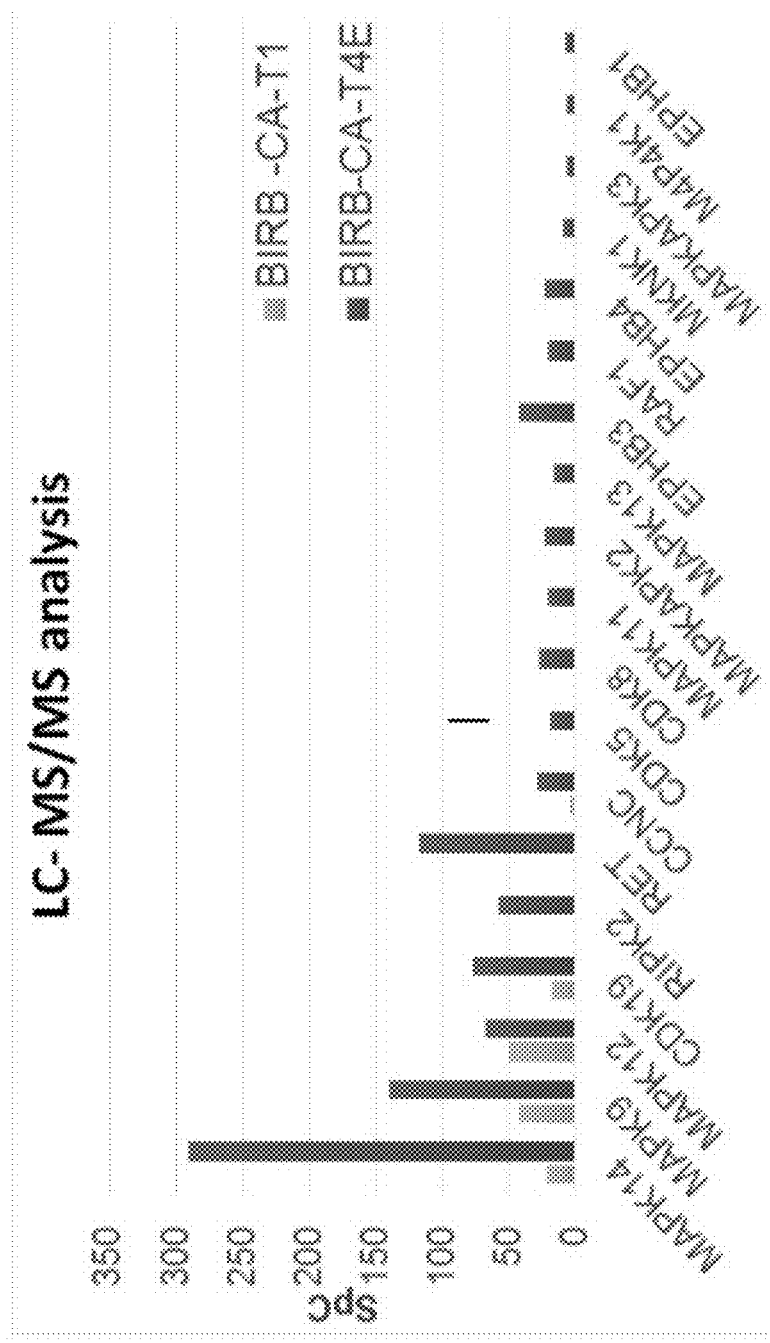
FIG. 34 shows mass spec analysis of target enriched from THP-1 cells by BIRB796 conjugated to CA-T1 and CA-T4E using competitive elution and chemical cleavage respectively.

The following example demonstrates the advantage of palladium-catalyzed elution over competitive elution for the enrichment of targets for compounds exhibiting prolonged residence time. Following a 2.5 hour treatment of THP-1 cells with a final concentration of 20 μM BIRB796-CA-T1 and BIRB796-CA-T4E (control cells remained untreated), cells were lysed, and the chloroalkane conjugates together with their bound targets were captured onto HALOTAG coated magnetic beads (Promega Corporation). Targets were then released by either 400 μM BIRB796 or 6 mM palladium catalyst and subjected to LC-MS/MS analysis (FIG. 34). Mass spectrometry analysis indicated higher enrichment of endogenous targets by the palladium catalyzed elution.

Example 26

Figure 35:
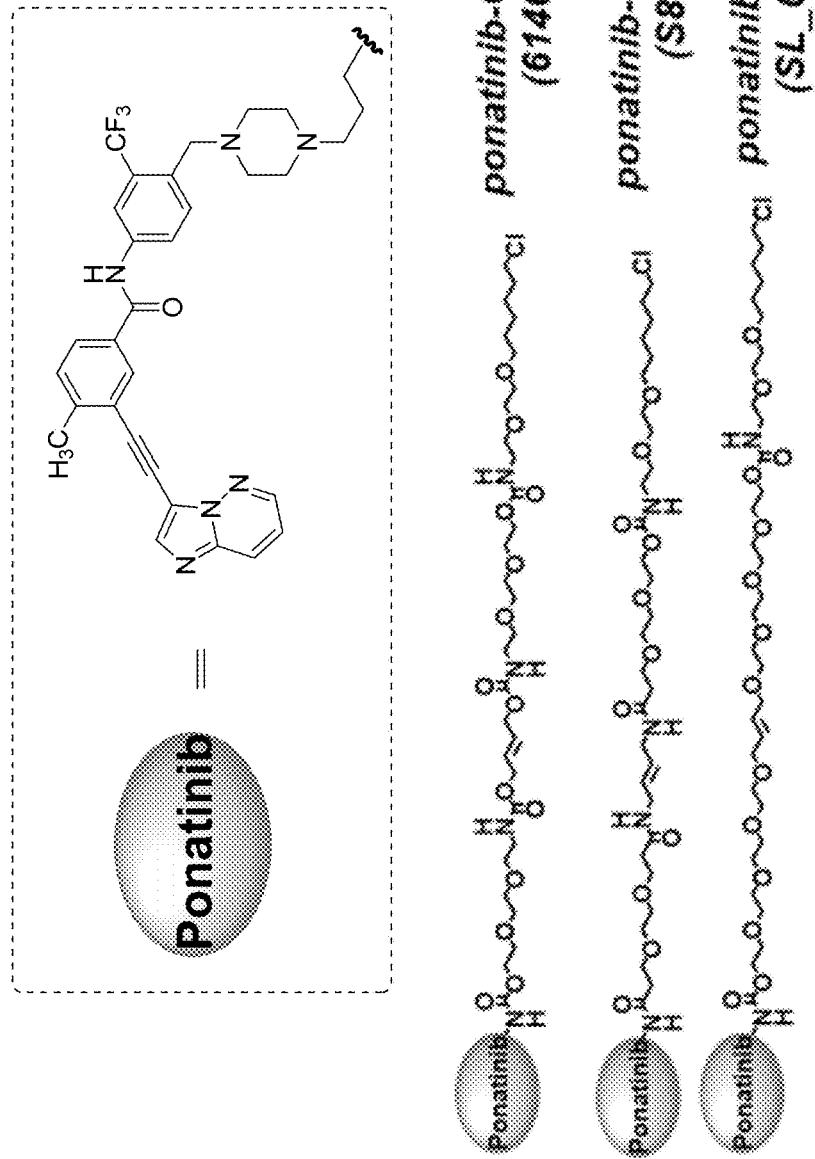
FIG. 35 shows structures of ponatinib-chloroalkanes conjugates.
Figure 36A:
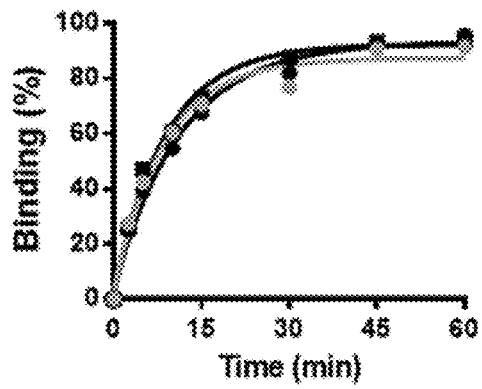
FIGS. 36A-36D shows the Influence of carbamate groups on properties of cleavable chloroalkane tag: (A) binding kinetics of ponatinib conjugates to HALOTAG in lysate; binding kinetics of ponatinib conjugates to HALOTAG inside intact cells; (C) inhibition of purified ABL1 by ponatinib conjugates; and (D) in-cell inhibition of STATS reporter expression by ponatinib conjugates.
Figure 36B:
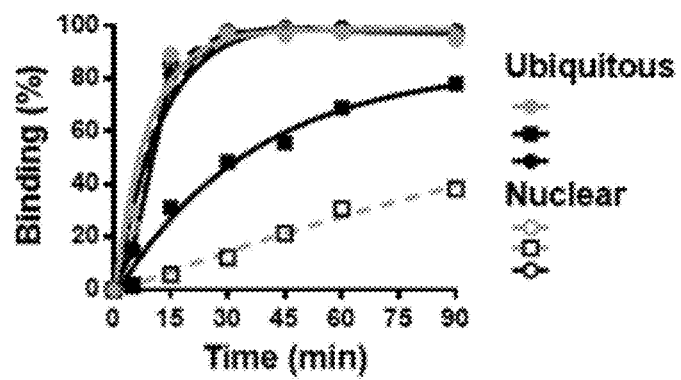
Figure 36C:
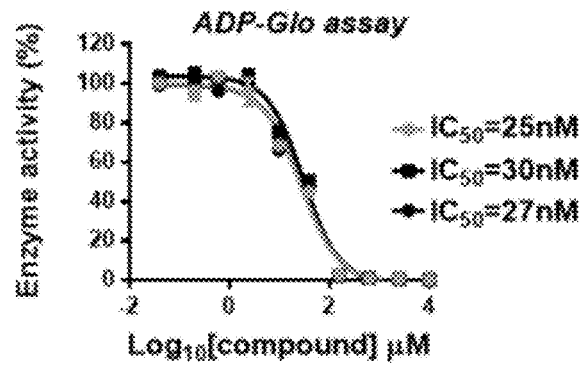
Figure 36D:
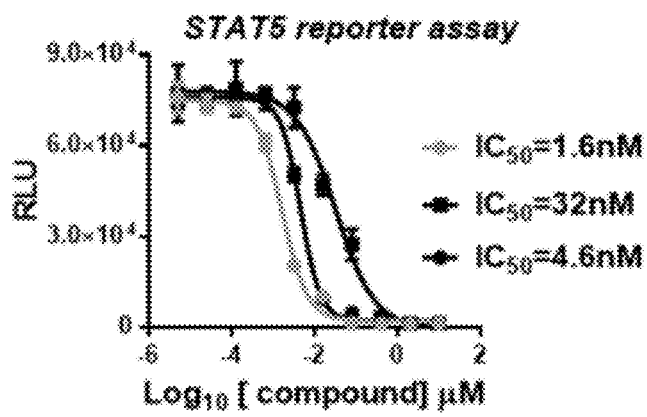

The following example demonstrates the contribution of carbamate groups to the features of the cleavable chloroalkane linker. CA-T4E contains 4 carbamate groups, one of them essential for rapid binding kinetics to HALOTAG. Two additional linkers were generated, one where the three other carbamates were replaced with amides, and the other where the two allyl carbamate groups were replaced with allyl ether linkages. All three linkers were conjugated to ponatinib (FIG. 35): Ponatinib-CA-T4E (6142), ponatinib-triamide (S83), and ponatinib all-PEG (SL_0729). The linkers were compared for their influence on binding to HALOTAG and ABL1 in biochemical and cellular assays. All three linkers exhibited similar binding kinetics to HALOTAG in lysate and comparable inhibition of purified ABL1 indicating the change to amides or PEG had no influence on binding to either protein (FIG. 36). In cellular assays, amides reduced binding kinetics to intracellular HALOTAG and decreased ponatinib potency by 20-fold relative to CA-T4E and all PEG linkers implying substantial impact on cell permeability (FIG. 36B and FIG. 36D). These results suggest carbamates contribute to the minimal influence of CA-T4E on cell permeability.

Example 27

The following are exemplary compositions within the scope of embodiments described herein, wherein a chemoselectively-cleavable linker moiety connects a chloroalkane functional element with a 4-nitrophenyl functional element (and a control composition (PBI4440) comprising a non-cleavable linker).
4-Nitrophenylcarbamate Chloroalkanes:

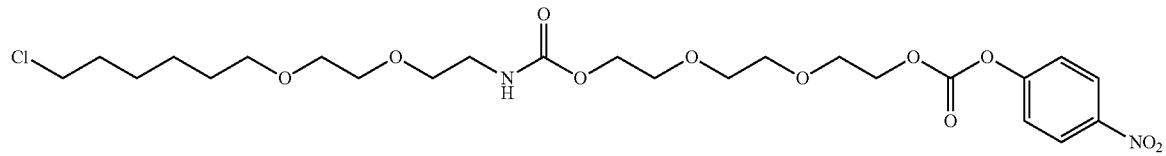

PBI4440

Synthesis of PBI4440 is described in *ACS Chem. Biol.* 2008, 3, 373-382.
Allyl Carbamate Linkers

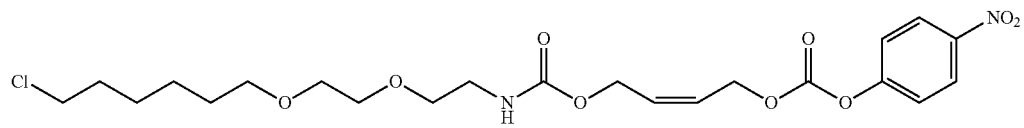

SL_0165

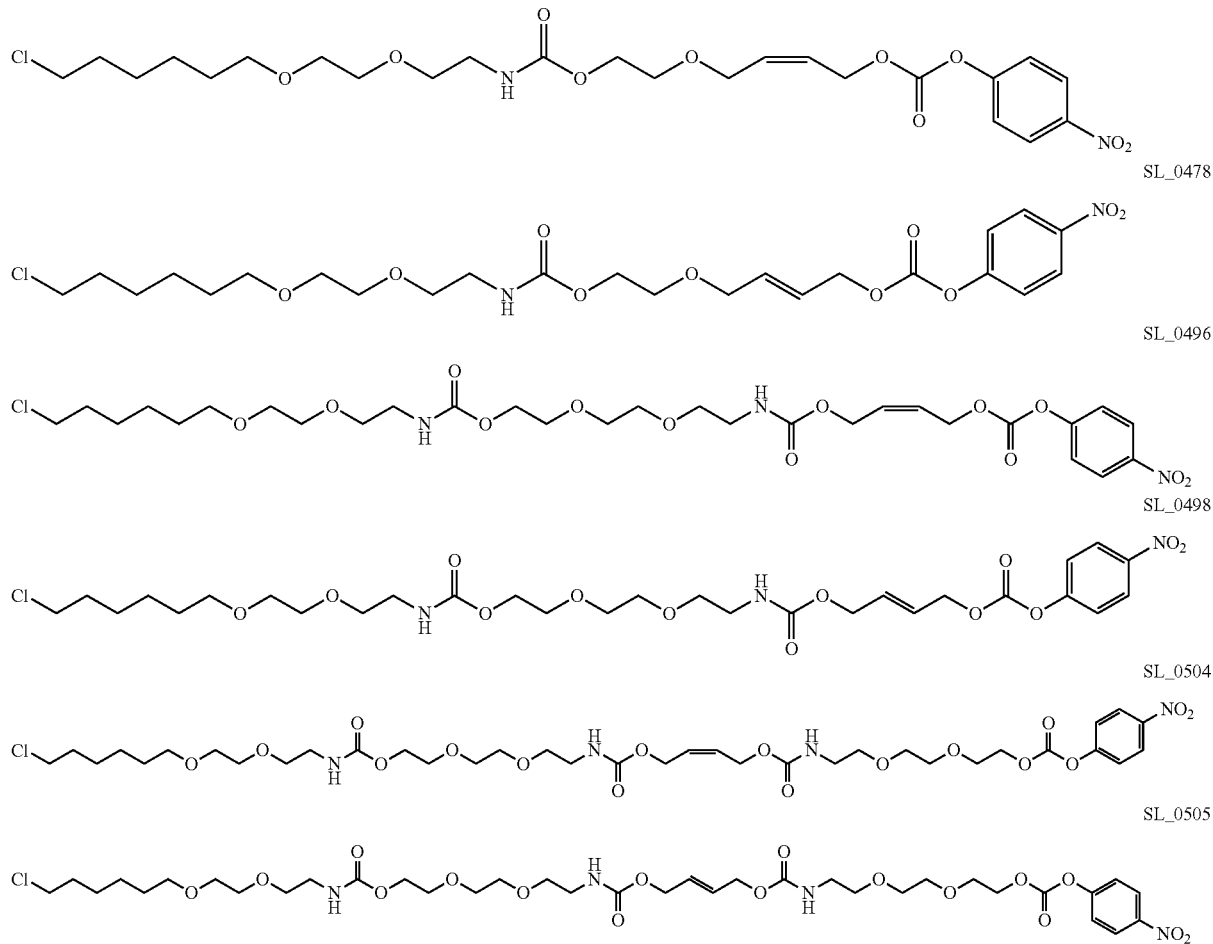

Example 28

Linker Synthesis:
General Procedure for 4-Nitrophenyl Carbamates Synthesis:
Pyridine (1.35 equiv.) and 4-nitrophenyl chloroformate (1.05 equiv.) were added to a stirred 0.25 M solution of alcohol in DCM (either at 0° C. or 25° C., as indicated on the reaction scheme) under nitrogen. The resulting solution/suspension was left at 25° C. or allowed to warm up to 25° C. (if started at 0° C.) over the period of 12 hours, at which point TLC indicated consumption of starting material. The reaction mixture was absorbed on silica and purified by silica gel chromatography (EtOAc/hexanes or MeOH/DCM).

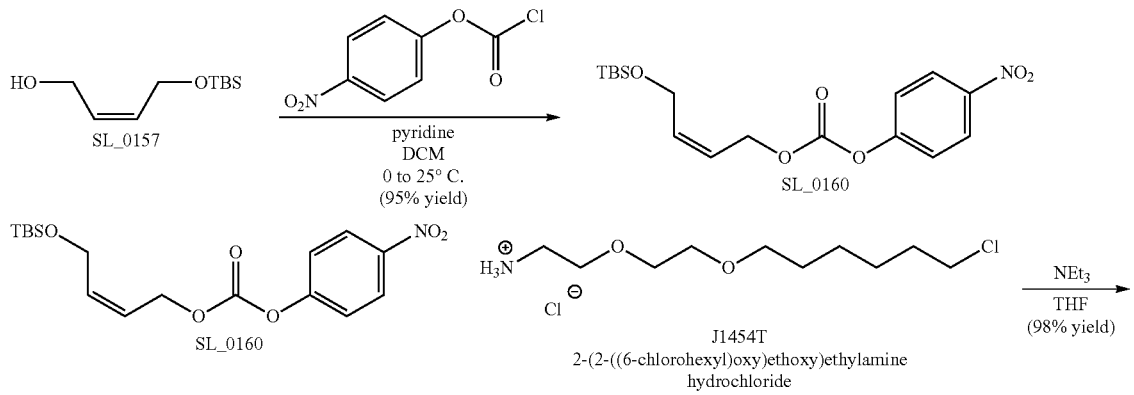

-continued

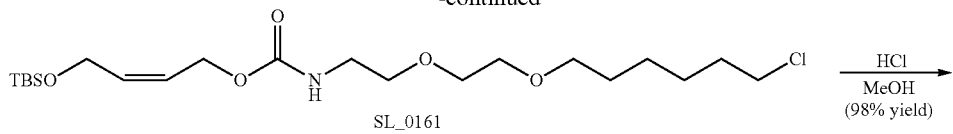

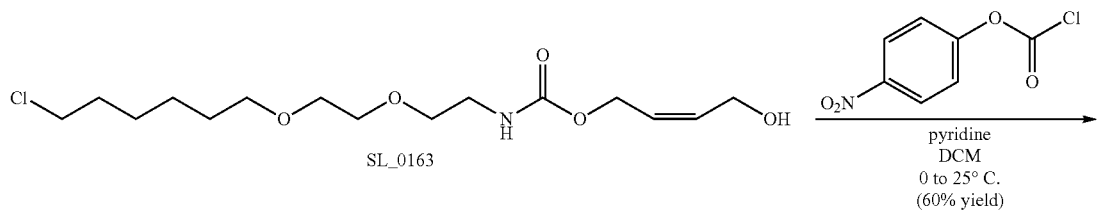

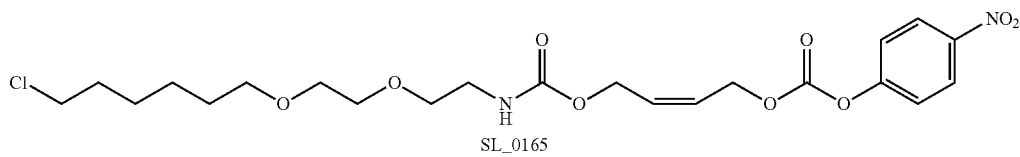

SL_0157 was synthesized according to: Nelson, B; Hiller, W; Pollex, A; Hiersemann, M. *Org. Lett.* 2011, 13, 4438.

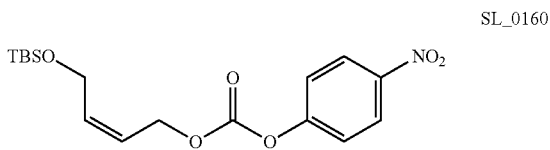 [SMILES: CC(C)(C)[Si](C)(C)OC/C=C\COC(=O)Oc1ccc([N+](=O)[O-])cc1]

Pyridine (382 µL, 4.74 mmol) and 4-nitrophenyl chloroformate (743 mg, 3.68 mmol) were added to a stirred solution of SL_0157 (710 mg, 3.51 mmol) in DCM (15 mL) 0° C. under nitrogen. The resulting solution was allowed to warm up to 25° C. over 12 hours, at which point TLC indicated consumption of starting material. The reaction mixture was absorbed on silica and purified by silica gel chromatography (0→10% EtOAc/hexanes) to provide 1.23 g (95% yield) of SL_0160 as a clear oil. $^1$H NMR (300 MHz, CDCl$_3$) δ 8.28 (d, J=9.0 Hz, 2H), 7.38 (d, J=9.1 Hz, 2H), 5.84 (dt, J=11.7, 5.7 Hz, 1H), 5.66 (dt, J=11.7, 7.0 Hz, 1H), 4.90 (d, J=7.0 Hz, 2H), 4.32 (d, J=5.7 Hz, 2H), 0.91 (s, 9H), 0.09 (s, 6H). MS (ESI+) calc'd for C$_{17}$H$_{25}$NaNO$_6$Si$^+$ [M+Na]$^+$ 390.13, found calc'd found 390.1.

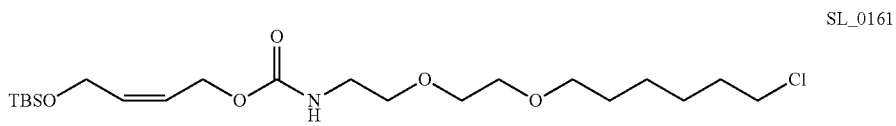 [SMILES: CC(C)(C)[Si](C)(C)OC/C=C\COC(=O)NCCOCCOCCCCCCCl]

To a solution of SL_0160 (400 mg, 1.09 mmol) was added 2-(2-((6-chlorohexyl)oxy) ethoxy) ethylamine hydrochloride (312 mg, 1.20 mmol) followed by Et$_3$N (290 µL, 20.7 mmol). The resulting yellow solution was left stirred for 18 hours at which point TLC indicated consumption of the starting material. The reaction mixture was absorbed on silica and purified by silica gel chromatography (0→30% EtOAc/hexanes) to provide 395 mg (80% yield) of SL_0161 as a clear oil. $^1$H NMR (300 MHz, CDCl$_3$) δ 5.71 (dt, J=11.4, 5.7 Hz, 1H), 5.56 (dt, J=11.3, 6.2 Hz, 1H), 5.19 (br. s, 1H), 4.63 (d, J=6.2 Hz, 2H), 4.27 (d, J=5.7 Hz, 2H), 3.67-3.50 (m, 8H), 3.47 (t, J=6.6 Hz, 2H), 3.37 (q, 5.2 Hz, 2H), 1.78 (p, J=6.8 Hz, 2H), 1.60 (p, J=6.8 Hz, 2H), 1.44-1.32 (m, 4H), 0.90 (s, 9H), 0.07 (s, 6H).

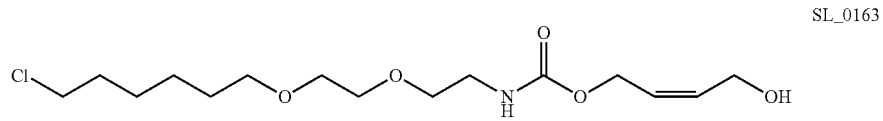 [SMILES: O=C(NCCOCCOCCCCCCCl)OC/C=C\CO]

SL_0163

To a solution of SL_0161 (395 mg, 874 µmol) in MeOH (20 mL) was added 3 drops of 2N HCl$_{(aq)}$. The resulting clear solution was left stirred for 10 minutes at which point TLC indicated consumption of the starting material. Solvent was removed in vacuo, and crude residue was purified by silica gel chromatography (0→5% MeOH/DCM) to provide 263 mg (98% yield) of SL_0163 as a clear oil. $^1$H NMR (300 MHz, CDCl$_3$) δ 5.87 (dt, J=11.5, 6.3 Hz, 0H), 5.64 (dt, J=10.8, 7.3 Hz, 0H), 5.24 (br. s, 1H), 4.67 (d, J=7.3 Hz, 1H), 4.24 (d, J=6.3 Hz, 1H), 3.65-3.51 (m, 8H), 3.46 (t, J=6.6 Hz, 2H), 3.36 (q, J=5.0 Hz, 2H), 1.78 (p, J=6.7 Hz, 2H), 1.60 (q, J=6.9 Hz, 2H), 1.43 (m, 4H). MS (ESI+) calc'd for C$_{15}$H$_{29}$ClNO$_5^+$ [M+H]$^+$ 338.17, found 338.1.

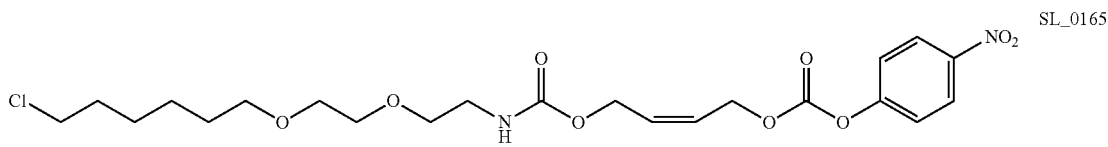 [SMILES: O=C(NCCOCCOCCCCCCCl)OC/C=C\COC(=O)Oc1ccc([N+](=O)[O-])cc1]

SL_0165

Pyridine (57 µL, 0.7 mmol) and 4-nitrophenyl chloroformate (110 mg, 0.55 mmol) were added to a stirred solution of SL_0163 (177 mg, 524 µmol) in DCM (15 mL) 0° C. under nitrogen. The resulting solution was allowed to warm up to 25° C. over 16 hours, at which point TLC indicated consumption of starting material. The reaction mixture was absorbed on silica and purified by silica gel chromatography (0→50% EtOAc/hexanes) to provide 159 mg (60% yield) of SL_0165 as a clear oil. $^1$H NMR (300 MHz, CDCl$_3$) δ 8.28 (d, J=9.1 Hz, 2H), 7.39 (d, J=9.1 Hz, 2H), 5.93-5.75 (m, 2H), 5.23 (br. s, 1H), 4.90 (d, J=5.8 Hz, 2H), 4.71 (d, J=5.3 Hz, 2H), 3.65-3.51 (m, 8H), 3.46 (t, J=6.4 Hz, 2H), 3.38 (q, J=4.9 Hz, 2H), 1.78 (p, J=6.6 Hz, 2H), 1.61 (p, J=6.6 Hz, 2H), 1.50-1.34 (m, 4H). MS (ESI+) calc'd for C$_{22}$H$_{32}$ClN$_2$O$_9^+$ [M+H]$^+$ 503.18, found 503.1.

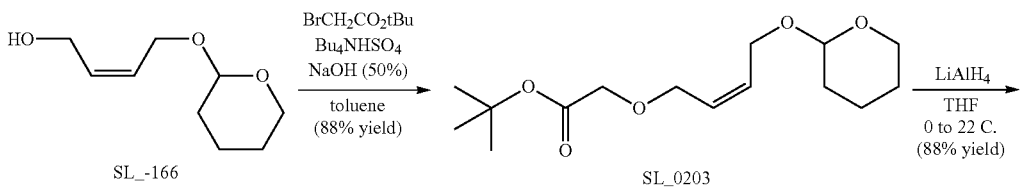

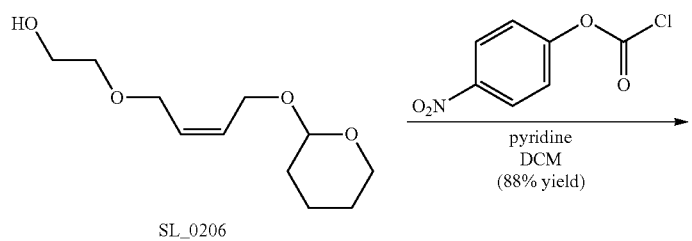

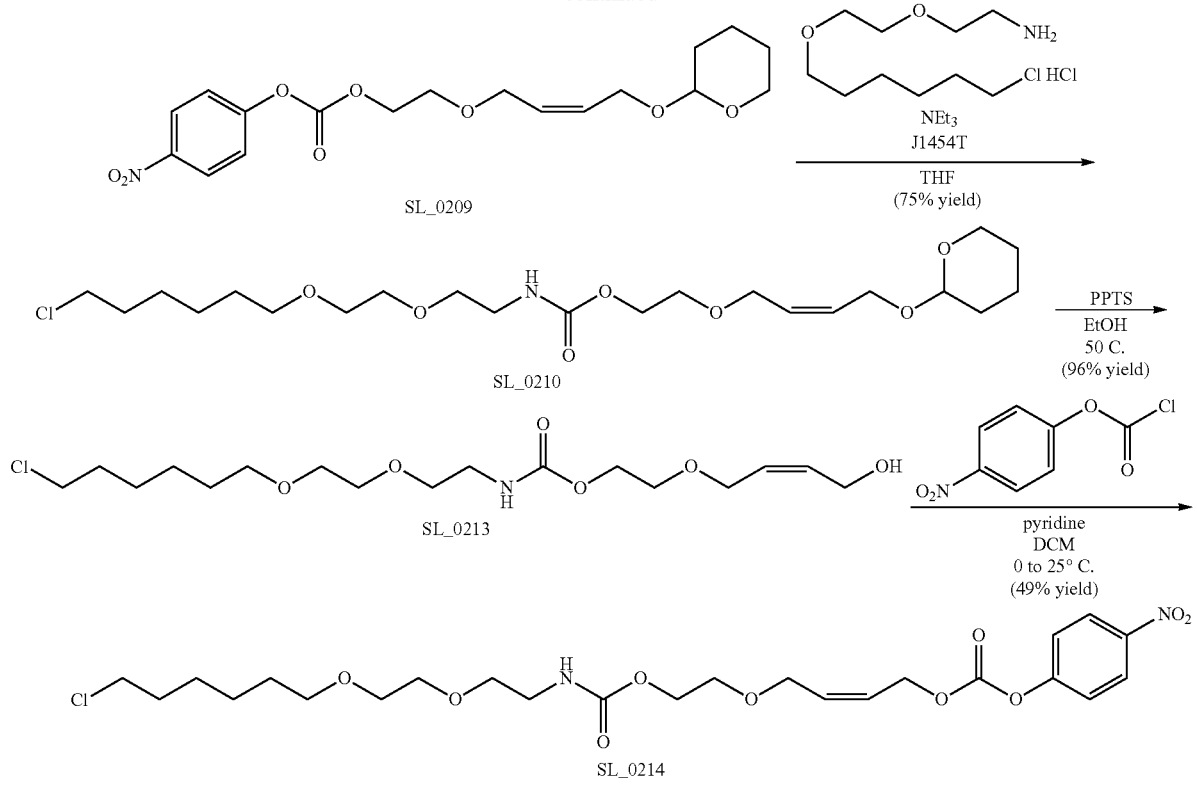

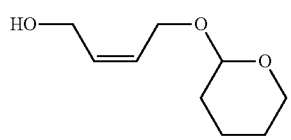

SL_0166 was synthesized according to: Könning, D; Hiller, W; Christmann, M. *Org. Lett.* 2012, 14, 5258-5261.

SL_0203

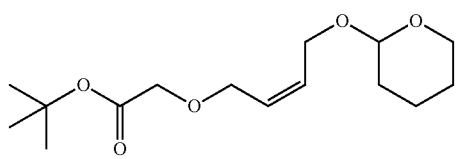

To a solution of SL_0166 (230 mg, 1.34 mmol) in toluene (2 mL) was added 50% aqueous NaOH (2.5 mL) followed by Bu₄NHSO₄ at 22° C. To the resulting vigorously stirred viscous mixture was slowly added tertbutylbromoacetate (0.59 mL, 4 mmol). The resulting solution was left stirred vigorously at 22° C. over 20 hours, at which point TLC analysis indicated consumption of starting material. 5 mL H₂O was added and 25 mL diethyl ether, aqueous layer separated and extracted 2×25 mL diethyl ether. Organic layers were combined, dried MgSO4 and concentrated in vacuo. Crude residue was purified by silica gel chromatography (0→30% EtOAc/hexanes) to provide 357 mg (93% yield) of SL_0203 as a clear oil. $^1$H NMR (300 MHz, CDCl₃) δ 5.76 (m, 2H), 4.62 (m, 1H), 4.27 (dd, J=12.5, 4.4 Hz, 1H), 4.18 (d, J=4.9 Hz, 2H), 4.09 (dd, J=12.6, 5.4 Hz, 0H), 3.95 (s, 2H), 3.85 (m, 1H), 3.52 (m, 1H), 1.90-1.70 (m, 2H), 1.62-1.51 (m, 4H), 1.48 (s, 9H).

SL_0206

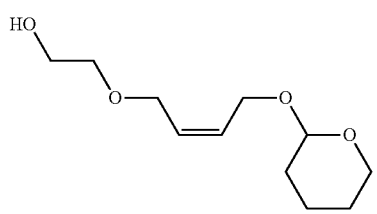

To a flame-dried 50 mL flask equipped with stir bar was added solution of SL_0203 (357 mg, 1.25 mmol) in THF (10 mL) under nitrogen and solution was cooled to 0° C. 1M LiAlH₄ solution in THF (6.2 mL, 6.2 mmol) was slowly added through syringe and reaction mixture was left to warm up to 22° C. overnight. After 16 hours TLC analysis indicated complete consumption of starting material, and the reaction mixture was cooled back to 0° C. and quenched with 30% aq. Rochelle salt solution (2 mL) while stirred vigorously. After 30 minutes white precipitate was filtered out and filtrate washed with THF (100 mL). THF solutions were combined and solvent was removed in vacuo. Crude residue was purified by silica gel chromatography (0→60% EtOAc/hexanes) to provide 197 mg (73% yield) of SL_0206 as a clear oil. $^1$H NMR (300 MHz, CDCl₃) δ 5.79-5.72 (m, 2H), 4.66 (m, 1H), 4.30-4.20 (m, 1H), 4.19-4.05 (m, 3H), 3.90-3.83 (m, 1H), 3.76-3.71 (m, 2H), 3.59-3.46 (m, 3H), 1.91-1.47 (m, 6H, overlap with H₂O). MS (ESI+) calc'd for $C_{11}H_{20}O_4Li^+$ [M+Li]⁺ 223.15, found 223.39.

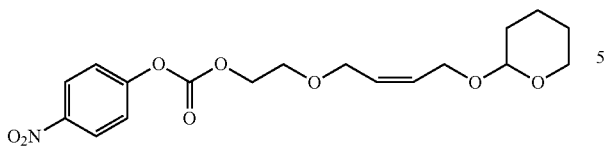

SL_0209

Pyridine (147 μL, 1.82 mmol) and 4-nitrophenyl chloroformate (275 mg, 1.37 mmol) were added to a stirred solution of SL_0206 (197 mg, 911 μmol) in DCM (20 mL) at 22° C. under nitrogen. The resulting solution was left stirred at 22° C. over 16 hours, at which point TLC indicated consumption of starting material. The reaction mixture was absorbed on silica and purified by silica gel chromatography (0→30% EtOAc/hexanes) to provide 307 mg (88% yield) of SL_0209 as a clear oil. $^1$H NMR (300 MHz, CDCl$_3$) δ 8.28 (d, J=9.2 Hz, 2H), 7.39 (d, J=9.2 Hz, 2H), 5.76 (m, 2H), 4.63 (t, J=3.5 Hz, 1H), 4.44 (m, 2H), 4.29 (dd, J=12.8, 5.4 Hz, 1H), 4.17 (d, J=5.5 Hz 2H), 4.10 (dd, J=12.8, 5.8 Hz, 1H), 3.86 (ddd, J=11.1, 7.6, 3.5 Hz, 1H), 3.74 (m, 2H), 3.52 (m, 1H), 1.88-1.66 (m, 2H), 1.61-1.47 (m, 4H, overlap with H$_2$O).

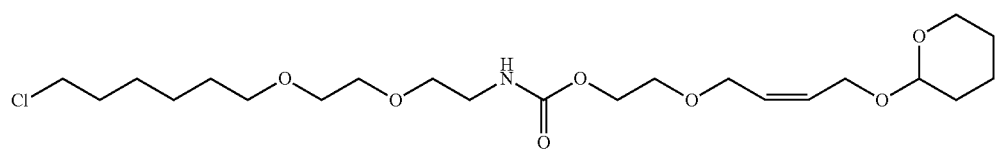

SL_0210

To a solution of SL_0209 (307 mg, 805 μmol) in THF (20 mL) was added J1454T (230 mg, 886 μmol) followed by triethylamine (340 μL, 2.41 mmol), white precipitate forms (NEt$_3$HCl). The resulting suspension was left stirred at 22° C. for 20 hours at which point TLC analysis indicated complete consumption of starting material. The solvent was removed in vacuo, and the residue was purified by silica gel chromatography (0→60% EtOAc/hexanes) to provide 280 mg (75% yield) of SL_0210 as a clear oil. $^1$H NMR (300 MHz, CDCl$_3$) δ 5.82-5.66 (m, 2H), 5.29 (br. s, 1H), 4.63 (m, 1H), 4.31-4.19 (m, 3H), 4.14-4.04 (m, 3H), 3.89-3.79 (m, 1H), 3.65-3.50 (m, 11H), 3.49-3.44 (m, 2H), 3.40-3.33 (m, 2H), 1.84-1.72 (m, 3H), 1.54-1.57 (m, 6H, overlap with H$_2$O), 1.94-1.31 (m, 5H, overlap with H$_2$O). MS (ESI+) calc'd for C$_{22}$H$_{41}$ClNO$_7{}^+$ [M+H]$^+$ 466.25, found 466.43.

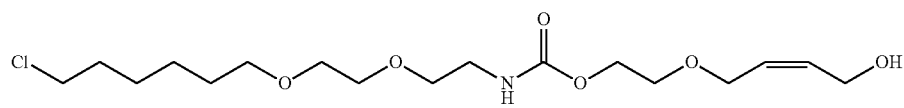

SL_0213

To a 20 mL microwave vial equipped with stir bar, was added SL_0210 (280 mg, 600 μmol), PPTS (15.1 mg, 60.0 μmol) and EtOH (10 mL). The resulting solution was heated in microwave at 50° C. for 60 minutes, at which point analysis indicated complete consumption of starting material. The solvent was removed in vacuo, and the residue was purified by silica gel chromatography (0→10% MeOH/DCM) to provide 220 mg (96% yield) of SL_0213 as a clear oil. MS (ESI+) calc'd for C$_{17}$H$_{33}$ClNO$_6{}^+$ [M+H]$^+$ 382.20, found 382.57.

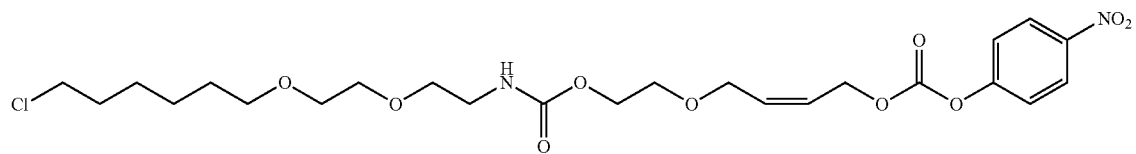

SL_0214

Pyridine (93 μL, 1.2 mmol) and 4-nitrophenyl chloroformate (174 mg, 864 μmol) were added to a stirred solution of SL_0213 (220 mg, 576 μmol) in DCM (15 mL) at 22° C. under nitrogen. The resulting solution was left stirred at 22° C. over 16 hours, at which point TLC indicated consumption of starting material. The reaction mixture was absorbed on silica and purified by silica gel chromatography (0→70% EtOAc/hexanes) to provide 153 mg (49% yield) of SL_0214 as a clear oil. $^1$H NMR (300 MHz, CDCl$_3$) δ 8.28 (d, J=9.1 Hz, 2H), 7.39 (d, J=9.1 Hz, 2H), 5.93-5.74 (m, 2H), 5.29 (br. s, 1H), 4.89 (d, J=6.4 Hz, 2H), 4.23 (m, 2H), 4.18 (d, J=5.7 Hz, 2H), 3.65 (m, 2H), 3.61-3.50 (m, 8H), 3.45 (t, J=6.6 Hz, 2H), 3.37 (q, J=5.3 Hz, 2H), 1.78 (p, J=6.7 Hz, 2H), 1.60 (dt, J=13.6, 6.5 Hz, 2H, overlap with H$_2$O), 1.50-1.33 (m, 4H). MS (ESI+) calc'd for C$_{24}$H$_{36}$ClN$_2$O$_{10}$$^+$ [M+H]$^+$ 547.21, found 547.20.

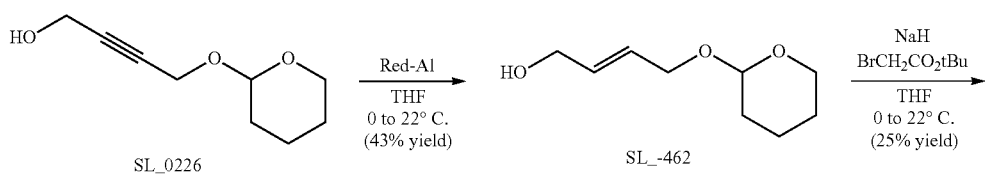

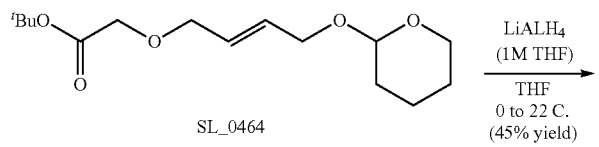

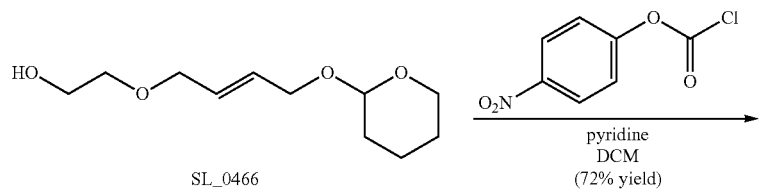

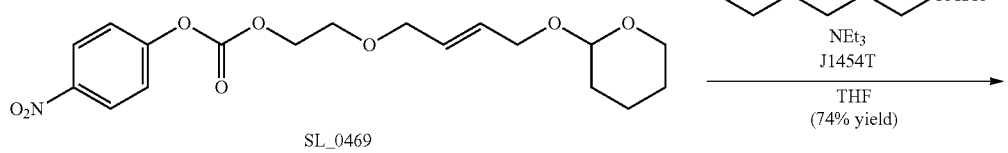

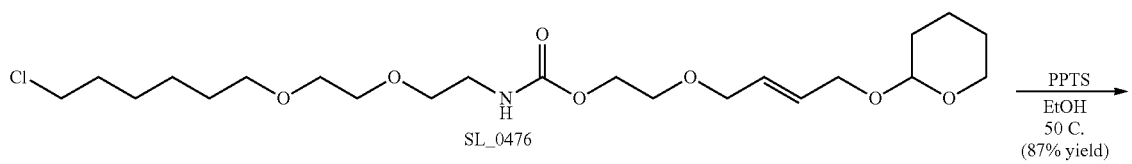

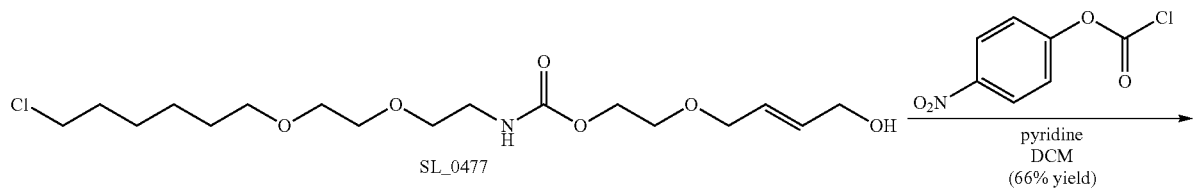

-continued

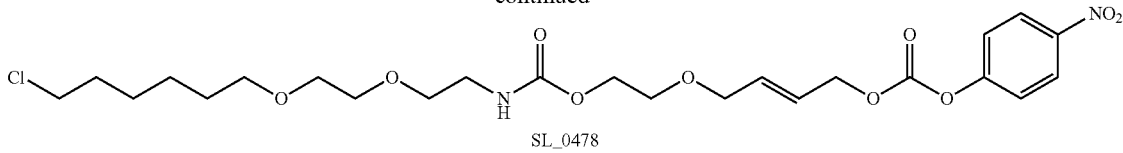
SL_0478

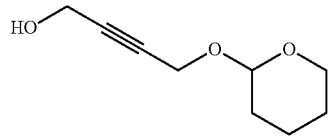

SL_0226 was synthesized according to: Konning, D; Hiller, W; Christmann, M. *Org. Lett.* 2012, 14, 5258-5261.

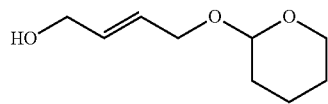
SL_0462

250 mL oven dried round bottom flask, equipped with a stir bar was charged with SL_0226 (3.48 g, 20.5 mmol). SL_0226 was dried by azeotrope with toluene (3×). Dry THF (100 mL) was added through cannula under $N_2$ and stirred solution was cooled to 0° C. on ice bath. Red-Al (7.12 mL, 25.6 mmol, 70% in toluene) was added drop wise to the stirred solution over the period of 15 minutes. The reaction mixture was left stirred at 0° C. for 60 minutes and allowed to warm up to 22° C. for another 60 minutes, at which point TLC analysis indicated almost complete disappearance of starting material. The reaction mixture was cooled back to 0° C. and quenched with 30% aqueous solution of Rochelle salt (50 mL), extracted 3×150 mL $Et_2O$, dried MgSO4, filtered and concentrated. Crude residue was purified by silica gel chromatography (0→70% EtOAc/hexanes) to provide 1.50 g (42% yield) of SL_0462 as a clear oil. $^1H$ NMR (300 MHz, $CDCl_3$) δ 5.98-5.79 (m, 2H), 4.65 (dd, J=4.0, 2.8 Hz, 1H), 4.26 (ddq, J=12.8, 4.9, 2.8 Hz, 1H), 4.19-4.16 (m, 2H), 4.00 (ddq, J=12.0, 5.8, 1.2 Hz, 1H), 3.88 (m, 1H), 3.52 (m, 1H), 1.91-1.68 (m, 2H), 1.66-1.49 (m, 4H).

SL_0464

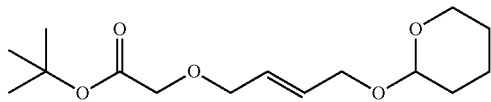

A 100 mL oven-dried flask was charged with NaH (358 mg, 60% dispersion mineral oil, 8.94 mmol), followed by THF (25 mL) under $N_2$. In a separate flask SL_0462 (1.40 g, 8.13 mmol) was dried by azeotrope with toluene (3×), and diluted with THF (25 mL). To the NaH/THF suspension pre-cooled to 0° C., was added the solution of SL_0462 via cannula. This brown mixture was stirred for 30 min at 0° C., after which time tBu-bromoacetate (1.38 mL, 9.35 mmol) was added dropwise. The resulting slurry was warmed to 22° C. and stirred for 18 h. Water (75 mL) was added, and the reaction extracted with $Et_2O$ (3×75 mL). The organic layer was dried ($MgSO_4$), concentrated, and purified by flash chromatography (0→50% EtOAc/hexanes) to provide 574 mg (25% yield) of SL_0464 as a clear oil. $^1H$ NMR (300 MHz, $CDCl_3$) δ 5.99-5.76 (m, 2H), 4.68 (d, 5.7 Hz, 1H), 4.64 (t, J=3.4 Hz, 1H), 4.31-4.22 (m, 1H), 4.11-4.07 (m, 1H), 4.03-3.82 (m, 4H), 3.55-3.47 (m, 1H), 1.92-1.78 (m, 1H), 1.77-1.66 (m, 1H), 1.66-4.51 (m, 4H), 1.48 (s, 9H). MS (ESI+) calc'd for $C_{15}H_{26}O_5Na^+$ [M+Na]$^+$ 309.17, found 309.22.

SL_0466

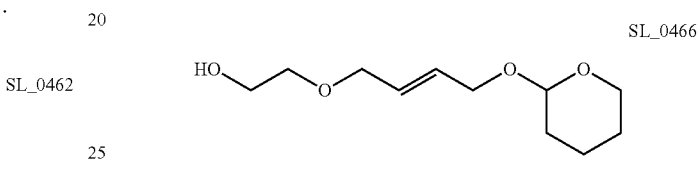

To a solution of SL_0464 (570 mg, 1.99 mmol) in THF (20 mL) at 0° C. was added 1M ethereal solution of $LiAlH_4$ (10 mL, 10 mmol). The reaction mixture was allowed to warm up to 22° C. and left stirred for 22 hours, at which time reaction mixture was cooled back to 0° C. and quenched by slow drop wise addition of 30% aqueous Rochelle salt until gas evolution ceased. Quenched reaction mixture was left stirred vigorously for another 30 minutes and white precipitate was filtered out on celite pad. Celite pad was washed with extra 50 mL THF and filtrate concentrated and purified by flash chromatography (0→100% EtOAc/hexanes) to provide 195 mg (45% yield) of SL_0466 as a clear oil. $^1H$ NMR (300 MHz, $CDCl_3$) δ 5.91-5.97 (m, 2H), 4.64 (dd, J=4.0, 2.9 Hz, 1H), 4.30-4.22 (m, 1H), 4.06-4.03 (m, 2H), 4.03-3.96 (m, 1H), 3.95-3.83 (m, 1H), 3.77-3.73 (m, 2H), 3.58-3.48 (m, 3H), 1.91-1.50 (m, 6H, overlap with $H_2O$). MS (ESI+) calc'd for $C_{11}H_{20}NaO_4^+$ [M+Na]$^+$ 239.13, found 239.13.

SL_0469

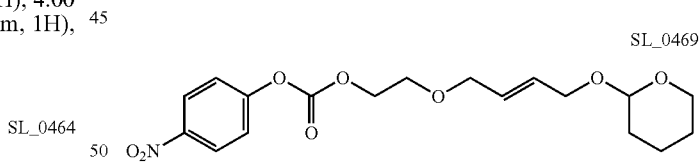

Pyridine (111 μL, 1.38 mmol) and 4-nitrophenyl chloroformate (208 mg, 1.03 mmol) were added to a stirred solution of SL_0466 (149 mg, 689 μmol) in DCM (15 mL) at 22° C. under nitrogen. The resulting solution was left stirred at 22° C. over 16 hours, at which point TLC indicated consumption of starting material. The reaction mixture was absorbed on silica and purified by silica gel chromatography (0→40% EtOAc/hexanes) to provide 188 mg (72% yield) of SL_0469 as a clear oil. $^1H$ NMR (300 MHz, DMSO-$d_6$) δ 8.32 (d, J=9.2 Hz, 2H), 7.57 (d, J=9.2 Hz, 2H), 5.82 (dd, J=15.7, 4.0 Hz, 1H), 5.74 (dd, J=15.7, 4.3 Hz, 1H), 4.59 (m, 1H), 4.40-4.37 (m, 2H), 4.14 (dd, J=12.9, 3.6 Hz, 1H), 4.01 (d, J=3.7 Hz, 2H), 3.93 (dd, J=12.8, 3.9 Hz, 1H), 3.77-3.71 (m, 1H), 3.70-3.661 (m, 2H), 3.46-3.39 (m, 1H), 1.78-1.56 (m, 2H), 1.53-1.40 (m, 4H). MS (ESI+) calc'd for $C_{18}H_{23}NaNO_4^+$ [M+H]$^+$ 404.13, found 404.1.

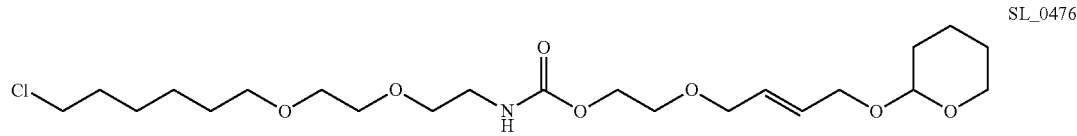 [SMILES: O=C(NCCOCCOCCCCCCCl)OCCOC/C=C/COC1CCCCO1]

SL_0476

To a solution of SL_0469 (104 mg, 273 µmol) in THF (10 mL) was added J1454T (78 mg, 300 µmol) followed by triethylamine (190 µL, 1.36 mmol), white precipitate forms (NEt₃HCl). The resulting suspension was left stirred at 22° C. for 5 hours at which point TLC analysis indicated complete consumption of starting material. The solvent was removed in vacuo, and the residue was purified by silica gel chromatography (0→100% EtOAc/hexanes) to provide 94 mg (74% yield) of SL_0476 as a clear oil. $^1$H NMR (300 MHz, DMSO-d6) δ 7.17 (t, J=5.6 Hz, 1H), 5.82-5.67 (m, 2H), 4.58 (s, 1H), 4.12 (m, 1H), 4.05 (m, 2H), 3.97-3.87 (m, 3H), 3.73 (m, 1H), 3.62 (t, J=6.6 Hz, 2H), 3.53 (m, 2H), 3.49-3.45 (m, 5H), 3.42-3.34 (m, 4H), 3.11 (q, J=6.0 Hz, 2H), 1.75-1.57 (m, 3H), 1.54-1.23 (m, 11H).

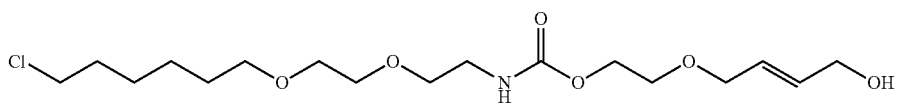

SL_0477

To a 10 mL microwave vial equipped with stir bar, was added SL_0477 (94.0 mg, 202 µmol), PPTS (5.1 mg, 20 µmol) and EtOH (5 mL). The resulting solution was heated in microwave at 50° C. for 60 minutes, at which point analysis indicated complete consumption of starting material. The solvent was removed in vacuo, and the residue was purified by silica gel chromatography (0→10% MeOH/DCM) to provide 67 mg (87% yield) of SL_0477 as a clear oil. $^1$H NMR (300 MHz, DMSO-d₆) δ 7.17 (t, J=5.7 Hz, 1H), 5.80 (dtd, J=15.7, 3.7, 0.7 Hz, 1H), 5.64 (dtt, J=15.7, 5.6, 1.3 Hz, 1H), 4.70 (t, J=5.4 Hz, 1H), 4.05 (m, 2H), 3.93 (d, J=4.4 Hz, 4H), 3.62 (t, J=6.6 Hz, 2H), 3.54-3.49 (m, 2H), 3.49-3.44 (m, 4H) 3.42-3.34 (m, 4H), 3.11 (q, J=6.0 Hz, 2H), 1.71 (p, J=6.6 Hz, 2H), 1.49 (p, J=6.8 Hz, 2H), 1.41-1.26 (m, 4H).

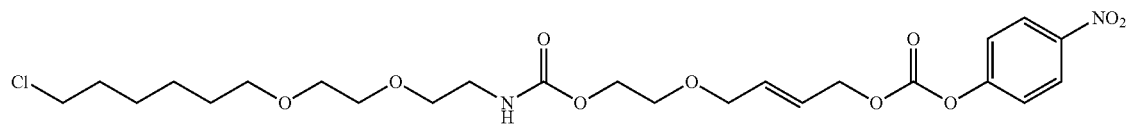

SL_0478

Pyridine (28 µL, 350 µmol) and 4-nitrophenyl chloroformate (53 mg, 263 µmol) were added to a stirred solution of SL_0477 (67.0 mg, 175 µmol) in DCM (5 mL) at 22° C. under nitrogen. The resulting solution was left stirred at 22° C. over 18 hours, at which point TLC indicated consumption of starting material. The reaction mixture was absorbed on silica and purified by silica gel chromatography (0→100% EtOAc/hexanes) to provide 63 mg (66% yield) of SL_0478 as a clear oil. $^1$H NMR (300 MHz, DMSO-d₆) δ 8.32 (d, J=9.1 Hz, 2H), 7.57 (d, J=9.1 Hz, 2H), 7.18 (t, J=5.2 Hz, 1H), 6.01-5.81 (m, 2H), 4.77 (d, J=5.2 Hz, 2H), 4.07 (m, 2H), 4.00 (d, J=4.1 Hz, 2H), 3.61 (t, J=6.6 Hz, 2H), 3.56 (m, 2H), 3.46 (m, 4H), 3.39 (m, 4H), 3.11 (q, J=5.9 Hz, 2H), 1.70 (p, J=6.7 Hz, 2H), 1.48 (p, J=6.6 Hz, 2H), 1.41-1.23 (m, 4H).

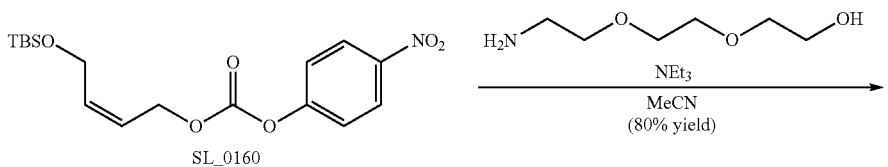

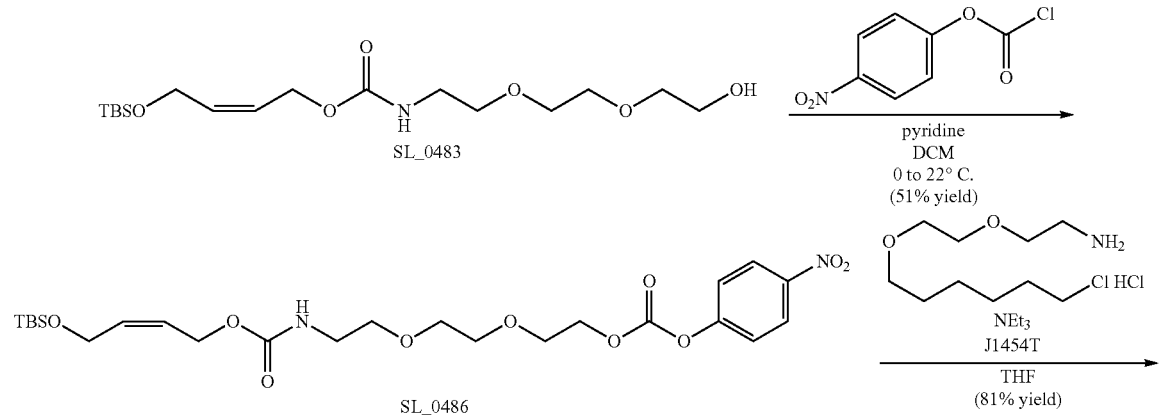

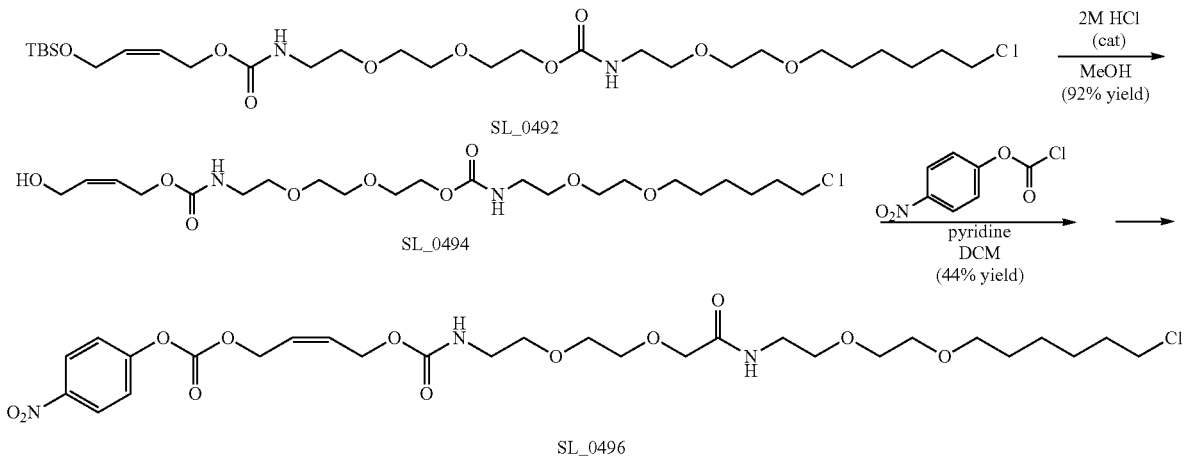

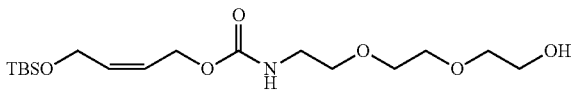

SL_0483

To a solution of SL_0160 (269 mg, 732 µmol) in MeCN (10 mL) was added 2-(2-(2-aminoethoxy)ethoxy)ethan-1-ol (109 mg, 732 µmol) followed by NEt$_3$ (200 µL, 145 µmol). The resulting yellow solution was left at 22° C. for 24 hours, at which point TLC analysis indicated complete consumption of starting material. Solvent was removed in vacuo, and crude residue was purified by silica gel chromatography (0→100% EtOAc/hexanes) to provide 220 mg (80% yield) of SL_0483 as a clear oil. $^1$H NMR (300 MHz, DMSO-d$_6$) δ 7.15 (t, J=5.4 Hz, 1H), 5.62 (dt, J=11.4, 5.7 Hz, 1H), 5.49 (dt, J=11.4, 6.5 Hz, 1H), 4.57-4.51 (m, 3H), 4.24 (d, J=5.7 Hz, 2H) 3.51-3.46 (m, 6H), 3.42-3.37 (m, 4H), 3.11 (q, J=5.9 Hz, 2H), 0.87 (s, 9H), 0.05 (s, 6H). MS (ESI+) calc'd for C$_{17}$H$_{35}$NaNO$_6$Si$^+$ [M+H]$^+$ 400.21, found 400.2.

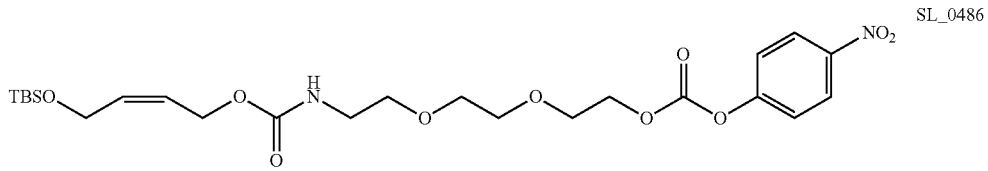 [SMILES: CC(C)(C)[Si](C)(C)OC/C=C\COC(=O)NCCOCCOCCOC(=O)Oc1ccc([N+](=O)[O-])cc1]

Pyridine (58 μL, 0.7 mmol) and 4-nitrophenyl chloroformate (113 mg, 0.56 mmol) were added to a stirred solution of SL_0483 (202 mg, 535 μmol) in DCM (15 mL) at 0° C. under nitrogen. The resulting solution was allowed to warm up to 25° C. over 20 hours, at which point TLC indicated consumption of starting material. The reaction mixture was absorbed on silica and purified by silica gel chromatography (0→40% EtOAc/hexanes) to provide 147 mg (51% yield) of SL_0486 as a clear oil. ¹H NMR (300 MHz, DMSO-$d_6$) δ 8.32 (d, J=9.2 Hz, 2H), 7.56 (d, J=9.2 Hz, 2H), 7.16 (t, J=5.5 Hz, 1H), 5.61 (dtt, J=11.5, 5.5, 1.3 Hz, 1H), 5.49 (dtt, J=11.5, 6.2, 1.7 Hz, 1H), 4.52 (m, 2H), 4.36 (m, 2H), 4.23 (d, J=5.8 Hz, 2H), 3.71 (m, 2H), 3.59-3.55 (m, 2H), 3.54-3.50 (m, 2H), 3.41 (t, J=6.0 Hz, 2H), 3.12 (q, J=6.0 Hz, 2H), 0.86 (s, 9H), 0.04 (s, 5H).

SL_0492

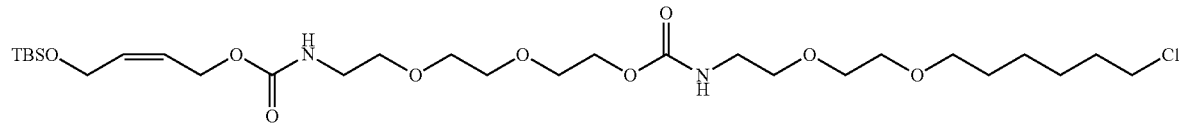

To a solution of SL_0486 (134 mg, 247 μmol) in THF (15 mL) was added J1454T (71 mg, 272 μmol) followed by triethylamine (172 μL, 1.23 μmol), murky solution forms (NEt$_3$.HCl precipitates). The resulting suspension was left stirred at 22° C. for 5 hours at which point TLC analysis indicated complete consumption of starting material. The solvent was removed in vacuo, and the residue was purified by silica gel chromatography (0→10% MeOH/DCM) to provide 126 mg (81% yield) of SL_0492 as a clear oil. ¹H NMR (300 MHz, DMSO-$d_6$) δ 7.16 (m, 2H), 5.62 (dt, J=11.2, 5.8 Hz, 1H), 5.49 (dt, J=12.6, 6.4 Hz, 1H), 4.53 (d, J=6.3 Hz, 2H), 4.24 (d, J=5.6 Hz, 2H), 4.04 (m, 2H), 3.62 (t, J=6.6 Hz, 2H), 3.55 (m, 2H), 3.52-3.45 (m, 8H), 3.42 3.34 (m, 6H), 3.11 (q, J=5.6 Hz, 4H), 1.70 (p, J=6.7 Hz, 2H), 1.49 (p, J=6.8 Hz, 2H), 1.38 (m, 4H), 0.86 (s, 9H), 0.05 (s, 5H).

SL_0494

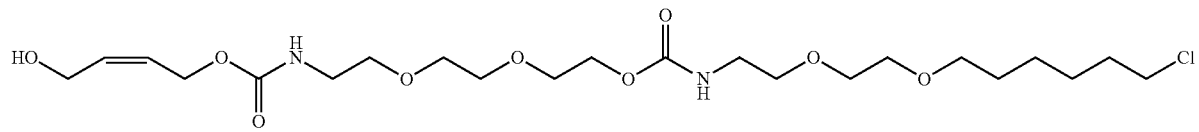

To a solution of SL_0494 (113 mg, 180 μmol) in MeOH (10 mL) was added 2 drops of 2N HCl$_{(aq)}$. The resulting clear solution was left stirred for 25 minutes at which point TLC indicated consumption of the starting material. Solvent was removed in vacuo, and crude residue was purified by silica gel chromatography (0→10% MeOH/DCM) to provide 85 mg (92% yield) of SL_0494 as a clear oil. ¹H NMR (300 MHz, DMSO-$d_6$) δ 7.15 (m, 2H), 5.64 (dt, J=11.8, 6.1 Hz, 1H), 5.46 (dt, J=11.5, 6.5 Hz, 1H), 4.72 (t, J=5.5 Hz, 1H), 4.52 (d, J=6.6 Hz, 2H), 4.03 (m, 4H), 3.62 (t, J=6.6 Hz, 2H), 3.55 (t, J=4.8 Hz, 2H), 3.51-3.44 (m, 8H), 3.42-3.32 (m, 6H), 3.11 (m, 4H), 1.71 (m, 2H), 1.49 (p, J=6.9 Hz, 2H), 1.41-1.25 (m, 4H).

SL_0496

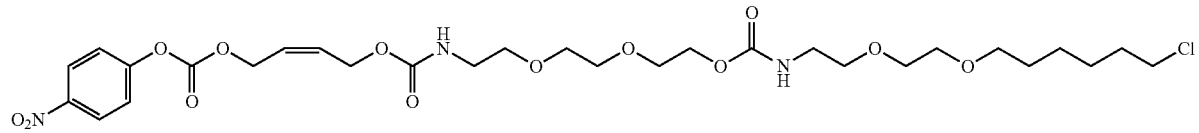

Pyridine (37 μL, 460 μmol) and 4-nitrophenyl chloroformate (47 mg, 230 μmol) were added to a stirred solution of SL_0494 (79 mg, 150 μmol) in DCM (10 mL) at 22° C. under nitrogen. The resulting solution was left stirred at 22° C. over 16 hours, at which point TLC indicated consumption of starting material. The reaction mixture was absorbed on silica and purified by silica gel chromatography (0→5% MeOH/DCM) to provide 46 mg (44% yield) of SL_0496 as a clear oil. $^1$H NMR (300 MHz, DMSO-$d_6$) δ 8.32 (d, J=8.7 Hz, 2H), 7.57 (d, J=8.7 Hz, 2H), 7.19 (m, 2H), 5.78 (m, 2H), 4.89 (d, J=4.4 Hz, 2H), 4.60 (d, J=4.3 Hz, 2H), 4.03 (t, J=4.7 Hz, 2H), 3.61 (t, J=6.8 Hz, 2H), 3.55 (t, J=4.8 Hz, 2H), 3.52-3.44 (m, 8H), 3.42-3.32 (m, 6H), 3.12 (p, J=5.8 Hz, 4H), 1.70 (p, J=6.7 Hz, 2H), 1.48 (p, J=6.8 Hz, 2H), 1.41-1.22 (m, 4H).

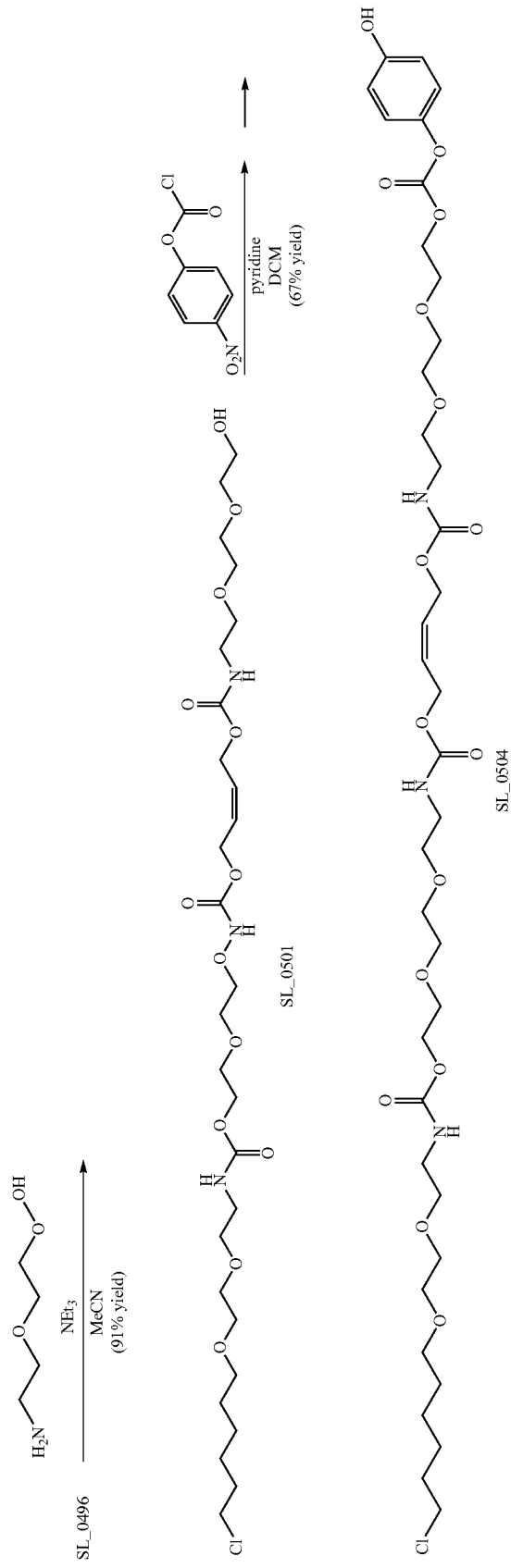

SL_0501

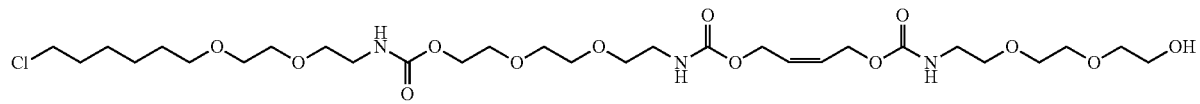

To a solution of SL_0496 (40 mg, 59 µmol) in MeCN (15 mL) was added 2-(2-(2-aminoethoxy)ethoxy)ethan-1-ol (8.8 mg, 59 µmol) followed by NEt₃ (25 µL, 177 µmol). The resulting yellow solution was left at 22° C. for 16 hours, at which point TLC analysis indicated complete consumption of starting material. Solvent was removed in vacuo, and crude residue was purified by silica gel chromatography (0→30% MeOH/DCM) to provide 37 mg (91% yield) of SL_0501 as a clear oil. $^1$H NMR (300 MHz, DMSO-d$_6$) δ 7.22-7.15 (m, 3H), 5.65-5.61 (m, 2H), 4.60-4.50 (m, 5H), 3.62 (t, J=6.6 Hz, 2H), 3.55 (dd, J=4.0, 5.5 Hz, 2H), 3.52-3.45 (m, 14H), 3.43-3.36 (m, 10H), 3.15-3.07 (m, 6H), 1.70 (p, J=6.5 Hz, 2H), 1.48 (p, J=6.8 Hz, 2H), 1.42-1.25 (m, 4H). MS (ESI+) calc'd for C$_{29}$H$_{55}$ClN$_3$O$_{13}$$^+$ [M+H]$^+$ 688.34, found 688.3.

Pyridine (21 µL, 250 µmol) and 4-nitrophenyl chloroformate (21 mg, 100 µmol) were added to a stirred solution of SL_0504 (35 mg, 51 µmol) in DCM (10 mL) at 22° C. under nitrogen. The resulting solution was left stirred at 22° C. over 16 hours, at which point TLC indicated consumption of starting material. The reaction mixture was absorbed on silica and purified by silica gel chromatography (0→5% MeOH/DCM) to provide 29 mg (67% yield) of SL_0504 as a clear oil. $^1$H NMR (300 MHz, DMSO-d$_6$) δ 8.32 (d, J=8.7 Hz, 2H), 7.56 (d, J=8.7 Hz,

SL_0504

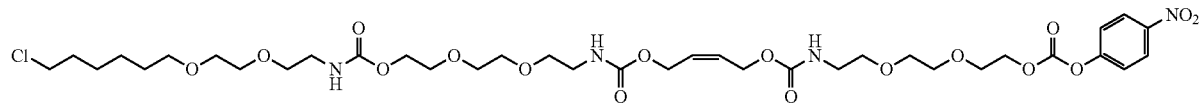

2H), 7.21-7.13 (m, 3H), 5.65-5.60 (m, 2H), 4.57-4.53 (m, 4H), 4.38-4.35 (m, 2H), 4.05-4.01 (m, 2H), 3.72-3.69 (m, 2H), 3.62 (t, J=6.5 Hz, 2H), 3.58-3.52 (m, 5H), 3.51-3.44 (m, 7H), 3.45-3.36 (m, 6H), 3.17-3.07 (m, 10H), 1.70 (p, J=6.7 Hz, 2H), 1.48 (p, J=6.8 Hz, 2H), 1.41-1.22 (m, 4H).

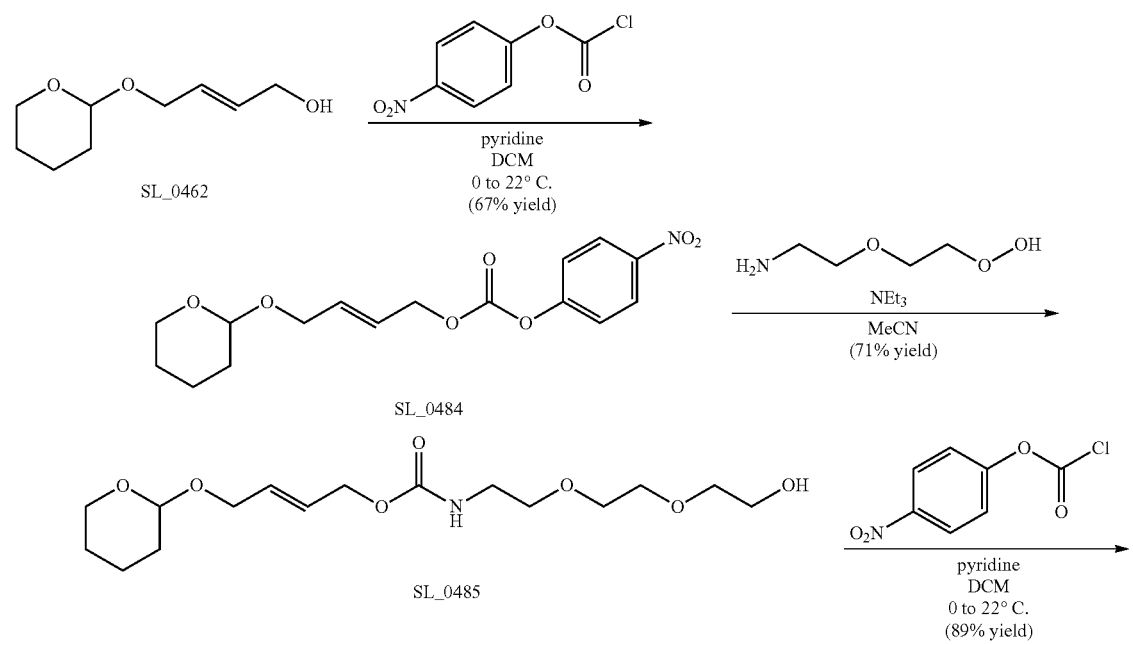

-continued

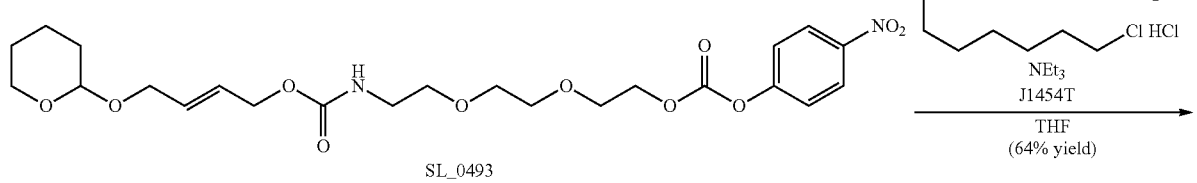
SL_0493

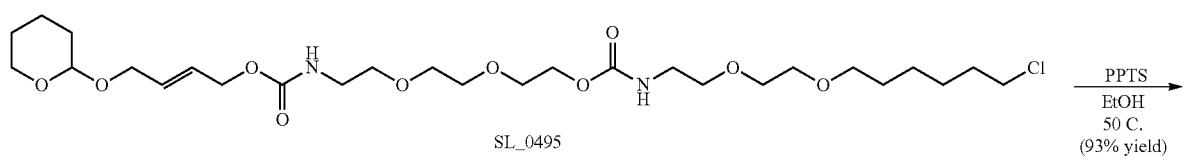
SL_0495

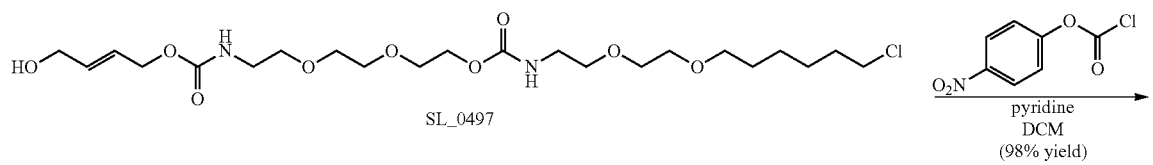
SL_0497

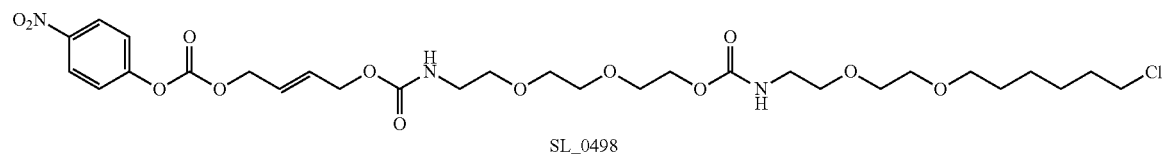
SL_0498

SL_0484

SL_0485

Pyridine (348 µL, 4.31 mmol) and 4-nitrophenyl chloroformate (676 mg, 3.35 mmol) were added to a stirred solution of SL_0462 (550 mg, 3.19 mmol) in DCM (15 mL) 0° C. under nitrogen. The resulting solution was allowed to warm up to 25° C. over 16 hours, at which point TLC indicated consumption of starting material. The reaction mixture was absorbed on silica and purified by silica gel chromatography (0→30% EtOAc/hexanes) to provide 0.72 g (67% yield) of SL_0484 as a clear oil. $^1$H NMR (300 MHz, DMSO-$d_6$) δ 8.32 (d, J=9.2 Hz, 2H), 7.57 (d, J=9.2 Hz, 2H), 5.99 (dt, J=15.6, 4.9 Hz, 1H), 5.87 (dt, J=15.6, 5.8 Hz, 1H), 4.78 (m, 2H), 4.61 (s, 1H), 4.18 (ddd, J=13.8, 4.6, 1.2 Hz, 1H), 3.98 (m, 1H), 3.74 (ddd, J=11.4, 8.0, 3.3 Hz, 1H), 3.44 (dt, J=10.7, 4.7 Hz, 1H), 1.80-1.61 (m, 2H), 1.54-1.37 (m, 4H). MS (ESI+) calc'd for $C_{16}H_{19}NaNO_7^+$ [M+Na]$^+$ 360.4, found 360.0. To a solution of SL_0212 (512 mg, 1.52 mmol) in MeCN (20 mL) was added 2-(2-(2-aminoethoxy)ethoxy)ethan-1-ol (226 mg, 1.52 mmol) followed by NEt$_3$ (424 µL, 3.04 mmol). The resulting yellow solution was left at 22° C. for 22 hours, at which point TLC analysis indicated complete consumption of starting material. Solvent was removed in vacuo, and crude residue was purified by silica gel chromatography (0→10% MeOH/DCM) to provide 376 mg (71% yield) of SL_0485 as a clear oil. $^1$H NMR (300 MHz, DMSO-$d_6$) δ 7.17 (t, J=5.7 Hz, 1H), 5.79 (m, 2H), 4.56 (m, 2H), 4.45 (d, J=4.2 Hz, 2H), 4.13 (dd, J=13.0, 3.9 Hz, 1H), 3.92 (dd, J=13.0, 4.3 Hz, 1H), 3.72 (td, J=9.5, 7.9, 3.4 Hz, 1H), 3.52-3.49 (m, 4H), 3.49-3.44 (m, 2H), 3.43-3.37 (m, 5H), 3.12 (q, J=5.9 Hz, 2H), 1.75-1.57 (m, 2H), 1.55-1.1 (m, 2H).

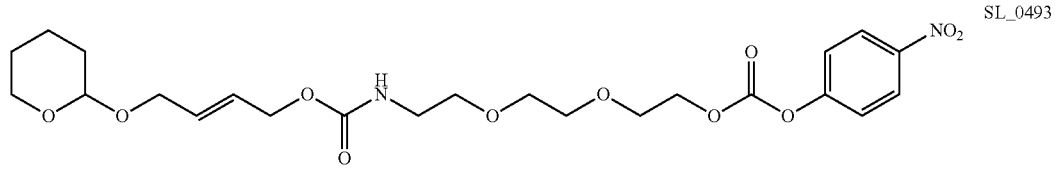 [SMILES: O=C(NCCOCCOCCOC(=O)Oc1ccc([N+](=O)[O-])cc1)OC/C=C/COC1CCCCO1]

SL_0493

Pyridine (57 μL, 0.7 mmol) and 4-nitrophenyl chloroformate (111 mg, 0.55 mmol) were added to a stirred solution of SL_0485 (182 mg, 524 μmol) in DCM (10 mL) at 0° C. under nitrogen. The resulting solution was allowed to warm up to 25° C. over 22 hours, at which point TLC indicated consumption of starting material. The reaction mixture was absorbed on silica and purified by silica gel chromatography (0→100% EtOAc/hexanes) to provide 240 mg (89% yield) of SL_0493 as a clear oil. $^1$H NMR (300 MHz, DMSO-d$_6$) δ 8.32 (d, J=9.2 Hz, 2H), 7.56 (d, J=9.2 Hz, 2H), 7.18 (t, J=5.5 Hz, 1H), 5.81 (dd, J=15.3, 4.3 Hz, 1H), 5.73 (dd, J=15.3, 4.9 Hz, 1H), 4.57 (m, 1H), 4.45 (d, J=4.0 Hz, 2H), 4.36 (m, 2H), 4.13 (m, 1H), 3.91 (dd, J=13.0, 4.3 Hz, 1H), 3.71 (m, 3H), 3.58 (m, 2H), 3.53 (m, 2H), 3.42 (t, J=5.9 Hz, 3H), 3.13 (q, J=5.9 Hz, 2H), 1.77-1.56 (m, 2H), 1.53-1.41 (m, 4H). MS (ESI+) calc'd for $C_{23}H_{32}NaN_2O_{11}^+$ [M+Na]$^+$ 535.2, found 535.2.

To a solution of SL_0493 (220 mg, 429 μmol) in THF (15 mL) was added J1454T (117 mg, 451 μmol) followed by triethylamine (120 μL, 859 μmol), murky solution forms (NEt$_3$.HCl precipitates). The resulting suspension was left stirred at 22° C. for 2 hours at which point TLC analysis indicated complete consumption of starting material. The solvent was removed in vacuo, and the residue was purified by silica gel chromatography (0→100% EtOAc/Heptane) to provide 164 mg (64% yield) of SL_0495 as a clear oil. $^1$H NMR (300 MHz, DMSO-d$_6$) δ 7.17 (t, J=5.6 Hz, 2H), 5.78 (m, 2H), 4.58 (m, 1H), 4.45 (m, 2H), 4.13 (dd, J=13.1, 3.8 Hz, 1H), 4.04 (m, 2H), 3.91 (dd, J=13.0, 4.3 Hz, 1H), 3.72 (ddd, J=11.4,

SL_0495

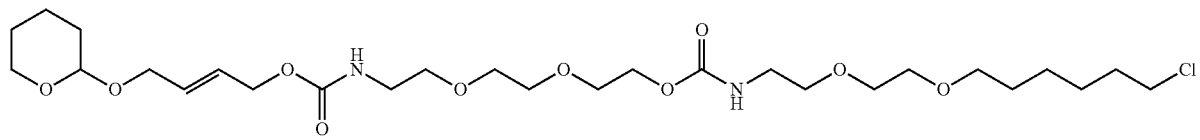

7.9, 3.4 Hz, 1H), 3.62 (t, J=6.6 Hz, 2H), 3.55 (dd, J=5.6, 3.9 Hz, 2H), 3.52-3.44 (m, 8H), 3.43-3.34 (m, 7H), 3.12 (m, 4H), 1.78-1.58 (m, 4H), 1.55-1.42 (m, 6H), 1.42-1.25 (m, 4H). MS (ESI+) calc'd for $C_{22}H_{42}ClN_2O_9^+$ [M−THP+H]$^+$ 513.26, found 513.2.

SL_0497

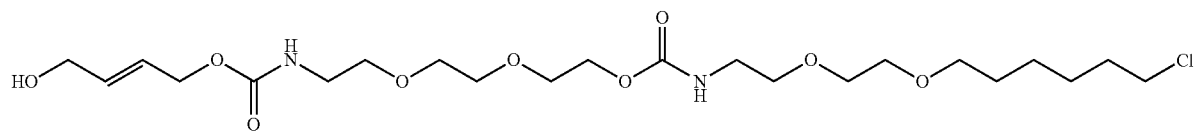

To a 20 mL microwave vial equipped with stir bar, was added SL_0495 (150.0 mg, 251 μmol), PPTS (6.3 mg, 25 μmol) and EtOH (15 mL). The resulting solution was heated in microwave at 50° C. for 60 minutes, at which point analysis indicated complete consumption of starting material. The solvent was removed in vacuo, and the residue was purified by silica gel chromatography (0→10% MeOH/DCM) to provide 120 mg (93% yield) of SL_0497 as a clear oil. ¹H NMR (300 MHz, DMSO-d₆) δ 7.17 (d, J=5.6 Hz, 1H), 7.12 (d, J=5.7 Hz, 1H), 5.80 (dt, J=15.6, 4.5 Hz, 1H), 5.68 (dt, J=15.6, 5.7 Hz, 1H), 4.74 (t, J=5.5 Hz, 1H), 4.44 (d, J=5.2 Hz, 2H), 4.04 (m, 2H), 3.94 (m, 2H), 3.62 (t, J=6.6 Hz, 2H), 3.55 (m, 2H), 3.52-3.43 (m, 8H), 3.43-3.34 (m, 6H), 3.11 (m, 4H), 1.70 (m, 2H), 1.49 (p, J=6.8 Hz, 2H), 1.43-1.24 (m, 4H). MS (ESI+) calc'd for C₂₂H₄₂ClN₂O₉⁺ [M+H]⁺ 513.26, found 513.2.

SL_0498

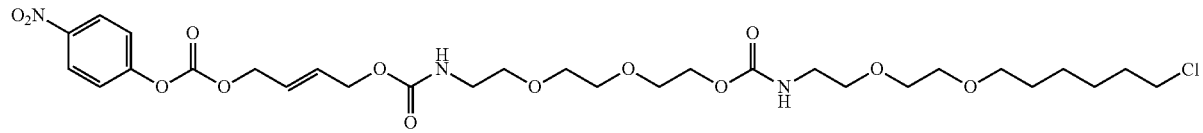

Pyridine (87 μL, 1.1 mmol) and 4-nitrophenyl chloroformate (86 mg, 429 μmol) were added to a stirred solution of SL_0497 (110 mg, 214 μmol) in DCM (10 mL) at 22° C. under nitrogen. The resulting solution was left stirred at 22° C. over 1 hour, at which point TLC indicated consumption of starting material. The reaction mixture was absorbed on silica and purified by silica gel chromatography (0→5% MeOH/DCM) to provide 141 mg (97% yield) of SL_0498 as a light yellow oil. ¹H NMR (300 MHz, DMSO-d₆) δ 8.31 (m, 2H), 7.56 (m, 2H), 7.27-7.07 (m, 2H), 6.03-5.82 (m, 2H), 4.76 (m, 2H), 4.50 (m, 2H), 4.03 (s, 2H), 3.70-3.25 (m, 18H), 3.11 (q, J=7.8 Hz, 4H), 1.76-1.61 (m, 2H), 1.54-1.43 (m, 2H), 1.42-1.26 (m, 2H). MS (ESI+) calc'd for C₂₉H₄₅ClN₃O₁₃⁺ [M+H]⁺ 678.26, found 678.2.

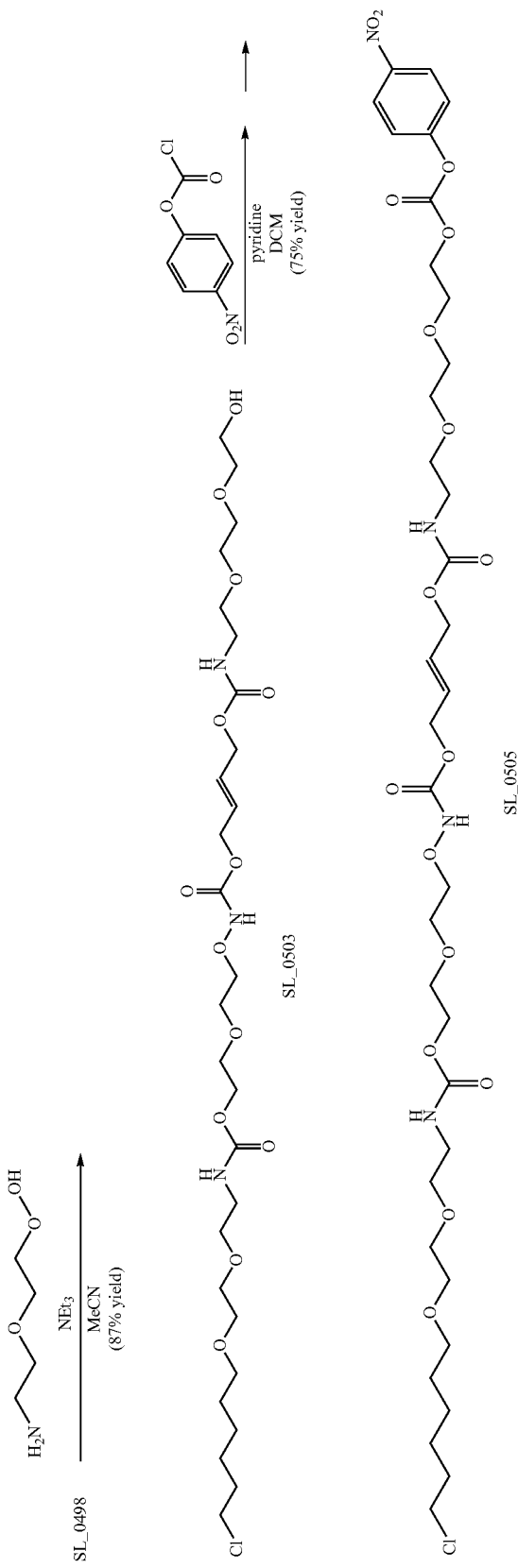

SL_0503

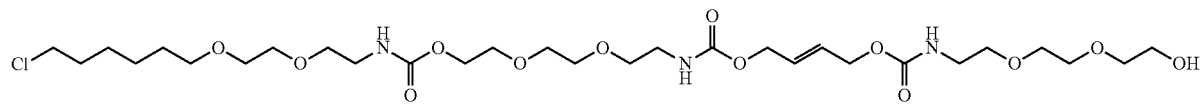

To a solution of SL_0498 (120 mg, 177 μmol) in MeCN (15 mL) was added 2-(2-(2-aminoethoxy)ethoxy)ethan-1-ol (26 mg, 177 μmol) followed by NEt₃ (74 μL, 531 μmol). The resulting yellow solution was left at 22° C. for 16 hours, at which point TLC analysis indicated complete consumption of starting material. Solvent was removed in vacuo, and crude residue was purified by silica gel chromatography (0→10% MeOH/DCM) to provide 106 mg (87% yield) of SL_0503 as a clear oil. $^1$H NMR (300 MHz, DMSO-$d_6$) δ 7.22-7.12 (m, 3H), 5.79 (m, 2H), 4.55 (t, J=5.5, 1H), 4.47-4.43 (m, 4H), 4.04 (t, J=4.8 Hz, 2H), 3.62 (t, J=6.6 Hz, 2H), 3.55 (t, J=4.8 Hz, 2H), 3.52-3.45 (m, 14H), 3.44-3.36 (m, 10H), 3.16-3.06 (m, 6H), 1.70 (p, J=6.7 Hz, 2H), 1.49 (p, J=6.9 Hz, 2H), 1.42-1.25 (m, 4H). MS (ESI+) calc'd for $C_{29}H_{55}ClN_3O_{13}^+$ [M+H]$^+$ 688.34, found 688.3.

SL_0505

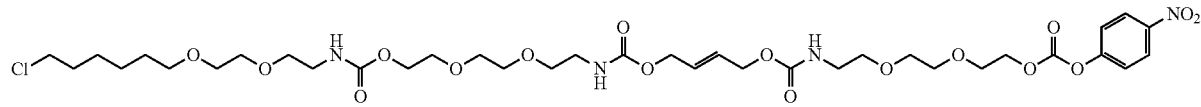

Pyridine (59 μL, 727 μmol) and 4-nitrophenyl chloroformate (59 mg, 291 μmol) were added to a stirred solution of SL_0503 (100 mg, 145 μmol) in DCM (10 mL) at 22° C. under nitrogen. The resulting solution was left stirred at 22° C. over 16 hours, at which point TLC indicated consumption of starting material. The reaction mixture was absorbed on silica and purified by silica gel chromatography (0→10% MeOH/DCM) to provide 93 mg (75% yield) of SL_0505 as yellowish oil. $^1$H NMR (300 MHz, DMSO-$d_6$) δ 8.32 (d, J=9.2 Hz, 2H), 7.56 (d, J=9.2 Hz, 2H), 7.18 (m, 3H), 5.78 (s, 2H), 4.45 (s, 4H), 4.38-4.34 (m, 2H), 4.06-4.00 (m, 2H), 3.72-3.68 (m, 2H), 3.62 (t, J=6.6 Hz, 2H), 3.58-3.52 (m, 6H), 3.52-3.45 (m, 8H), 3.44-3.33 (m, 8H), 3.17-3.07 (m, 6H), 1.70 (p, J=6.6 Hz, 2H), 1.48 (p, J=6.9 Hz, 2H), 1.42-1.25 (m, 4H). MS (ESI+) calc'd for $C_{36}H_{58}ClN_4O_{17}^+$ [M+H]$^+$ 853.35, found 853.30.

Ibrutinib Chloroalkane Syntheses:

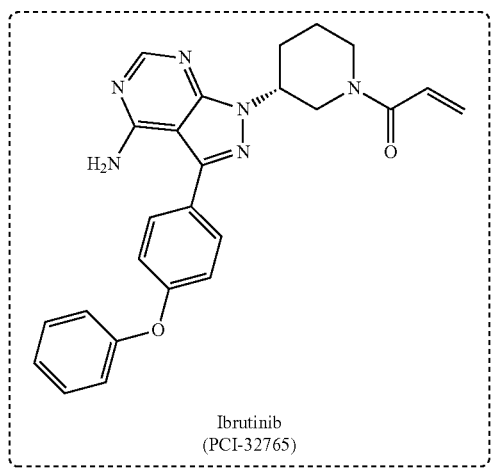 [SMILES: C=CC(=O)N1CCC[C@@H](n2nc(-c3ccc(Oc4ccccc4)cc3)c3c(N)ncnc32)C1]

Ibrutinib
(PCI-32765)

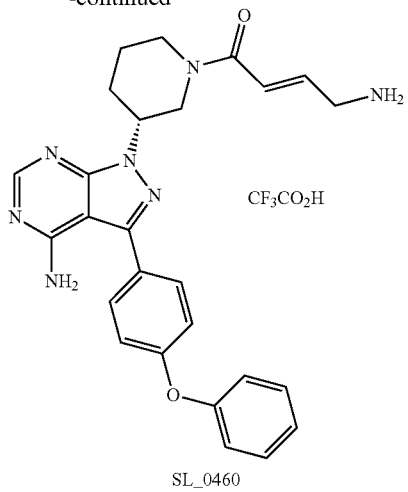

SL_0460

SL_0460 was synthesized according to: Turetsky, A., Kim, E., Kohler, R. H., Miller, M. A., Weissleder, R. *Sci Rep.* 2014, 4, 4782, from commercially available advanced intermediate ((R)-3-(4-phenoxyphenyl)-1-(piperidin-3-yl)-1H-pyrazolo[3,4-d]pyrimidin-4-amine)

General Procedure for Ibrutinib-CA Synthesis:

To a solution of SL_0460 (10 µmol) in DMF (5 mL) was added 4-nitrophenyl carbamate of the appropriate chloroalkane (10 µmol), followed by Et$_3$N (50 µmol) at 22° C. The resulting yellow solution was left at 22° C. for 16 hours at which point, solvent was removed in vacuo and crude residue was purified silica gel chromatography (0→20% MeOH/DCM) to provide Ibrutinib-CA conjugate as clear oil.

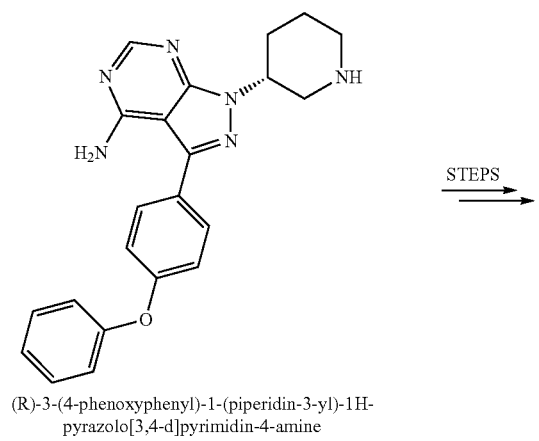

(R)-3-(4-phenoxyphenyl)-1-(piperidin-3-yl)-1H-pyrazolo[3,4-d]pyrimidin-4-amine

STEPS

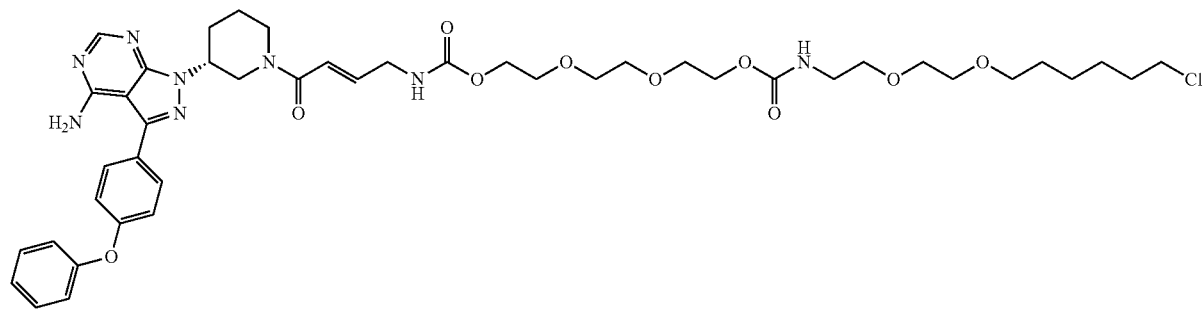

PBI6040

>96% purity HPLC@254 nm. MS (ESI+) calc'd for $C_{44}H_{60}ClN_8O_{10}^+$ [M+H]$^+$ 895.41, found 895.52.

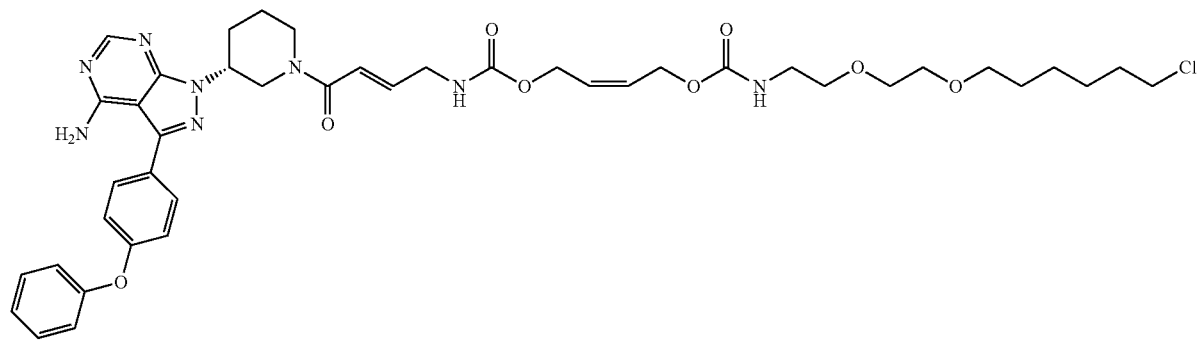
PBI6041
>99% purity HPLC@254 nm. MS (ESI+) calc'd for $C_{42}H_{54}ClN_8O_8^+$ [M+H]$^+$ 833.38, found 833.28.
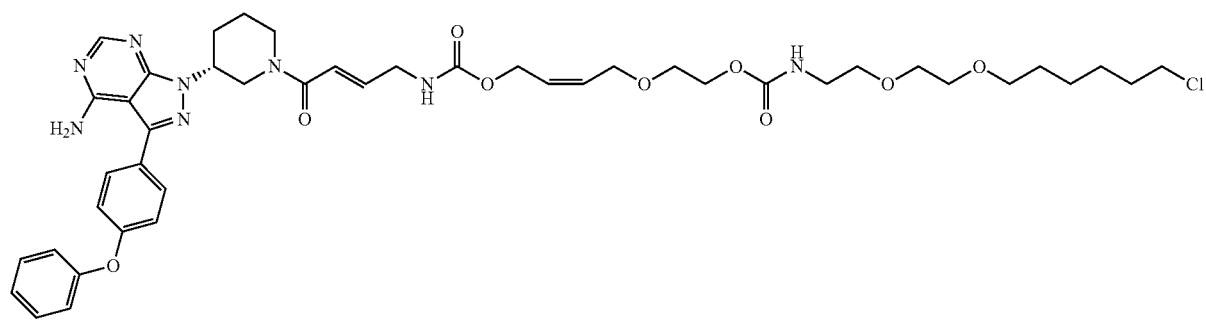
PBI6025
>99% purity HPLC@254 nm. MS (ESI+) calc'd for $C_{44}H_{58}ClN_8O_9^+$ [M+H]$^+$ 877.40, found 877.40.
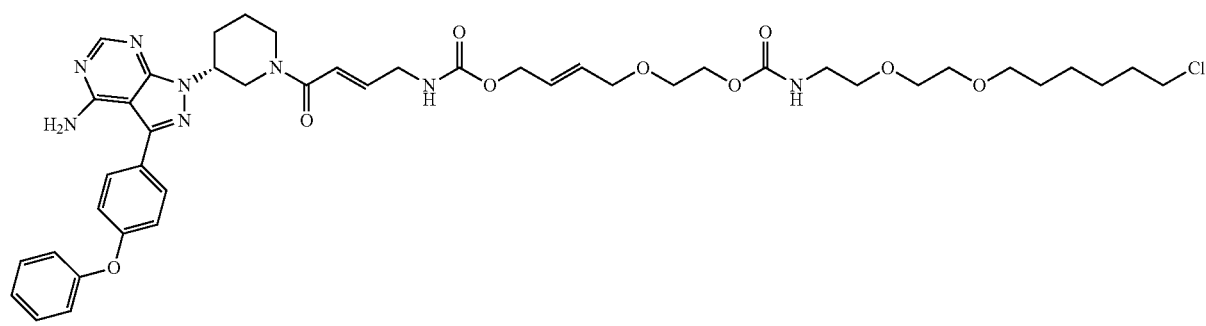
PBI6027
>99% purity HPLC@254 nm. MS (ESI+) calc'd for $C_{44}H_{58}ClN_8O_9^+$ [M+H]$^+$ 877.40, found 877.64.

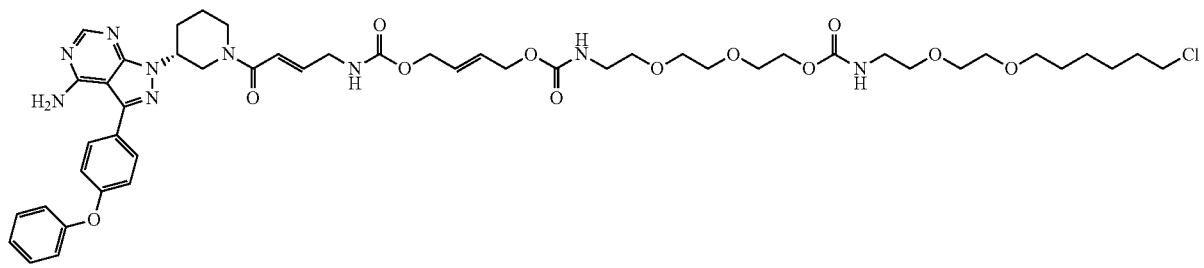
PBI6029
>99% purity HPLC@254 nm. MS (ESI+) calc'd for
$C_{49}H_{67}ClN_9O_{12}^+$ [M+H]$^+$ 1008.46, found 1008.50.
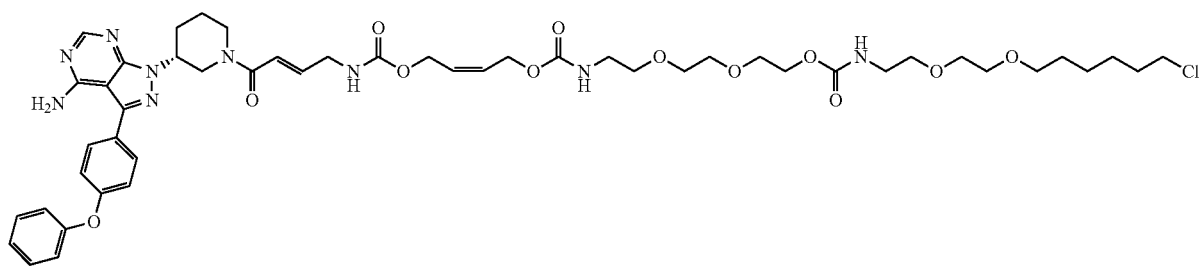
PBI6030
>99% purity HPLC@254 nm. MS (ESI+) calc'd for
$C_{49}H_{67}ClN_9O_{12}^+$ [M+H]$^+$ 1008.46, found 1008.50.
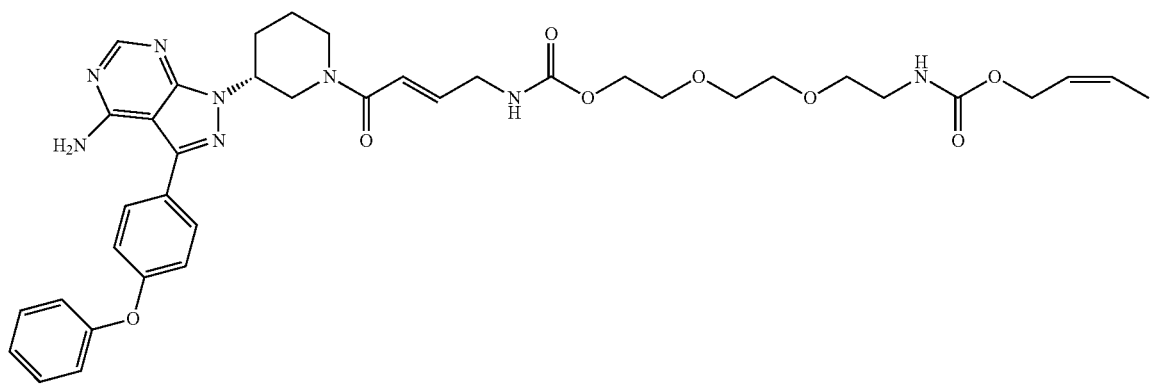
PBI6030
>96% purity HPLC@254 nm. MS (ESI+) calc'd for
$C_{56}H_{80}ClN_{10}O_{16}^+$ [M+H]$^+$ 1183.54, found 1183.50.

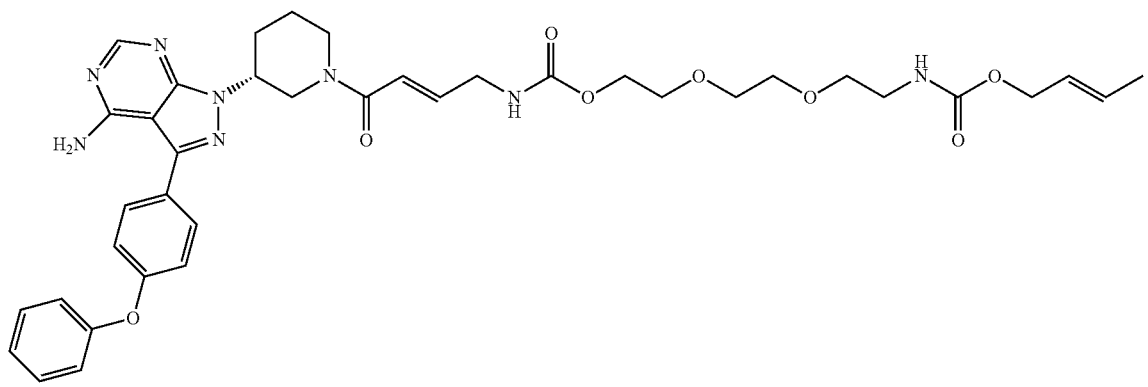

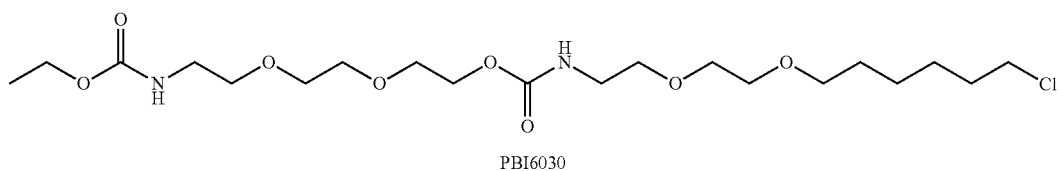

PBI6030

>99% purity HPLC@254 nm. MS (ESI+) calc'd for $C_{56}H_{80}ClN_{10}O_{16}{}^{+}$ [M+H]$^{+}$ 1183.54, found 1183.97.

General Procedure for the Preparation of Catalyst Solution:

$$Na_2PdCl_4 + 8\,PR_3 + H_2O \xrightarrow[\text{degrassed water}]{\text{Argon atmosphere}} Pd(PR_3)_x + O{=}PR_3 + (7-x)Pr_3 + 2NaCl + 2HCl$$

All operations are performed under Argon atmosphere. Water was degassed by 3× freeze-pump-thaw cycles on liquid nitrogen.

Example for 4 mM Pd-oDANPHOS 1:8 Solution o-DANPHOS (188 mg, 0.32 mmol, 97% pure) was placed in a sealed vial, equipped with stir bar. Air was evacuated and vial was backfilled with argon (3× repetitions). Degassed water (9 mL) was added via cannula resulting in a clear solution formation. In a separate sealed vial was placed Na$_2$PdCl$_4$ (11.8 mg, 0.04 mmol) air was evacuated and vial was backfilled with argon (3× repetitions). Degassed water (1 mL) was added to solid Na$_2$PdCl$_4$, resulting in brown solution formation. Brown aqueous solution of Na$_2$PdCl$_4$ (1 mL, 11.8 mg/mL) solution was added to the stirred phosphine solution, resulting in a clear yellow solution formation. Clear yellow solution of Pd-o-DAN-PHOS complex was allowed to mix for 30 minutes and transferred to a sealed vials (1 mL each) under Argon. Stock solutions are stored at ambient temperature, protected from light.

Example 29

BIRB796 Conjugates

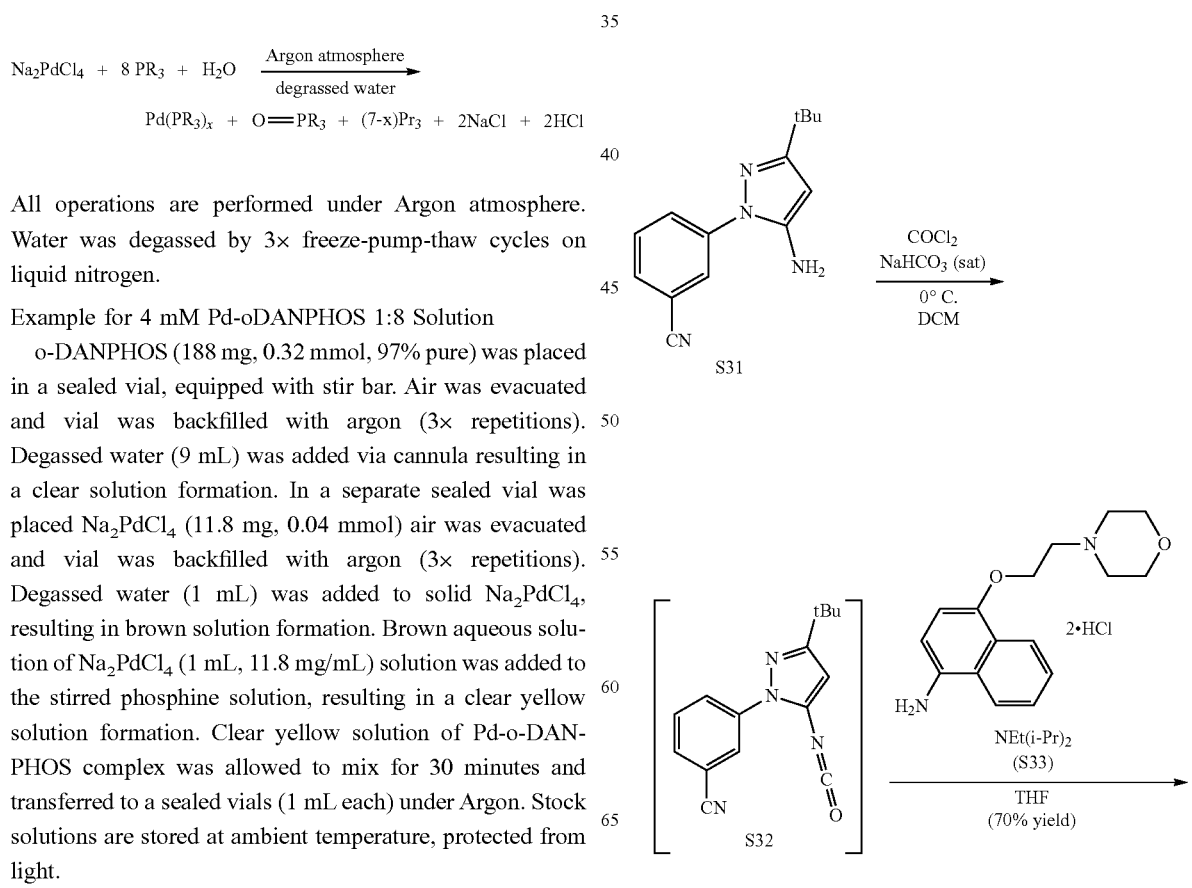

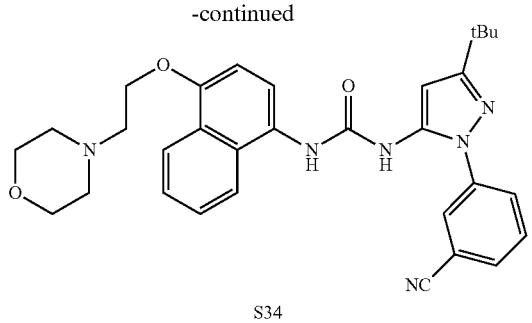

S34

To a vigorously stirred biphasic mixture of S31 (Chem. Biol. Drug. Des. 2009, 74, 547-559) (900 mg, 3.75 mmol) in DCM (100 mL) and aqueous saturated $NaHCO_3$ (100 mL), a solution of phosgene (10.7 mL, 15 wt % in toluene, 15.0 mmol) at 0° C. was added. After 25 minutes, the organic layer was separated, dried over $MgSO_4$, and concentrated. The resulting yellow oil was dissolved in THF (50 mL) and added to a solution of S33 (J. Med. Chem. 2002, 45, 2994-3008) (1.26 g, 4.09 mmol) and DIPEA (1.94 mL, 11.2 mmol) in THF (100 mL) at 22° C. The resulting solution was stirred under nitrogen for 22 hours. Solvent was removed under vacuum, and the crude reaction mixture was purified by silica gel chromatography (0→20% MeOH/DCM to provide 1.41 g (70% yield) of S34 as a white solid. $^1$H NMR (300 MHz, DMSO-$d_6$) δ 8.73 (s, 1H), 8.65 (s, 1H), 8.15 (dd, J=7.0, 1.9 Hz, 1H), 8.06 (t, J=1.8 Hz, 1H), 7.93 (ddd, J=8.1, 2.3, 1.2 Hz, 1H) 7.87 (m, 1H), 7.84 (q, J=1.4 Hz, 1H), 7.72 (t, J=7.9 Hz, 1H), 7.58-7.48 (m, 2H), 7.48 (d, J=8.4 Hz, 1H), 6.94 (d, J=8.4 Hz, 1H), 6.37 (s, 1H), 4.24 (t, J=5.6 Hz, 2H), 3.65-3.50 (m, 4H), 2.83 (t, J=5.6 Hz, 2H), 2.53 (dd, J=5.6, 3.7 Hz, 4H), 1.27 (s, 9H); $^{13}$C NMR (75 MHz, CD$_3$OD) δ 164.3, 156.9, 154.5, 141.0, 138.7, 132.1, 132.0, 131.6, 130.2, 128.8, 128.1, 127.4, 126.9, 126.5, 125.25, 123.5, 123.1, 119.0, 114.3, 105.5, 100.3, 67.6, 67.2, 58.7, 55.2, 33.4, 30.6; MS (ESI+) calc'd for $C_3H_{35}N_6O_3^+$ [M+H]$^+$ 539.28, found 539.29.

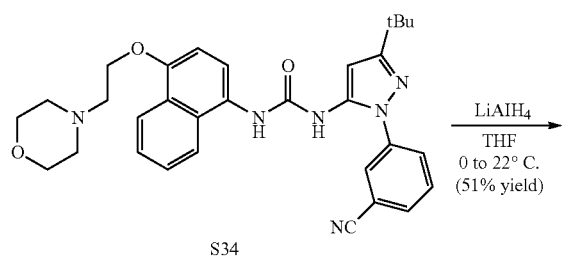

S34

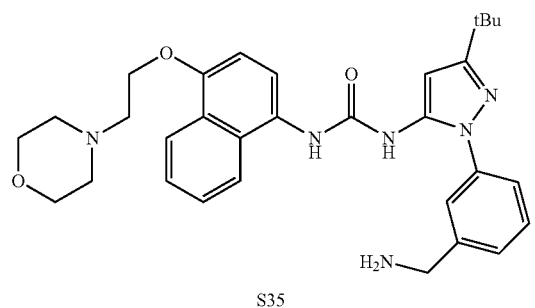

S35

To a stirred solution of dried (azeotroped with toluene 3×25 mL) S34 (1.36 g, 2.52 mmol) in dry THF (100 mL) at 0° C. (ice bath) under nitrogen, a 1M ethereal solution of LiAlH$_4$ (25.3 mL, 25.3 mmol) was added. The resulting solution was allowed to warm up to 22 C over a period of 16 hours at which point HPLC indicated consumption of the starting material. The reaction mixture was cooled back to 0° C. and quenched by slow addition of 0.2 mL H$_2$O, followed by 15% aq. KOH solution (2 mL), and finally H$_2$O (5 mL). (Caution H$_2$ evolution!). The resulting suspension was stirred at 0° C. for 30 minutes and filtered. Filtrate cake was washed with additional THF (5 mL), and combined organics were dried over MgSO$_4$, solvent removed under vacuum, and residue purified by silica gel chromatography (0→30% MeOH/DCM to provide 700 mg (51% yield) of S35 as a yellow solid. $^1$H NMR (300 MHz, CD$_3$OD) δ 8.45-8.10 (m, 1H), 7.86-7.66 (m, 1H), 7.59-7.44 (m, 4H), 7.43-7.33 (m, 3H), 6.82 (d, J=8.3 Hz, 1H), 6.42 (s, 1H), 4.26 (t, J=5.4 Hz, 2H), 3.83 (s, 2H), 3.80-3.56 (m, 4H), 2.93 (t, J=5.2 Hz, 1H) 2.75-2.47 (m, 4H), 1.33 (s, 9H); $^{13}$C NMR (75 MHz, CD$_3$OD) δ 163.5, 156.0, 154.0, 145.1, 139.7, 138.9, 131.4, 130.6, 128.4, 127.9, 127.3, 127.0, 126.4, 125.6, 125.4, 124.2, 123.5, 122.9, 105.5, 97.1, 67.7, 67.2, 58.6, 55.2, 46.2, 33.3, 30.8; MS (ESI+) calc'd for $C_{31}H_{39}N_6O_3^+$ [M+H]$^+$ 543.31, found 543.28.

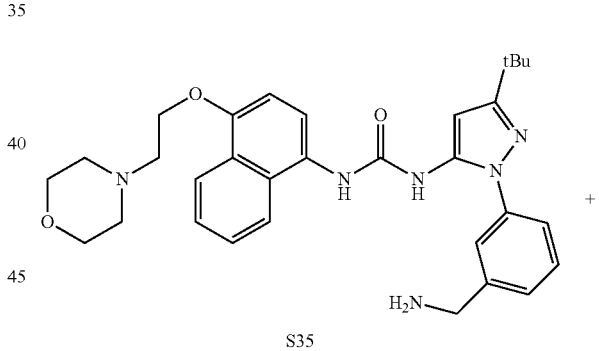

S35

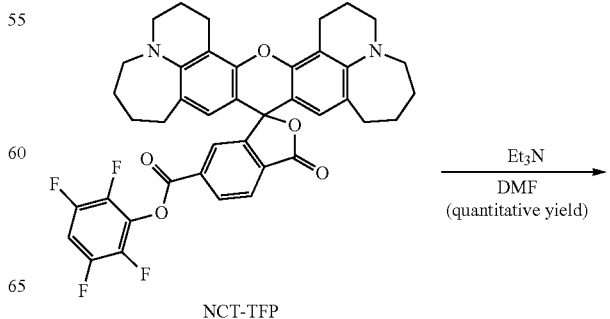

NCT-TFP

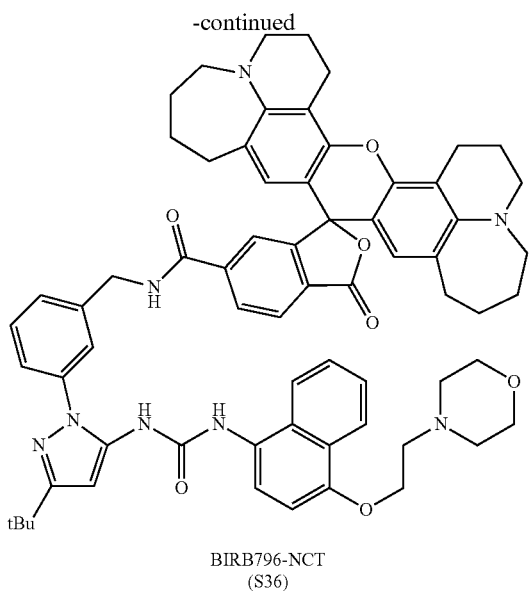

BIRB796-NCT
(S36)

To a solution of S35 (14.0 mg, 25.8 µmol) and NCT-TFP (20.2 mg, 28.4 µmol) in DMF (3 mL), Et$_3$N (18.0 µL, 129 µmol) was added, and the resulting solution was stirred at 22° C. for 12 hours at which point HPLC analysis indicated consumption of the starting material. The reaction mixture was directly loaded onto C18 column and purified by preparative HPLC (C$_{18}$, 5→95% MeCN/H$_2$O, 0.05% TFA). Solvent was removed by lyophilization to provide 30.0 mg of BIRB796-NCT (S36) (107% yield) as a deep blue solid. $^1$H NMR (300 MHz, CD$_3$OD) δ 8.26 (d, J=8.2 Hz, 2H), 8.15 (dd, J=8.2, 1.8 Hz, 1H), 7.83 (d, J=1.8 Hz, 1H), 7.77 (dd, J=7.3, 2.1 Hz, 1H), 7.56-7.48 (m, 4H), 7.47-7.42 (m, 1H), 7.43-7.33 (m, 2H), 6.91 (d, J=8.4 Hz, 1H), 6.56 (s, 2H), 4.69 (s, 2H), 4.57 (dd, J=5.8, 3.7 Hz, 2H), 3.93 (br. S, 4H), 3.79 (dd, J=5.5, 4.0 Hz, 2H), 3.68 (dt, J=8.8, 5.6 Hz, 4H), 3.52 (t, J=5.7 Hz, 8H), 3.03-2.88 (m, 4H), 2.77-2.69 (m, 4H), 2.10-1.98 (m, 4H), 1.96-1.85 (m, 4H), 1.82-1.71 (m, 4H), 1.30 (s, 9H); MS (ESI+) calc'd for C$_{66}$H$_{７i}$N$_8$O$_7^+$ [M+H]$^+$ 1087.54, found 1087.74.

General Procedure for BIRB796-CA Synthesis:

To a solution of S35 (10 µmol) in DMF (5 mL), the 4-nitrophenyl carbonate of the appropriate chloroalkane (10 µmol) was added, followed by Et$_3$N (50 µmol) at 22° C. The resulting yellow solution was left at 22° C. for 16 hours, at which point the solvent was removed under vacuum, and crude residue was purified silica gel chromatography (0→30% MeOH/DCM) to provide BIRB-CA conjugate as clear or yellow(ish) oil.

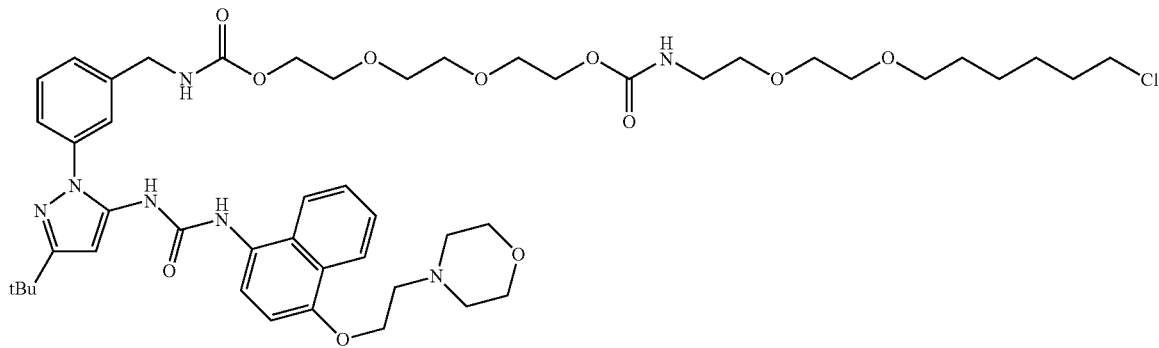

PBI5446
(BIRB796-CA-T1 (S37))

$^1$H NMR (300 MHz, CD$_3$OD) δ 8.29-8.25 (m, 1H), 7.86-7.70 (m, 1H), 7.60-7.25 (m, 7H), 6.89 (d, J=8.3 Hz, 1H), 6.41 (s, 1H), 4.36 (s, 2H), 4.33 (t, J=5.4 Hz, 2H), 4.17-4.07 (m, 4H), 3.76-3.70 (m, 4H), 3.66-3.58 (m, 4H), 3.58-3.49 (m, 10H), 3.49-3.39 (m, 3H), 3.24 (t, J=5.5 Hz, 2H), 2.97 (t, J=5.4 Hz, 2H), 2.74-2.55 (m, 4H), 1.74 (dq, J=7.9, 6.5 Hz, 2H), 1.65-1.50 (m, 2H), 1.50-1.36 (m, 4H), 1.33 (s, 9H); $^{13}$C NMR (75 MHz, CD$_3$OD) δ 163.6, 159.1, 158.9, 159.0, 154.2, 142.5, 139.7, 139.0, 131.6, 130.7, 128.3, 128.0, 127.3, 127.0, 126.5, 125.5, 125.4, 124.4, 123.5, 123.0, 105.6, 97.1, 72.2, 71.5, 71.2, 71.2, 70.9, 70.5, 67.7, 67.3, 65.3, 65.1, 58.7, 55.2, 45.7, 45.1, 41.7, 33.7, 33.7, 30.8, 30.5, 27.7, 26.5; MS (ESI+) calc'd for C$_{49}$H$_{71}$ClN$_7$O$_{11}^+$ [M+H]$^+$ 968.49, found 968.74.

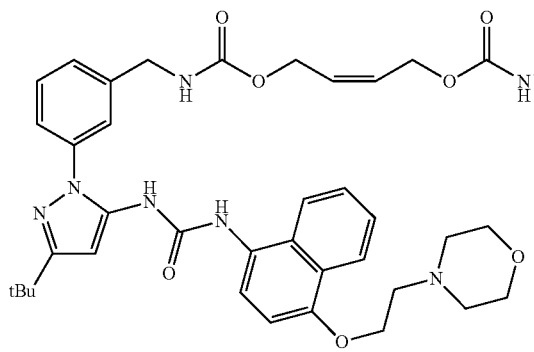
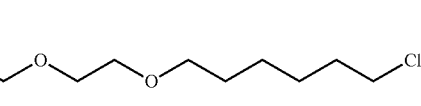
BIRB796-CA-T0
(S38)
¹H NMR (300 MHz, CD₃OD) δ 8.31-8.25 (m, 1H), 7.81-7.76 (m, 1H), 7.57-7.51 (m, 1H), 7.51-7.47 (m, 2H), 7.47-7.36 (m, 4H), 6.90 (d, J=8.3 Hz, 1H), 6.40 (s, 1H), 5.69-5.58 (m, 2H), 4.62 (d, J=4.4 Hz, 2H), 4.56 (d, J=4.2 Hz, 2H), 4.41-4.25 (m, 4H), 3.77-3.70 (m, 4H), 3.62-3.52 (m, 5H), 3.51-3.41 (m, 5H), 3.24 (t, J=5.5 Hz, 2H), 3.00 (t, J=5.4 Hz, 2H), 2.81-2.64 (m, 4H), 1.74 (dq, J=8.1, 6.6 Hz, 2H), 1.65-1.51 (m, 2H), 1.49-1.35 (m, 4H), 1.33 (s, 9H); ¹³C NMR (75 MHz, CD₃OD) δ 163.7, 158.9, 158.6, 156.1, 154.2, 142.5, 139.7, 139.0, 131.6, 130.7, 129.4, 129.2, 128.3, 128.0, 127.3, 127.1, 126.5, 125.6, 125.4, 124.5, 123.5, 123.0, 105.6, 97.3, 72.2, 71.2, 71.2, 70.9, 67.6, 67.2, 61.7, 61.5, 58.7, 55.2, 45.7, 45.2, 41.7, 33.7, 33.4, 30.8, 30.5, 27.7, 26.5; MS (ESI+) calc'd for $C_{47}H_{65}ClN_7O_9^+$ [M+H]⁺ 906.45, found 906.59.
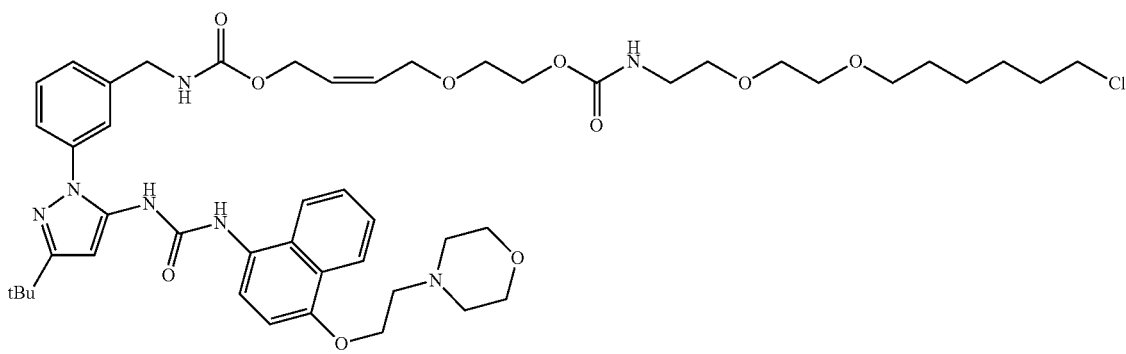
PBI5913
(BIRB796-CA-T2Z
(S39))
¹H NMR (300 MHz, CD₃OD) δ 8.31-8.24 (m, 1H), 7.83-7.77 (m, 1H), 7.57-7.31 (m, 7H), 6.90 (d, J=8.3 Hz, 1H), 6.41 (s, 1H), 5.63 (m, 2H), 4.59 (d, J=4.1 Hz, 2H), 4.36 (s, 2H), 4.34 (t, J=5.5 Hz, 2H), 4.09 (t, J=4.7 Hz, 2H), 4.01 (d, J=3.9 Hz, 2H), 3.82-3.66 (m, 4H), 3.61-3.35 (m, 12H), 3.25 (t, J=5.6 Hz, 2H), 2.98 (t, J=5.4 Hz, 2H), 2.77-2.59 (m, 4H), 1.74 (dq, J=8.0, 6.6 Hz, 2H), 1.66-1.51 (m, 2H), 1.51-1.35 (m, 4H), 1.33 (s, 9H); MS (ESI+) calc'd for $C_{49}H_{69}ClN_7O_{10}^+$ [M+H]⁺ 950.48, found 950.64.

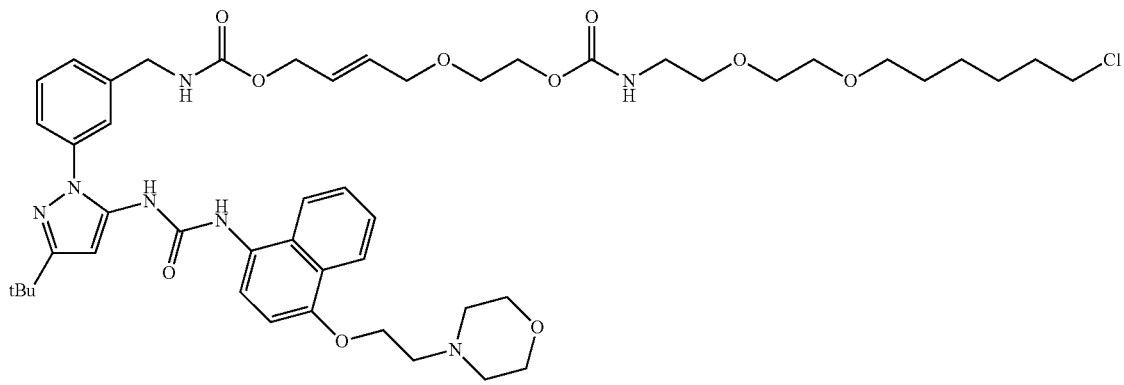
BIRB796-CA-T2E
(S40)
¹H NMR (300 MHz, CD₃OD) δ 8.30-8.25 (m, 1H), 7.89-7.70 (m, 1H), 7.61-7.30 (m, 7H), 6.90 (d, J=8.3 Hz, 1H), 6.41 (s, 1H), 5.82-5.67 (m, 2H), 4.54-4.45 (m, 2H), 4.37 (s, 2H), 4.33 (t, J=5.4 Hz, 2H), 4.16-4.09 (m, 2H), 3.96-3.90 (m, 2H), 3.75-3.67 (m, 4H), 3.60-3.52 (m, 7H), 3.53-3.38 (m, 5H), 3.25 (t, J=5.5 Hz, 2H), 2.98 (t, J=5.4 Hz, 2H), 2.77-2.49 (m, 4H), 1.74 (dq, J=7.9, 6.5 Hz, 2H), 1.56 (q, J=6.8 Hz, 2H), 1.51-1.36 (m, 4H), 1.33 (s, 9H); MS (ESI+) calc'd for C₄₉H₆₉ClN₇O₁₀⁺ [M+H]⁺ 950.48, found 950.88.
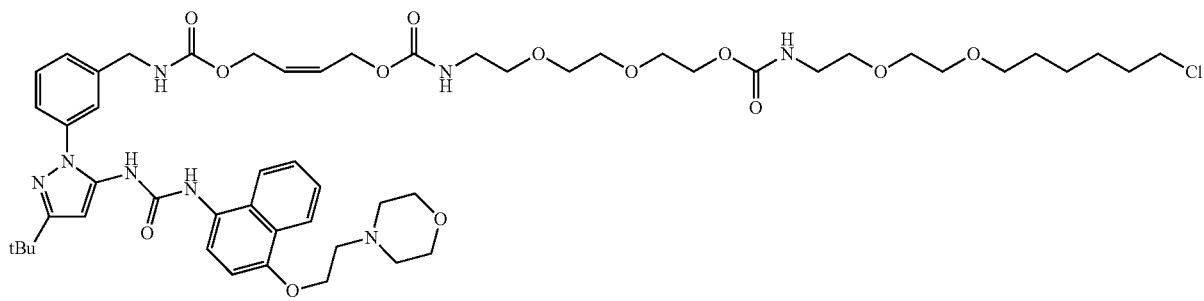
BIRB796-CA-T3Z
(S41)
¹H NMR (300 MHz, CD₃OD) δ 8.30-8.25 (m, 1H), 7.81-7.73 (m, 1H), 7.54-7.34 (m, 7H), 6.89 (d, J=8.3 Hz, 1H), 6.41 (s, 1H), 5.68-5.59 (m, 2H), 4.65-4.58 (m, 2H), 4.58-4.51 (m, 2H), 4.35 (s, 2H), 4.32 (t, J=5.4 Hz, 2H), 4.16-4.12 (m, 2H), 3.75-3.70 (m, 4H), 3.67-3.62 (m, 2H), 3.61-3.53 (m, 9H), 3.53-3.46 (m, 5H), 3.44 (d, J=6.5 Hz, 2H), 3.29-3.20 (m, 4H), 2.97 (t, J=5.4 Hz, 2H), 2.71-2.63 (m, 4H), 1.74 (dq, J=8.0, 6.6 Hz, 2H), 1.57 (p, J=6.9 Hz, 2H), 1.50-1.36 (m, 4H), 1.33 (s, 9H); MS (ESI+) calc'd for C₅₄H₇₈ClN₈O₁₃⁺ [M+H]⁺ 1081.54, found 1081.71.

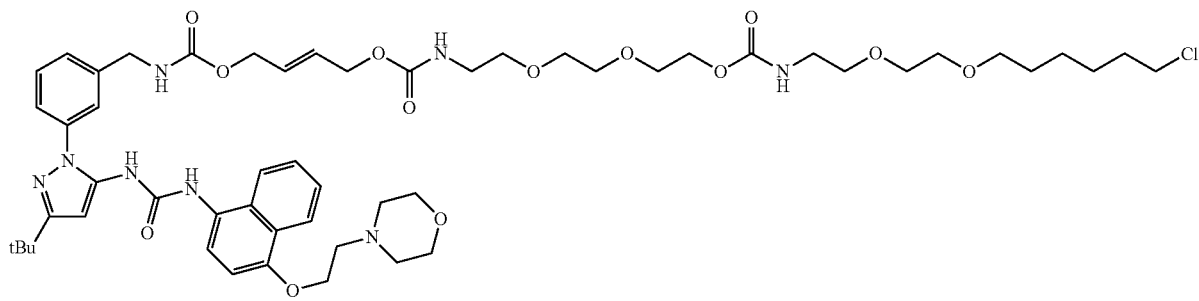
BIRB796-CA-T3E
(S42)
$^1$H NMR (300 MHz, CD$_3$OD) δ 8.30-8.23 (m, 1H), 7.87-7.71 (m, 1H), 7.59-7.33 (m, 7H), 6.89 (d, J=8.3 Hz, 1H), 6.41 (s, 1H), 5.84-5.72 (m, 2H), 4.53-4.45 (m, 4H), 4.36 (s, 2H), 4.32 (t, J=5.4 Hz, 2H), 4.14 (t, J=4.8 Hz, 2H), 3.79-3.69 (m, 4H), 3.64 (t, J=4.8 Hz, 2H), 3.61-3.53 (m, 9H), 3.53-3.46 (m, 5H), 3.44 (d, J=6.5 Hz, 2H), 3.25 (td, J=5.6, 2.2 Hz, 4H), 2.97 (t, J=5.4 Hz, 2H), 2.78-2.56 (m, 4H), 1.74 (dq, J=8.0, 6.6 Hz, 2H), 1.57 (p, J=6.9 Hz, 2H), 1.50-1.36 (m, 4H), 1.33 (s, 9H); MS (ESI+) calc'd for C$_{54}$H$_{78}$ClN$_8$O$_{13}$$^+$ [M+H]$^+$ 1081.54, found 1081.80.
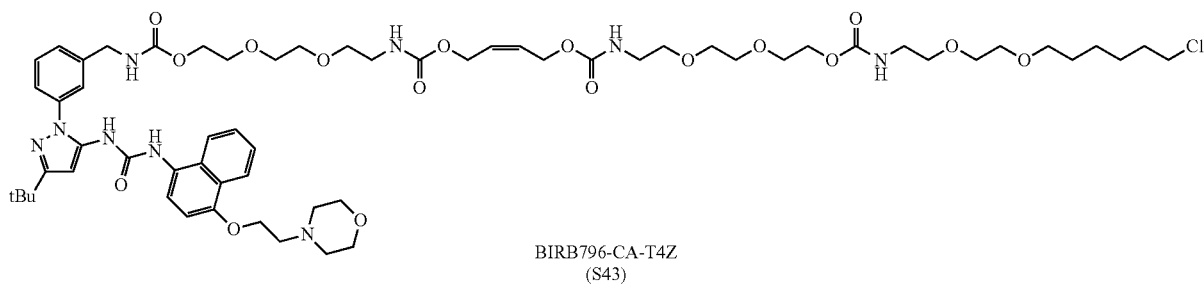 [SMILES: CC(C)(C)c1cc(NC(=O)Nc2ccc(OCCN3CCOCC3)c3ccccc23)n(-c2cccc(CNC(=O)OCCOCCOCCNC(=O)OC/C=C\COC(=O)NCCOCCOCCOC(=O)NCCOCCOCCCCCCCl)c2)n1]
BIRB796-CA-T4Z
(S43)
$^1$H NMR (300 MHz, CD$_3$OD) δ 8.30-8.24 (m, 1H), 7.83-7.74 (m, 1H), 7.61-7.25 (m, 7H), 6.89 (d, J=8.3 Hz, 1H), 5.68 (s, 2H), 5.74-5.65 (m, 2H), 4.68-4.56 (m, 4H), 4.37 (s, 2H), 4.32 (t, J=5.4 Hz, 2H), 4.23-4.03 (m, 4H), 3.78-3.68 (m, 4H), 3.68-3.39 (m, 27H), 3.30-3.15 (m, 7H), 2.97 (t, J=5.4 Hz, 2H), 2.74-2.56 (m, 4H), 1.75 (dq, J=8.1, 6.6 Hz, 2H), 1.65-1.51 (m, 2H), 1.51-1.35 (m, 4H), 1.33 (s, 9H); MS (ESI+) calc'd for C$_6$H$_{91}$ClN$_9$O$_{17}$$^+$ [M+H]$^+$ 1256.82, found 1256.96.
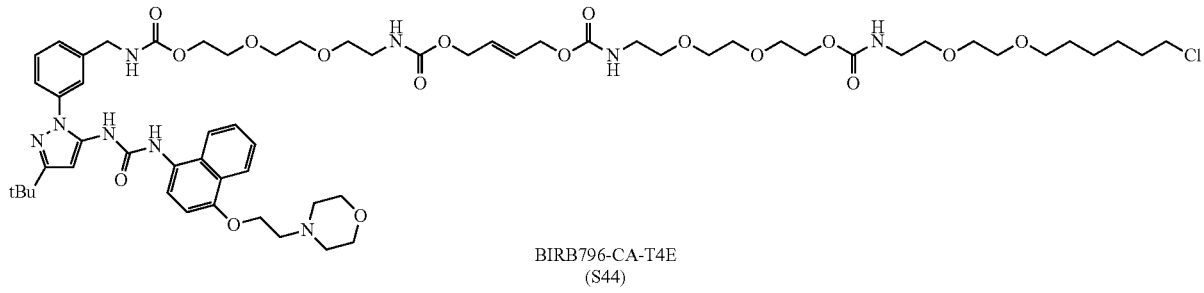 [SMILES: CC(C)(C)c1cc(NC(=O)Nc2ccc(OCCN3CCOCC3)c3ccccc23)n(-c2cccc(CNC(=O)OCCOCCOCCNC(=O)OC/C=C/COC(=O)NCCOCCOCCOC(=O)NCCOCCOCCCCCCCl)c2)n1]
BIRB796-CA-T4E
(S44)

$^1$H NMR (300 MHz, CD$_3$OD) δ 8.31-8.25 (m, 1H), 7.84-7.77 (m, 1H), 7.61-7.23 (m, 7H), 6.91 (d, J=8.4 Hz), 6.41 (s, 1H), 5.82 (s, 2H), 4.50 (s, 4H), 4.38 (s, 2H), 4.34 (t, J=5.4 Hz, 2H), 4.15 (t, J=4.7 Hz, 4H), 3.81-3.70 (m, 4H), 3.70-3.37 (m, 27H), 3.29-3.16 (m, 6H), 2.98 (t, J=5.3 Hz, 2H), 2.77-2.50 (m, 4H), 1.74 (dt, J=7.9, 6.6 Hz, 2H), 1.57 (q, J=6.8 Hz, 2H), 1.52-1.36 (m, 4H), 1.33 (s, 9H); MS (ESI+) calc'd for C$_{61}$H$_{91}$ClN$_9$O$_{17}^+$ [M+H]$^+$ 1256.82, found 1256.96.
Ponatinib Conjugates
Synthesis of Modified Ponatinib (Procedures Adapted from *J. Med. Chem.* 2010, 53, 4701-4719.)
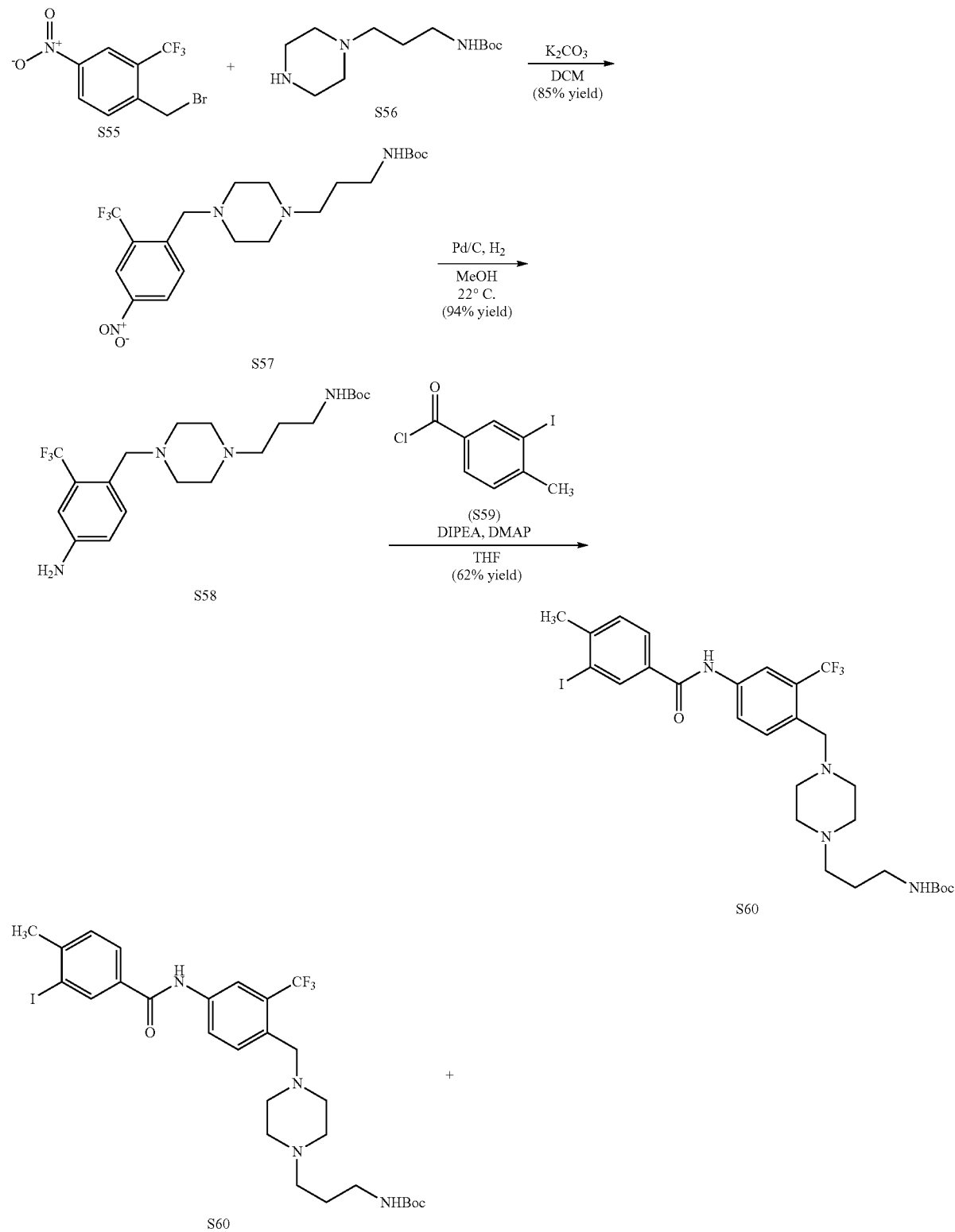

-continued

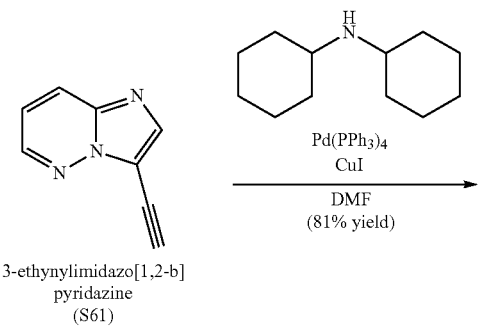

3-ethynylimidazo[1,2-b]
pyridazine
(S61)

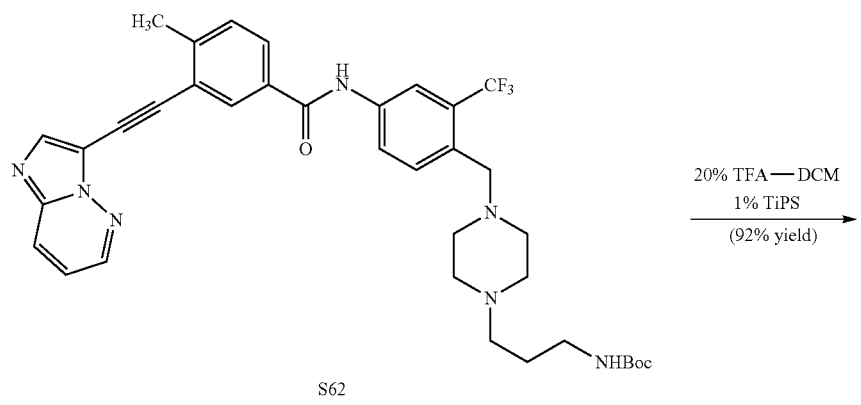

S62

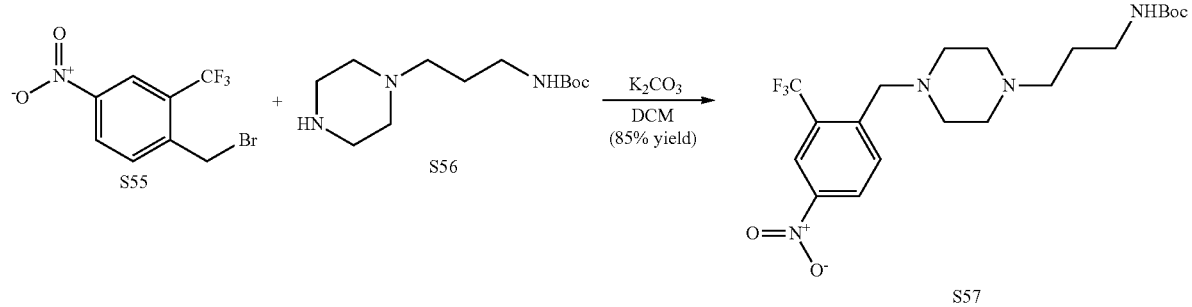

Potassium carbonate (333 mg, 2.41 mmol) was added to a stirred solution of bromide (S55)[8] (685 mg, 2.41 mmol) and S56 (880 mg, 3.62 mmol) in DCM (25 mL) at 22° C. The resulting suspension was stirred at 22° C. for 60 hours, at which point TLC indicated consumption of the starting material. The solution was concentrated to 20 mL, absorbed on silica, and purified by silica gel chromatography (0→10% MeOH/DCM) to provide 915 mg (85% yield) of S57 as a yellowish oil. $^1$H NMR (300 MHz, DMSO-$d_6$) δ 8.52 (dd, J=8.6, 2.4 Hz, 1H), 8.41 (d, J=2.4 Hz, 1H), 8.08 (d, J=8.6 Hz, 1H), 6.79 (s, 1H), 3.74 (m, 2H), 2.94 (m, 2H), 2.46-2.35 (m, 8H), 2.27 (m, 2H), 1.53 (m, 2H), 1.37 (s, 9H); MS (ESI+) calc'd for $C_{20}H_{30}F_3N_4O_4^+$ [M+H]$^+$ 447.22, found 447.25.

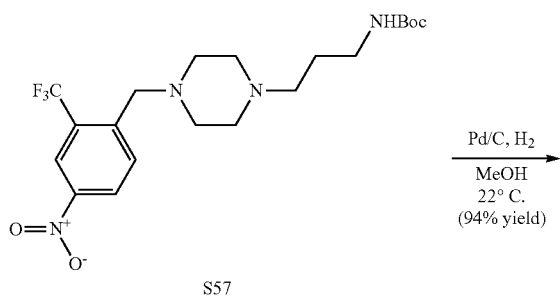

S57

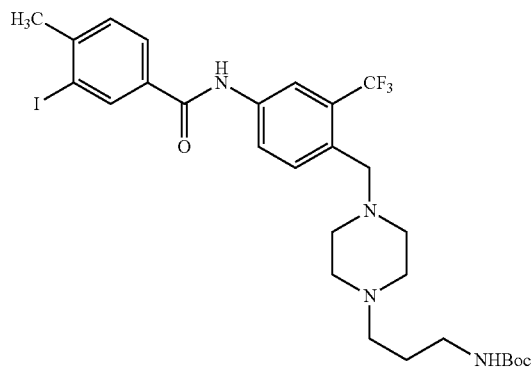

S60

3-Iodo-4-methylbenzoic acid (1.28 g, 4.88 mmol) was suspended in DCM (25 mL). Oxalyl chloride (420 μL, 4.9 mmol) was added, followed by DMF (1 drop). The reaction was stirred at 22° C., and gas evolution was observed for around 60 minutes, at which point HPLC analysis indicated almost complete consumption of the starting material. The solvent was removed under vacuum to provide 1.38 g (101% yield) of orange oil that solidified on storage. This material was used in the next step without further purification or characterization.

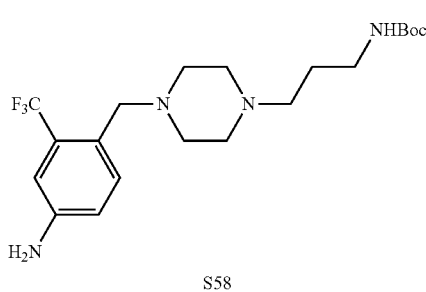

S58

A 250 mL flask equipped with stir bar was charged with Pd/C (80 mg, 10% wt.). A solution of S57 (840 mg, 1.88 mmol) in MeOH (75 mL) was added through cannula under nitrogen atmosphere, and the flask evacuated/backfilled with hydrogen gas (3 times). The suspension was vigorously stirred under a hydrogen atmosphere ($H_2$ balloon) for 50 minutes, at which point HPLC indicated consumption of the starting material. The reaction mixture was filtered through a Celite pad, and the cake was washed with extra 200 mL MeOH. The resulting methanolic solution was concentrated to provide 735 mg (94% yield) of S58 as a yellowish oil. $^1$H NMR (300 MHz, DMSO-$d_6$, reported for major rotamer) δ 7.28 (d, J=8.3 Hz, 1H), 6.85 (d, J=2.3 Hz, 1H), 6.81-6.72 (m, 2H), 5.43 (s, 2H), 3.38 (s, 2H), 2.91 (m, 2H), 2.40-2.8 (m, 10H), 1.58-1.45 (m, 2H), 1.37 (s, 9H); MS (ESI+) calc'd for $C_{20}H_{32}F_3N_4O_2^+$ [M+14]$^+$ 417.25 found 417.66.

S59 (270 mg, 0.96 mmol) was added to a solution of S58 (400 mg, 0.96 mmol), DMAP (11.7 mg, 96.0 μmol), and DIPEA (214 μL, 1.20 mmol) in THF (20 mL). The resulting solution was stirred at 22° C. for 90 minutes, at which point HPLC indicated consumption of the starting material. Solvent was removed under vacuum, and residue redissolved in DCM (10 mL) and purified by silica gel chromatography (0→10% MeOH/DCM) to provide 391 mg (62% yield) of S59 as a yellowish solids. $^1$H NMR (300 MHz, DMSO-$d_6$) δ 10.49 (s, 1H), 8.42 (d, J=1.8 Hz, 1H), 8.17 (d, J=2.2 Hz, 1H), 8.04 (dd, J=8.6, 2.2 Hz, 1H), 7.92 (dd, J=7.9, 1.8 Hz, 1H), 7.70 (d, J=8.5 Hz, 1H), 7.48 (d, J=8.0 Hz, 1H), 6.80 (t, J=6.0 Hz, 1H), 3.57 (s, 2H), 2.93 (q, J=6.6 Hz, 2H), 2.50-2.30 (partial overlap with DMSO-$d_5$, m, 12H), 1.54 (m, 2H), 1.37 (s, 9H); MS (ESI+) calc'd for $C_{28}H_{37}F_3IN_4O_3^+$ [M+H]$^+$ 661.19, found 661.27.

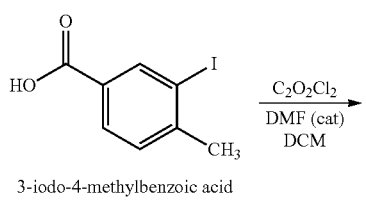

3-iodo-4-methylbenzoic acid

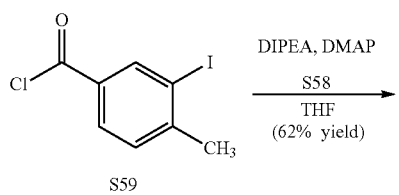

S59

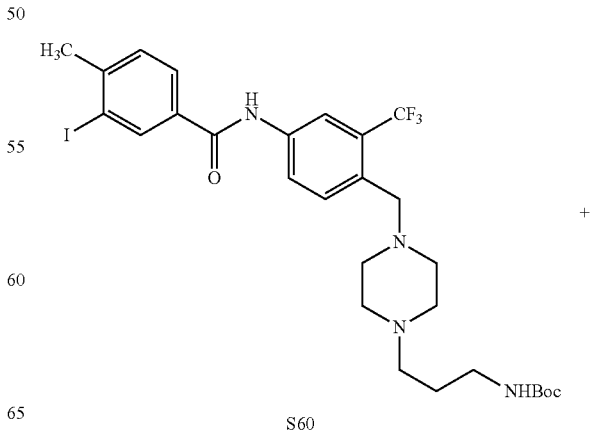

S60

-continued

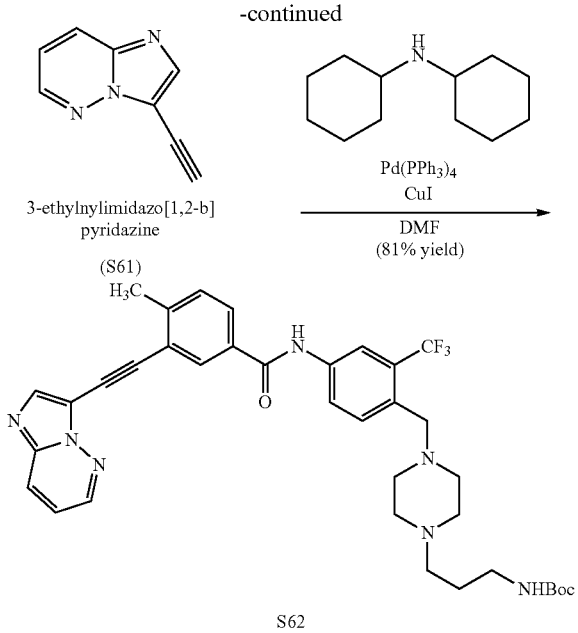

S60 (250 mg, 0.38 mmol), Pd(PPh$_3$)$_4$ (21.9 mg, 19 μmol), CuI (5.4 mg, 28 μmol), and 3-ethynylimidazo[1,2-b]pyridazine (S61) (J. Med. Chem 2010, 53, 4701-4719) (70 mg, 0.49 mmol) were placed in vial sealed with a septa and equipped with stir bar. The vial was evacuated and backfilled with argon (3× times). Dry DMF (5 mL) was added, followed by dicyclohexylamine (113 μL, 0.57 mmol). The suspension was stirred at 22° C. for 15 hours, at which point HPLC indicated consumption of the starting material. Water (20 mL) was added, and reaction was extracted with EtOAc (3×25 mL). The organic layers were combined, dried over Na$_2$SO$_4$, filtered, and concentrated. Crude material was purified by preparative HPLC (C$_{18}$, 3→97% MeCN/H$_2$O, 0.05% TFA) to provide 208 mg (81% yield) of S62 as a yellow oil. $^1$H NMR (300 MHz, DMSO-d$_6$) δ 10.56 (s, 1H), 8.72 (dd, J=4.4, 1.6 Hz, 1H), 8.26 (dd, J=9.2, 1.6 Hz, 1H), 8.23 (s, 1H), 8.21 (d, J=2.0 Hz, 2H), 8.07 (dd, J=8.6, 2.2 Hz, 1H), 7.95 (dd, J=8.0, 1.9 Hz, 1H), 7.70 (d, J=8.5 Hz, 1H), 7.54 (d, J=8.2 Hz, 1H), 7.39 (dd, J=9.2, 4.5 Hz, 1H), 3.57 (s, 2H), 2.93 (q, J=6.6 Hz, 2H), 2.61 (s, 3H), 2.48-2.35 (m, 7H), 2.35-2.20 (m, 3H), 1.54 (q, J=6.9 Hz, 2H), 1.37 (s, 9H); $^{13}$C NMR (75 MHz, DMSO-d$_6$) δ 164.5, 155.5, 145.0, 143.5, 139.6, 138.2, 138.1, 132.18, 132.0, 131.2, 130.1, 130.0, 128.5, 127.3 (q, J=32 Hz), 126.11, 126.07, 123.5, 122.5, 119.0, 117.2 (q, J=6.5 Hz), 111.7, 96.4, 81.1, 77.3, 57.4, 55.3, 52.6, 38.3, 28.2, 26.5, 20.4; MS (ESI+) calc'd for C$_{36}$H$_{41}$F$_3$N$_7$O$_3^+$ [M+H]$^+$ 676.31, found 676.30.

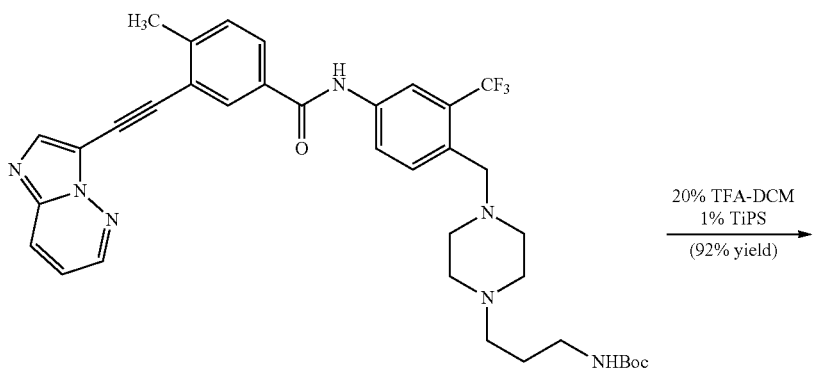

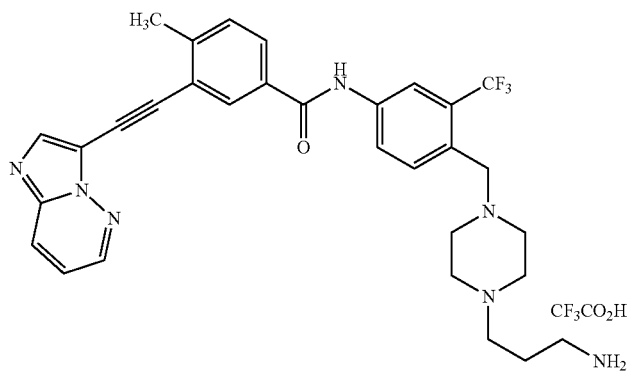

S62 (150 mg, 166 µmol) was treated with 15 mL cleavage cocktail (100:20:1 DCM:TFA:TiPS) for 1 hour, at which point HPLC indicated consumption of the starting material and conversion to a single product. Solvent was removed under vacuum to provide 140 mg (92% yield) of S63 as a yellow solid, which was used in the next step without further characterization and purification.

General Procedure for Ponatinib-CA Synthesis:

To a solution of S63 (10 µmol) in DMF (5 mL), 4-nitrophenyl carbonate of the appropriate chloroalkane (CA-T1 4-Nitrophenylcarbonate (S87) synthesis)[3] (10 µmol) was added, followed by Et$_3$N (50 µmol) at 22° C. The resulting yellow solution was left at 22° C. for 16 hours, at which point the solvent was removed under vacuum, and the crude residue was purified by silica gel chromatography (0→30% MeOH/DCM) to provide ponatinib-CA conjugate as clear or yellow(ish) oil.

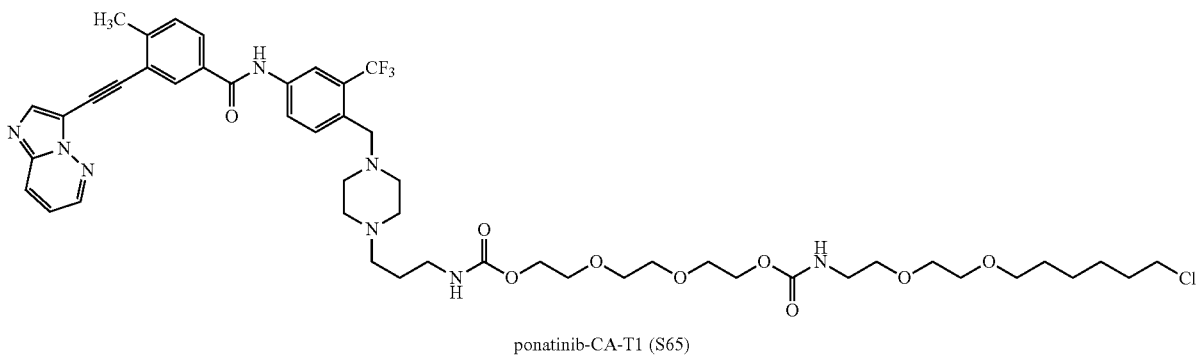 [SMILES: Cc1ccc(C(=O)Nc2ccc(CN3CCN(CCCNC(=O)OCCOCCOCCOC(=O)NCCOCCOCCCCCCCl)CC3)c(C(F)(F)F)c2)cc1C#Cc1cnc2cccnn12]

ponatinib-CA-T1 (S65)

$^1$H NMR (300 MHz, CD$_3$OD) δ 8.63 (dd, J=4.4, 1.5 Hz, 1H), 8.16 (dd, J=6.6, 2.1 Hz, 2H), 8.10 (dd, J=9.2, 1.6 Hz, 1H), 8.06 (s, 1H), 7.95 (dd, J=8.5, 2.2 Hz, 1H), 7.90 (dd, J=8.0, 2.0 Hz, 1H), 7.77 (d, J=8.7 Hz, 1H), 7.48 (d, J=8.1 Hz, 1H), 7.36 (dd, J=9.3, 4.6 Hz, 1H), 4.20-4.12 (m, 4H), 3.75-3.64 (m, 6H), 3.63 (s, 4H), 3.60-3.50 (m, 8H), 3.47 (t, J=6.5 Hz, 2H), 3.35-3.26 (m, 2H, overlap with CD$_2$HOD), 3.15 (t, J=6.7 Hz, 2H), 2.66 (s, 4H), 2.63-2.54 (m, 6H), 2.50 (t, J=7.7 Hz, 2H), 1.74 (h, J=7.0 Hz, 4H), 1.58 (p, J=6.8 Hz, 2H), 1.51-1.29 (m, 4H); MS (ESI+) calc'd for C$_{49}$H$_{65}$ClF$_3$N$_8$O$_9{}^+$ [M+H]$^+$ 1001.45, found 1001.57.

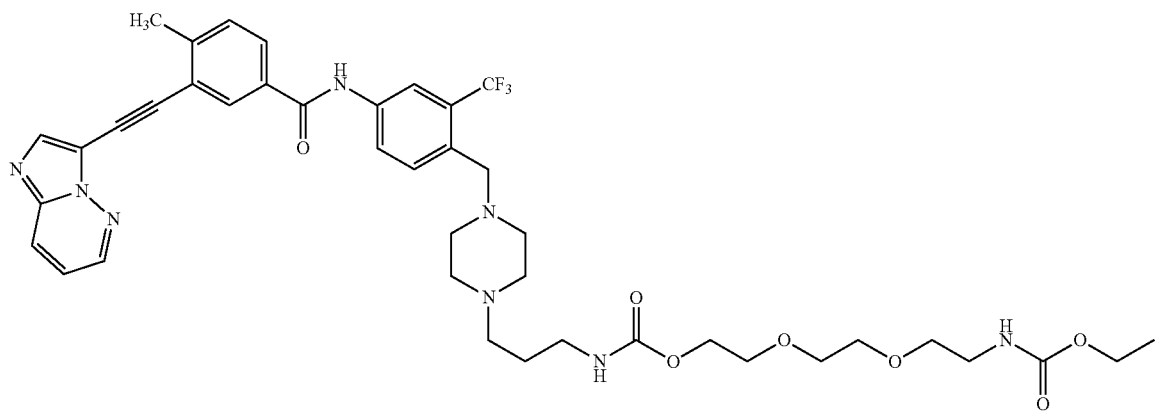

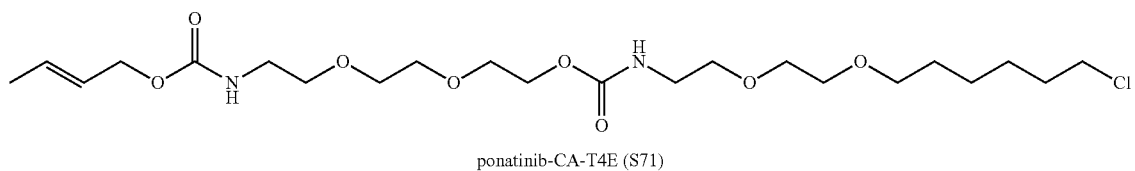

ponatinib-CA-T4E (S71)

¹H NMR (300 MHz, CD₃OD) δ 8.65 (dd, J=4.5, 1.6 Hz, 1H), 8.19 (d, J=2.0 Hz, 1H), 8.17-8.15 (m, 1H), 8.13 (dd, J=9.2, 1.6 Hz, 1H), 8.10 (s, 1H), 8.03 (dd, J=2.0, 8.5 Hz, 1H), 7.91 (dd, J=8.0, 2.0 Hz, 1H), 7.77 (d, J=8.5 Hz, 1H), 7.50 (d, J=8.1 Hz, 1H), 7.39 (dd, J=9.5, 4.2 Hz, 1H), 5.85 (m, 2H), 4.53 (m, 5H), 4.22-4.11 (m, 5H), 3.79 (s, 3H), 3.73-3.65 (m, 5H), 3.65-3.56 (m, 14H), 3.55-3.49 (m, 9H), 3.49-3.43 (t, J=6.5 Hz, 4H), 3.28-3.15 (m, 8H), 3.14-3.01 (m, 1H), 2.67 (s, 3H), 2.61-2.41 (m, 1H), 1.94 (m, 2H), 1.76 (p, J=6.8 Hz, 2H), 1.60 (q, J=6.9 Hz, 2H), 1.50-1.28 (m, 4H); (ESI+) calc'd for $C_{61}H_{85}ClF_3N_{10}O_{15}^+$ [M+H]⁺ 1289.58, found 1289.79.

Synthesis of Ponatinib Tri-Amide Chloroalkane Conjugate
Synthesis of Tri-Amide Chloroalkane Linker

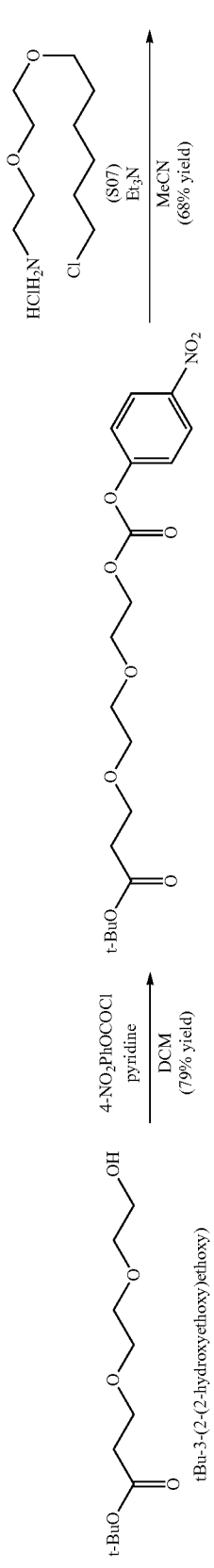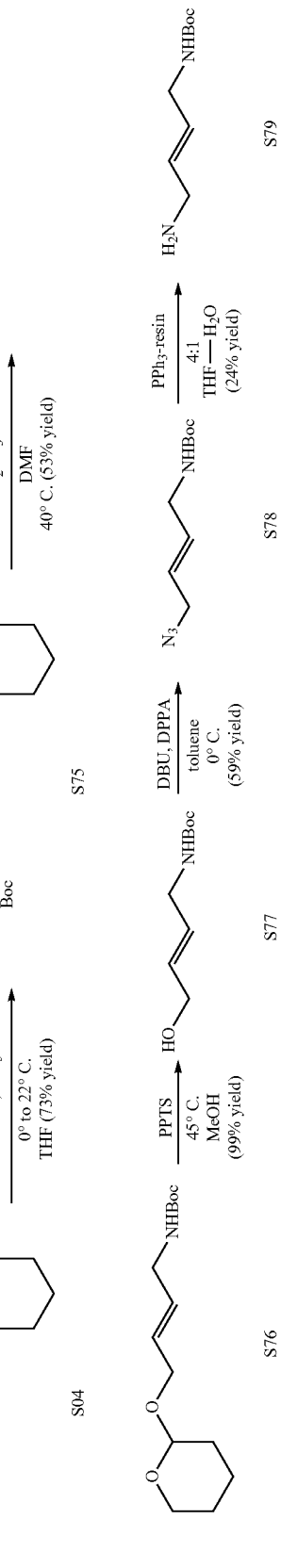

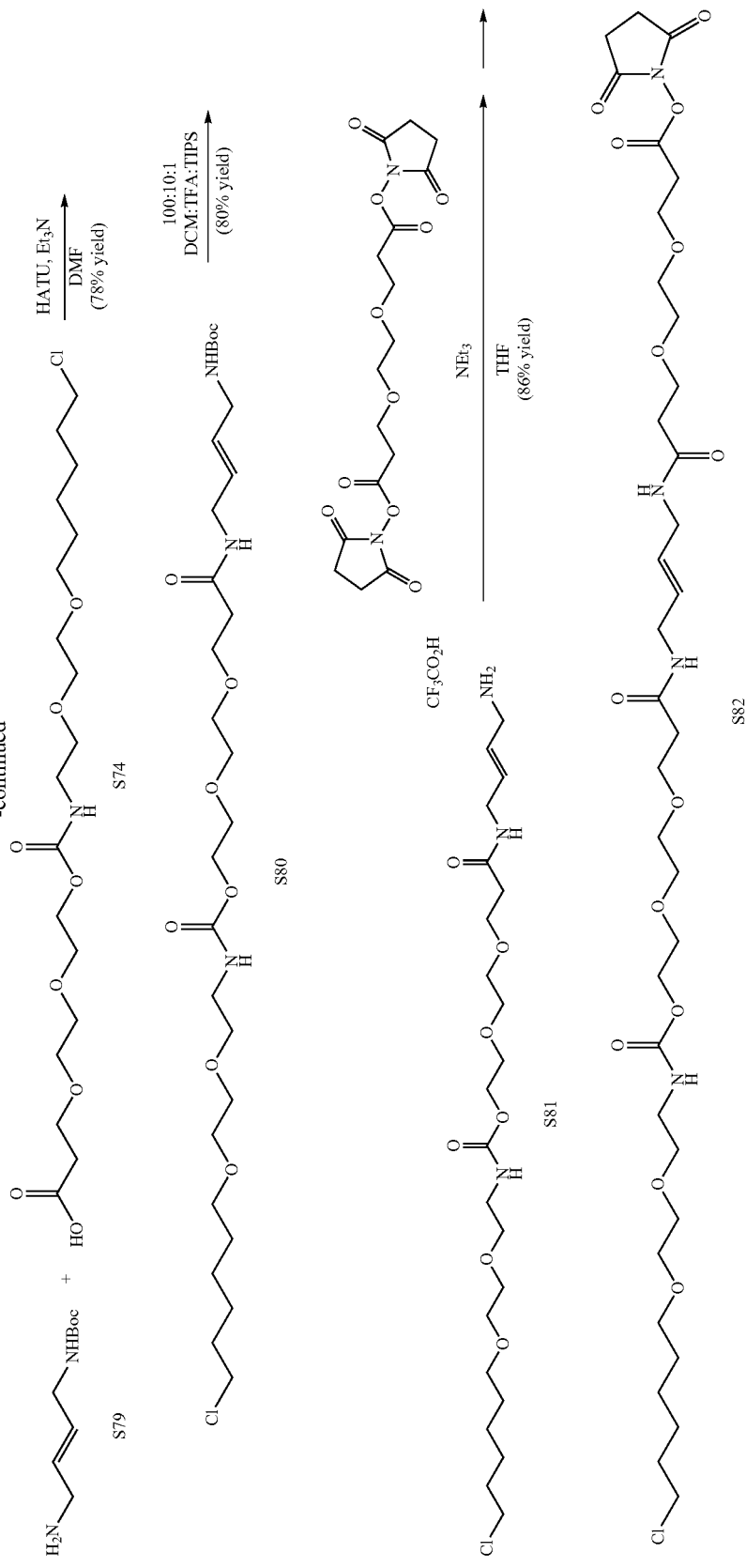

-continued
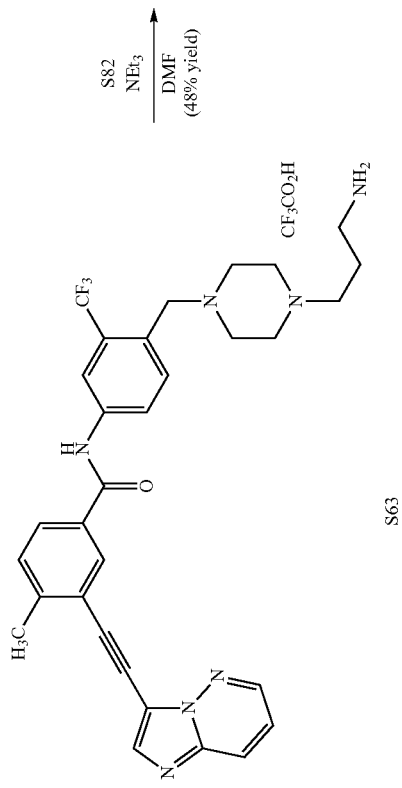
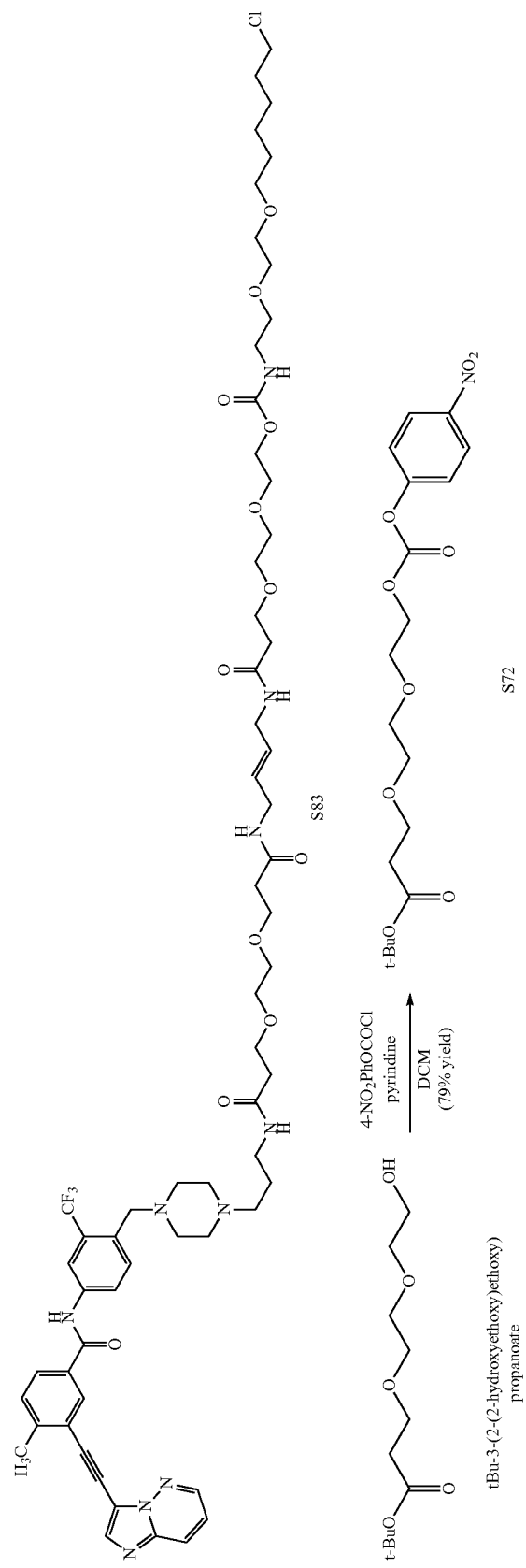

To a stirred solution of tert-butyl 3-(2-(2-hydroxyethoxy)ethoxy)propanoate (1.00 g, 4.27 mmol) in DCM (100 mL), 4-nitrophenylchloroformate (1.29 g, 6.40 mmol) was added, followed by pyridine (1.72 mL, 21.3 mmol). The resulting murky solution was stirred at 22° C. for 20 hours, at which point TLC analysis indicated complete consumption of the starting material. The reaction mixture was concentrated to approximately 20 mL under vacuum and purified by silica gel chromatography (0→40% EtOAc/Heptane) to provide 1.35 g (79% yield) of S72 as a clear oil. $^1$H NMR (300 MHz, DMSO-d$_6$) δ 8.47-8.18 (m, 2H), 7.68-7.44 (m, 2H), 4.54-4.16 (m, 2H), 3.76-3.65 (m, 2H), 3.60 (t, J=6.2 Hz, 2H), 3.58-3.46 (m, 4H), 2.42 (t, J=6.2 Hz, 2H), 1.39 (s, 9H); 13C NMR (75 MHz, DMSO-d$_6$) δ 170.4, 155.3, 152.0, 145.1, 125.4, 122.5, 79.7, 69.7, 69.6, 68.3, 67.9, 66.2, 35.8, 27.7; MS (ESI+) calc'd for C$_{18}$H$_{25}$NNaO$_9$$^+$ [M+Na]$^+$ 422.1, found 422.1.

To a solution of S73 (564 mg, 1.17 mmol) in DCM (20 mL), TiPS (0.25 mL) was added, followed by TFA (5 mL). The resulting solution was stirred for 5 hours, at which point TLC analysis indicated complete consumption of the starting material. The solvent was removed under vacuum, and crude S74 was used in further steps without extra purification.

$^1$H NMR (300 MHz, DMSO-d$_6$) δ 7.18 (t, J=5.5 Hz, 1H), 4.11-3.93 (m, 2H), 3.70-3.58 (m, 3H), 3.58-3.51 (m, 3H), 3.51-3.42 (m, 7H), 3.38 (qd, J=6.8, 1.2 Hz, 5H), 3.11 (q, J=5.9 Hz, 2H), 2.44 (t, J=6.3 Hz, 2H), 1.69 (dt, J=8.0, 6.5 Hz, 2H), 1.49 (p, J=6.9 Hz, 2H), 1.42-1.20 (m, 4H); MS (ESI+) calc'd for C$_{18}$H$_{35}$ClNO$_8$$^+$ [M+H]$^+$ 428.21, found 428.49.

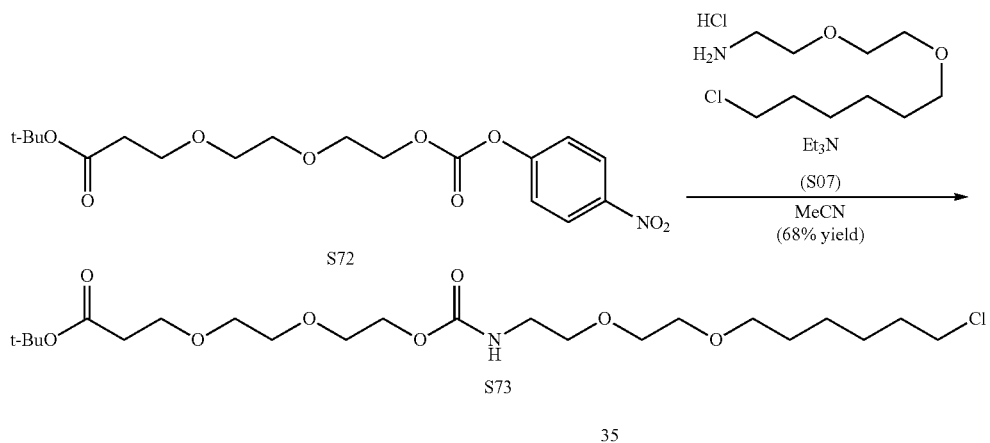

To a solution of S72 (820 mg, 2.05 mmol) in MeCN (20 mL), 2-(2-((6-chlorohexyl)oxy)ethoxy)ethan-1-amine hydrochloride (S07) (588 mg, 2.26 mmol) was added, followed by trimethylamine (1.43 mL, 10.3 mmol). The resulting yellow solution was stirred for 18 hours, at which point TLC analysis indicated complete consumption of starting material. The reaction mixture was concentrated approximately under vacuum and purified by silica gel chromatography (0→100% EtOAc/Heptane) to provide 674 mg (68% yield) of S73 as a clear oil. $^1$H NMR (300 MHz, DMSO-d$_6$) δ 7.16 (t, J=5.5 Hz, 1H), 4.16-3.89 (m, 2H), 3.72-3.53 (m, 6H), 3.53-3.43 (m, 8H), 3.38 (m, 4H), 3.11 (q, J=6.0 Hz, 2H), 2.41 (t, J=6.2 Hz, 2H), 1.70 (dq, J=8.0, 6.5 Hz, 2H), 1.58-1.44 (m, 2H), 1.39 (s, 13H); $^{13}$C NMR (75 MHz, DMSO-d$_6$) δ 170.4, 156.2, 79.7, 70.2, 69.6, 69.5, 69.4, 69.1, 68.8, 66.2, 63.1, 45.3, 35.8, 32.0, 29.0, 27.7, 26.1, 24.9; MS (ESI+) calc'd for C$_{22}$H$_{42}$ClNNaO$_8$$^+$ [M+Na]$^+$ 506.3, found 506.2.

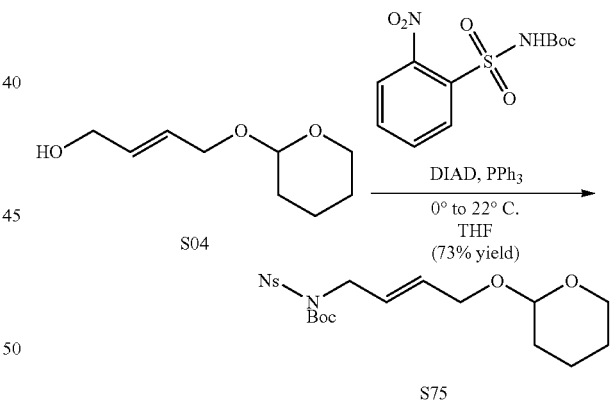

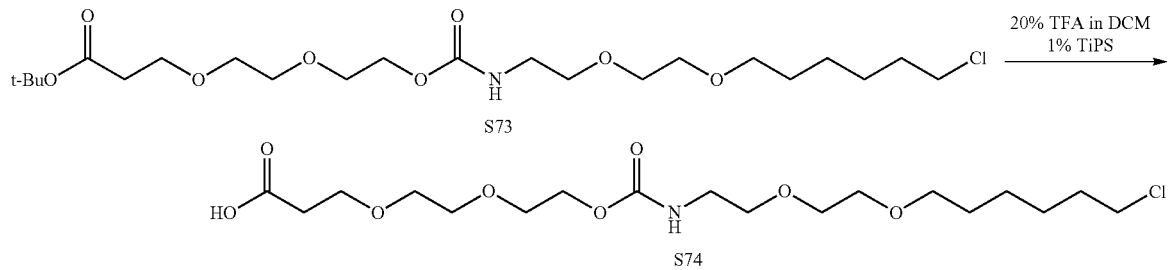

To a stirred solution of S04 (1.20 g, 6.95 mmol), NosN-HBoc (2.10 g, 6.95 mmol) and PPh$_3$ (2.73 g, 10.4 mmol) in THF (30 mL) at 0° C. under argon, DIAD (2.33 mL, 11.1 mmol, 94%) was added. The resulting yellow solution was allowed to warm up to 22° C. and stirred for 17 hours, at which point TLC analysis indicated complete consumption of the starting material. Solvent was removed under vacuum, and crude residue was purified by silica gel chromatography (0→50% EtOAc/Heptane) to provide 2.3 g (73% yield) of S75 as a yellow oil. $^1$H NMR (300 MHz, DMSO-d$_6$) δ 8.26-8.12 (m, 1H), 8.12-8.03 (m, 1H), 8.03-7.78 (m, 2H), 5.90-5.63 (m, 2H), 4.27 (m, 2H), 4.29-4.23 (m, 2H), 4.20-4.07 (m, 1H), 4.02-3.86 (m, 1H), 3.72 (ddd, J=11.4, 8.0, 3.2 Hz, 1H), 3.51-3.34 (m, 1H), 1.84-1.54 (m, 2H), 1.53-1.38 (m, 4H), 1.23 (s, 9H); $^{13}$C NMR (75 MHz, DMSO-d$_6$) δ 149.5, 147.1, 135.5, 132.7, 131.7, 131.4, 130.1, 126.6, 124.8, 97.2, 84.9, 65.9, 61.3, 48.1, 30.2, 27.2, 25.0, 19.1; MS (ESI+) calc'd for C$_{20}$H$_{29}$N$_2$O$_8$S$^+$ [M+H]$^+$ 457.16, found 457.4.

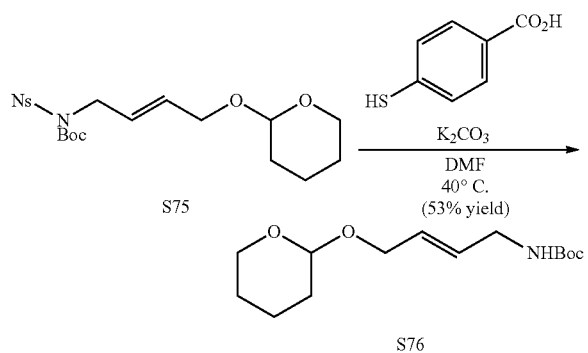

To a solution of S75 (690 mg, 1.51 mmol) and 4-mercaptobenzoic acid (466 mg, 3.02 mmol), potassium carbonate (836 mg, 6.05 mmol) was added, and the resulting suspension was warmed up to 40° C. and stirred for 20 hours, at which point TLC analysis indicated complete consumption of the starting material. The solvent was removed under vacuum, and the crude residue was partitioned between water (50 mL) and DCM (50 mL). The organic layer was removed, and the aqueous layer was extracted twice with additional DCM (50 mL). Organic layers were combined, dried MgSO$_4$, and concentrated. The crude residue was purified by silica gel chromatography (0→40% EtOAc/Heptane) to provide 219 mg (53% yield) of S76 as a yellow oil. $^1$HNMR (300 MHz, DMSO-d$_6$) δ 6.98 (s, 1H), 5.80-5.44 (m, 2H), 4.58 (d, J=4.0 Hz, 1H), 4.19-3.99 (m, 1H), 3.88 (dd, J=12.7, 3.7 Hz, 1H), 3.72 (ddd, J=11.4, 7.9, 3.3 Hz, 1H), 3.53 (s, 2H), 3.43 (dd, J=11.0, 5.7 Hz, 1H), 1.85-1.54 (m, 2H), 1.45 (d, J=5.3 Hz, 4H), 1.37 (s, 9H); $^{13}$C NMR (75 MHz, DMSO-d$_6$) δ 155.4, 129.9, 126.8, 97.1, 77.6, 66.3, 61.2, 41.1, 30.2, 28.2, 25.0, 19.1; MS (ESI+) calc'd for C$_{14}$H$_{25}$NNaO$_4^+$ [M+Na]$^+$ 294.2, found 294.0.

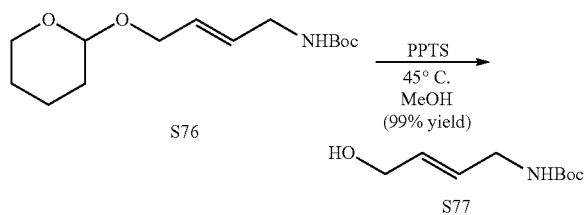

To a solution of S76 (218 mg, 803 μmol) in MeOH (10 mL), PPTS (20 mg, 80 μmol) was added. The reaction mixture was kept at 45° C. for 90 minutes, at which point TLC analysis indicated complete consumption of the starting material. Solvent was removed under vacuum, and the crude residue was purified by silica gel chromatography (0→70% EtOAc/Heptane) to provide 150 mg (99% yield) of S77 as a clear oil. $^1$HNMR (300 MHz, DMSO-d$_6$) δ 6.94 (m, 1H), 5.81-5.27 (m, 2H), 4.65 (s, 1H), 3.90 (s, 2H), 3.51 (m, 2H), 1.37 (s, 9H); $^{13}$C NMR (75 MHz, DMSO-d$_6$) δ 155.5, 131.0, 126.8, 77.5, 60.9, 41.2, 28.3; MS (ESI+) calc'd for C$_9$H$_{18}$N$_8$O$_3^+$ [M+H]$^+$ 188.13, found 188.17.

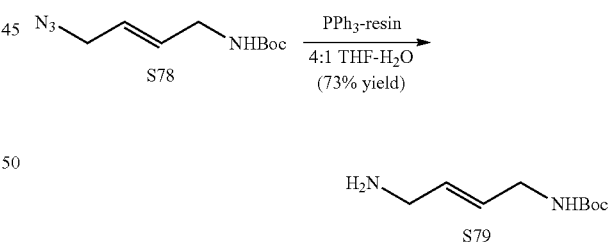

To a stirred solution of S77 (150 mg, 801 μmol) in toluene (5 mL) at 0° C., DPPA (270 mg, 961 μmol) was added, followed by DBU (145 μL, 961 μmol). The reaction mixture was kept at 0° C. for 2 hours, at which point TLC analysis indicated complete consumption of the starting material, and the reaction mixture was directly loaded onto silica gel column and purified by silica gel chromatography (0→50% EtOAc/Heptane) to provide 100 mg (59% yield) of S78 as a clear oil (5:1 mixture of isomers by $^1$H NMR). $^1$H NMR (300 MHz, CD$_2$Cl$_2$, reported for major (linear) isomer) δ 5.95-5.51 (m, 2H), 4.70 (br. s, 1H), 3.76 (m, 4H), 1.43 (s, 9H); MS (ESI+) calc'd for C$_{18}$H$_{33}$N$_8$O$_3^+$ [2M+H]$^+$ 425.26, found 425.45.

To a stirred solution of S78 (100 mg, 471 μmol) in a mixture of THF (10 mL) and H$_2$O (2.5 mL), resin-bound PPh$_3$ (1 g, 1.4-2.00 mmol/g,) was added. The reaction mixture was kept at 22° C. for 18 hours, at which point TLC analysis indicated complete consumption of the starting material. Solids were filtered out, solvent removed under vacuum, and crude residue purified by silica gel chromatography (0→90% MeOH/DCM) to provide 21 mg (24% yield) of S79 as a yellowish solid. $^1$H NMR (300 MHz, DMSO-d$_6$) δ 6.89 (m, 1H), 5.72-5.51 (m, 1H), 5.51-5.31 (m, 1H), 3.48 (m, 2H), 3.08 (dd, J=5.1, 1.5 Hz, 3H), 1.35 (s, 9H).

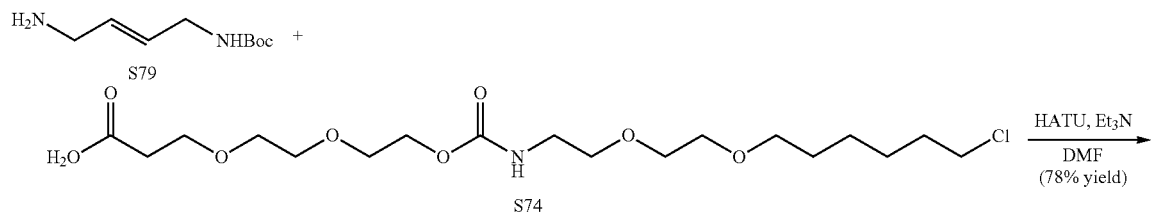

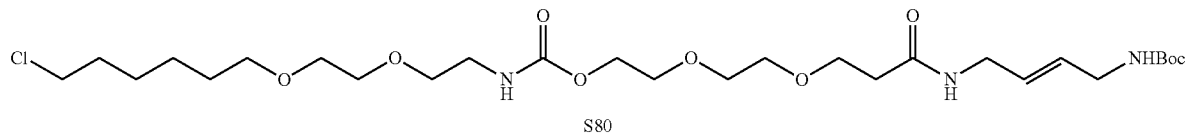

To a solution of S79 (20.0 mg, 107 µmol) in DMF (2 mL), a solution of S74 (57.4 mg, 134 µmol), HATU (51.0 mg, 134 µmol), and Et$_3$N (75 µL, 537 µmol) in DMF (4 mL) was added. The resulting yellow solution was stirred at 40° C. for 2 hours, at which point TLC analysis indicated complete consumption of the starting material. Solvent was removed under vacuum, and crude residue purified by silica gel chromatography (0→30% MeOH/DCM) to provide 50 mg (78% yield) of S80 as a clear oil. $^1$H NMR (300 MHz, DMSO-d$_6$) δ 7.96 (t, J=5.7 Hz, 1H), 7.19 (t, J=5.7 Hz, 1H), 6.94 (t, J=5.6 Hz, 1H), 5.50-5.44 (m, 2H), 4.02 (m, 2H), 3.69-3.44 (m, 16H), 3.42-3.34 (m, 4H), 3.11 (q, J=5.8 Hz, 4H), 2.32 (t, J=6.5 Hz, 2H), 1.70 (p, J=6.8 Hz, 2H), 1.49 (p, J=6.9 Hz, 2H), 1.37 (s, 9H), 1.35-1.27 (m, 2H), 1.18 (t, J=7.4 Hz, 2H); MS (ESI+) calc'd for C$_{27}$H$_{51}$ClN$_3$O$_9$$^+$ [M+H]$^+$ 596.33, found 596.48.

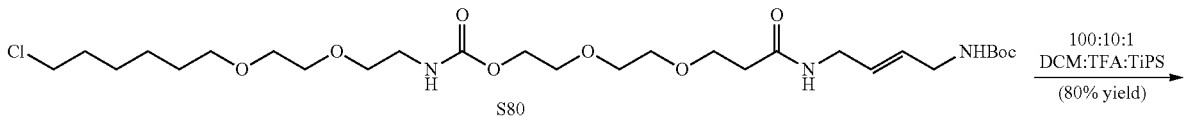

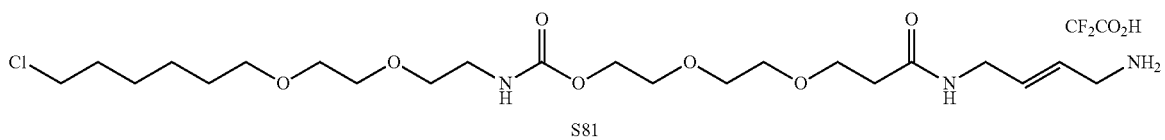

S80 (50 mg, 84 µmol) was dissolved in 10 mL of cleavage cocktail (100:10:1 DCM-TFA-TiPS), and the reaction mixture was stirred at 22° C. for 40 minutes, at which point TLC analysis indicated complete consumption of the starting material. Solvent was removed under vacuum, and crude residue purified, and triturated with Et$_2$O to provide 41 mg (80% yield) of S81 as a clear oil. $^1$H NMR (300 MHz, DMSO-d$_6$) δ 8.08 (t, J=5.9 Hz, 1H), 7.78 (s, 3H), 7.18 (t, J=5.5 Hz 1H), 6.85-5.71 (m, 1H), 5.62-5.45 (m, 1H), 4.04 (m, 2H), 3.71 (t, J=5.5 Hz, 2H), 3.66-3.53 (m, 6H), 3.53-3.41 (m, 12H), 3.11 (q, J=6.0 Hz, 4H), 2.33 (d, J=6.4 Hz, 2H), 1.71 (p, J=6.7 Hz, 2H), 1.49 (p, J=6.8 Hz, 2H), 1.35 (m, 4H); MS (ESI+) calc'd for C$_{22}$H$_{43}$ClN$_3$O$_7$$^+$ [M+H]$^+$ 496.28, found 496.36.

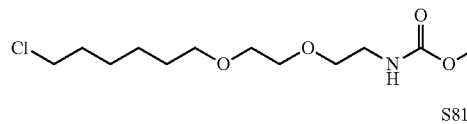
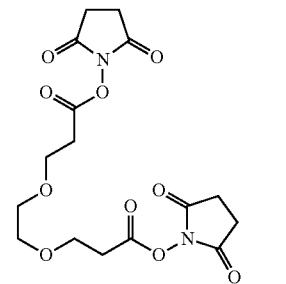

(bis(2,5-dioxopyrrolidin-1-yl) 3,3'-(ethane-1,2-diylbis(oxy)) dipropionate)
→
THF
(86% yield)

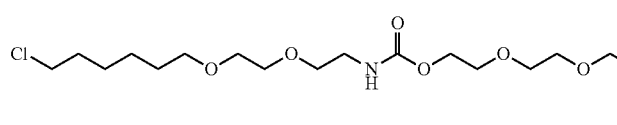

To a vigorously stirred solution of bis(2,5-dioxopyrrolidin-1-yl) 3,3'-(ethane-1,2-diylbis(oxy))dipropionate (52.0 mg, 131 μmol) and NEt$_3$ (9 μL, 0.07 mmol) in THF (20 mL), a solution of S81 (20 mg, 33 μmol) in THF (5 mL) was added over 15 minutes at 22° C. Upon completion of addition, the reaction mixture was allowed to react for an additional 40 minutes. Solvent was removed under vacuum, and crude residue was purified by silica gel chromatography (0→30% MeOH/DCM), a fraction of which provided the desired m/z in MS was collected to provide 22 mg (86% yield) of S82 as a clear oil. MS (ESI+) calc'd for $C_{34}H_{58}ClN_4O_{14}^+$ [M+H]$^+$ 781.36, found 781.53.

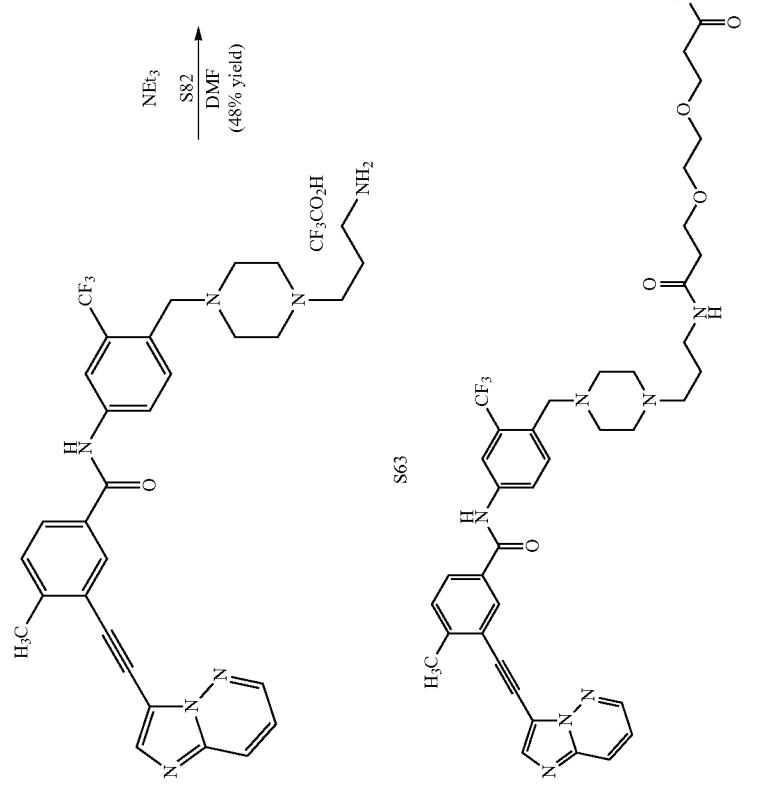

A solution of S63 (8.5 mg, 9.3 μmol), S82 (22 mg, 28 μmol), and Et$_3$N (7 μL, 48 μmol) in DMF (3 mL) was stirred at 22° C. for 90 minutes, at which point TLC analysis indicated complete consumption of the starting material. Solvent was removed under vacuum, and crude residue was purified by silica gel chromatography (0→100% MeOH/DCM) to provide 5.5 mg (48% yield) of S83 as a clear oil. $^1$H NMR (300 MHz, CD$_3$OD) δ 8.63 (dd, J=4.3, 1.5 Hz, 1H), 8.16 (dd, J=10.0, 2.1 Hz, 1H), 8.10 (dd, J=9.2, 1.6 Hz, 1H), 8.06 (s, 1H), 7.94 (dd, J=8.5, 2.2 Hz, 1H), 7.90 (dd, J=8.0, 2.0 Hz, 1H), 7.77 (d, J=8.5 Hz, 1H), 7.49 (d, J=8.1 Hz, 1H), 7.36 (dd, J=8.9, 4.1 Hz, 1H), 5.63 m, 2H), 4.15 (t, J=4.8 Hz, 2H), 3.84-3.76 (m, 4H), 3.75-3.69 (m, 6H), 3.67 (m, 3H), 3.63-3.54 (m, 11H), 3.54-3.50 (m, 2H), 3.47 (t, J=6.5 Hz, 2H), 3.28 (m, 2H), 3.26-3.16 (m, 2H), 2.66 (s, 3H), 2.51 (d, J=25.9 Hz, 8H), 2.43 (td, J=6.1, 4.4 Hz, 6H), 1.85-1.66 (m, 4H), 1.58 (p, J=6.8 Hz, 2H), 1.50-1.33 (m, 4H); MS (ESI+) calc'd for $C_{61}H_{85}ClF_3N_{10}O_{12}^+$ [M+H]$^+$ 1241.60, found 1241.81.

Synthesis of Ponatinib All-PEG Chloroalkane Conjugate
Synthesis (Unoptimized) of All-PEG Chloroalkane Linker

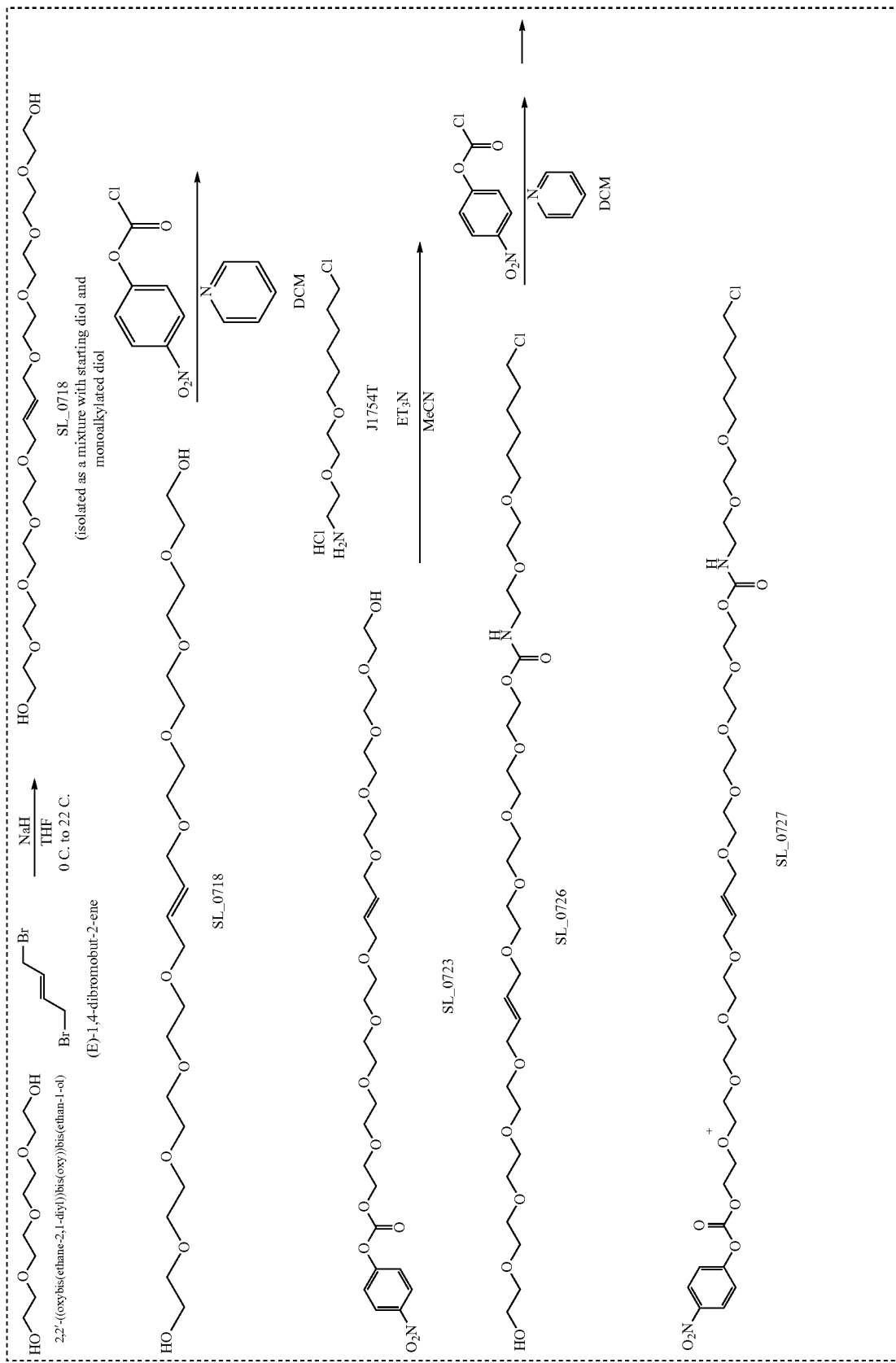

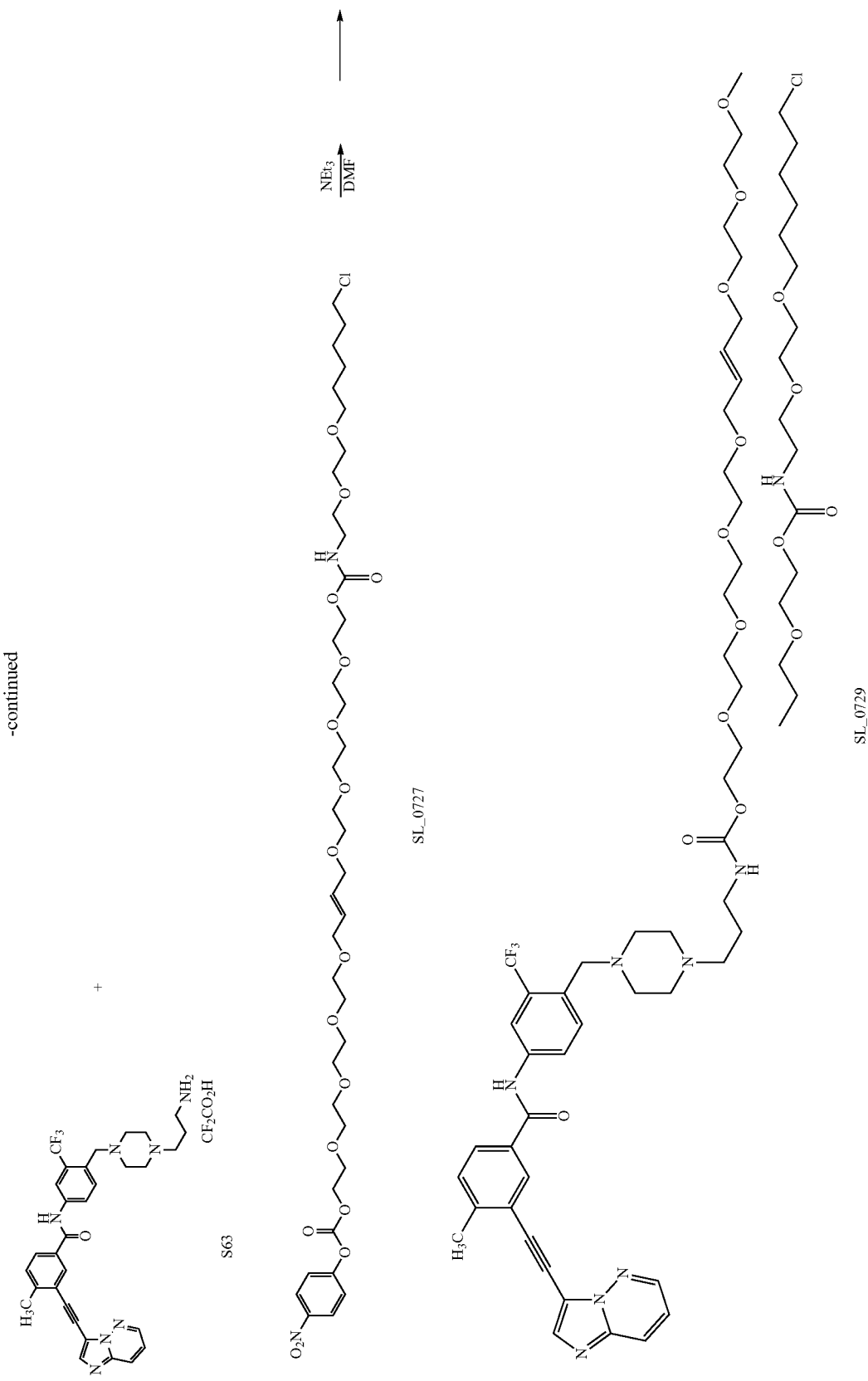

A 500 mL oven-dried flask equipped with stir bar was charged with NaH (988 mg, 60% dispersion mineral oil, 24.7 mmol), followed by THF (100 mL) under $N_2$ at 0° C. Neat 2,2'-((oxybis(ethane-2,1-diyl))bis(oxy))bis(ethan-1-ol) (4.0 g, 21 mmol) was added dropwise over the period of 10 minutes, followed by (E)-1,4-dibromobut-2-ene (2.20 g, 10.3 mmol) in THF (10 mL) added in one portion. The reaction mixture was allowed to warm up to 22° C. over a period of 20 hours, and the reaction mixture quenched by addition of 1 mL of AcOH. The reaction mixture was absorbed onto celite, and solvent was removed under vacuum. Purification by silica gel chromatography (0→30% MeOH/DCM) was performed. Fractions enriched with bis-alkylated product (m/z=441.26 [M+H]$^+$) were combined and concentrated to provide 360 mg of yellow oil as a mixture of starting diol, mono and bis-alkylated (SL_0718) products.

Mixture SL_0718 (360 mg) was dissolved in DCM (25 mL) and treated with 4-nitrophenylchloroformate (494 mg, 2.45 mmol) followed by pyridine (0.66 mL, 8.2 mmol). The resulting solution was left stirred at 22° C. for 18 hours and then loaded directly on silica gel column. Purification by silica gel chromatography (0→10% MeOH/DCM). Minor fraction yielded 27 mg of clean product SL_0723 as yellowish oil. $^1$H NMR (300 MHz, DMSO-$d_6$) δ 8.44-8.12 (m, 2H), 7.78-7.30 (m, 2H), 5.71-5.68 (m, 2H), 4.53 (t, J=5.4 Hz), 4.41-4.25 (m, 2H), 3.91 (m, 4H), 3.71-3.65 (m, 2H), 3.55 (m, 2H), 3.52-3.42 (m, 24H), 3.41-3.36 (m, 2H); MS (ESI+) calc'd for $C_{27}H_{43}NNaO_{14}^+$ [M+Na]$^+$ 628.26, found 628.24.

To a solution of SL_0723 (27 mg, 45 μmol) in MeCN (7 mL), J1454T (13 mg, 50 μmol) was added, followed by NEt$_3$ (31 μL, 0.22 mmol). The resulting yellow solution was allowed to react for 20 hours, at which point TLC analysis indicated complete consumption of starting material. Solvent was removed under vacuum, and crude residue was purified by silica gel chromatography (0→10% MeOH/DCM) to provide 26 mg (85% yield) of SL_0725 as a yellow oil. $^1$H NMR (300 MHz, DMSO-$d_6$) δ 7.18 (t, J=5.1 Hz, 1H), 5.74-5.67 (m, 2H), 4.55 (t, J=5.4 Hz, 1H), 4.07-4.01 (m, 2H), 3.99-3.84 (m, 4H), 3.62 (t, J=6.6 Hz, 2H), 3.58-3.44 (m, 32H), 3.44-3.33 (m, 6H), 3.11 (q, J=5.9 Hz, 2H), 1.70 (p, J=6.7 Hz, 2H), 1.49 (p, J=6.8 Hz, 2H), 1.43-1.22 (s, 4H); MS (ESI+) calc'd for $C_3H_{61}ClNO_{13}^+$ [M+H]$^+$ 690.38, found 690.62.

To a stirred solution of SL_0725 (26 mg, 38 μmol) in DCM (10 mL), 4-nitrophenylchloroformate (15 mg, 75 μmol) was added, followed by pyridine (15 μL, 0.19 mmol). The resulting solution was stirred at 22° C. for 20 hours, at which point TLC analysis indicated complete consumption of the starting material. The reaction mixture was concentrated to approximately 5 mL under vacuum and purified by silica gel chromatography (0→10% MeOH/DCM) to provide 5 mg (16% yield) of SL_0727 as a clear oil. $^1$H NMR (300 MHz, DMSO-$d_6$) δ 8.45-8.14 (m, 2H), 7.67-7.45 (m, 2H), 7.18 (t, J=5.6 Hz, 1H), 5.72 (m, 2H), 4.47-4.27 (m, 2H), 4.03 (t, J=4.8 Hz, 2H), 3.99-3.87 (m, 4H), 3.78-3.66 (m, 2H), 3.62 (t, J=6.7 Hz, 2H), 3.58-3.42 (m, 30H), 3.42-3.33 (m, 4H), 3.10 (q, J=6.0 Hz, 2H), 1.70 (p, J=6.7 Hz, 2H), 1.47 (q, J=6.9 Hz, 2H), 1.41 (s, 4H); MS (ESI+) calc'd for $C_{38}H_{64}ClN_2O_{17}^+$ [M+H]$^+$ 855.39, found 855.54.

To a solution of S63 (5 mg, 6 μmol) in DMF (5 mL), SL_0727 (5 mg, 6 μmol) was added, followed by a drop of NEt$_3$. The resulting yellowish solution was left stirred at 22° C. for 19 hours, at which point HPLC analysis indicated complete consumption of the starting material. The reaction mixture was concentrated under vacuum and purified by silica gel chromatography (0→30% MeOH/DCM) to provide 5.5 mg (74% yield) of SL_0729 as a clear oil. $^1$H NMR (300 MHz, CD$_3$OD) δ 8.63 (dd, J=4.5, 1.6 Hz, 1H), 8.16 (dd, J=7.7, 2.1 Hz, 2H), 8.09 (dd, J=9.3, 1.6 Hz, 1H), 8.06 (s, 1H), 7.96 (dd, J=8.5, 2.0 Hz, 1H), 7.90 (dd, J=8.0, 2.0 Hz, 1H), 7.76 (d, J=8.8 Hz, 1H), 7.48 (d, J=8.2 Hz, 1H), 7.36 (dd, J=9.2, 4.4 Hz, 1H), 5.79 (m, 2H), 4.34-4.07 (m, 4H), 4.07-3.86 (m, 4H), 3.71-3.59 (m, 28H), 3.59-3.50 (m, 12H), 3.50-3.43 (m, 2H), 3.27 (t, J=5.5 Hz, 2H), 3.14 (q, J=8.4, 7.5 Hz, 2H), 2.76-2.67 (br. S, 4H), 2.65 (s, 3H), 2.62-2.50 (m, 6H), 1.75 (p, J=6.6 Hz, 4H), 1.58 (p, J=6.7 Hz, 2H), 1.51-1.26 (m, 4H); MS (ESI+) calc'd for $C_{63}H_{91}ClF_3N_8O_{15}^+$ [M+H]$^+$ 1291.63, found 1291.79.

All publications and patents mentioned in the present application are herein incorporated by reference. Various modification, recombination, and variation of the described features and embodiments will be apparent to those skilled in the art without departing from the scope and spirit of the invention. Although specific embodiments have been described, it should be understood that the invention as claimed should not be unduly limited to such specific embodiments. Indeed, various modifications of the described modes and embodiments that are obvious to those skilled in the relevant fields are intended to be within the scope of the following claims.

We claim:

1. A dual-function, cell-permeable, cell-compatible, chemoselectively-cleavable composition, comprising:
   (a) a cellular interaction element, wherein the cellular interaction element is capable of non-covalently binding to a cellular target protein;
   (b) a capture element comprising a haloalkane group; and
   (c) a linker covalently tethering the cellular interaction element to the capture element, wherein said linker comprises a chemoselectively cleavable moiety selected from the group consisting of an allyl-heteroatom group, a propargyl-heteroatom group.

2. The composition of claim 1, wherein the cellular interaction element is a small molecule or peptide.

3. The composition of claim 1, wherein the capture element is a covalent substrate for an enzyme.

4. The composition of claim 1, wherein the capture element is an affinity element.

5. The composition of claim 1, wherein the chemoselectively cleavable moiety comprises an allyl-heteroatom group selected from the group consisting of: allyl ether, allyl amine, allyl ester, allyl amide, allyl urea, allyl carbonate, and allyl carbamate.

6. The composition of claim 5, wherein the chemoselectively-cleavable moiety comprises an allyl carbamate group.

7. The composition of claim 1, wherein the chemoselectively-cleavable moiety comprises a propargyl-heteroatom group selected from the group consisting of: propargyl ether, propargyl amine, propargyl ester, propargyl amide, propargyl urea, propargyl carbonate, and propargyl carbamate.

8. A method comprising:
   (a) administering the dual-function, cell-permeable, cell compatible, chemoselectively-cleavable composition of claim 1 to a cell;
   (b) allowing binding of the chemoselectively-cleavable composition via the cellular interaction element with a corresponding intracellular cellular target to provide chemoselectively-cleavable composition bound intracellular target;
   (c) lysing said cell to produce a cell lysate; and
   (d) providing surface immobilized intracellular target by contacting the cell lysate with a surface immobilized capture agent specific for the capture element of the chemoselectively-cleavable composition to immobilize the chemoselectively-cleavable composition bound intracelluar target on the surface.

9. The method of claim 8, further comprising:
   (e) contacting the surface immobilized intracellular target with a chemoselective agent capable of cleaving the chemoselectivly-cleavable linker, thereby releasing the cellular interaction element and the bound intracellular target from the surface.

10. A system comprising:
   (a) the dual-function, cell-permeable, cell-compatible, chemoselectively-cleavable composition of claim 1; and
   (b) one or more of:
      (i) a cell,
      (ii) a cellular target,
      (iii) a surface-displayed capture agent, and
      (iv) a chemoselective agent.

\* \* \* \* \*